United States Patent
White et al.

(10) Patent No.: US 7,115,558 B2
(45) Date of Patent: Oct. 3, 2006

(54) P450RAI-2(P450 CYTOCHROME 26B), ENCODING NUCLEIC ACID MOLECULES AND METHODS AND USES THEREOF

(75) Inventors: Jay A. White, Newmarket (CA); Martin P. Petkovich, Kingston (CA); Glenville Jones, Kingston (CA); Heather Ramshaw, Napanee (CA)

(73) Assignee: Cytochroma Inc., Markham (CA)

( * ) Notice: Subject to any disclaimer, the term of this patent is extended or adjusted under 35 U.S.C. 154(b) by 20 days.

(21) Appl. No.: 10/433,485

(22) PCT Filed: Dec. 17, 2001

(86) PCT No.: PCT/CA01/01805

§ 371 (c)(1), (2), (4) Date: Nov. 13, 2003

(87) PCT Pub. No.: WO02/48334

PCT Pub. Date: Jun. 20, 2002

(65) Prior Publication Data

US 2004/0131617 A1   Jul. 8, 2004

Related U.S. Application Data

(63) Continuation-in-part of application No. PCT/CA00/01493, filed on Dec. 15, 2000.

(60) Provisional application No. 60/178,314, filed on Jan. 27, 2000, provisional application No. 60/171,110, filed on Dec. 16, 1999.

(30) Foreign Application Priority Data

Dec. 17, 2001  (CA) .................................... 0101805

(51) Int. Cl.
*C07K 16/00* (2006.01)
*C12P 21/08* (2006.01)

(52) U.S. Cl. .................... 514/2; 530/387.1; 530/388.1; 530/388.8; 530/389.1; 435/810

(58) Field of Classification Search ............ 530/387.1, 530/388.1, 388.15, 388.8, 389.1
See application file for complete search history.

(56) References Cited

FOREIGN PATENT DOCUMENTS

| WO | WO 97/49815 | 12/1997 |
|---|---|---|
| WO | WO 9749832 A2 * | 12/1997 |
| WO | WO 200058473 A2 * | 10/2000 |

OTHER PUBLICATIONS

White, Jay A. et al. "Identification of the human cytochrome P450, P450RAI-2, which is predominantly expressed in the adult cerebellum and is responsible for all-trans-retinoic acid metabolism." Proceedings of the National Academy of Sciences of the United States, 97 (2): 6403-6408 (2000).

Miller, Wilson H. Jr. "The emerging role of retinoids and retinoic acid metabolism blocking agents in the treatment of cancer." Cancer, 83 )8_1471-1482 (1998).

Database EMBL 'Online! EBI; Acc. No. AC007002, Mar. 12, 1999 Sulston J.E., Waterston R.: "Homo sapiens BAC clone RP11-493L16 from 2, complete cds" XP002168113 abstract.

Njar, V.C.O. et al. "Potent inhibition of retinoic acid metabolism enzyme(s) by novel azolyl retinoids." Bioorganic & Medicinal Chemistry Letters, 10 (17): 1905-1908 (2000).

* cited by examiner

*Primary Examiner*—Jeffrey Siew
*Assistant Examiner*—Brandon Fetterolf
(74) *Attorney, Agent, or Firm*—Micheline Gravelle; Bereskin & Parr

(57) ABSTRACT

The present invention provides a novel all-trans-RA inducible all-trans-RA metabolizing cytochrome P450, P450RAI-2, that is predominantly expressed in the brain, cerebellum in particular. It is also expressed in normal and tumour lung tissue and in breast cancer cells and may have a correlation with lung and breast cancer. Human P450RAI-2 show 42% amino acid identity to human P450RAI-1 and when transfected into COS-1 cells causes the rapid conversion of all-trans-RA into more polar metabolites including the inactive products 4-oxo-RA, 4-OH-RA and 18-OH-RA. P450RAI-2, as with P450RAI-1, is also inducible in certain cultured cell lines exposed to all-trans-RA. Methods for and uses of the new polynucleotide, polypeptide, fragments thereof and inhibitors thereof, include the treatment of dermatological disorders, cancer and certain brain disorders.

6 Claims, 37 Drawing Sheets

FIGURE 2A

```
ATGCTCTTTGAGGGGCTTGGATCTCGGTGTCGGCGCTTGGCCACCCTCGCCGCGTGCCTGGTG   60
 M  L  F  E  G  L  D  L  V  S  A  L  A  T  L  A  A  C  L  V

TCCGTGACGCTGCTGCTGGCCGTGTCGCAGCTGCGGTGGCAGCTGCGCTGGGCTGCCACT    120
 S  V  T  L  L  L  A  V  S  Q  L  R  W  Q  L  R  W  A  A  T

CGGGACAAGAGCTGCAAGCTGCCCATCCCCCAAGGGATCCATGGGCTTCCCGCTCATCGGA    180
 R  D  K  S  C  K  L  P  I  P  K  G  S  M  G  F  P  L  I  G

GAGACCGGCCACTGGCTGCTGCAGGGTTCTGGCTTCCAGTCGCGGAGGAGAAGTAT     240
 E  T  G  H  W  L  L  Q  G  S  G  F  Q  S  R  R  E  K  Y

GGCAACGTGTTCAAGACGCATTTGTTGGGGCGGCCGCTGATACGCGTGACCGGCGAG     300
 G  N  V  F  K  T  H  L  L  G  R  P  L  I  R  V  T  G  A  E

AACGTGCGCAAGATCCTCATGGGGCCCAACACGCTCGTGAGCACCGAGTGGCCTCGCAGC    360
 N  V  R  K  I  L  M  G  P  N  T  L  V  S  T  E  W  P  R  S

ACCCGCATGTTGCTGGGCCCCAATTCCAATGTGTCCAGCCACGAGGCCCTGGAGAGTTACCTGCCCAAC    420
 T  R  M  L  L  G  P  N  S  N  V  S  S  H  E  A  L  E  S  Y  L  P  K

AAGCGCAAGGTCTTCTCCAAGATCTTCAGCCACTGCGCGCCTGGAGCAGCCACCCGAGGCCATCAAC    480
 K  R  K  V  F  S  K  I  F  S  H  C  A  L  R  A  S  H  P  E  A  I  N

ATCCAGCTGGTGATCCAGGACGCGCAGAAGCTGACCTTCCGCATGGCCATCCGGGTGCTGCTGGGCTTC    540
 I  Q  L  V  I  Q  D  A  Q  K  L  T  F  R  M  A  I  R  V  L  L  G  F

GTGTACCAGGAGGCGGAGGACCTTGGGCACCTCTTTGAGGTCTACCAGCAGTTGTGACAAT    600
 V  Y  Q  E  A  E  D  L  G  H  L  F  E  V  Y  Q  Q  F  V  D  N

AGCATCCCTGAGGAGGACCTGTCCGACACCGGCTACTGGCAGTCAGTTCAGGCATTCAGGCTCGG    660
 S  I  P  E  E  D  L  S  D  T  G  Y  W  Q  S  V  Q  F  R  G  I  Q  A  R

GTCTTCTCCCTGCCTCGACCTTCAGTGCCCTTGCCCTGCCCTGCCCTTCCCTCTGG     720
 V  F  S  L  P  V  D  L  P  F  S  G  Y  R  R  G  I  A  R
```

FIGURE 2B

```
CAGATCCTGCAGAAGGGGCTGGAGAAGGCCATCCGGGAGAAGCTGCAGTGCACACAGGGC  780
 Q  I  L  Q  K  G  L  E  K  A  I  R  E  K  L  Q  C  T  Q  G
AAGGACTACTTGGACGCCCTGGACCTCCTCATTGAGAGCAGCAAGGAGCACGGAAAGGAG  840
 K  D  Y  L  D  A  L  D  L  L  I  E  S  S  K  E  H  G  K  E
ATGACCATGCAGGAGCTGAAGGACACGGGACCCTGGAGCTGATCTTTGCGGCCTATGCCACC  900
 M  T  M  Q  E  L  K  D  G  T  L  E  L  I  F  A  A  Y  A  T
ACGGCCAGCGCCAGCACCTCACTCATCATGCAGCTGCTGAAGCACCCCACTGTGCTGGAG  960
 T  A  S  A  S  T  S  L  I  M  Q  L  L  K  H  P  T  V  L  E
AAGCTGCGGGATGAGCTGCGCGCTCATGGCATCCTGCACAGTGGCGGGGGCTGCCCTGCGAG 1020
 K  L  R  D  E  L  R  A  H  G  I  L  H  S  G  G  C  P  C  E
GGCACACTGCGCCTGGACACGCTCAGTGGGCTGCGCTACCTGGACTGCGTCATCAAGGAG 1080
 G  T  L  R  L  D  T  L  S  G  L  R  Y  L  D  C  V  I  K  E
GTCATGCGCCTGTTCACGCCCATTTCCGGCCCAAAGGCTGAGTGTGTCATGCTGCAGACCTTCGAG 1140
 V  M  R  L  F  T  P  I  S  G  Y  R  T  V  L  Q  T  F  E
CTTGATGGTTTCCAGATCCCCGTGTTCAAAGACGTGAACGTGTTCGACCCCGATCGCTTCAGCCAGGCG 1200
 L  D  G  F  Q  I  P  V  F  K  D  V  N  V  F  D  P  D  R  F  S  Q  A
GACACCAGCGCCCGTGTTCAAAGATGGCCGCTTCCATTACCTCCCGTTCGGTGGCGTGTCCGGACC 1260
 D  T  S  A  P  V  F  K  D  G  R  F  H  Y  L  P  F  G  G  V  R  T
CGGAGGAGGACAAGCACCTGGCCAAGCTGTTCCTGAAGGTGCTGGCGGTGGAGCTGGCTAGC 1320
 R  S  E  D  K  H  L  A  K  L  F  L  K  V  L  A  V  E  L  A  S
TGCCTGGGCAAGCACCTTGAGCTGGCCTTCCCCCGCATCACCTTGGTCCCCGTCCTG 1380
 C  L  G  K  H  L  E  L  A  F  P  R  I  T  L  V  P  V  L
ACCAGCCGCTTTGAGCTGGCCTTGAGCTGGCCACAGGACTTCTTTGGCCTTGATAGCAACCAGAACGAGATC 1440
 T  S  R  F  E  L  A  T  R  T  F  P  R  I  T  L  V  P  V  L
CACCCCGTGGATGGCCTCAGCGTCAAGTTCTTTGGCCTTGACAGTCCAACCAGAACGAGATC 1500
 H  P  V  D  G  L  S  V  K  F  F  G  L  D  S  N  Q  N  E  I
CTGCCGGAGACGGAGGCCATGCTGAGCGCCACAGTCTAACCCAAGACCCACCCGCCCTCAG 1560
 L  P  E  T  E  A  M  L  S  A  T  V
```

FIGURE 2C

```
CCCAGCCCAGGCAGCGGGGTGGTTGTGGGAGGTAGAAACCTGTGTGTGGGAGGGGC    1620
CGGAACGGGAGGGGCGAGTGGCCCCATACTTGCCCTCCCTTGCTCCCCTGGCAA      1680
ACCCTACCCAAAGCCAGTGGGCGCCCCATTCCTAGGGCTGGGCCTCCCCTTCTGGCTCCAGCT  1740
TCCCTCCAGCCACTCCCGTGGCCCATTTACCATCAGCTCAGCCCCTGGGAAGGGCGTGGCAGGGGC  1800
TCTGCATGCCCGTGACAGTGTTAGGTGTCAGCGCGTGCTACAGTGTTTTTGTGATGTCT  1860
GAACTGCTCCCTTCCCTCCGTTCCTTCCTTCGGACCCCTTTTAGCTCCTCTGGGTTGGGGACGGGAA  1920
GAGCCGTGCCCCCTTGGGCGCACTCTTCAGCGCGTCTCCTGCGCCCACTGCGTC      1980
TGCCCAGGAACAGAGCATCCTGGGTAGCAGAGAACAGGAGTCAACCTTGGCTCCCTCCACCAGTTTG  2040
CGTCCAACCTGGAGATTACCTATTGCTGCCCTCCCACGGTTCTGTCCTCTGACCCTTGGGCAAAGGA  2100
GACAATTTGAAATTACCTATTGCTACTTGTTCTGTCCTCTGACCCTTGGGCAAAGGA   2160
GCCCCAGGCCCCTGTCTCCCCAGCATCCTCCCCTGCTGAACCAGCCCTGTTACACAGCCGCCACACC 2220
CCCACCCTTCCCATCCCCTGCTGAACCAGCCCTGTTACACAGAGAATCTGTTCTAGCTCTGGGG 2280
GCTCATGTGCTGCCCCCCATATTTATTCACTGCCCTAGCTGTGTTCTAGCTCTGGGGATGCTGGGG  2340
TCTGGAGTGAACATCTCCCTCCCCTTCATGCCCCTAGCTGTGTTCTAGCTCTGGCGAG  2400
ACTTCTGTGAGTGAAGAGGAAGGGTCTGGTCAAACCCAGCCCCCAGGGCCTAGGGTT   2460
GAAAGCCTTCCCCGGCCTCTGCCTTATTTGGGTTTAATCTCGGAGCCTCACTCCTGGAC 2520
TGAAGTCCGGTGCCTCTGCCTTATCCCTGGTGGAGATGGAATGTGGCCCACGATTTCCTGTTTGG  2580
CCTCTCCTGTTCACCCAGTGCACTGCACCTGGCCCTGACTCGAGTATGGGAAGGATACGG 2700
CCCCTGTTCACCCAGTGCACTGCACCTGGCCCTGACTCGAGTATGGGAAGGATACGG   2760
GTTCTTTCTGACGGGAGCAAGGTGTCCTTGAAGTCCCCTTCCACCTCTATGCCACTGCTGCCTTAGC 2820
TCCGCCCTGAAAAAGGTGGGGGTGCAGGGCCGAAAGCGTGTGTGCCGGTTGTCAGGGGAGGTGAGCG  2880
CCAGCTCAGGAGCTGATTGCAGGGGCGGCACAGCTGCGGTTTGTCAGGGGAGGTGAGCGCAGCGGTTCTG  2940
CCTGAAGCTGAAGAGGCGGCTACAGTGCGGTTTGTCAGGGGATTGGGTTGAAAACTGGCC 3000
AGTCGGGATGACTGGGTGAAAGAGGAGTAGCTCCTGCCACTGGCGTTTTGAGTGTTGGCA 3060
```

FIGURE 2D

```
ATTTGGGATGCCTCCTGGGGAAGGTTTCCGGGCGTTTGGTGAGTCTCTAGATTTTCCTT  3120
GCTTTCTGTGTTTATTGGTTTTGATGTTGTAAAAGCAATGAATCCCCTTACAAGAAAA   3180
TCGAAAACACAGAAGAATGAAGGACATGCCAGTCCCCGATCGCTGCTGTGAGCACCTCAG 3240
TGGCTCCCTCAGACCCGTAGGCAGCCCCACAGACCGACCCCTGACCCCACTCACA      3300
GCCACCCTGAAGATAGACTATAGGAACGGGCCCATACCACACAGACTGCTCTCCAATCCC 3360
TGAGTCTCAGATGTTTCATTTATTCCTACTTTTCCACTAAAAACAGTGTGGAATA      3420
GACATTATTGGCAAAATTGCTCATCCCTAATCCTGAAAAACAGGCCAGAATGGGTAAAGA 3480
CTTGTCAAAGCTTGCAACATAGCTACATGGTCACCCGGACCCTGTACCCCTCCCCCAA   3540
CACAAAACCAGTGTCTGGGAGTTCATTTTCCTTTAAACTGATCCAGCTGCCCTGAACC   3600
AATTGTTTTGACTGAGTATCTAGGAGAGAGCAGTGGAACTTCAGACAAGCCCACTGG    3660
GTCTGGTCCAGGTGAGGGCAGGGGCATGGGGGCTGGGAGGTCTCAGGGGGTCCCTGG    3720
GGGTGGCCAGCCTGTAGGGGCAGAGAAGGAAAAGCTGAGGGGGTCCCTGTGAGGGAG    3780
GAAAGAAGGATCATTTGCCCCCGGGTCCAAAGGCAGTGTCCCCTTTCAGCTCTCTAGTG  3840
CTCTGGCTGGCTGACAGGATCCCTGTGTTGTAATTGGTCATACAGCCTTAAAAGACAAACCCCACAA 3900
AGATGCCCGTGTCTGTGCCTAACTATTGCAACTTGACCTTAAAAAGACAAACCCCACAA  3960
GTTTCTTACTTATCATCCGCCACGGGCTTGCAGATTGAAGCACTTTGATGTTGGGCGCTGGCGTTTG 4020
AACTCTTCCTGGGCACCACCGTGACCCTGCCCAGATGGCTATAATATTTATACACAAACC 4080
TGTTCTGGGCACCACCGTGACCCTGCCCAGATGGCTATAATATTTATACACAAACC    4140
TTTTTTCATAAATGTTATAATTTGTCTCTTTATAAACTATTATAAGTATTTGTTATT    4200
TTGTTATAAATAGAATTTGCTTATTGTAAACATGGTTCAAAATTAATATGTTTTAT    4260
TAGTAAAATATGAATTTAATATTGAAAAAGCACTGTGTTTGTTTTGATATGAAACTGGTAC 4320
CACAGTCGTTTTAATATTGAAAAAGCACTGTGTTTGTTTTGATATGAAACTGGTAC    4380
CGTGTGAGTGTGTTTTTGCTGTCGTGGTTTTAATCTGTATATAAATATTCCATGTTGCATATT 4440
AAAAA                                                         4445
```

FIGURE 3A

| | | | | | | | | | | | | | |
|---|---|---|---|---|---|---|---|---|---|---|---|---|---|
| P450RAI-2 | M | L | F | E | G | L | D | L | V | S | A | L | A | A | C | L | V | S | V | T | L | L | 25 |
| P450RAI-1 | – | – | – | – | M | G | L | P | A | L | L | A | S | A | L | C | T | F | V | L | P | L | L | L | 20 |

| | | | | | | | | | | | | | |
|---|---|---|---|---|---|---|---|---|---|---|---|---|---|
| P450RAI-2 | L | A | V | S | Q | Q | L | W | Q | L | R | W | A | A | T | R | D | K | S | C | K | L | P | I | P | 50 |
| P450RAI-1 | F | L | A | A | I | K | L | W | D | L | Y | C | V | S | G | R | D | R | S | C | A | L | P | L | P | 45 |

| | | | | | | | | | | | | | |
|---|---|---|---|---|---|---|---|---|---|---|---|---|---|
| P450RAI-2 | K | G | S | M | G | F | P | L | I | G | E | T | G | H | W | L | L | Q | S | G | F | Q | S | S | 75 |
| P450RAI-1 | P | G | T | M | G | F | P | F | F | G | E | T | H | L | Q | M | V | L | Q | R | R | K | F | L | Q | M | 70 |

| | | | | | | | | | | | | | |
|---|---|---|---|---|---|---|---|---|---|---|---|---|---|
| P450RAI-2 | R | R | E | K | Y | G | N | V | F | K | T | H | L | L | G | R | P | L | I | R | V | T | G | A | E | 100 |
| P450RAI-1 | K | R | R | K | Y | G | H | I | Y | K | T | H | L | F | G | R | P | T | V | R | V | M | G | A | D | 95 |

| | | | | | | | | | | | | | |
|---|---|---|---|---|---|---|---|---|---|---|---|---|---|
| P450RAI-2 | N | V | R | I | L | M | G | E | H | H | L | V | S | T | E | W | P | R | S | T | R | M | L | L | 125 |
| P450RAI-1 | N | V | R | I | L | L | G | D | R | D | L | V | S | V | H | W | P | A | S | V | R | T | I | L | 120 |

| | | | | | | | | | | | | | |
|---|---|---|---|---|---|---|---|---|---|---|---|---|---|
| P450RAI-2 | G | P | N | T | V | S | N | I | H | D | I | H | R | N | R | K | R | K | V | F | S | K | I | F | S | 150 |
| P450RAI-1 | G | S | G | C | L | S | N | L | H | D | S | S | H | K | Q | R | R | K | V | I | M | R | A | F | S | 145 |

FIGURE 3B

| | | | | | | | | | | | | | | |
|---|---|---|---|---|---|---|---|---|---|---|---|---|---|---|
| P450RAI-2 | H | E | A | L | E | S | Y | L | P | K | I | Q | L | V | I | Q | D | T | L | R | A | W | S | S | H | 175 |
| P450RAI-1 | R | E | A | L | E | C | Y | V | P | V | I | T | E | E | V | G | S | S | L | E | Q | W | L | S | C | 170 |

| P450RAI-2 | P | - | E | A | I | N | V | Y | Q | E | A | Q | K | L | T | F | R | M | A | I | R | V | L | L | G | 199 |
| P450RAI-1 | G | E | R | G | L | L | V | Y | P | E | V | K | R | L | M | F | R | I | A | M | R | I | L | L | G | 195 |

| P450RAI-2 | F | S | I | P | E | E | D | L | G | - | - | - | H | L | F | E | V | Y | Q | Q | F | V | D | N | 220 |
| P450RAI-1 | C | E | P | Q | L | A | G | D | G | D | S | E | Q | Q | L | V | E | A | F | E | E | M | T | R | N | 220 |

| P450RAI-2 | V | F | S | L | P | V | D | L | P | F | S | G | Y | R | R | G | I | Q | A | R | Q | I | L | Q | K | 245 |
| P450RAI-1 | L | F | S | L | P | I | D | V | P | F | S | G | L | Y | R | G | M | K | A | R | N | L | I | H | A | 245 |

| P450RAI-2 | G | L | E | K | A | I | R | E | K | L | Q | C | T | Q | - | - | - | - | G | K | D | Y | L | D | A | 266 |
| P450RAI-1 | R | I | E | Q | N | I | R | A | K | I | C | G | L | R | A | S | E | A | G | Q | G | C | K | D | A | 270 |

| P450RAI-2 | L | D | L | I | E | S | S | K | E | H | G | K | E | M | T | M | Q | E | L | K | D | G | T | L | 291 |
| P450RAI-1 | L | Q | L | I | E | H | S | W | E | R | G | E | R | L | D | M | Q | A | L | K | Q | S | T | 295 |

| | | | | | | | | | | | | | | | | | | | | | |
|---|---|---|---|---|---|---|---|---|---|---|---|---|---|---|---|---|---|---|---|---|---|
| P450RAI-2 | L | G | K | H | L | A | K | L | F | V | L | A | V | E | L | A | S | T | S | R | F | E | L | 466 |
| P450RAI-1 | V | G | K | E | F | A | K | I | L | K | I | F | T | V | E | L | A | R | H | C | D | W | Q | L | 467 |

| | | | | | | | | | | | | | | | | | | |
|---|---|---|---|---|---|---|---|---|---|---|---|---|---|---|---|---|---|---|
| P450RAI-2 | A | T | R | T | F | P | R | I | T | L | V | P | V | L | H | P | V | D | G | L | S | V | K | F | F | 491 |
| P450RAI-1 | L | N | - | G | P | P | T | M | K | T | S | P | T | V | Y | P | V | D | N | L | P | A | R | F | T | 491 |

| | | | | | | | | | | | | | | | | | |
|---|---|---|---|---|---|---|---|---|---|---|---|---|---|---|---|---|---|
| P450RAI-2 | G | L | D | S | N | Q | N | E | I | L | P | E | T | E | A | M | L | S | A | T | V | 512 |
| P450RAI-1 | H | F | H | G | - | - | - | E | I | | | | | | | | | | | | | 497 |

FIGURE 4C

|   | 1 | 2 | 3 | 4 | 5 | 6 | 7 | 8 | 9 | 10 | 11 | 12 |
|---|---|---|---|---|---|---|---|---|---|---|---|---|
| a | Whole Brain | Cere-bellum Left | Substan-tia nigra | Heart | Esophagus | Colon transverse | Kidney | Lung | Liver | leukemia HL-60 | Fetal brain | yeast total RNA |
| b | Cere-bral Cortex | Cere-bellum right | Accum-bens nucleus | Aorta | Stomach | Colon decending | Skeletal muscle | Placenta | Pan-creas | HeLa S3 | Fetal heart | yeast tRNA |
| c | Frontal Lobe | Corpus Callosum | Thalamus | Atrium Left | Duodenum | Rectum | Spleen | Bladder | Adrenal gland | leukemia K-562 | Fetal kidney | E.coli rRNA |
| d | Perietal Lobe | Amy-gdala | Pituitary gland | Atrium right | Jejunum |   | Thymus | Uterus | Thyroid gland | leukemia MOLT-4 | Fetal liver | E.coli DNA |
| e | Occip-ital Lobe | Caudate nucleus | Spinal cord | Ventricle Left | Ileum |   | Peripheral blood leuk | Prostate | Salivary gland | Burkitt's lym., Raji | Fetal spleen | Poly r (A) |
| f | Temp-oral Lobe | Hippo-campus |   | Ventricle right | Ilocecum |   | lymph node | Testis | mam-mary gland | Burkitt's lym., Daudi | Fetal thymus | human Cot-1 DNA |
| g | p.g. of cerebral | Medulla oblon-gata |   | Inter-ventric septum | Appendix |   | Bone | Ovary |   | Colo-rectal SW480 | Fetal lung | human DNA 100 ng |
| h | Pons | Putamen |   | Apex of heart | Colon, ascending |   | Trachea |   |   | lung carc. A549 |   | human DNA 500 ng |

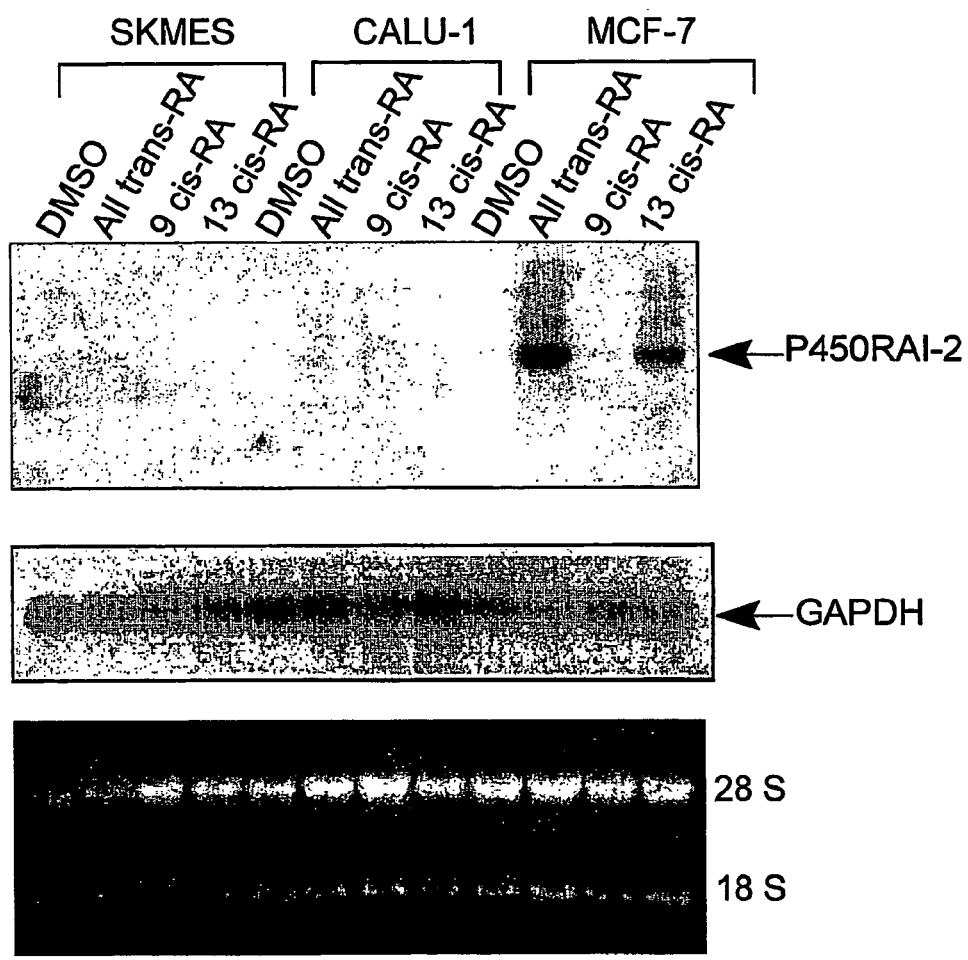

FIGURE 22A
FIGURE 22B
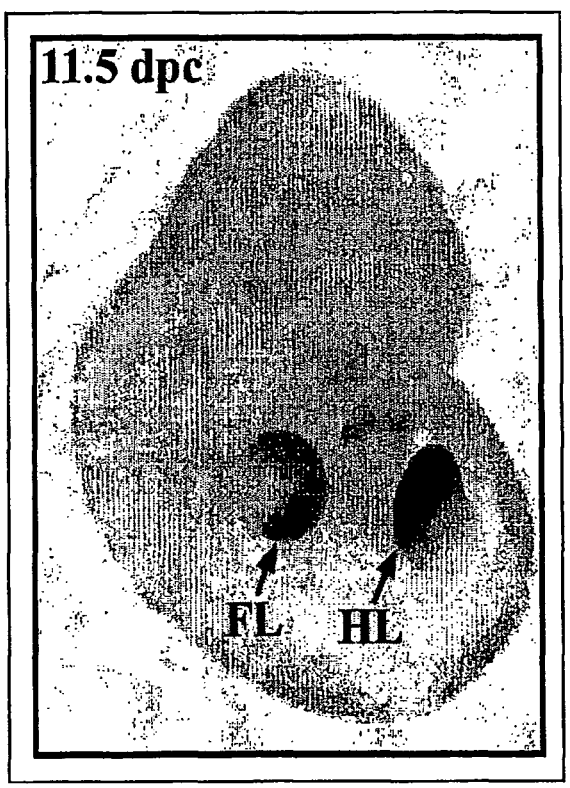
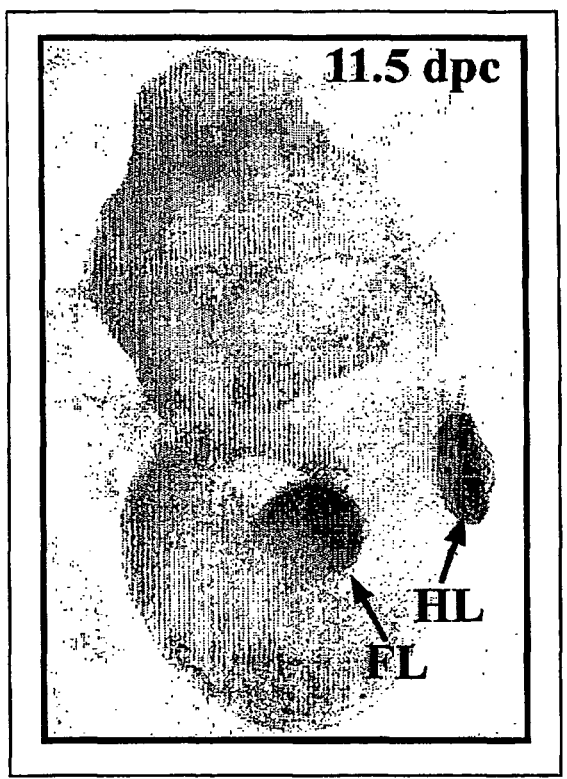

P450RAI-2(P450 CYTOCHROME 26B), ENCODING NUCLEIC ACID MOLECULES AND METHODS AND USES THEREOF

PRIOR APPLICATIONS

This application is the national stage of international application number PCT/CA01/01805, filed on Dec. 17, 2001. This application claims the benefit and is a continuation-in-part of international application PCT/CA00/01493, filed on Dec. 15, 2000, which was pubfished in English as WO 01/44443. PCT/CA00/01493 entered national phase in the United States of America and was assigned application Ser. No. 10/148,883. PCT/CA00/01493 in turn claims priority from U.S. provisional applications 60/171,110 and 60/178,314, filed on Dec. 16, 1999 and Jan. 27, 2000, respectively. All of these patent applications are herein incorporated by reference.

FIELD OF THE INVENTION

The present invention relates to a novel gene encoding a polypeptide that is a member of the cytochrome P450 family. More particularly the present invention relates to a polynucleotide encoding the novel polypeptide, to an antisense polynucleotide thereof and to fragments thereof. The invention further relates to the novel cytochrome P450 as well as to vectors, host cells and antibodies to the polypeptide and the recombinant methods for producing the same. Uses and methods relating to any of the foregoing are also included within the scope of the invention.

BACKGROUND OF THE INVENTION

Cytochrome P450s

The cytochromes P450 comprise a large gene superfamily that encodes over 500 distinct heme-thiolate proteins that catalyze the oxidation of drugs and numerous other compounds in the body [Nelson et al., (1996); Guengerich (1991)]. Since there are at least 500 different cytochrome P450 enzymes, it is of considerable interest in the pharmaceutical and other fields to identify which of these enzymes are most important in the metabolism of individual compounds. There are now numerous examples of adverse drug-drug interactions and side effects that can now be understood in terms of the cytochrome P450 enzymes.

P450 proteins are ubiquitous in living organisms, and have been identified in bacteria, yeast, plants and animals [Nelson et al (1996); and Nelson, (1999a)]. The P450 enzymes catalyze the metabolism of a wide variety of drugs, xenobiotics carcinogens, mutagens, and pesticides, and are responsible for the bioactivation of numerous endogenous compounds including steroids, prostaglandins, bile acids and fatty acids body [Nelson et al., (1996); Guengerich (1991); Nebert et al., (1989)].

Cytochrome P450 metabolism of xenobiotics can result in detoxification of toxic compounds by their conjugation into excretable forms or can result in activation of compounds into metabolites that are toxic, mutagenic, or carcinogenic. Many steroids are deactivated by cytochrome P450-catalyzed oxidation.

Vitamin A and Retinoic Acid

Vitamin A metabolism gives rise to several active forms of retinoic acid (RA) which are involved in regulating gene expression during development, regeneration, and in the growth and differentiation of epithelial tissues. [Maden, 1992; Chambon, 1995; Mangelsdorf, 1995; Gudas, 1994; Lotan, 1995; Morriss-Kay, 1996] RA has been linked to apoptosis, or programmed cell death in a number of cell types; and to have anticarcinogenic and antitumoral properties [Lotan, 1996].

Early studies of retinol deficiency indicated a correlation between vitamin A depletion and a higher incidence of cancer and increased susceptibility to chemical carcinogenesis [Chytil, 1984]. Several animal models have been used to demonstrate the effectiveness of retinoids in suppressing carcinogenesis in a variety of tissues including skin, mammary epithelia, oral cavity, aerodigestive tract, liver, bladder and prostate [Moon, 1994]. These studies have led to the preventative use of retinoids to treat premalignant lesions including actinic keratosis and oral leukoplakia, as well as in the prevention of secondary tumors of the head and neck and the recurrence of non-small cell lung carcinomas, and basal cell carcinomas [Hong, 1994; Lippman, 1995]. RA itself has been found to be useful therapeutically, notably in the treatment of cancers, including acute promyelocytic leukemia (APL), tumors of the head and neck, and skin cancer, as well as in the treatment of skin disorders such as the premalignancy associated actinic keratoses, acne, psoriasis and ichthyosis. There is evidence that the effectiveness of RA as an anti-tumor agent is at least partially due to induction of cellular differentiation and/or inhibition of proliferation [Lotan, 1996]. Studies over the past several years indicate that a high proportion of patients with acute promyelocytic leukemia (APL) achieve complete remission after a short period of treatment with all-trans RA. Unfortunately, this high rate of remission is in most cases brief. Following relapse, patients are clinically resistant to further treatment with RA [Warrell, 1994; Warrell, et al., 1994; Chomienne, 1996; Muindi, 1992]. The nature of this resistance is unknown. Interestingly, leukemic cells taken from patients exhibiting clinical resistance to RA have been shown to be sensitive to the differentiating action of RA when grown in vitro [Muindi, 1992; Muindi, 1994]. This suggests that pharmacokinetic mechanisms may account for the acquired resistance to RA. This possibility is supported by studies showing that peak plasma concentrations of RA were much higher in patients after initial administration than in patients treated following relapse. This decrease in peak plasma RA concentration was accompanied by a 10-fold increase in urinary 4-oxo-retinoic acid concentration. In addition, ketoconazole, a broad spectrum inhibitor of cytochrome P450 function was shown to modulate RA pharmacokinetics in vivo [Muindi, 1992; Muindi, 1994]. It is therefore likely that RA increases the rate of its own metabolism which in turn results in the inability to sustain effective therapeutic doses of RA. Therapeutic administration of RA can result in a variety of undesirable side effects and it is therefore important to establish and maintain the minimal requisite doses of RA in treatment. For example, RA treatments during pregnancy can lead to severe teratogenic effects on the fetus. Adverse reactions to RA treatment also include headache, nausea, chelitis, facial dermatitis, conjunctivitis, and dryness of nasal mucosa. Prolonged exposure to RA can cause major elevations in serum triglycerides and can lead to severe abnormalities of liver function, including hepatomegaly, cirrhosis and portal hypertension.

RA metabolism may also account for the lack of response of certain tumors to RA treatment. For example, recent studies have shown that cytochrome P450 inhibitors that block RA metabolism, resulting in increased tissue levels of RA, may be useful therapeutic agents in the treatment of prostate cancer [Wouters, 1992; De Coster, 1996]. Thus RA metabolizing cytochrome P450s may be useful targets for the treatment of a number of different types of cancer.

The classical view of vitamin A metabolism holds that all trans-RA, the most active metabolite is derived from conversion of retinol to retinaldehyde to RA through two oxidation steps and that RA is further metabolized to the polar derivatives 4-OH RA and 4-oxo RA [Blaner, 1994; Napoli, 1995; Formelli, 1996; Napoli, 1996]. It is unknown whether the 4-oxo- and 4-OH— metabolites are simply intermediates in the RA catabolic pathway or whether they can also have specific activities which differ from those of all-trans RA and 9-cis RA. Pijnappel et al. [Pijnappel, 1993] have shown that, in Xenopus, 4-oxo-RA can efficiently modulate positional specification in early embryos and exhibits a more potent ability to regulate Hoxb-9 and Hoxb4 gene expression than all-trans RA. 4-oxo-RA has been found to bind to retinoic acid receptor-β (RAR-β) with affinity comparable to all-trans RA [Pijnappel, 1993] but poorly to RAR-γ [Reddy, 1992], suggesting that this metabolite exhibits some receptor selectivity. 4-oxo-RA also binds to cellular retinoic acid binding protein (CRABP) but with an affinity slightly lower than that of all-trans RA [Fiorella, 1993]. Takatsuka et al. [Takatsuka, 1996] have shown that growth inhibitory effects of RA correlate with RA metabolic activity but it is unknown whether there is a causal relationship between production of RA metabolites and growth inhibition. The asymmetric distribution of- these metabolites in developing embryos suggests that they may be preferentially sequestered or generated by tissue specific isomerases [Creech Kraft, 1994]. The normal balance of these metabolites is dependent upon rate of formation from metabolic precursors, retinol and retinaldehyde [Leo, 1989], and rate of catabolism. Little is presently known about the enzymes involved in this metabolic scheme, in particular the catabolism of RA.

The catabolism of RA is thought to be initiated by hydroxylation either at the C4-, or C18-position of the β-ionone ring of RA [Napoli, 1996]. The C4-hydroxylation step is mediated by cytochrome P450 activity, as judged by the ability of broad spectrum P450 inhibitors such as ketoconazole and liarazole to block 4-hydroxylation [Williams, 1987, Van Wauwe, 1988; Van Wauwe, 1990, Van Wauwe, 1992, Wouters, 1992]. In certain tissues, including testis, skin and lung and in numerous cell lines, such as NIH3T3 fibroblasts, HL 60 myelomonocytic leukemic cells, F9 and P19 murine embryonal carcinoma cell lines and MCF7, RA metabolism can be induced by RA pretreatment [Frolik, 1979, Roberts, 1979a and b; Duell, 1992; Wouters, 1992]. Studies involving targeted disruption of RAR genes in F9 cells suggest that RAR-α and RAR-γ isoforms may play a role in regulating the enzymes responsible for this increased metabolism [Boylan, 1995].

The glucuronidation of RA is a significant metabolic step in the inactivation of RA [Blaner, 1994; Formelli, 1996]. The elimination of RA may require oxidation to 4-oxo, followed by conjugation to form the 4-oxo all-trans RA glucuronide. This is supported by studies in both primates and humans showing that the 4-oxo RA glucuronide is the only retinoid conjugate found in urine [Muindi, 1992; Muindi, 1994]. The fact that following RA therapy, 4-oxo RA is not present or barely detectable in serum, suggests that oxidation may be the rate limiting step in this process.

It has recently been shown that 4-oxoretinol (4-oxo-ROL) can have greater biological activity than retinol. The 4-oxo-ROL is inducible by RA in F9 and P19 mouse teratocarcinoma cells [Blumberg et al., 1995; Achkar et al., 1996].

It is known that zebrafish fins regenerate through an RA sensitive process which utilizes many gene regulatory pathways involved in early vertebrate development [White, 1994; Akimenko, 1995a & b].

Cytochome P450s and Retinoic Acid Metabolism

In 1979, Roberts et al., [Roberts (1979a] first postulated that the catabolism of retinoic acid (RA) was mediated by a cytochrome P450 enzyme. Several P450s have since been shown to metabolize RA, including P450 proteins from human, zebrafish and mouse. For example, human P450RAI, which is induced by RA, metabolizes RA to more poplar derivatives including 4-hydroxy retinoic acid (4-OHRA) and 4-oxo retinoic acid (4-oxo RA) [White et al. (1996a)]. Since RA is useful as an antitumor agent, it is desirable to maintain high tissue levels of RA. Thus, cytochrome P450 inhibitors that block RA metabolism, resulting in increased tissue levels of RA, may be useful therapeutic agents in the treatment of cancers, such as prostate cancer [Wouters et al., (1992); and De Coster et al., (1996)].

International Patent Publication No. WO 97/49815, published Dec. 31, 1997, describes a family retinoid metabolizing proteins, CYP26A, including proteins from human, zebrafish and mouse and their coding sequences. This earlier publication is incorporated herein in its entirety. cDNAs encoding a cytochrome P450-dependent enzyme (P450RAI) which is induced by RA have been cloned and characterized from zebrafish and the protein metabolizes RA to more polar derivatives including 4-hydroxy retinoic acid (4-OH RA) and 4-oxo retinoic acid (4-oxo RA) [White et al., 1996a]. The identification of P450RAI gene is an important step in the understanding of RA signaling but its presence has been known since Roberts et al. (1979a) first postulated that the catabolism of RA was mediated by a P450 enzyme [Frolik et al., 1979; Roberts et al., 1979a]. More recently, the isolation of cDNAs which encode the full-length human and mouse P450RAI orthologs whose expression, like that of the fish cytochrome, is highly inducible by RA has been achieved [Fujii et al., 1997; Ray et al., 1997]. Human and mouse genomic P450RAI-1 sequences are identified herein as SEQ ID NOS: 15 and 16. The mouse sequence encoding P450RAI-1 is identified herein as SEQ ID NO: 17. Homologs have also been isolated from human, mouse, chick and xenopus all exhibiting a high degree of sequence conservation [Abu-Abed et al., 1998; Hollermann et al., 1998; White et al., 1997]. There is extensive identity between the human and fish P450RAI genes which overall is 68% at the amino acid level (over 90% between mouse and human).

MCF7 cells have been shown to have RA inducible RA metabolism [Butler and Fontana, 1992; Wouters et al., 1992]. The expression of P450RAI in these cells is dependent on the continuous presence of RA [White et al., 1997]. This suggests that P450RAI regulation by RA forms an autoregulatory feedback loop that functions to limit local concentrations of RA, such that when normal physiological levels of RA are exceeded, induction of P450RAI acts to normalize RA levels. The inducible expression of P450RAI in mouse embryos also suggests that a similar autoregulatory mechanism may limit exposure to RA sensitive tissues during development [Iulianella et al., 1999].

Retinoic Acid, Cytochrome p450 and Embryonic Development

All-trans-RA is a critical regulator of gene expression during embryonic development and in the maintenance of adult epithelial tissues [Gudas, et al. (1994).; Lotan, R. M. (1995); Lotan, R. (1996); Morriss-Kay, G. M. (1996)). The effects of all-trans-RA are mediated by heterodimers of nuclear receptors for retinoic acid (RARs) and retinoid-X-receptors, which are regulated by by the 9-cis isomer of RA. Three different subtypes exist for each of these receptors (RARα, β and γ; RXR RAR α, β and γ) which individually are expressed in a tissue specific manner but collectively can be found in essentially all cell types, both during embryonic development and in the adult [Chambon, P. (1995).]. The activity of RA in these tissues is controlled, to a large extent, by enzymes involved in its synthesis from retinaldehyde (ALDH-1 and RAIDH-2) and its catabolism to 4-OH, 4-oxo and 18-OH products (P450RAI) [White J. A., et al. (1997); Iulianella, A. et al. (1999); McCaffery P. et al., (1999) Niederreither, K. et al. (1999) Swindell E., et al. (1999)].

The present inventor and others have shown that P450RAI-1 (CYP26A) from zebrafish, mouse, human, chick and xenopus which is responsible for the metabolism of active all-trans-RA to inactive polar metabolites including 4-OH-RA, 4-oxo-RA and 18-OH-RA [White J., et al. (1997); Swindell E., et al. (1999); White, J. & Petkovich, M. (1996); Abu-Abed, et al.(1998); Fujii, H. et al., (1997); Ray, W. et al. (1997); Hollermann, T et al. (1998)]. P450RAI-1 expression can be induced by all-trans-RA pre-treatment in multiple tissues, and cell types, and this expression is concomitant with increased all-trans-RA catabolism. In MCF7 cells, all all-trans-RA suggesting a feedback-loop mechanism is dependent on the continued presence of all-trans-RA suggesting a feedback-loop mechanism for the regulation of all-trans-RA levels [White J., et al. (1997)]. Inducible expression of P450RAI-1 has also been observed in vivo in zebrafish, chick, xenopus and mouse embryos suggesting that this autoregulatory feedback-loop plays an important role in balancing all-trans-RA levels in certain developing tissues.

Studies from several groups show that tissues such as neural folds in chick embryos [Swindell E., et al. (1999)], caudal neuroepithelia [Iulianella, A et al. (1999); Fujii, H. et al. (1997)] and developing retina [McCaffery P. et al. (1999)] from mouse express P450RAI-1 constitutively thus forming a barrier to all-trans-RA exposure. Comparison of the expression patterns of RALDH-2 and P450RAI-1 in these models suggest that these enzymes act together to form regions of RA synthesis and activity (where RALDH-2 is expressed). RALDH-2 expressing tissues have been shown to contain retinoid activity as measured by both retinoid responsive reporter gene activity and direct measurement of RA levels from tissue extracts; by similar analyses, P450RAI-1 expressing tissues do not [Iulianella, A et al. (1999); McCaffery P. et al. (1999)]. In addition, over expression of P450RAI-1 in xenopus embryos has been shown to abrogate the teratogenic effects of exogenously applied RA, consistent with a catabolic role for its enzyme [Hollermann, T et al. (1998)].

SUMMARY OF THE INVENTION

The present inventors have identified and characterized a novel cytochrome P450 that can metabolize retinoic acid, preferably all-trans retinoic acid, (hereinafter referred to as P450RAI-2) and the nucleic acid sequence encoding therefor. In one embodiment the novel cytochrome P450 metabolizes all-trans retinoic acid from into more polar metabolites.

In one embodiment the P450RAI-2 is a mammalian P450RAI-2, and preferably a murine (such as comprising amino acid sequence depicted in SEQ. ID. NO. 11 or 17), rat (such as that comprising SEQ. ID. NO. 27) or human P450RAI-2(such as that of SEQ. ID. NO. 5). In an another embodiment the P450RAI-2 is a zebrafish P450RAI-2 (such as that comprising SEQ. ID. NO. 12). In another embodiment, the invention provides functional homologs of the above-noted sequences, or functional homologous fragments thereof.

Although, the P450RAI-2 and encoding nucleic acid sequence of the invention can be isolated and characterized from a number of different tissues such as spleen, kidney, skeletal muscle, brain, liver, retina, heart or small intestine, it is preferably isolated and characterized from brain cells, such as from from the cerebellum, cerebal cortex, medulla, occipital pole, frontal lobe and temporal lobe, and most preferably from the cerebellum. In another embodiment, P450RAI-2 is isolated from lung cells, preferably tumour lung cells, such as human lung tissue or SKMES cells.

Accordingly, the present invention provides an isolated nucleic acid molecule comprising a sequence encoding a P450RAI-2, preferably a human P450RAI-2 (such as SEQ. ID. NO. 4 or 28 or degenerate or corresponding RNA sequences (where T is U) thereof) or a murine P450RAI-2 (such as comprising any one of SEQ. ID. NO. 17–26 or degenerate or corresponding RNA sequences (where T is U)) or fragments thereof, preferably fragments encoding functional fagments of P450RAI-2.

In a preferred embodiment, an isolated nucleic acid molecule is provided having: (a) a nucleic acid sequence as shown in SEQ ID NOS: 4, 5, 28, 27, 7, 18, 26, 21, 22, 23, 24, or 25 where T can also be U; (b) nucleic acid sequences complementary to (a); (c) nucleic acid sequences which are homologous to (a) and (b); (d) a nucleic acid molecule differing from any of the nucleic acid molecules of (a) to (c) in codon sequences due to the degeneracy of the genetic code; or (e) a fragment of (a) to (d) that is at least 15 bases, preferably 20 to 30 bases, and which will hybridize to (a) to (c) under stringent hybridization conditions.

The present invention also includes the P450RAI-2 polypeptide itself. Accordingly, the invention provides a polypeptide having an amino acid sequence of a P450RAI-2. Preferably, the invention provides a polypeptide having either the human (SEQ ID NO: 5) or a homologous mouse sequence or fragment thereof. The invention also comprises peptides comprising fragments of the amino acid sequence of SEQ ID NO: 5. Preferably the fragments comprise amino acid sequences of SEQ ID NOS: 11 or 12 or encoded by nucleic acid sequences SEQ ID NOS. 18, 26, or 21 to 25. In another embodiment the fragments preferably comprise at least 14 amino acid residues and are most preferably antigenic or immunogenic. In one embodiment the invention provides peptides encoded by a nucleic acid sequence of SEQ ID NO: 4 or fragments thereof and to an antisense nucleic acid molecule to all or part of the nucleic acid molecule encoding P450RAI-2.

In another embodiment, homologs, analogs, and modfied proteins of the invention as described herein are encompassed within the scope of this invention.

In one embodiment, the invention also provides a nucleic acid molecule of the invention operationally linked to an expression control sequence in a suitable expression vector. In another embodiment, the expression vector comprising the nucleic acid molecule of the invention is capable of being activated to express the peptide which is encoded by the nucleic acid molecule and is capable of being transformed or transfected into a suitable host cell. Such transformed or transfected cells are also encompassed with the scope of this invention.

The invention also provides a method of preparing a P450RAI-2 protein of the invention utilizing a nucleic acid molecule of the invention. In one embodiment, a method for preparing a P450RAI-2 protein of the invention is provided comprising: transforming a host cell with a recombinant expression vector comprising a nucleic acid sequence of the invention; (b) selecting transformed host cells from untransformed host cells; (c) culturing a selected transformed host cell under conditions which allow expression of the protein; and (d) isolating the protein.

The invention also encompasses an antibody specific for one or more epitopes of a protein of the invention, such as a peptide specific antibody or a polyclonal antibody, and more preferably a monoclonal antibody. The invention also encompasses methods for preparing the antibodies. Preferably the epitopes are selected from the group consisting of SEQ ID NOS: 5, 11, 12, or those encoded by nucelic acid sequences SEQ ID NOS: 4, 6, 8, 18, 21–25, 27 or 28 or immunogenic fragments thereof.

The invention also includes a method for detecting a disease or medical condition associated with P450RAI-2 expression or RA metabolism in an animal. "A disease or medical condition associated with P450RAI-2 expression" as used herein means any disease that can be affected or characterized by the level of P450RAI-2 expression. This includes, without limitation, diseases affected by, high, normal, reduced or non-existent expression of P450RAI-2 or expression of mutated P450RAI-2. A disease or medical condition associated with P450RAI-2 expression includes diseases associated with RA metabolism such as cell cycle regulation, particularly cell growth and apoptosis, for instance cancer, dysplasia, autoimmune disease, dermatological disorders and disabilities associated with high order brain functions, such as learning and memory. The method comprises assaying for the P450RAI-2 from a sample, such as a blood sample, a biopsy, or other cellular or tissue sample, from an animal susceptible of having such a disease. In one embodiment, the method comprises contacting the sample with an antibody of the invention that binds P450RAI-2, and measuring the amount of antibody bound to P450RAI-2 in the sample, or unreacted antibody. In another embodiment, the method involves detecting the presence of a nucleic acid molecule having a sequence encoding a P450RAI-2, comprising contacting the sample with a nucleotide probe which hybridizes with the nucleic acid molecule, preferably mRNA or cDNA to form a hybridization product under conditions which permit the formation of the hybridization product, and assaying for the hybridization product.

The invention further includes a kit for detecting a disease or condition associated with P450RAI-2 expression in a sample comprising an antibody of the invention, preferably a monoclonal antibody. Preferably directions for its use is also provided. The kit may also contain reagents that are required for binding of the antibody to a P450RAI-2 protein in the sample.

The invention also provides a kit for detecting the presence of a nucleic acid molecule having a sequence encoding a polypeptide related to or analogous to a polypeptide of the invention, comprising a nucleotide probe which hybridizes with the nucleic acid molecule, reagents required for hybridization of the nucleotide probe with the nucleic acid molecule, and directions for its use.

The invention further provides a method of treating or preventing a medical condition disease associated with P450RAI-2 or RA expression comprising administering an effective amount of an agent that activates, simulates or inhibits P450RAI-2 expression, as the situation requires, to an animal in need thereof. In one embodiment, P450RAI-2, a therapeutically active fragment thereof, or an agent which activates or simulates P450RAI-2 expression is administered to the animal in need thereof to treat cancer, dysplasia, autoimmune disease or dermatological disorders or to improve high order brain functions or dermatological disorders that is related to the presence of too much RA or all-trans-RA. In another embodiment the disease is associated with over expression of P450RAI-2 or too little RA, or all-trans-RA or apoptosis, and the method of treatment comprises adminstration of an effective amount of an agent that inhibits P450RAI-2 expression such as an antibody to P450RAI-2, a mutation thereof, or an antisense nucleic acid molecule to all or part of the P450RAI-2 gene.

In another embodiment, the invention provides pharmaceutical compositions comprising the nucleic acid molecules of proteins, antibodies, vectors or cells of the invention and a pharmaceutically acceptable carrier.

In another embodiment, the invention further provides a method for identifying modulators of P450RAI-2 expression or P450RAI-2 activity. In one emobodiment, this involved incubating the gene under conditions conducive to gene expression with a potential modulator of gene expression and then assaying, for instance by southern, norther or western blot for the presence of expression of the gene and the effect of the modulator on such expression (increased expression, inhibited expression or no effect on expression). In another embodiment, the effect of the modulator on such expression is determined by comparison to various controls run without the potential modulator and/or with the potential modulator but without the gene. Expression of P450RAI-2 can also be done by radioactive or othe labeling for such expression or by antibody screening, such as using the P450RAI-2 polyclonal antibody discloses herein.

In yet another embodiment, the invention further provides a method of rational drug design.

In one embodiment the invention provides methods or uses of the proteins and nucleic acid molecules of the invention, such as in relation to medical treatment (where inhibitors of P450RAI-2, such as antibodies or antisense molecules can be used to treat a condition associated with too much RA metabolism (e.g., too little RA), preferably all-trans RA metabolism. In another embodiment, P450RAI-2 gene or protein or stimulators or functional fragments or homologs thereof can be used in cases where there is too much RA or all-trans-RA.

Other objects, features and advantages of the present invention will become apparent from the following detailed description. It should be understood, however, that the detailed description and the specific examples, while indicating preferred embodiments of the invention, are given by way of illustration only. Various changes and modifications within the spirit and scope of the invention will become apparent to those skilled in the art from this detailed description.

BRIEF DESCRIPTION OF THE DRAWINGS

FIG. 2 Human P450RAI-2 cDNA and amino acid sequence (SEQ ID NO: 28) comprising the coding sequence and the 3' untranslated sequence. The full-length cDNA clone was isolated from human retina cDNA. The deduced primary sequence using single-letter amino acid codes, identifies a 512 amino acid protein which is shown directly below the corresponding nucleotide sequence. Numbers on the right refer to the nucleotide positions.

FIG. 3 Amino acid eequence comparison between human P450RAI-2 (SEQ. ID. NO. 5) and human P450RAI-1 (amino acid sequence shown in SEQ. ID. NO. 13). Predicted amino acid sequences were aligned using Omiga software (Oxford Molecular, CA). Identical amino acids are highlighted by the black boxes with white letters. Conservatively substituted amino acids are indicated by the open boxes. Gaps, indicated by the dashes, have been introduced in several regions in order to optimize amino acid identity between the two proteins. Overall the two protein sequences show 42% identity at the amino acid level. Numbers on the right hand side refer to the corresponding amino acid positions.

FIG. 5 shows northern blot analysis of human cell lines probed with an $\alpha$-[$^{32}$P]-dATP labeled probe having the sequence identified as SEQ ID NO:4 SKMES; CALU-1 and MCF-7 (A). Cells were treated with DMSO, all-trans retinoic acid, 9-cis retinoic acid or 13-cis retinoic acid. Cells were exposed to $10^{-6}$ M final concentrations of each retinoid dissolved in DMSO. Transcripts corresponding to P450RAI-2 are indicated by the arrowhead. The blot was also probed with the human β-actin probe to control for RNA loading of the gel, shown in the middle panel (B). The 18S and 28S portions of the mRNA as seen on the ethidium bromide stained agarose gel are shown in the bottom panel (C).

FIG. 22 shows P450RAI2 expression in 11.5 dpc embryos treated with retinoic acid. (A) 11.5 dpc lateral view, P450RAI2 expression is observed in both the developing hind and fore limb. (B) 11.5 dpc, ventral view, as in embryos untreated with retinoic acid, P450RAI2 expression is not observed in the aptical ectodermal ridge.

DETAILED DESCRIPTION OF THE INVENTION

Figure 1:
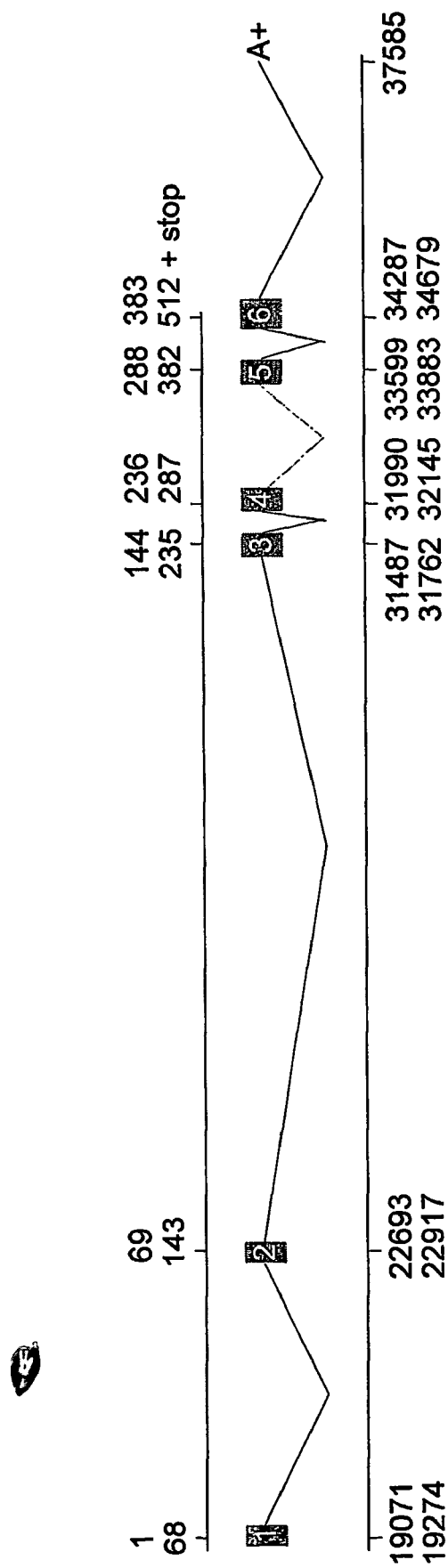
FIG. 1 is a schematic diagram showing the 6 exons of human cytochrome p450RAI-2 on human clone having GenBank Accession No. AC007002 (SEQ ID NO:3). The numbers above the schematic diagram indicate the amino acid regions of the exons and the numbers below the schematic refer to nucleotide positions on the human sequence.

Retinoids, particularly all-trans retinoic acid (all-trans-RA), are potent regulators of cell differentiation, cell proliferation and apoptosis. As noted above, the role of all-trans-RA during development and in the maintenance of adult tissues has been well established. The control of all-trans-RA in cells and tissues is regulated by the balance between its biosynthesis and its catabolism to inactive metabolites. The cytochrome P450 enzyme P450RAI-1 is partially responsible for this inactivation of all-trans-RA.

The present inventors have now identified ,cloned and characterized a second related enzyme, here termed P450RAI-2, which is also involved in the specific inactivation or metabolism of all-trans-RA. A cDNA has been isolated from human retina and sequenced. A protein encoded by the cDNA has been expressed and shown to have the ability to metabolize all-trans-RA to more polar metabolites. The metabolites so formed include products that have been oxidized at the 4-position of the β-ionone ring, including the corresponding acid hydroxylated at the 4-position of the β-ionone ring. The MRNA has been found to be inducible in multiple cell types including but not limited to human lung and human skin upon the addition of all-trans retinoic acid. It has also been shown to be expressed in human brain tissue and breast and lung cancer cells.

The present inventors herein show that tansiently transfected P450RAI-2 can convert all-trans-RA to more polar metabolites including 4-oxo, 4-OH, and 18-OH-retinoic acid. Competition experiments with other retinoids suggest that all-trans-RA is the preferred substrate, but not necessarily the only retinoid substrate. The high level of expression of P450RAI-2 particularly in the cerebellum and pons of human adult brain, suggests a unique role for this enzyme in the protection of specific tissues from exposure to retinoids.

Homologs of the cloned sequence have also been identified. Partial nucleotide sequences have been determined for the mouse, rat and zebrafish P450RAI-2 coding sequence.

Definitions

The term "retinoids" as used herein means a group of compounds which includes retinoic acid, vitamin A (retinol) and a series of natural and synthetic derivatives that can exert profound effects on development and differentiation in a wide variety of systems. For purposes of this disclosure "retinoid" is also intended to encompass an equivalent thereof having the same functional characteristics which may be produced, for example, by computational chemistry.

The following standard abbreviations for the amino acid residues are used throughout the specification: A, Ala—alanine; C, Cys—cysteine; D, Asp—aspartic acid; E, Glu— glutamic acid; F, Phe—phenylalanine; G, Gly—glycine; H, His—histidine; I, Ile—isoleucine; K, Lys—lysine; L, Leu—leucine; M, Met—methionine; N, Asn—asparagine; P, Pro—proline; Q, Gln—glutamine; R, Arg—arginine; S, Ser—serine; T, Thr—threonine; V, Val—valine; W, Trp—tryptophan; Y, Tyr—tyrosine; and p.Y., P.Tyr—phosphotyrosine.

I. Nucleic Acid Molecules of the Invention

The present invention provides an isolated nucleic aid molecule comprising a sequence encoding a cytochrome P450RAI-2 polypeptide.

The term "isolated" refers to a nucleic acid substantially free of cellular material or culture medium when produced by recombinant DNA techniques, or chemical precursors, or other chemicals when chemically synthesized.

The term "nucleic acid molecule" is intended to include unmodified DNA or RNA or modified DNA or RNA. For example, the nucleic acid molecules or polynucleotides of the invention can be composed of single- and double stranded DNA, DNA that is a mixture of single- and double-stranded regions, single- and double stranded RNA, and RNA that is a mixture of single- and double-stranded regions, hybrid molecules comprising DNA and RNA that may be single-stranded or, more typically double stranded or a mixture of single- and double stranded regions. In addition, the P450RAI-2 nucleic acid molecules can be composed of triple-stranded regions comprising RNA or DNA or both RNA and DNA. The nucleic acid molecules of the invention may also contain one or more modified bases or DNA or RNA backbones modified for stability or for other reasons. "Modified" bases include, for example, tritiated bases and unusual bases such as inosine. A variety of modifications can be made to DNA and RNA; thus "nucleic acid molecule" embraces chemically, enzymatically, or metabolically modified forms. The term "polynucleotide" shall have a corresponding meaning.

One aspect of the present invention is thus an isolated nucleic acid molecule comprising a nucleotide sequence selected from the group consisting of:

(a) a nucleotide sequence as shown in SEQ ID NOS: 4 or 28, but preferably SEQ ID NO: 4, wherein T can also be U;

(b) nucleotide sequences complementary to (a);

(c) nucleotide sequences which are homologous to (a) or (b);

(d) a nucleotide sequence differing from any of the nucleotide sequences of (a) to (c) in codon sequences due to the degeneracy of the genetic code; or (e) a fragment of (a) to (d) that is at least 15 bases, preferably 20 to 30 bases, and which would hybridize to (a) to (d) under stringent hybridization conditions. In another embodiment, the fragment is at least 35, 40, 45, 50, 55, or 60 or more nucleotides in length. In another embodiment the fragment is capable of oxidizing a retinoid. In yet another embodiment it preferably has at least about 55 percent homology with the protein encoded by a nucleotide sequence of (a) or (b).

In another embodiment, the nucleotide sequence in (a) above is a human P450RAI-2 sequence. In one embodiment, the nucleic acid sequence can be used as a probe or a primer, such as for PCR, like SEQ ID NOS: 9, 10, 29, 30, 33, 37 or 38, more preferably SEQ. ID. Nos. 37 and/or 38. In yet another embodiment, the nucleotide sequence of (a) above is selected from the group consisting of: a mouse P450RAI-2 sequence, such as SEQ ID NO: 6, 18, 26, 21, 22, 23, 24 or 25; a rat P450RAI-2 sequence, SEQ ID NO: 27; or a zebrafish P450RAI-2 sequence, SEQ ID NO: 8.

In one embodiment, the nucleic acid molecule of the invention encodes a protein that is capable of oxidizing a retinoid, preferably retinoic acid, preferably at the 4-position of the β-ionone ring. In another embodiment the nucleic acid molecule of the invention encodes a protein having SEQ ID NO: 5. In another embodiment, the nucleotide sequence inhibits P450RAI-2 expression, such as certain complimentary sequences to SEQ ID NO 4.

In one embodiment of the invention, the nucleic acid molecule consists of any of the nucleotide sequences described herein.

In all of the sequences referred to above, T can also be U. As previously stated, the invention includes isolated DNA molecules having such sequences of nucleotides, and RNA molecules having such sequences. The invention thus includes isolated mRNA transcribed from DNA having such a sequence. The invention further encompasses nucleic acid molecules that differ from any of the nucleic acid molecules of the invention in codon sequences due to the degeneracy of the genetic code.

The invention also encompasses nucleic acid sequences or molecules that are analogs of the nucleic acid sequences and molecules described herein. The term "a nucleic acid sequence which is an analog" means a nucleic acid sequence which has been modified as compared to the sequences described herein, such as sequences of (a), (b), (c), (d), or (e), above wherein the modification does not alter the utility of the sequences described herein. The modified sequence or analog may have improved properties over the sequence shown in (a), (b),(c), (d) or (e). One example of a modification to prepare an analog is to replace one of the naturally occurring bases (i.e. adenine, guanine, cytosine or thymidine) of the sequence shown in SEQ ID NO: 4, 6, 8–10, 18, or 21–28 with a modified base such as such as xanthine, hypoxanthine, 2-aminoadenine, 6-methyl, 2-propyl and other alkyl adenines, 5-halo uracil, 5-halo cytosine, 6-aza uracil, 6-aza cytosine and 6-aza thymine, pseudo uracil, 4-thiouracil, 8-halo adenine, 8-aminoadenine, 8-thiol adenine, 8-thiolalkyl adenines, 8-hydroxyl adenine and other 8-substituted adenines, 8-halo guanines, 8 amino guanine, 8-thiol guanine, 8-thiolalkyl guanines, 8-hydroxyl guanine and other 8-substituted guanines, other aza and deaza uracils, thymidines, cytosines, adenines, or guanines, 5-trifluoromethyl uracil and 5-trifluoro cytosine.

Another example of a modification is to include modified phosphorous or oxygen heteroatoms in the phosphate backbone, short chain alkyl or cycloalkyl intersugar linkages or short chain heteroatomic or heterocyclic intersugar linkages in the nucleic acid molecule shown in SEQ ID NOS: 4, 6, 8–10, 18, or 21–28. For example, the nucleic acid sequences may contain phosphorothioates, phosphotriesters, methyl phosphonates, and phosphorodithioates.

A further example of an analog of a nucleic acid molecule of the invention is a peptide nucleic acid (PNA) wherein the deoxyribose (or ribose) phosphate backbone in the DNA (or RNA), is replaced with a polyamide backbone which is similar to that found in peptides (P. E. Nielsen, et al Science 1991, 254, 1497). PNA analogs have been shown to be resistant to degradation by enzymes and to have extended lives in vivo and in vitro. PNAs also bind stronger to a complimentary DNA sequence due to the lack of charge repulsion between the PNA strand and the DNA strand. Other nucleic acid analogs may contain nucleotides containing polymer backbones, cyclic backbones, or acyclic backbones. For example, the nucleotides may have morpholino backbone structures (U.S. Pat. No. 5,034,506). The analogs may also contain groups such as reporter groups, a group for improving the pharmacokinetic or pharmacodynamic properties of nucleic acid sequence.

It will be appreciated that the invention includes nucleic acid molecules encoding truncations of proteins of the invention, and analogs and homologs of proteins of the invention and truncations thereof, as described below. It will further be appreciated that variant forms of nucleic acid molecules of the invention which arise by alternative splicing of an mRNA corresponding to a cDNA of the invention are encompassed by the invention. The invention further includes biologically active fragments of the nucleic acid molecules of the invention. Such fragments would include, but is not necessarily limited to any nucleic acid molecules which are beneficial in the modulation, including but not limited to simulation, inhibition or stimulation of P450RAI-2 activity or P450RAI-2 expression, or in the identification or production of such agents.

A nucleic acid molecule of the invention can encode a protein (polypeptide) having a homology of at least about 50, at least about 55, or more preferably at least about 58 percent with a protein encoded by SEQ ID NO:4 or the full length anti-sense sequence thereto. The level of homology, according to various aspects of the invention is at least about 60 percent; at least about 63 percent; at least about 65 percent; at least about 68 percent; at least about 70 percent; at least about 73 percent; at least about 75 percent; at least about 78 percent; at least about 80 percent; at least about 83 percent; at least about 85 percent; at least about 88 percent; at least about 90 percent; at least about 93 percent; at least about 95 percent; or at least about 98 percent. Methods for aligning the sequences to be compared and determining the level of homology between the sequences are described in detail below.

In another aspect, the present invention includes a fragment of the nucleotide sequence encoding P450RAI-2 (SEQ ID NO:4). Such a fragment can find usefulness as a probe or depending on the fragment may even have biological activity itself. The complement of the probe can find utility in, for example, manufacture of the probe or inhibition of any activity of the fragment, as the case may be. In a particular use, the probe can be used to determine the presence of an RNA molecule in a sample which might, or might not, also include an RNA molecule encoding P450RAI-1. Such a probe would generally be 20 nucleotides long or be at least 20 nucleotides long. The probe could also be 25, 30, 35, 40, 45, 50, 55, 60 or more nucleotides in length and the probe can include the full length of the complement to the sequence to which it is intended to bind. The sequence of the probe would also be sufficiently distinguishable from any portion of the sequence encoding P450RAI-1 that it would not cross-hybridize to a significant extent to a nucleotide sequence that encodes P450RAI-1, or portion thereof, particularly to an RNA encoding P450RAI-1. Such a probe would thus be sufficiently different from any sequence of contiguous nucleotides selected from the nucleotide sequence encoding human P450RAI-1 (SEQ ID NO:13) that there is no more than about 60% homology between the two sequences when the two sequences are directly aligned with each other. More preferably, the percent homology would be less than about 55%, or less than about 50%, or less than about 45%, or even less than about 40%. Certain probes of the invention are selected so as span borders between introns of the coding sequence as determined from the genomic sequence (SEQ ID NO:3). A preferred P450RAI-2 specific probe or PCR primer are SEQ. ID. NOs. 37 and/or 38.

The invention includes the method of determining the presence of a nucleic acid molecule encoding P450RAI-2 in a sample containing RNA isolated from a human cell, using such a probe.

In the context of this specification, the term "conserved" describes similarity between sequences. The degree of conservation between two sequences can be determined by optimally aligning the sequences for comparison. Here, sequences were aligned using the Omiga software program, Version 1.13. (Oxford Molecular Group, Inc., Campbell, Calif.). The Omiga software uses the Clustal W Alignment algorithms [Higgins et al., 1989; Higgins et al., 1991; Thompson et al. 1994] Default settings used are as follows: Open gap penalty 10.00; Extend gap penalty 0.05; Delay divergent sequence 40 and Scoring matrix—Gonnet Series. Percent identity or homology between two sequences is determined by comparing a position in the first sequence with a corresponding position in the second sequence. When the compared positions are occupied by the same nucleotide or amino acid, as the case may be, the two sequences are conserved at that position. The degree of conservation between two sequences is often expressed, as it is here, as a percentage representing the ratio of the number of matching positions in the two sequences to the total number of positions compared.

In one particular aspect, the present invention is a nucleic acid molecule of any preceding claim which encodes a protein that is a conservatively substituted variant of the protein encoded by the nucleotide sequence of SEQ ID NO:4.

Further, it will be appreciated that the invention includes nucleic acid molecules comprising nucleic acid sequences having substantial sequence homology with the nucleic acid sequences as shown in SEQ ID NO. 4, 6, 8–10, 18, or 21–28 and fragments thereof. The term "sequences having substantial sequence homology" means those nucleic acid sequences that have slight or inconsequential sequence variations from these sequences, i.e., the sequences function in substantially the same manner to produce functionally equivalent proteins. The variations may be attributable to local mutations or structural modifications.

Nucleic acid sequences having substantial homology include nucleic acid sequences having at least 85%, preferably 90–95% identity with the nucleic acid sequence as shown in SEQ ID NO: 4, 6, 8–10, 18, or 21–28. However, the invention is not to be restricted by this homology, for instance, nucleic acid sequences having at least a 50% homology with the sequence shown in 4, 6, 8–10, 18, or 21–28 are also encompassed within the scope of the present invention.

"Stringent hybridization conditions" is a term known to a person skilled in the art. Appropriate stringency conditions which promote nucleic acid hybridization, for example, 6×sodium chloride/sodium citrate (SSC) at about 45° C. are know. The following examples are found in Current Protocols in Molecular Biology, John Wiley & Sons, NY (1989), 6.3.1–6.3.6: For 50 ml of a first suitable hybridization solution, mix together 24 ml formamide, 12 ml 20×SSC, 0.5 ml 2 M Tris-HCl pH 7.6, 0.5 ml 100×Denhardt's solution, 2.5 ml deionized $H_2O$, 10 ml 50% dextran sulfate, and 0.5 ml 10% SDS. A second suitable hybridization solution can be 1% crystalline BSA (fraction V), 1 mM EDTA, 0.5 M $Na_2HPO_4$ pH 7.2, 7% SDS. The salt concentration in the wash step can be selected from a low stringency of about 2×SSC at 50° C. to a high stringency of about 0.2×SSC at 50° C. Both of these wash solutions may contain 0.1% SDS. In addition, the temperature in the wash step can be increased from low stringency conditions at room temperature, about 22° C., to high stringency conditions, at about 65° C. The cited reference gives more detail, but appropriate wash stringency depends on degree of homology and length of probe. If homology is 100%, a high temperature (65° C. to 75° C.) may be used. If homology is low, lower wash temperatures must be used. However, if the probe is very short (<100 bp), lower temperatures must be used even with 100% homology. In general, one starts washing at low temperatures (37° C. to 40° C.), and raises the temperature by 3–5° C. intervals until background is low enough not to be a major factor in autoradiography.

Isolated nucleic acid molecules having sequences which differ from the nucleic acid sequence shown in SEQ ID NO: 4, 6, 8–10, 18, or 21–28 due to degeneracy in the genetic code are also within the scope of the invention. Such nucleic acids encode functionally equivalent proteins but differ in sequence from the above mentioned sequences due to degeneracy in the genetic code.

An isolated nucleic acid molecule of the invention which comprises DNA can be isolated by preparing a labelled nucleic acid probe based on all or part of the nucleic acid sequences as shown in SEQ ID NO: 4, 6, 8–10, 18, or 21–28 and using this labelled nucleic acid probe to screen an appropriate DNA library (e.g. a cDNA or genomic DNA library). For example, a genomic library isolated can be used to isolate a DNA encoding a novel protein of the invention by screening the library with the labelled probe using standard techniques. Nucleic acids isolated by screening of a cDNA or genomic DNA library can be sequenced by standard techniques.

An isolated nucleic acid molecule of the invention which is DNA can also be isolated by selectively amplifying a nucleic acid encoding a novel protein of the invention using the polymerase chain reaction (PCR) methods and cDNA or genomic DNA. It is possible to design synthetic oligonucleotide primers from the nucleic acid sequence as shown in SEQ ID NO: 4, 6, 8–10, 18, or 21–28 for use in PCR. A nucleic acid can be amplified from cDNA or genomic DNA using these oligonucleotide primers and standard PCR amplification techniques. The nucleic acid so amplified can be cloned into an appropriate vector and characterized by DNA sequence analysis. It will be appreciated that cDNA may be prepared from mRNA, by isolating total cellular mRNA by a variety of techniques, for example, by using the guanidinium-thiocyanate extraction procedure of Chirgwin et al., Biochemistry, 18, 5294 5299 (1979). cDNA is then synthesized from the mRNA using reverse transcriptase (for example, Moloney MLV reverse transcriptase available from Gibco/BRL, Bethesda, Md., or AMV reverse transcriptase available from Seikagaku America, Inc., St. Petersburg, Fla.).

An isolated nucleic acid molecule of the invention which is RNA can be isolated by cloning a cDNA encoding a novel protein of the invention into an appropriate vector which allows for transcription of the cDNA to produce an RNA molecule which encodes a protein of the invention. For example, a cDNA can be cloned downstream of a bacteriophage promoter, (e.g., a T7 promoter) in a vector, cDNA can be transcribed in vitro with T7 polymerase, and the resultant RNA can be isolated by standard techniques.

A nucleic acid molecule of the invention may also be chemically synthesized using standard techniques. Various methods of chemically synthesizing polydeoxynucleotides are known, including solid-phase synthesis which, like peptide synthesis, has been fully automated in commercially available DNA synthesizers (See e.g., Itakura et al. U.S. Pat. No. 4,598,049; Caruthers et al. U.S. Pat. No. 4,458,066; and Itakura U.S. Pat. Nos. 4,401,796 and 4,373,071).

Determination of whether a particular nucleic acid molecule encodes a novel protein of the invention may be accomplished by expressing the cDNA in an appropriate host cell by standard techniques, and testing the activity of the protein using the methods as described herein. A cDNA having the activity of a novel protein of the invention so isolated can be sequenced by standard techniques, such as dideoxynucleotide chain termination or Maxam-Gilbert chemical sequencing or by automated DNA sequencing, to determine the nucleic acid sequence and the predicted amino acid sequence of the encoded protein.

The initiation codon and untranslated sequences of nucleic acid molecules of the invention may be determined using currently available computer software designed for the purpose, such as PC/Gene (IntelliGenetics Inc., CA). Regulatory elements can be identified using conventional techniques. The function of the elements can be confirmed by using these elements to express a reporter gene which is operatively linked to the elements. These constructs may be introduced into cultured cells using standard procedures. In addition to identifying regulatory elements in DNA, such constructs may also be used to identify proteins interacting with the elements, using techniques known in the art.

The sequence of a nucleic acid molecule of the invention may be inverted relative to its normal presentation for transcription to produce an antisense nucleic acid molecule. The term "antisense" nucleic acid molecule is a nucleotide sequence that is complementary to its target. Preferably, an antisense sequence is constructed by inverting a region preceding or targeting the initiation codon or an unconserved region. In another embodiment the antisense sequence targets all or part of the mRNA or cDNA of P450RAI-2. In particular, the nucleic acid sequences contained in the nucleic acid molecules of the invention or a fragment thereof may be inverted relative to its normal presentation for transcription to produce antisense nucleic acid molecules. In one embodiment the antisense molecules can be used to inhibit P450RAI-2 expression and/or RA metabolism, The antisense nucleic acid molecules of the invention or a fragment thereof, may be chemically synthesized using naturally occurring nucleotides or variously modified nucleotides designed to increase the biological stability of the molecules or to increase the physical stability of the duplex formed with mRNA or the native gene e.g. phosphorothioate derivatives and acridine substituted nucleotides. The antisense sequences may be produced biologically using an expression vector introduced into cells in the form of a recombinant plasmid, phagemid or attenuated virus in which antisense sequences are produced under the control of a high efficiency regulatory region, the activity of which may be determined by the cell type into which the vector is introduced.

The invention also provides nucleic acids encoding fusion proteins comprising a novel protein of the invention and a selected protein, or a selectable marker protein (see below).

II. Polypeptides of the Invention

The invention further contemplates an isolated P450RAI-2 protein. In an embodiment of the invention, an isolated protein is provided which has the human amino acid sequence as shown in SEQ ID NO. 5 or a fragment , preferably biologically active fragment, thereof. The present invention also encompasses peptides encoded by the nucleic acid sequence of SEQ ID NO: 4 and all embodiments therefor as described in reference to the peptides in SEQ ID NO. 5 described below.

Within the context of the present invention, a protein of the invention may in one embodiment include various structural forms of the primary protein which retain biological activity of the cytochrome P450RAI-2. For example, a protein of the invention may be in the form of acidic or basic salts or in neutral form. In addition, individual amino acid residues may be modified by oxidation or reduction. The biological activity of a active cytochrome P450RAI-2 is the ability to oxidize a retinoid. Such activity can be tested for as deccribed herein.

In addition to the full length amino acid sequence (SEQ ID NO: 5), the proteins of the present invention may also include truncations of the proteins, and analogs, and homologs of the proteins and truncations thereof as described herein. Truncated proteins may comprise peptides of at least 10 and preferably at least fourteen amino acid residues.

In one embodiment, the invention provides a peptide fragment of human SEQ ID NO: 5. In another embodiment the invention provides a peptide having an amino acid sequence of the partial mouse P450RAI-2 sequence, SEQ ID NO: 11 or Zebrafish sequence (SEQ ID NO: 12). In another embodiment the invention provides a peptide encoded by any of the nucleic acid molecules of the invention as described above. In yet another embodiment the invention provides an antigenic immunogenic fragment of the proteins of the invention.

Analogs of the proteins having the amino acid sequences shown in SEQ ID NO: 5 and/or truncations thereof as described herein, may include, but are not limited to an amino acid sequence containing one or more amino acid substitutions, insertions, and/or deletions. Amino acid substitutions may be of a conserved or non-conserved nature. Conserved amino acid substitutions involve replacing one or more amino acids of the proteins of the invention with amino acids of similar charge, size, and/or hydrophobicity characteristics. When only conserved substitutions are made the resulting analog should be functionally equivalent. Non-conserved substitutions involve replacing one or more amino acids of the amino acid sequence with one or more amino acids which possess dissimilar charge, size, and/or hydrophobicity characteristics.

Without the intention of being limited thereby, in one embodiment it is preferable that substitutions of amino acids are made that preserve the structure responsible for retinoid metabolizing activity of the proteins disclosed herein. Conservative substitutions are described in the patent literature, as for example, in U.S. Pat. No. 5,264,558. It is thus expected, for example, that interchange among non-polar aliphatic neutral amino acids, glycine, alanine, proline, valine and isoleucine, would be possible. Likewise, substitutions among the polar aliphatic neutral amino acids, serine, threonine, methionine, asparagine and glutamine could possibly be made. Substitutions among the charged acidic amino acids, aspartic acid and glutamic acid, could probably be made, as could substitutions among the charged basic amino acids, lysine and arginine. Substitutions among the aromatic amino acids, including phenylalanine, histidine, tryptophan and tyrosine would also likely be possible. These sorts of substitutions and interchanges are well known to those skilled in the art. Other substitutions might well be possible. Of course, it would also be expected that the greater the percentage of homology, i.e., sequence similarity, of a variant protein with a naturally occurring protein, the greater the retention of metabolic activity. Of course, as protein variants having the activity of P450RAI-2 as described herein are intended to be within the scope of this invention, so are nucleic acids encoding such variants.

One or more amino acid insertions may be introduced into the amino acid sequences shown in SEQ ID NO: 5. Amino acid insertions may consist of single amino acid residues or sequential amino acids ranging from 2 to 15 amino acids in length. For example, amino acid insertions may be used to destroy target sequences so that the protein is no longer active. This procedure may be used in vivo to inhibit the activity of a protein of the invention.

Deletions may consist of the removal of one or more amino acids, or discrete portions from the amino acid sequence shown in SEQ ID NO: 5. The deleted amino acids may or may not be contiguous. The lower limit length of the resulting analog with a deletion mutation is about 10 amino acids, preferably 100 amino acids.

Analogs of the proteins of the invention may be prepared by introducing mutations in the nucleotide sequence encoding the protein. Mutations in nucleotide sequences constructed for expression of analogs of a protein of the invention must preserve the reading frame of the coding sequences. Furthermore, the mutations will preferably not create complementary regions that could hybridize to produce secondary mRNA structures, such as loops or hairpins, which could adversely affect translation of the mRNA.

Mutations may be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion.

Alternatively, oligonucleotide-directed site specific mutagenesis procedures may be employed to provide an altered gene having particular codons altered according to the substitution, deletion, or insertion required. Deletion or truncation of a protein of the invention may also be constructed by utilizing convenient restriction endonuclease sites adjacent to the desired deletion. Subsequent to restriction, overhangs may be filled in, and the DNA religated. Exemplary methods of making the alterations set forth above are disclosed by Sambrook et al (Molecular Cloning: A Laboratory Manual, 2nd Ed., Cold Spring Harbor Laboratory Press, 1989).

Insertions, deletions or substitution mutations of P450RAI-2 can be used to generate dominant negative forms of P450RAI-2 that can act as transdominant repressors of P450RAI-2 activity.

The proteins of the invention also include homologs of the amino acid sequence shown in SEQ ID NO: 5 and/or truncations thereof as described herein. Such homologs are proteins whose amino acid sequences are encoded by nucleic acid sequences that hybridize under stringent hybridization conditions (see discussion of stringent hybridization conditions herein) with a probe used to obtain a protein of the invention. Homologs of a protein of the invention will have the same regions which are characteristic of the protein.

A homologous protein includes a protein with an amino acid sequence having at least 60%, preferably at least 76%, preferably 80–90% identity with the amino acid sequence as shown in SEQ ID NO: 5.

The invention also contemplates isoforms of the proteins of the invention. An isoform contains the same number and kinds of amino acids as a protein of the invention, but the isoform has a different molecular structure. The isoforms contemplated by the present invention are those having the same properties as a protein of the invention as described herein.

The present invention also includes a protein of the invention conjugated with a selected protein, or a selectable marker protein (see below) to produce fusion proteins. Additionally, immunogenic portions of a protein of the invention are within the scope of the invention. Immunogenic portions of a protein is that portion that if administered to a patient can induce an immune response and preferably an antibody response.

A further advantage may be obtained through chimeric forms of the protein, as known in the art. A DNA sequence encoding the entire protein, or a portion of the protein, could thus be linked, for example, with a sequence coding for the C-terminal portion of E. coli β-galactosidase to produce a fusion protein. GST-P450RAI-2 fusion proteins are described in the above examples. An expression system for human respiratory syncytial virus glycoproteins F and G is described in U.S. Pat. No. 5,288,630 issued Feb. 22, 1994 and references cited therein, for example.

The proteins of the invention (including truncations, analogs, etc.) may be prepared using recombinant DNA methods. These proteins may be purified and/or isolated to various degrees using techniques known in the art. Accordingly, nucleic acid molecules of the present invention having a sequence which encodes a protein of the invention may be incorporated according to procedures known in the art into an appropriate expression vector which ensures good expression of the protein. Possible expression vectors include but are not limited to cosmids, plasmids, or modified viruses (e.g., replication defective retroviruses, adenoviruses and adeno-associated viruses), so long as the vector is compatible with the host cell used. The expression "vectors suitable for transformation of a host cell", means that the expression vectors contain a nucleic acid molecule of the invention and regulatory sequences, selected on the basis of the host cells to be used for expression, which are operatively linked to the nucleic acid molecule. "Operatively linked" is intended to mean that the nucleic acid is linked to regulatory sequences in a manner which allows expression of the nucleic acid.

The invention therefore contemplates a recombinant expression vector of the invention containing a nucleic acid molecule of the invention, or a fragment thereof, and the necessary regulatory sequences for the transcription and translation of the inserted protein-sequence. Suitable regulatory sequences may be derived from a variety of sources, including bacterial, fungal, or viral genes (For example, see the regulatory sequences described in Goeddel, Gene Expression Technology: Methods in Enzymology 185, Academic Press, San Diego, Calif. (1990). Selection of appropriate regulatory sequences is dependent on the host cell chosen, and may be readily accomplished by one of ordinary skill in the art. Examples of such regulatory sequences include: a transcriptional promoter and enhancer or RNA polymerase binding sequence, a ribosomal binding sequence, including a translation initiation signal. Additionally, depending on the host cell chosen and the vector employed, other sequences, such as an origin of replication, additional DNA restriction sites, enhancers, and sequences conferring inducibility of transcription may be incorporated into the expression vector. It will also be appreciated that the necessary regulatory sequences may be supplied by the native protein and/or its flanking regions.

The invention further provides a recombinant expression vector comprising a DNA nucleic acid molecule of the invention cloned into the expression vector in an antisense orientation. That is, the DNA molecule is operatively linked to a regulatory sequence in a manner which allows for expression, by transcription of the DNA molecule, of an RNA molecule which is antisense to a nucleotide sequence of the invention preferably comprising the nucleotides as shown in SEQ ID NO: 4 or fragments thereof. Regulatory sequences operatively linked to the antisense nucleic acid can be chosen which direct the continuous expression of the antisense RNA molecule.

The recombinant expression vectors of the invention may also contain a selectable marker gene that facilitates the selection of host cells transformed or transfected with a recombinant molecule of the invention. Examples of selectable marker genes are genes encoding a protein which confers resistance to certain drugs, such as G418 and hygromycin. Examples of other markers which can be used are: green fluorescent protein (GFP), β-galactosidase, chloramphenicol acetyltransferase, or firefly luciferase. Transcription of the selectable marker gene is monitored by changes in the concentration of the selectable marker protein such as β-galactosidase, chloramphenicol acetyltransferase, or firefly luciferase. If the selectable marker gene encodes a protein conferring antibiotic resistance such as neomycin resistance transformant cells can be selected with G418. Cells that have incorporated the selectable marker gene will survive, while the other cells die. This makes it possible to visualize and assay for expression of recombinant expression vectors of the invention and in particular to determine the effect of a mutation on expression and phenotype. It will be appreciated that selectable markers can be introduced on a separate vector from the nucleic acid of interest.

The recombinant expression or cloning vectors of the invention may also contain genes which encode a fusion moiety which provides increased expression of the recombinant protein; increased solubility of the recombinant protein; and aid in the purification of a target recombinant protein by acting as a ligand in affinity purification. For example, a proteolytic cleavage site may be added to the target recombinant protein to allow separation of the recombinant protein from the fusion moiety subsequent to purification of the fusion protein.

Recombinant expression vectors can be introduced into host cells to produce a transformed host cell. The term "transformed host cell" is intended to include prokaryotic and eukaryotic cells which have been transformed or transfected with a recombinant expression vector of the invention. The terms "transformed with", "transfected with", "transformation" and "transfection" are intended to encompass introduction of nucleic acid (e.g. a vector) into a cell by one of many possible techniques known in the art. Prokaryotic cells can be transformed with nucleic acid by, for example, electroporation or calcium chloride mediated transformation. Nucleic acid can be introduced into mammalian cells via conventional techniques such as calcium phosphate or calcium chloride co precipitation, DEAE-dextran-mediated transfection, lipofectin, electroporation or microinjection. Suitable methods for transforming and transfecting host cells can be found in Sambrook et al. (Molecular Cloning: A Laboratory Manual, 2nd Edition, Cold Spring Harbor Laboratory press (1989)), and other such laboratory textbooks.

Suitable host cells include a wide variety of prokaryotic and eukaryotic host cells. For example, the proteins of the invention may be expressed in bacterial cells such as E. coli, insect cells (using baculovirus), yeast cells or mammalian cells, COS1 cells. Other suitable host cells can be found in Goeddel, Gene Expression Technology: Methods in Enzymology 185, Academic Press, San Diego, Calif. (1991).

The invention includes a microbial cell that contains and is capable of expressing a heterologous a nucleic acid molecule having a nucleotide sequence as broadly encompassed by the invention. The heterologous nucleic acid molecule can be DNA.

Isolated DNA of the invention can be contained in a recombinant cloning vector.

The invention includes a stably transfected cell line which expresses any one or more proteins as broadly defined by the invention.

The invention includes a culture of cells transformed with a recombinant DNA molecule having a nucleotide sequence as broadly encompassed by the invention. Such a culture of cells can be eukaryotic. They can be piscine—particularly zebrafish, mammalian—particularly human, rat or mouse, for example.

The invention is also a process for producing any protein as broadly defined by the invention. The process includes such steps as:

preparing a DNA fragment including a nucleotide sequence which encodes said protein;

incorporating the DNA fragment into an expression vector to obtain a recombinant DNA molecule which includes the DNA fragment and is capable of undergoing replication;

transforming a host cell with said recombinant DNA molecule to produce a transformant which can express said protein;

culturing the transformant to produce said protein; and recovering said protein from resulting cultured mixture.

More particularly, the invention provides a method of preparing a purified protein of the invention comprising introducing into a host cell a recombinant nucleic acid encoding the protein, allowing the protein to be expressed in the host cell and isolating and purifying the protein. Preferably, the recombinant nucleic acid is a recombinant expression vector. Proteins can be isolated from a host cell expressing the protein and purified according to standard procedures of the art, including ammonium sulfate precipitation, column chromatography (e.g. ion exchange, gel filtration, affinity chromatography, etc.), electrophoresis, and ultimately, crystallization [see generally, "Enzyme Purification and Related Techniques", *Methods in Enzymology,* 22, 233–577 (1971)].

Alternatively, the protein or parts thereof can be prepared by chemical synthesis using techniques well known in the chemistry of proteins such as solid phase synthesis [Merrifield 1964] or synthesis in homogeneous solution [Houbenwycl, 1987].

III. Applications

1. Diagnostic Applications

The above nucleic acid and peptide molecules of the invention can be used to diagnose a disease affected by P450RAI-2 expression, such as a disease or medical condition associated with or where RA, P450RAI-2 or inhibitors thereof treatment may be indicated. Examples of such conditions have been outlined herein, such as diseases associated with angiogenesis the regulation of the cell cycle or apoptosis, such as cancer, dysplasia, various autoimmune diseases and conditions related to cerebellum or pond functions, such as memory or learning. Determination of peptide or nucleic acid expression levels could assist not only in identifying a medical condition but in determining the appropriate course of treatment.

(i) Nucleic Acids

The above described nucleic acid molecules of the invention, allow those skilled in the art to construct nucleotide probes for use in the detection of nucleotide sequences homologous to P450RAI-2 or a fragment thereof in a sample.

Accordingly, the present invention also relates to a method of detecting the presence of nucleic acid molecules encoding a P450RAI-2 in a sample comprising contacting the sample under hybridization conditions with one or more nucleotide probes which hybridize to the nucleic acid molecules and are labelled with a detectable marker, and, determining the degree of hybridization between the nucleic acid molecule in the sample and the nucleotide probe(s).

A nucleotide probe may be labelled with a detectable marker such as a radioactive label which provides for an adequate signal and has sufficient half life such as 32P, 3H, 14C or the like. Other detectable markers which may be used include antigens that are recognized by a specific labelled antibody, fluorescent compounds, enzymes, antibodies specific for a labelled antigen, and chemiluminescent compounds. An appropriate label may be selected having regard to the rate of hybridization and binding of the probe to the nucleotide to be detected and the amount of nucleotide available for hybridization.

Hybridization conditions which may be used in methods of the invention are known in the art and are described for example in Sambrook J, Fritch E F, Maniatis T. In: Molecular Cloning, A Laboratory Manual,1989. (Nolan C, Ed.), Cold Spring Harbor Laboratory Press, Cold Spring Harbor, N.Y. The hybridization product may be assayed using techniques known in the art. The nucleotide probe may be labelled with a detectable marker as described herein and the hybridization product may be assayed by detecting the detectable marker or the detectable change produced by the detectable marker.

A nucleic acid molecule of the invention also permits the identification and isolation, or synthesis of nucleotide sequences which may be used as primers to amplify a nucleic acid molecule of the invention, for example, in a polymerase chain reaction (PCR) which is discussed in more detail below. The primers may be used to amplify the genomic DNA or mRNA of other P450RAI-2 genes or coding sequences. The PCR amplified sequences can be examined to determine the relationship between the various P450RAI-2 genes.

The length and bases of primers for use in a PCR are selected so that they will hybridize to different strands of the desired sequence and at relative positions along the sequence such that an extension product synthesized from one primer when it is separated from its template can serve as a template for extension of the other primer into a nucleic acid of defined length. Primers which may be used in the invention are oligonucleotides, i.e., molecules containing two or more deoxyribonucleotides of the nucleic acid molecule of the invention which occur naturally as in a purified restriction endonuclease digest or are produced synthetically using techniques known in the art such as for example phosphotriester and phosphodiester methods (See Good et al. Nucl. Acid Res 4:2157, 1977) or automated techniques (See for example, Conolly, B. A. Nucleic Acids Res. 15:15 (7): 3131, 1987). The primers are capable of acting as a point of initiation of synthesis when placed under conditions which permit the synthesis of a primer extension product which is complementary to a DNA sequence of the invention, i.e., in the presence of nucleotide substrates, an agent for polymerization such as DNA polymerase and at suitable temperature and pH. Preferably, the primers are sequences that do not form secondary structures by base pairing with other copies of the primer or sequences that form a hair pin configuration. The primer preferably contains between about 7 and 25 nucleotides.

The primers may be labelled with detectable markers which allow for detection of the amplified products. Suitable detectable markers are radioactive markers such as P-32, S-35, I-125, and H-3, luminescent markers such as chemiluminescent markers, preferably luminol, and fluorescent markers, preferably dansyl chloride, fluorcein-5-isothiocyanate, and 4-fluor-7-nitrobenz-2-axa-1,3 diazole, enzyme markers such as horseradish peroxidase, alkaline phosphatase, β-galactosidase, acetylcholinesterase, or biotin.

It will be appreciated that the primers may contain non-complementary sequences provided that a sufficient amount of the primer contains a sequence which is complementary to a nucleic acid molecule of the invention or oligonucleotide fragment thereof, which is to be amplified. Restriction site linkers may also be incorporated into the primers allowing for digestion of the amplified products with the appropriate restriction enzymes facilitating cloning and sequencing of the amplified product.

In an embodiment of the invention a method of determining the presence of a nucleic acid molecule having a sequence encoding a protein of the invention is provided comprising treating the sample with primers which are capable of amplifying the nucleic acid molecule or a predetermined oligonucleotide fragment thereof in a polymerase chain reaction to form amplified sequences, under conditions which permit the formation of amplified sequences and, assaying for amplified sequences.

Polymerase chain reaction as used herein refers to a process for amplifying a target nucleic acid sequence as generally described in Innis et al, Academic Press, 1990 in Mullis el al., U.S. Pat. No. 4,863,195 and Mullis, U.S. Pat. No. 4,683,202. Conditions for amplifying a nucleic acid template are described in M. A. Innis and D. H. Gelfand, PCR Protocols, A Guide to Methods and Applications M. A. Innis, D. H. Gelfand, J. J. Sninsky and T. J. White eds, pp 3–12, Academic Press 1989.

The amplified products can be isolated and distinguished based on their respective sizes using techniques known in the art. For example, after amplification, a DNA sample can be separated on an agarose gel and visualized, after staining with ethidium bromide, under ultra violet (uv) light. DNA may be amplified to a desired level and a further extension reaction may be performed to incorporate nucleotide derivatives having detectable markers such as radioactive labelled or biotin labelled nucleoside triphosphates. The primers may also be labelled with detectable markers as discussed above. The detectable markers may be analyzed by restriction enzyme digestion and electrophoretic separation or other techniques known in the art.

Conditions which may be employed in the methods of the invention using PCR are those which permit hybridization and amplification reactions to proceed in the presence of DNA in a sample and appropriate complementary hybridization primers. Conditions suitable for a polymerase chain reaction are generally known in the art. For example, see M. A. Innis and D. H. Gelfand, PCR Protocols, A guide to Methods and Applications M. A. Innis, D. H. Gelfand, J. J. Sninsky and T. J. White eds, pp 3–12, Academic Press 1989. To amplify DNA template strands, preferably, the PCR utilizes polymerase obtained from the thermophilic bacterium Thermus aquatics (Taq polymerase, GeneAmp Kit, Perkin Elmer Cetus) or other thermostable polymerase.

It will be appreciated that other techniques such as the Ligase Chain Reaction (LCR) and NASBA may be used to amplify a nucleic acid molecule of the invention (Barney in "PCR Methods and Applications", August 1991, Vol.1(1), page 5, and European Published Application No. 0320308, published Jun. 14, 1989, and U.S. Ser. No. 5,130,238 to Malek).

(ii) Antibodies

A P450RAI-2 protein of the invention or antigenic portion thereof can be used to prepare antibodies specific for the proteins of the invention, preferably to a protein having SEQ ID NO: 5 or partial sequence SEQ ID NO: 11 or 12. Antibodies can be prepared which bind a distinct epitope in an unconserved region of the protein. An unconserved region of the protein is one which does not have substantial sequence homology to other proteins. Alternatively, a region from a well-characterized domain can be used to prepare an antibody to a conserved region of a protein of the invention. Antibodies having specificity for a protein of the invention may also be raised from fusion proteins.

Conventional methods can be used to prepare the antibodies. For example, by using a peptide of a protein of the invention, polyclonal antisera or monoclonal antibodies can be made using standard methods. A mammal, (e.g., a mouse, hamster, or rabbit) can be immunized with an immunogenic form of the peptide which elicits an antibody response in the mammal. Techniques for conferring immunogenicity on a peptide include conjugation to carriers or other techniques well known in the art. For example, the peptide can be administered in the presence of adjuvant. The progress of immunization can be monitored by detection of antibody titers in plasma or serum. Standard ELISA or other immunoassay procedures can be used with the immunogen as antigen to assess the levels of antibodies. Following immunization, antisera can be obtained and, if desired, polyclonal antibodies isolated from the sera.

To produce monoclonal antibodies, antibody producing cells (lymphocytes) can be harvested from an immunized animal and fused with myeloma cells by standard somatic cell fusion procedures thus immortalizing these cells and yielding hybridoma cells. Such techniques are well known in the art, (e.g., the hybridoma technique originally developed by Kohler and Milstein (Nature 256, 495–497 (1975)) as well as other techniques such as the human B-cell hybridoma technique (Kozbor et al., Immunol. Today 4, 72 (1983)); the EBV-hybridoma technique to produce human monoclonal antibodies (Cole et al. Monoclonal Antibodies in Cancer Therapy (1985) Allen R. Bliss, Inc., pages 77–96); and screening of combinatorial antibody libraries (Huse et al., Science 246, 1275 (1989)). Hybridoma cells can be screened immunochemically for production of antibodies specifically reactive with the peptide and the monoclonal antibodies can be isolated. Therefore, the invention also contemplates hybridoma cells secreting monoclonal antibodies with specificity for a protein of the invention.

The term "antibody" as used herein is intended to include fragments thereof which also specifically react with a protein of the invention, or peptide thereof. Antibodies can be fragmented using conventional techniques and the fragments screened for utility in the same manner as described above. For example, F(ab')2 fragments can be generated by treating antibody with pepsin. The resulting F(ab')2 fragment can be treated to reduce disulfide bridges to produce Fab' fragments.

Chimeric antibody derivatives, i.e., antibody molecules that combine a non-human animal variable region and a human constant region are also contemplated within the scope of the invention. Chimeric antibody molecules can include, for example, the antigen binding domain from an antibody of a mouse, rat, or other species, with human constant regions. Conventional methods may be used to make chimeric antibodies containing the immunoglobulin variable region which recognizes a P450RAI-2 protein of the invention (See, for example, Morrison et al., Proc. Natl Acad. Sci. U.S.A. 81,6851 (1985); Takeda et al., Nature 314, 452 (1985), Cabilly et al., U.S. Pat. No. 4,816,567; Boss et al., U.S. Pat. No. 4,816,397; Tanaguchi et al., European Patent Publication EP171496; European Patent Publication 0173494, United Kingdom patent GB 2177096B).

Monoclonal or chimeric antibodies specifically reactive with a protein of the invention as described herein can be further humanized by producing human constant region chimeras, in which parts of the variable regions, particularly the conserved framework regions of the antigen-binding domain, are of human origin and only the hypervariable regions are of non-human origin. Such immunoglobulin molecules may be made by techniques known in the art (e.g., Teng et al., Proc. Natl. Acad. Sci. U.S.A., 80, 7308–7312 (1983); Kozbor et al., Immunology Today, 4, 7279 (1983); Olsson et al., Meth. Enzymol., 92, 3–16 (1982); and PCT Publication WO92/06193 or EP 0239400). Humanized antibodies can also be commercially produced (Scotgen Limited, 2 Holly Road, Twickenham, Middlesex, Great Britain.)

Specific antibodies, or antibody fragments reactive against a protein of the invention may also be generated by screening expression libraries encoding immunoglobulin genes, or portions thereof, expressed in bacteria with peptides produced from nucleic acid molecules of the present invention. For example, complete Fab fragments, VH regions and FV regions can be expressed in bacteria using phage expression libraries (See for example Ward et al., Nature 341, 544–546: (1989); Huse et al., Science 246, 1275–1281 (1989); and McCafferty et al. Nature 348,552–554 (1990)).

The antibodies may be labelled with a detectable marker including various enzymes, fluorescent materials, luminescent materials and radioactive materials. Examples of suitable enzymes include horseradish peroxidase, alkaline phosphatase, β-galactosidase, or acetylcholinesterase; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include S-35, Cu-64, Ga-67, Zr-89, Ru-97, Tc-99m, Rh-105, Pd-109, In-111, I-123, I-125, I-131, Re-186, Au-198, Au-199, Pb-203, At-211, Pb-212 and Bi-212. The antibodies may also be labelled or conjugated to one partner of a ligand binding pair. Representative examples include avidin-biotin and riboflavin-riboflavin binding protein. Methods for conjugating or labelling the antibodies discussed above with the representative labels set forth above may be readily accomplished using conventional techniques.

Antibodies reactive against P450RAI-2 proteins of the invention (e.g., enzyme conjugates or labelled derivatives) may be used to detect a protein of the invention in various samples, for example they may be used in any known immunoassays which rely on the binding interaction between an antigenic determinant of a protein of the invention and the antibodies. Examples of such assays are radioimmunoassays, western immunoblotting, enzyme immunoassays (e.g., ELISA), immunofluorescence, immunoprecipitation, latex agglutination, hemagglutination, and histochemical tests. Thus, the antibodies may be used to identify or quantify the amount of a protein of the invention in a sample.

A sample may be tested for the presence or absence of a P450RAI-2 by contacting the sample with an antibody specific for an epitope of a P450RAI-2 protein which antibody is capable of being detected after it becomes bound to a P450RAI-2 protein in the sample, and assaying for antibody bound to a P450RAI-2 protein in the sample, or unreacted antibody.

In a method of the invention a predetermined amount of a sample or concentrated sample is mixed with antibody or labelled antibody. The amount of antibody used in the method is dependent upon the labelling agent chosen. The resulting protein bound to antibody or labelled antibody may be isolated by conventional isolation techniques, for example, salting out, chromatography, electrophoresis, gel filtration, fractionation, absorption, polyacrylamide gel electrophoresis, agglutination, or combinations thereof.

The sample or antibody may be insolubilized, for example, the sample or antibody can be reacted using known methods with a suitable carrier. Examples of suitable carriers are Sepharose or agarose beads. When an insolubilized sample or antibody is used protein bound to antibody or unreacted antibody is isolated by washing. For example, when the sample is blotted onto a nitrocellulose membrane, the antibody bound to a protein of the invention is separated from the unreacted antibody by washing with a buffer, for example, phosphate buffered saline (PBS) with bovine serum albumin (BSA).

When labelled antibody is used, the presence of a P450RAI-2 can be determined by measuring the amount of labelled antibody bound to a protein of the invention in the sample or of the unreacted labelled antibody. The appropriate method of measuring the labelled material is dependent upon the labelling agent.

When unlabelled antibody is used in a method of the invention, the presence of a P450RAI-2 can be determined by measuring the amount of antibody bound to the P450RAI-2 using substances that interact specifically with the antibody to cause agglutination or precipitation. In particular, labelled antibody against an antibody specific for a protein of the invention, can be added to the reaction mixture. The antibody against an antibody specific for a protein of the invention can be prepared and labelled by conventional procedures known in the art which have been described herein. The antibody against an antibody specific for a protein of the invention may be a species specific anti-immunoglobulin antibody or monoclonal antibody, for example, goat anti-rabbit antibody may be used to detect rabbit antibody specific for a protein of the invention.

(iii) Methods of the Invention

The invention includes a protein of the invention for use in metabolizing retinoic acid in an organism or cell in need of such metabolizing. The invention also includes use of a protein of the invention in the preparation of a medicament for use in metabolizing retinoic acid in an organism. Preferably the protein has sequence of SEQ ID NO: 5.

The invention includes a method for metabolizing retinoic acid, particularly all-trans retinoic acid, in an organism or cell comprising administering a protein as broadly defined by the invention, most preferably of SEQ ID NO: 5.

The invention is also a method for inhibiting retinoic acid hydroxylation in an organism in need of such inhibition, comprising administering to the organism an effective amount of an antisense nucleic acid or oligonucleotide substantially complementary to at least a portion of the sequence identified as SEQ ID NO:4. In such a method, the portion can be at least 5 bases in length, or at least about 10 bases in length, or at least about 15 bases in length, or at least about 20 bases in length, or at least about 25 bases in length, or at least about 30 bases in length, or at least about 35 bases in length, or at least about 40 bases in length, or at least about 45 bases in length, or at least about 50 bases in length. Other inhibitors, of RA metabolism such as antibodies to P450RAI-2, or inhibitors of P450RAI-2 activity could also be used.

A preferred organism to be treated is human but could be any organism with an RA metabolism or P450RAI-2 related condition.

The organism may be being treated for a medical condition or disease wherein RA treatment may be indicated. In one embodiment the disease or medical condition is selected from the group consisting of cancer, angiogenesis, actinic keratosis, oral leukoplakia, a secondary tumor of the head and/or neck, a non-small cell lung carcinoma, a basal cell carcinoma, acute promyelocytic leukemia, skin cancer, and a premalignancy associated actinic keratosis, acne, psoriasis and/or ichthyosis, and particularly, acute promyelocytic leukemia. In another embodiment the peptides and nucleic and molecules of the invention may be used to treat disorders of the brain such as memory loss or learning dificiencies.

In one embodiment the invention includes a kit for determining the presence of a protein as broadly described above, or containing an amino acid sequence as identified by SEQ ID NO:5 (human P450RAI-2) SEQ ID NO:11 (mouse CYP26B) or SEQ ID NO:12 (zebrafish CYB26B), comprising an antibody to the protein linked to a reporter system, wherein the reporter system produces a detectable response when a predetermined amount of the protein and the antibody are bound together. In a preferred aspect, the antibody is specific for a protein that includes the amino acid sequence identified as SEQ ID NO:5.

The invention also includes a kit for determining the presence of a first said nucleic acid molecule as broadly defined by the invention. The kit includes a second nucleic acid molecule capable of hybridizing with at least a portion of a the first nucleic acid molecule under the high stringency conditions of paragraph (a), above, in which the second nucleic acid molecule is linked to a reporter system wherein the reporter system produces a detectable response when a predetermined amount of the first and second molecules are hybridized together. The second nucleic acid molecule can be at least 5 bases in length, or at least about 10 bases in length, or at least about 15 bases in length, or at least about 20 bases in length, or at least about 25 bases in length, or at least about 30 bases in length, or at least about 35 bases in length, or at least about 40 bases in length, or at least about 45 bases in length, or at least about 50 bases in length.

The invention is also a method of screening drugs for their modulating effect on activity of a protein as broadly defined by the invention, which method includes exposing a purified said protein to a said drug and determining the effect on the activity. Usually, the modulating effect would be to inhibit the activity of the protein in question. Typically, the activity of the protein is oxidation, e.g., hydroxylation of a retinoic acid, particularly all-trans retinoic acid. In a preferred embodiment, the activity is oxidation of all-trans retinoic acid and the protein includes the amino identified as SEQ ID NO:5.

The invention also includes a method of screening drugs for their effect on expression of a gene, wherein the gene is an inducible gene containing a nucleotide sequence as broadly defined by the invention, by all-trans retinoic acid. The method includes exposing a eukaryotic cell to a said drug and determining the effect on gene expression. Preferably, the gene includes the nucleotide sequence identified as SEQ ID NO:4.

The cell can be a mammalian cell, particularly, a human cell.

The invention includes any drug identified according to a method of the invention, particularly for a purpose related to its related to its modulating effect on the activity of a protein of the invention.

The invention includes a method for inhibiting retinoic acid metabolism in an organism in need of such inhibition, or in cells obtained from such an organism, comprising administering to the organism an effective amount of a drug of the invention.

The invention includes a method of oxidizing a retinoid. The method includes exposing the retinoid to a protein as broadly defined by the invention, and particularly where the protein includes the amino acid sequence identified as SEQ ID NO:5. The retinoid can be a retinoic acid, particularly, all-trans retinoic acid.

In another aspect, the invention is a method of screening a drug for its activity on a protein. The method includes steps of:

(i) providing a cell line having heterologous DNA encoding a functional protein as broadly defined by the invention incorporated thereinto so as to be capable of expressing said protein;

(ii) exposing the cell line to the drug under conditions in which said protein is expressed in an active form to expose the protein to the drug; and (iii) determining the effect of the drug on the activity of the protein.

The method can include exposing the cell line to a substrate of the protein under conditions in which the protein is expressed in an active form to expose the protein to the substrate.

In a particular aspect, the activity is oxidation.

Step (ii) of the method can include exposing the cell line to the drug and the substrate simultaneously.

The substrate can be a retinoid, particularly, a retinoic acid, more particularly, all-trans retinoic acid.

The oxidative activity can be oxidation of the β-ionone ring of the substrate, particularly, hydroxylation.

According to a particular aspect, the heterologous DNA encodes the protein identified as SEQ ID NO:5.

The invention is also a method for screening an agent for its effect on an activity of a first protein relative to its effect on the activity of a second protein. This method includes steps of:

(a) providing a first protein, wherein the protein one defined according this invention;

(b) providing a second protein, wherein the second protein is a cytochrome P450;

(c) exposing the first protein to the agent;

(d) exposing the second protein to the agent; and (e) determining the effect of the agent on the activity of the first protein relative to its effect on the activity of the second protein.

According to the method, the activity of each protein under consideration can be the ability of the proteins to oxidize a retinoid and it optionally limited to the ability to oxidize a retinoid at the 4-position of the β-ionone ring and/or to hydroxylate a retinoid at the 4-position of the β-ionone ring.

The retinoid can be a retinoic acid, and it can simply be all-trans retinoic acid.

The first protein can be a human protein and it can include the sequence identified as SEQ ID NO:5.

The method can be such that the second protein is selected from the group of proteins encoded by: (a) a nucleotide sequence that hybridizes under high stringency conditions, wherein high stringency conditions include a wash step of about 0.2×SSC at 50° C., to the nucleotide sequence shown as SEQ ID NO:13 or SEQ ID NO:14 or SEQ ID NO:17, and encodes a protein that oxidizes a retinoid; and (b) a nucleotide sequence that hybridizes under high stringency conditions, wherein high stringency conditions include a wash step of about 0.2×SSC at 50° C., to the nucleotide sequence shown as SEQ ID NO:13 or SEQ ID NO:14, and encodes a protein that hydroxylates retinoic acid at the 4 position of the β-ionone ring.

The second protein can be a human protein and it can include a protein which includes the amino acid sequence encoded by the nucleotide sequence identified as SEQ ID NO:13.

Step (c) of the method can include exposing the first protein to a retinoid.

Step (d) of the method can include exposing the second protein to a retinoid.

Each of steps (c) and (d) can include exposing the first protein to a retinoid.

Step (c) can include exposing the first protein to said retinoid at various concentrations and/or step (d) can include exposing the second protein to said retinoid at various concentrations.

In another broad aspect, the invention is a method for screening an agent for its effect on an activity of a first protein relative to its effect on the activity of a second protein where the proteins are each expressed in a cell or group of cells. Such method thus includes:
(a) providing a group of first cells having expressibly incorporated thereinto heterologous DNA encoding a first protein wherein the protein is a protein of the invention as defined herein;
(b) providing a group of second cells having expressibly incorporated thereinto heterologous DNA encoding a second protein, where the second protein is a cytochrome P450;
(c) exposing the first cells to the agent under conditions in which the first protein is expressed;
(d) exposing the second cells to the agent under conditions in which the second protein is expressed; and
(e) determining the effect of the agent on the activity of the first protein relative to its effect on the activity of the second protein.

Step (e) of the method can include monitoring the disappearance of the agent in the presence the first cells and monitoring the disappearance of the agent in the presence of the second cells.

Step (e) can include monitoring the appearance of an oxidized product or products formed from the agent on exposure to the first cells and monitoring the appearance of the oxidized product or products formed from the agent on exposure to the second cells.

Step (c) can include exposing the first cells to a substrate of the first protein in the presence of the agent and step (d) can include exposing the second cells to the substrate in the presence of the agent.

Step (e) can include monitoring the production of a reaction product or products formed from the substrate on exposure to the first protein in step (c) and, further, step (e) can include monitoring the production of the reaction product or products formed from the substrate on exposure to the second protein in step (d).

Step (e) can include monitoring reduction in the amount of substrate on exposure to the first protein in step (c) and step (e) can include monitoring the reduction in the amount of the substrate on exposure to the second protein in step (d).

The substrate can be a retinoid, which can be a retinoic acid, which can be all-trans retinoic acid.

The observed activity of each protein can be its ability to oxidize a retinoid, particularly, the ability to oxidize a retinoid at the 4-position of the β-ionone ring, or the ability to hydroxylate a retinoid at the 4-position of the β-ionone ring.

The first protein can be a human protein and it can have the sequence identified as SEQ ID NO:5.

The second protein can be selected from the group of proteins encoded by: (a) a nucleotide sequence that hybridizes under high stringency conditions, wherein high stringency conditions include a wash step of about 0.2×SSC at 50° C., to the nucleotide sequence shown as SEQ ID NO:13 or SEQ ID NO:14, and encodes a protein that oxidizes a retinoid; and (b) a nucleotide sequence that hybridizes under high stringency conditions, wherein high stringency conditions include a wash step of about 0.2×SSC at 50° C., to the nucleotide sequence shown as SEQ ID NO:13 or SEQ ID NO:14, and encodes a protein that hydroxylates retinoic acid at the 4 position of the β-ionone ring.

The second protein can be a human protein and it can include the amino acid sequence encoded by the nucleotide sequence identified as SEQ ID NO:13.

Step (c) of the method can include exposing the first cells to a retinoid.

Step (d) can include exposing the second cells to a retinoid.

Step (c) can include exposing the first cells to said retinoid at various concentrations.

Step (d) can also include exposing the second cells to a retinoid at various concentrations.

In another aspect, the present invention is a method of inducing in an eukaryotic cell, production of RNA comprising the nucleotide sequence identified as SEQ ID NO:4 The method includes the steps of:
exposing the cell to a retinoid; and
hybridizing the RNA with a probe comprising a nucleic acid molecule comprising a nucleotide sequence which encodes a protein of the present invention.

The cell can be a mammalian cell, particularly a human cell.

The retinoid can be a retinoic acid, particularly, all-trans retinoic acid.

The nucleic acid sequence can be a non-coding sequence complementary to a coding sequence of a nucleic acid molecule encoding the protein comprising the amino acid sequence identified as SEQ ID NO: 5 and the probe is at least 10 nucleotide residues in length, or the probe is at least 15 nucleotide residues in length, or the probe is at least 20 nucleotide residues in length, or the probe is at least 25 nucleotide residues in length, or the probe is at least 30 nucleotide residues in length, or the probe is at least 35 nucleotide residues in length, or the probe is at least 40 nucleotide residues in length, or the probe is at least 45 nucleotide residues in length, or the probe is at least 50 nucleotide residues in length, or the probe is at least 55 nucleotide residues in length, or the probe is at least 56 nucleotide residues in length, or the probe is at least 60 nucleotide residues in length.

The invention includes a method of inducing expression in an eukaryotic cell, a protein comprising the amino acid sequence identified as SEQ ID NO: 5, the method comprising the steps of:

exposing the cell to a retinoid in an amount sufficient to induce said expression; and isolating the protein from the cell.

Isolating the protein can include exposing proteins produced by the cell after said exposure step to an antibody which binds specifically to the desired protein.

In the context of this invention, an antibody which "specifically binds" (and grammatical equivalents) to a protein refers to the phenomenon in which an antibody recognizes and binds to a specific binding entity, e.g., protein, but substantially does not recognize or bind to any other specific binding entity.

The cell can be a mammalian cell, particularly, a human cell.

The retinoid can be a retinoic acid, particularly, all-trans retinoic acid.

Human and mouse genomic P450RAI-1 sequences are identified herein as SEQ ID NOs:15 and 16, respectively. The mouse sequence encoding P450RAI-1 is identified herein as SEQ ID NO:17.

In another aspect, the present invention includes a fragment of the nucleotide sequence encoding P450RAI-2 (SEQ ID NO:4). Such a fragment can find usefulness as a probe. The complement of the probe can find utility in, for example, manufacture of the probe. In a particular use, the probe can be used to determine the presence of an RNA molecule in a sample which might, or might not, also include an RNA molecule encoding P450RAI-1. Such a probe would generally be 20 nucleotides long or be at least 20 nucleotides long. The probe could also be 25, 30, 35, 40, 45, 50, 55, 60 or more nucleotides in length and the probe can include the full length of the complement to the sequence to which it is intended to bind. The sequence of the probe would also be sufficiently distinguishable from any portion of the sequence encoding P450RAI-1 that it would not cross-hybridize to a significant extent to a nucleotide sequence that encodes P450RAI-1, or portion thereof, particularly to an RNA encoding P450RAI-1. Such a probe would thus be sufficiently different from any sequence of contiguous nucleotides selected from the nucleotide sequence encoding human P450RAI-1 (SEQ ID NO: 13) that there is no more than about 60% homology between the two sequences when the two sequences are directly aligned with each other. More preferably, the percent homology would be less than about 55%, or less than about 50%, or less than about 45%, or even less than about 40%. Certain probes of the invention are selected so as span borders between introns of the coding sequence as determined from the genomic sequence (SEQ ID NO:3).

The invention includes the method determining the presence of a nucleic molecule encoding P450RAI-2 in a sample containing RNA isolated from human cell, using such a probe.

In the context of this specification, the term "conserved" describes similarity between sequences. The degree of conservation between two sequences can be determined by optimally aligning the sequences for comparison. Here, sequences were aligned using the Omiga software program, Version 1.13. (Oxford Molecular Group, Inc., Campbell, Calif.). The Omiga software uses the Clustal W Alignment algorithms [Higgins et al., 1989; Higgins et al., 1991; Thompson et al. 1994] Default settings used are as follows: Open gap penalty 10.00; Extend gap penalty 0.05; Delay divergent sequence 40 and Scoring matrix—Gonnet Series. Percent identity or homology between two sequences is determined by comparing a position in the first sequence with a corresponding position in the second sequence. When the compared positions are occupied by the same nucleotide or amino acid, as the case may be, the two sequences are conserved at that position. The degree of conservation between two sequences is often expressed, as it is here, as a percentage representing the ratio of the number of matching positions in the two sequences to the total number of positions compared.

The generic term "retinoids" means a group of compounds which includes retinoic acid, vitamin A (retinol) and a series of natural and synthetic derivatives that can exert profound effects on development and differentiation in a wide variety of systems. For purposes of this disclosure "retinoid" is also intended to encompass an equivalent thereof having the same functional characteristics which may be produced, for example, by computational chemistry.

"Stringent hybridization conditions" takes on its common meaning to a person skilled in the art here. Appropriate stringency conditions which promote nucleic acid hybridization, for example, 6×sodium chloride/sodium citrate (SSC) at about 45° C. are known to those skilled in the art. The following examples are found in Current Protocols in Molecular Biology, John Wiley & Sons, NY (1989), 6.3.1–6.3.6: For 50 ml of a first suitable hybridization solution, mix together 24 ml formamide, 12 ml 20×SSC, 0.5 ml 2 M Tris-HCl pH 7.6, 0.5 ml 100×Denhardt's solution, 2.5 ml deionized $H_2O$, 10 ml 50% dextran sulfate, and 0.5 ml 10% SDS. A second suitable hybridization solution can be 1% crystalline BSA (fraction V), 1 mM EDTA, 0.5 M $Na_2HPO_4$ pH 7.2, 7% SDS. The salt concentration in the wash step can be selected from a low stringency of about 2×SSC at 50° C. to a high stringency of about 0.2×SSC at 50° C. Both of these wash solutions may contain 0.1% SDS. In addition, the temperature in the wash step can be increased from low stringency conditions at room temperature, about 22° C., to high stringency conditions, at about 65° C. The cited reference gives more detail, but appropriate wash stringency depends on degree of homology and length of probe. If homology is 100%, a high temperature (65° C. to 75° C.) may be used. If homology is low, lower wash temperatures must be used. However, if the probe is very short (<100 bp), lower temperatures must be used even with 100% homology. In general, one starts washing at low temperatures (37° C. to 40° C.), and raises the temperature by 3–5° C. intervals until background is low enough not to be a major factor in autoradiography.

The invention also includes a method of inhibiting retinoic acid hydroxylation in an organism in need of such inhibition by administering to the organism an effective amount of an antibody, such antibodies being described herein. A particularly useful antibody for the treatment of a human would be an antibody to the protein having the amino acid sequence identified as SEQ ID NO:5, or a portion thereof. It would be advantageous to adapt such an antibody for administration to a human by "humanizing" the antibody, as is understood by those skilled in the art [Hozumi, 1993].

(iv) Kits

Reagents suitable for conducting the above described diagnostic and/or methods of the invention may be packaged into convenient kits providing the necessary materials, packaged into suitable containers. Such kits may include all the reagents required to detect P450RAI-2 in a sample by means of the methods described herein, and optionally suitable supports useful in performing the methods of the invention.

In one embodiment of the invention the kit contains a nucleotide probe which hybridizes with a nucleic acid molecule of the invention, reagents required for hybridization of the nucleotide probe with the nucleic acid molecule, and directions for its use. In another embodiment of the invention the kit includes antibodies of the invention and reagents required for binding of the antibody to a P450RAI-2 protein in a sample. In still another embodiment of the invention, the kit includes primers which are capable of amplifying a nucleic acid molecule of the invention or a predetermined oligonucleotide fragment thereof, all the reagents required to produce the amplified nucleic acid molecule or predetermined fragment thereof in the polymerase chain reaction, and means for assaying the amplified sequences.

The methods and kits of the present invention have many practical applications. For example, the methods and kits of the present invention may be used to detect P450RAI-2 in any medical sample suspected of containing or lacking P450RAI-2 and used to diagnose diseases associated with P450RAI-2 or RA, expression or metabolism or where RA, P450RAI-2 inhibitor or P450RAI-2 treatment may be indicated. Examples of such diseases include cancer, dysplasia, certain autoimmune diseases or dermatological disorders, angiogenesis, conditions of high order brain functions or other conditions as noted herein. Samples which may be tested include bodily materials such as blood, urine, serum, tears, saliva, feces, tissues and the like.

Before testing a sample in accordance with the methods described herein, the sample may be concentrated using techniques known in the art, such as centrifugation and filtration. For hybridization and/or PCR-based methods described herein, nucleic acids may be extracted from cell extracts of the test sample using techniques known in the art.

2. Therapeutic Applications

Methods of Treatment/Pharmaceutical Compositions

P450RAI-2 may play a role in a number of diseases, such as those associated with regulation of the cell cycle or apoptosis. In particular P450RAI-2 may play a role in cancer or dysplasia by activating apoptosis. In one embodiment, it is associated with lung and/or breast cancer. In another embodiment, P450RI-2 may play role in learning, memory and other brain functions, such as those controlled by the cerebellum or pons. As such , the invention comprises methods for modulating or simulating P450RAI-2 activity or P450RAI-2 expression, preferably for treating or preventing a P450RAI-2 or RA related condition. The invention further comprises uses of the modulating or simulating agents disclosed herein for the preparation of a medicament for treating or preventing a condition associated with P450RAI-2 expression or activity. Such a condition could be anny condition that may benefit from the treatment with a P450RAI-2 or a modulator thereof. In another embodiment the invention provides a use of the modulating or simulating agents for the treatment or prevention of a P450RAI-2 related condition. In another embodiment, the invention provides for inhibitors of P450RAI-2 for the treatment of a related condition. Such inhibitors could include antibodies to P450RAI-2 or antisense molecules to P450RAI-s nucleic acid sequence or other compounds such as ketoconazole.

Accordingly, the present invention provides a method of treating or preventing a disease associated with P450RAI-2 expression or activity comprising administering an agent that modulates or simulates P450RAI-2 expression or activity to an animal in need thereof, such as in an animal with cancer (such as lung or breast cancer), dysplasia, an autoimmune disease, a dermatological disorder or a learning or memory or other brain functions, such as those controlled by the cerebellum or pons. It may also be used in the treatment of various embryonic development disorders. In one embodiment, such modulators can be adminsistered to a pregnant women or to be pregnant women or delivered to the fetus to avoid or correct certain developmental disorders.

In a one embodiment, such agents stimulate or simulate P450RAI-2 activity. Examples of agents that activate or simulate P450RAI-2 activity would include without limitations, P450RAI-2, the gene encoding for P450RAI-2 with suitable promoters, such promoters preferably being tissue specific promoters and therapeutically effective fragments of the nucleic acid and amino acid sequences of the invention.

Examples of agents that inhibit P450RAI-2 include antisense nucleic acid molecules, antibodies and transdominant inhibitors, as described herein.

Agents that inhibit, activate, or stimulate P450RAI-2 can be formulated into pharmaceutical compositions with or without RA for adminstration to subjects in a biologically compatible form suitable for administration in vivo. As used herein "biologically compatible form suitable for administration in vivo" means a form of the substance to be administered in which therapeutic effects outweigh any toxic effects. The substances may be administered to animals in need thereof. Animals, as used herein refers to any animal susceptible to a disease associated with P450RAI-2 expression preferably dogs, cats, mice, horses and humans.

Administration of an "effective amount" of pharmaceutical compositions of the present invention is defined as an amount of the pharmaceutical composition, at dosages and for periods of time necessary to achieve the desired result. For example, a therapeutically active amount of a substance may vary according to factors such as disease state, age, sex, and weight of the recipient, and the ability of the substance to elicit a desired response in the recipient. Dosage regima may be adjusted to provide an optimum Therapeutic response. For example, several divided doses may be administered daily or the dose may be proportionally reduced as indicated by the exigencies of the therapeutic situation.

An active substance may be administered in a convenient manner such as by injection (subcutaneous, intravenous, topical, intratumoral etc.), oral administration, inhalation, transdermal application, or rectal administration. Depending on the route of administration, the active substance may be coated in a material to protect the compound from the action of enzymes, acids and other natural conditions which may inactivate the compound.

The compositions described herein can be prepared by known methods for the preparation of pharmaceutically acceptable compositions which can be administered to subjects, such that an effective quantity of the active substance is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., USA 1985). On this basis, the compositions include, albeit not exclusively, solutions of the substances in association with one or more pharmaceutically acceptable vehicles or diluents, and contained in buffered solutions with a suitable pH and iso-osmotic with the physiological fluids.

Recombinant nucleic acid molecules comprising a sense, an antisense sequence or oligonucleotide fragment thereof, may be directly introduced into cells or tissues in vivo using delivery vehicles known in the art such as retroviral vectors, adenoviral vectors and DNA virus vectors. They may also be introduced into cells in vivo using physical techniques known in the art such as microinjection and electroporation or chemical methods such as coprecipitation and incorporation of DNA into liposomes. Recombinant molecules may also be delivered in the form of an aerosol or by lavage.

The utility of the substances, antibodies, sense and antisense nucleic acid molecules, and compositions of the invention may be confirmed in animal experimental model systems. Suitable animal model systems which can be used to determine P450RAI-2 activity may include, but is not limited or P450RAI-2 knock-out transgenic animals.

3. Other Applications

Screening for P450RAI-2 Modulating Compounds

In another embodiment, the invention provides a method for identifying a compound or molecule that modulates P450RAI-2 protein activity or gene expression. "Modulate" as used herein can include activation or increase of P450RAI-2 protein activity or gene expression or suppression of P450RAI-2 protein activity or gene expression. The method includes incubating components comprising the compound and P450RAI-2 peptide or a recombinant cell expressing P450RAI-2 peptide, under conditions sufficient to allow the components to interact and determining the effect of the compound on P450RAI-2 activity or expression. The effect of the compound on P450RAI-2 activity can be measured by a number of assays and may include measurements before and after incubation in the presence of the compound. Compounds that affect P450RAI-2 activity or gene expression include peptides, chemical compounds and biologic agents. Assays include Northern blot analysis of P450RAI-2 mRNA (for gene expression), Western blot analysis (for protein level) and luciferase, apoptosis or growth suppression assays (for protein activity).

In one embodiment, the above screening assays may be used for detecting the compounds or molecules that bind to the P450RAI-2 protein or peptide, in isolating molecules that bind to the P450RAI-2 gene, for measuring the amount of P450RAI-2 in a sample, either peptide or RNA (mRNA), for identifying molecules that may act as agonists or antagonists, and the like.

Incubating includes conditions which allow contact between the test compound and P450RAI-2 peptide or with a recombinant cell expressing P450RAI-2 peptide. Contacting includes in solution and in solid phase, or in a cell. The test compound may optionally be a combinatorial library for screening a plurality of compounds. Compounds identified in the method of the invention can be further evaluated, detected, cloned, sequenced and the like, either in solution or after binding to a solid support by any method usually applied to the detection of a specific DNA sequence such as PCR, oligomer restriction, allele-specific oligonucleotide probe analysis, and the like.

In another embodiment, modulators of P450RAI-2 activity can be screened by incubating the potential modulator with P450RAI-2 and its substrate, such as all-trans-RA under conditions that permit interaction between P450RAI-2 and the substrate and assaying for substrate levels or levels of binding or other interaction between P450RAI-2 and the substrate, or assaying for binding or lack thereof between the potential modulator and/or P450RAI-2 and/or the substrate. Assaying for binding or activity levels can be done by assays known in the art such as radiolabelling or colourmetric assays, or ELISAs. Other ways of screening for potential modulators of P450RAI-2 is to run the P450RAI-2 peptide or nucleic acid molecule on a Southern, Northern or Western gel, as the case may be and probing with a labeled (or radiolabelled) potential modulator to check of binding. The potential modulator can then be subsequently screened for modulating effects on RA metabolism in the presence of P450RAI-2 and the all-trans-RA or other suitable substrate. The gels can also be run in the reverse by running the potential modulator on an appropriate gel and screening for binding activity with P450RAI-2 and.or all-trans-RA.

Competition assays can also be conducted to screen for potential modulators of P450RAI-2 such as shown in FIG. 16.

Screening for P450RAI-2 or RA Related Disorders

Method for screening of P450RAI-2 protein activity and or gene expression as described above, can also be used to screen for P450RAI-2 related disorders. For instance, biological samples from patients with a particular conditions, such as cancer or APL, or other disorders outlined herein, such as dysplasia, lung or breast cancer can be screened for P450RAI-2 protein activity and or gene expression. P450RAI-2 gene can also be sequenced from patients with a disorder to identify any mutations in the P450RAI-2 gene. Correlation between P450RAI-2 activity and/or gene expression/ and or any mutations and the disorder can be determined by a number of methods known in the art. For instance, P450RAI-2 activity and/or gene expression in a biological sample, such as a tissue, blood or other sample of a subject to be screened can be compared with that from "healthy" individuals or healthy tissues. In one embodiment, the level of P450RAI-2 activity and/or gene expression can be compared with a cut off level for normal P450RAI-2 activity and/or gene expression. In one embodiment, the cutoff level can be determined by analysis of a database of levels from "healthy" individuals.

Transgenic Animals and Methods of Making Same

Nucleic acids which encode proteins having biological activity of P450RAI-2 can be used to generate either transgenic animals or "knock out" animals which, in turn, are useful in the development and screening of therapeutically useful reagents. Preferably, non-human transgenic animals are encompassed within the scope of this invention. A transgenic animal (e.g., a mouse) is an animal having cells that contain a transgene, which transgene was introduced into the animal or an ancestor of the animal at a prenatal, e.g., an embryonic stage. A transgene is a DNA which is integrated into the genome of a cell from which a transgenic animal develops. In one embodiment, a P450RAI-2, preferably mouse or human cDNA shown in SEQ ID NO: 4, or an appropriate sequence, can be used to clone a murine P450RAI-2 gene in accordance with established techniques and the genomic nucleic acid used to generate transgenic animals that contain cells which express P450RAI-2 protein. Methods for generating transgenic animals, particularly animals such as mice, have become conventional in the art and are described, for example, in U.S. Pat. Nos. 4,736,866 and 4,870,009, 5,616,491. In a preferred embodiment, plasmids containing recombinant molecules of the invention are microinjected into mouse embryos. In particular, the plasmids are microinjected into the male pronuclei of fertilized one-cell mouse eggs; the injected eggs are transferred to pseudo-pregnant foster females; and, the eggs in the foster females are allowed to develop to term. [Hogan, B. et al., (1986) A Laboratory Manual, Cold Spring Harbor, New York, Cold Spring Harbor Laboratory]. Alternatively, an embryonal stem cell line can be transfected with an expression vector containing nucleic acid encoding a protein having P450RAI-2 activity and cells containing the nucleic acid can be used to form aggregation chimeras with embryos from a suitable recipient mouse strain. The chimeric embryos can then be implanted into a suitable pseudopregnant female mouse of the appropriate strain and the embryo brought to term. Progeny harbouring the transfected DNA in their germ cells can be used to breed uniformly transgenic mice.

Typically, particular cells would be targeted for P450RAI-2 transgene incorporation by use of tissue specific enhancers operatively linked to the P450RAI-2-encoding gene. For example, promoters and/or enhancers which direct expression of a gene to which they are operatively linked preferentially in cardiac muscle cells can be used to create a transgenic animal which expresses a P450RAI-2 protein. Examples of suitable promoters and enhancers include those which regulate the expression of the genes for cardiac myosin and cardiac actin. Transgenic animals that include a copy of a P450RAI-2 transgene introduced into the germ line of the animal at an embryonic stage can also be used to examine the effect of increased P450RAI-2 expression in various tissues.

The pattern and extent of expression of a recombinant molecule of the invention in a transgenic mouse is facilitated by fusing a reporter gene to the ecombinant molecule such that both genes are co-transcribed to form a polycistronic mRNA. The reporter gene can be introduced into the recombinant molecule using conventional methods such as those described in Sambrook et al., 1989, Molecular Cloning, A Laboratory Manual. Cold Spring Harbor Laboratory press. Efficient expression of both cistrons of the polycistronic mRNA encoding the protein of the invention and the reporter protein can be achieved by inclusion of a known internal translational initiation sequence such as that present in poliovirus mRNA. The reporter gene should be under the control of the regulatory sequence of the recombinant molecule of the invention and the pattern and extent of expression of the gene encoding a protein of the invention can accordingly be determined by assaying for the phenotype of the reporter gene. Preferably the reporter gene codes for a phenotype not displayed by the host cell and the phenotype can be assayed quantitatively. Examples of suitable reporter genes include lacZ (b-galactosidase), neo (neomycin phosphotransferase), CAT (chloramphenicol acetyltransferase) dhfr (dihydrofolate reductase), aphIV (hygromycin phosphotransferase), lux (luciferase), uidA (b glucuronidase). Preferably, the reporter gene is lacZ which codes for b-galactosidase. b galactosidase can be assayed using the lactose analogue X-gal(5-bromo-4-chloro-3-indolyl b-D-galactopyranoside) which is broken down by b-galactosidase to a product that is blue in color. (See for example Old R. W. & Primrose S. B. Principles of Gene Manipulation. An Introduction to Genetic Engineering, 4th ed. Oxford University Press at pages 63–66 for a discussion of procedures for screening for recombinants).

Additionally, the non-human homologues of genes encoding proteins having P450RAI-2 activity can be used to construct a P450RAI-2 "knock out" animal which has a defective or altered P450RAI-2 gene. For example, a human P450RAI-2 cDNA, comprising the nucleotide sequence shown in SEQ ID NO: 5, or a mouse P450RAI-2 cDNA appropriate sequence thereof, can be used to clone a murine P450RAI-2 gene in accordance with established techniques. A portion of the genomic P450RAI-2 DNA (e.g., an exon) can be deleted or replaced with another gene, such as a gene encoding a selectable marker which can be used to monitor integration. The altered P450RAI-2 DNA can then be transfected into an embryonal stem cell line. The altered P450RAI-2 DNA will homologously recombine with the endogenous P450RAI-2 gene in certain cells and clones containing the altered gene can be selected. Cells containing the altered gene are injected into a blastocyst of an animal, such as a mouse, to form aggregation chimeras as described for transgenic animals. Chimeric embryos are implanted as described above. Transmission of the altered gene into the germline of a resultant animal can be confirmed using standard techniques and the animal can be used to breed animals having an altered P450RAI-2 gene in every cell. Accordingly, a knockout animal can be made which cannot express a functional P450RAI-2 protein. Such a knockout animal can be used, for example, to test the effectiveness of an agent in the absence of a P450RAI-2 protein.

Although experimental animals used in the preferred embodiment disclosed are mice, the invention should not be limited thereto. It can be desirable to use other species such as rats, hamsters and rabbits.

The transgenic animals of the invention can be used to investigate the effect of P450RAI-2 expression and activity or lack thereof and to test other compounds and molecules that can perhaps be used to suppress or restore the P450RAI-2 or RA activity. The transgenic animals of the invention can also be used to test substances for the ability to prevent, slow or reverse apoptosis. A transgenic animal can be treated with the substance in parallel with an untreated control transgenic animal.

Cells from the transgenic animals of the invention can be cultured using standard tissue culture techniques. In particular, cells carrying the recombinant molecule of the invention can be cultured and used to test substances for the ability to prevent, slow or reverse apoptosis.

EXAMPLES

General Materials and Methods

Cell Culture

HPK1a-ras (ras-transformed human keratinocyte), COS-1 (African green monkey kidney and V79 cells (Chinese Hamster lung) were maintained in DMEM supplemented with 10% FBS (5% for V79). WTE (human non-small cell lung carcinoma and SW900 (human non-small cell lung carcinoma) cells were maintained in RPMI supplemented with 10% FBS. SK-Luci-6 (human non-small cell lung carcinoma) and SK-MS-1 (human non-small cell lung carcinoma) cells in RPMI with 5% FBS. NB4(human acute prmyelocytic leukemia-serived) cells were maintained in RPMI supplemented with 10% FBS and gentamicin (10 mg/ml) HeLa cells (human cervical carcinoma) were maintained in MEM supplemented with 10% FBS. Previous cell lines were supplemented with penicillin (50 units/ml) streptomycin (50 ug/ml) and fungizone (0.1% final concentration). MCF-7 cells (human breast epithelial adenocarcinoma) were grown in MEM supplemented with 10% FBS, insulin (10 ng/ml), sodium pyruvate (0.5 mM), non-essential amino acids (100 nM), L-glutamine (2 mM), penicillin (5 ug.ml), streptomycin (5 ug/ml), fungizone (200 ng/ml), and gentamicin (10 mg/ml). All reagents were supplied by Life Technologies, NY. Cells lines were maintained at 37° C. in an atmosphere of 5% $CO_2$ and 95% air.

Transient Transfection of Cos-1 Cells

Exponentially growing cells were plated in triplicate into 6-well plates and transfected with 1 ug of pcDNA3.1-P450RAI-1 or pcDNA3.1-P450RAI-2 using Fugene 6 transfection reagent with 3 ul per sample as described by the manufacturer (Roche Molecular Biochemicals, IN). Cells were maintained in media supplemented with 10% FBS during transfection.

RNA Preparation and Northern Blot Analysis

Total RNA was isolated from cultured cells uding the Oligotex Direct mRNA kit (Qiagen, CA) and electrophoresed on a formaldehyde-agarose gel. Gels were photographed under ultraiolet light and then blotted onto Hybond ECL nitrocellulose membrane (Amersham Pharmacia Biotech, UK) and fixed to the membrane by baking at 80° C. for 2 hours under vacuum. Prehybridization and hybridization steps were performed using ExpressHyb (Clontech, CA) according to the manufacturer's directions. Full length P450RAI-1 and P450RAI-2 cDNA were labeled with α-[$^{32}$P]dATP using Prime-A-Gene Labeling System (Promega, Wis.). The blot was washed two times for 15 minutes in 2×SSC, 0.1% SDS at room temperature then for 15 minutes at 60° C. in 0.1×SSC, and 0.1% SDS and exposed at −70° C. for 19 hours to Kodak X-Omat AR film (Eastman Kodak Company, NY).

Example 1

Determination cDNA Sequence Encoding P450RAI-2

The human expressed sequence tagged (EST) database at the National Center for Biotechnology Information (NCBI), was searched using an amino acid sequence encoding a typical heme binding motif found in all Cytochrome P450s. The database was queried using the following sequence: KKETFIPFGIGKRVCMGEQLAKMELFLMFV (SEQ ID NO1). The TBLASTN algorithm of the Advanced BLAST program was used to search all 6 possible reading frames for translation of all the human EST sequences against the query sequence (SEQ ID NO:1). Parameters for all searching were the defaults of Blosum 62 which use a gap existence cost of 11, per residue cost of 1 and lambda ratio of 0.85. Subject amino acid sequences which showed similarity to SEQ ID NO:1 were retrieved from the GenBank database and their nucleotide sequences used to search GenBank for nucleotide sequences showing similarity to the EST nucleotide query sequence using the BLASTN algorithm.

One of the subject sequences obtained from GenBank (AA012833, identified here as SEQ ID NO:2, a 3.5 kb clone from the Soares retina N2b4H2 library) showing similarity to the nucleotide sequence encoding amino acid sequence identified as SEQ ID NO:1, also showed similarity to a human genomic DNA sequence from GenBank (Accession#, AC007002 (clone name NH0493L16), identified here as SEQ ID NO:3). As described below, the present inventors determined that this clone comprised within it the polynucleotide sequence encoding the novel cytochrome P450 of the invention, P450RAI-2. A BLASTN search of the EST database using SEQ ID NO:2 failed to identify any more EST sequences showing similarity. In order to check for protein sequences which may show similarity to the 6 possible reading frames for translation of SEQ ID NO:2, the BLASTX program was run on the non-redundant GenBank database. Several sequences with the highest degrees of amino acid similarity were identified and included, human, mouse, Xenopus and zebrafish P450RAI (CYP26A; protein encoded by SEQ ID NO:13 (human), protein encoded by SEQ ID NO:14 (zebrafish)).

Figure 3C:
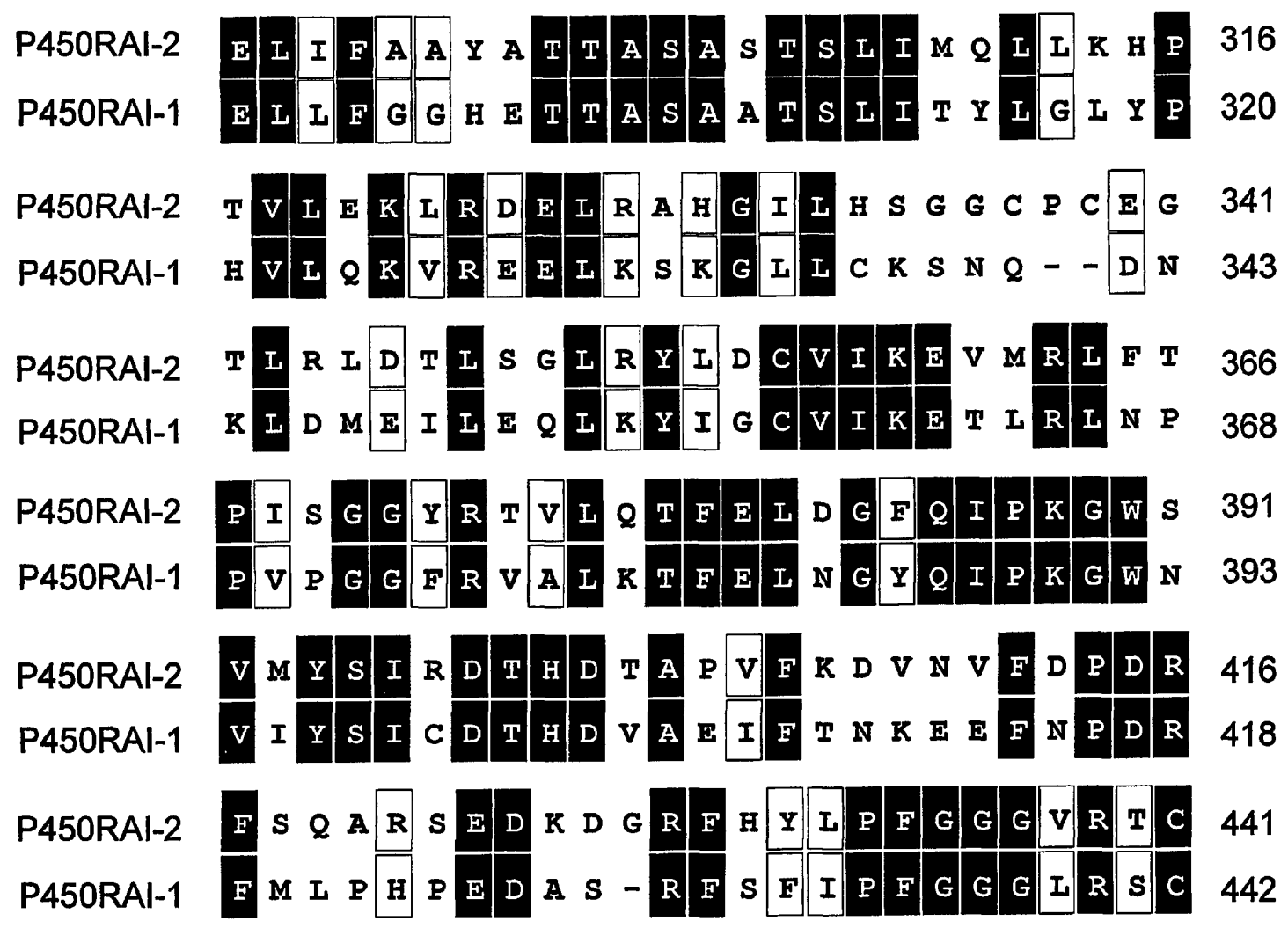

Using the amino acid sequence of human P450RAI-1 (SEQ ID NO. 4 of WO 97/49815) aligned to the 3 possible reading frame translations of SEQ ID NO:3, a potential full-length amino acid sequence for a novel CYP cDNA family member was assembled. The intron/exon boundaries were deduced based on the loss of amino acid similarity. The intron/exon boundaries of the novel cytochrome P450 is shown in FIG. 1. The amino acids within the respective exons are identified above the schematic diagram and nucleotide positions in relation to human sequence are provided below the diagram. However, it would be appreciated that the positions of the exons noted in FIG. 1 are approximate and may vary slightly from the actual boundaries. The sequence has been termed P450RAI-2 based on its sequence homology with CYP26A. An amino acid sequence comparison between human P450RAI-2 and human p450RAI-1 is shown in FIG. 3. Overall the two protein sequences show 42% identity at the amino acid level and 52% at the nucleotide level over the region of the predicted open reading frame. The overall similarity of the two putative open reading frames is somewhat higher when conservatively substittued amino acids are considered.

Human retina Marathon-Ready cDNA (Clontech, California) was used as a template to amplify P450RAI-2 using the polymerase chain reaction (PCR) according to the manufacturer's directions Using the potential nucleotide sequence derived from the intron/exon mapping exercise, two primers, (SEQ ID NO. 9 and SEQ ID NO. 10) one upstream of the putative initial methionine and one downstream of the putative stop codon, were synthesized and used to PCR amplify a fragment of approximately 1600 base pairs representing the coding region SEQ. ID NO. 4 See FIG. 2 [SEQ ID NO:28] which depicts the original clone within the 1598 bp coding sequence and the 3 untranslated region which was cloned and sequenced. The 1598 bp fragment including the coding sequence of the cDNA is indicated as SEQ ID NO. 4 and appears to correspond to a full-length cDNA. SEQ ID. 4 shows a single nucleotide change from "C" in the genomic sequence SEQ ID NO. 3 to "T" at nucleotide 1401 of SEQ ID NO. 4 which, due to the degeneracy of the genetic code, does not change the corresponding amino acid sequence, identified as SEQ ID NO. 5.

The cDNA 1600 bp PCR amplified product was gel purified using the QIAEXI Gel Extraction kit (Qiagen, California) and ligated into the pT-Adv vector using T4 DNA Ligase, heat shocked into competent TOP10F' *Escherichia coli*, plated on Luria Bertoni-kanamycin plates and incubated overnight at 37° C., as per the manufactures instruction for the AdvanTAge PCR Cloning Kit (Clontech, CA). White colonies were grown up in Luria Bertoni-kanamycin medium, and DNA was prepared using the QIAprep Spin Miniprep kit (Quiagen, CA). For transient expression studies the P450RAI-2 cDNA was subcloned into the EcoR1 restriction endonucleoase site of pcDNA3.1 (Invitrogen, CA).

Example 2

P450RAI-2 Tissue Expression

Given the presence of a full-length cDNA in a retinal cDNA library, expression in human retinal tissues could be expected. In order to find tissues in which P450RAI-2 is expressed, a multi-tissue RNA dot blot containing samples from 76 different normal human tissues a human poly A+ blot (Clontech, CA) was probed using a labeled probe encoding the full length P450RAI-2 α-[$^{32}$P]dATP-labeled probe for the corresponding cDNAs were hybridized to blots using the conditions as described in the manufacturers directions. A human brain multi-tissue northern blot (Clontech, CA) was also hybridized with full-length α-[$^{32}$P] dATP-labelled P450RAI-2 probe according to the manufacurer's directions. The blots were stripped and re-probed with α-[$^{32}$P]dATP-labelled ubiquitin and β-actin controls.

Figure 4A:
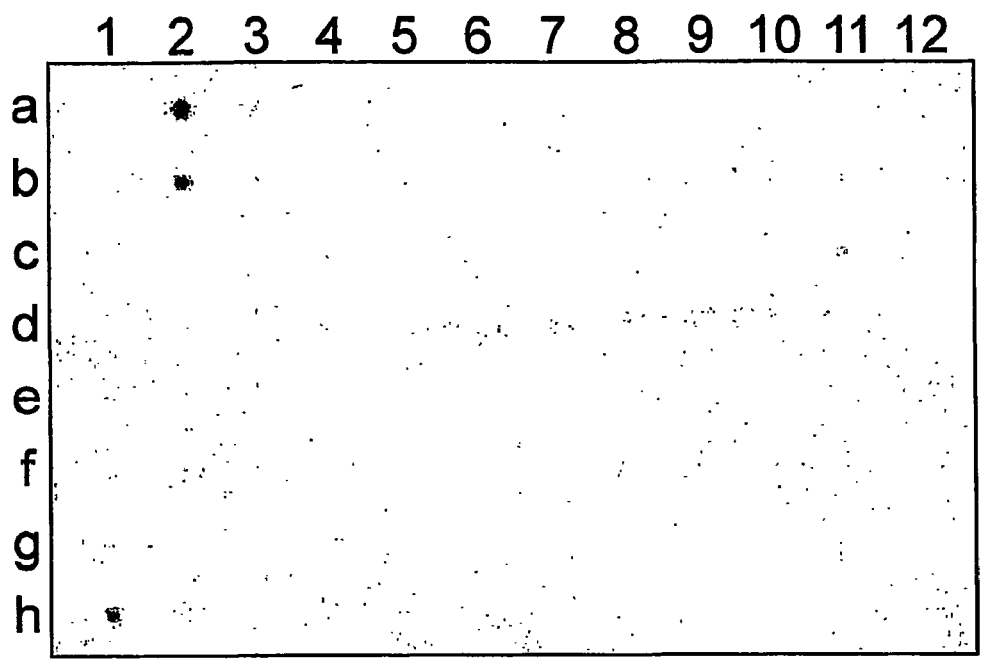
FIG. 4 Expression of P450RAI-2 in human tissues. RNA samples from 76 normal human tissues were probed for expression of P450RAI-2 transcripts using a commercially available dot blot (A). Signals representing P450RAI-2 transcripts are observed in three samples, a2, b2 and h1 representing left and right cerebellum and pons respectively. Sample a1 is whole brain and a11 is fetal brain for comparison. Control hybridization with a human ubiquitin probe (B) shows differences in RNA loading. Northern blot analyses for expression of P450RAI-2 expression in human brain (D). 2 µg poly A+ mRNA each from eight different human brain tissues was used to analyze P450RAI-2 expression. Transcripts at approximately 5 Kb corresponding to P450RAI-2 are indicated, with the highest levels of expression seen in cerebellum.
FIG. 4C shows the location of the different human mRNAs on the blot used in FIG. 4A.
Figure 4B:
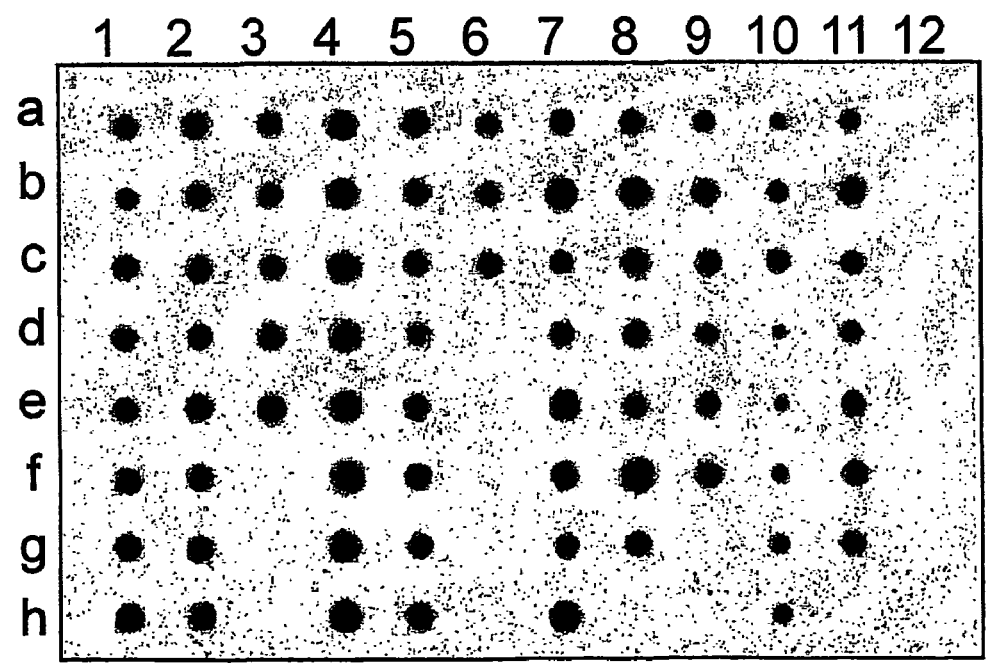
Figure 4D:
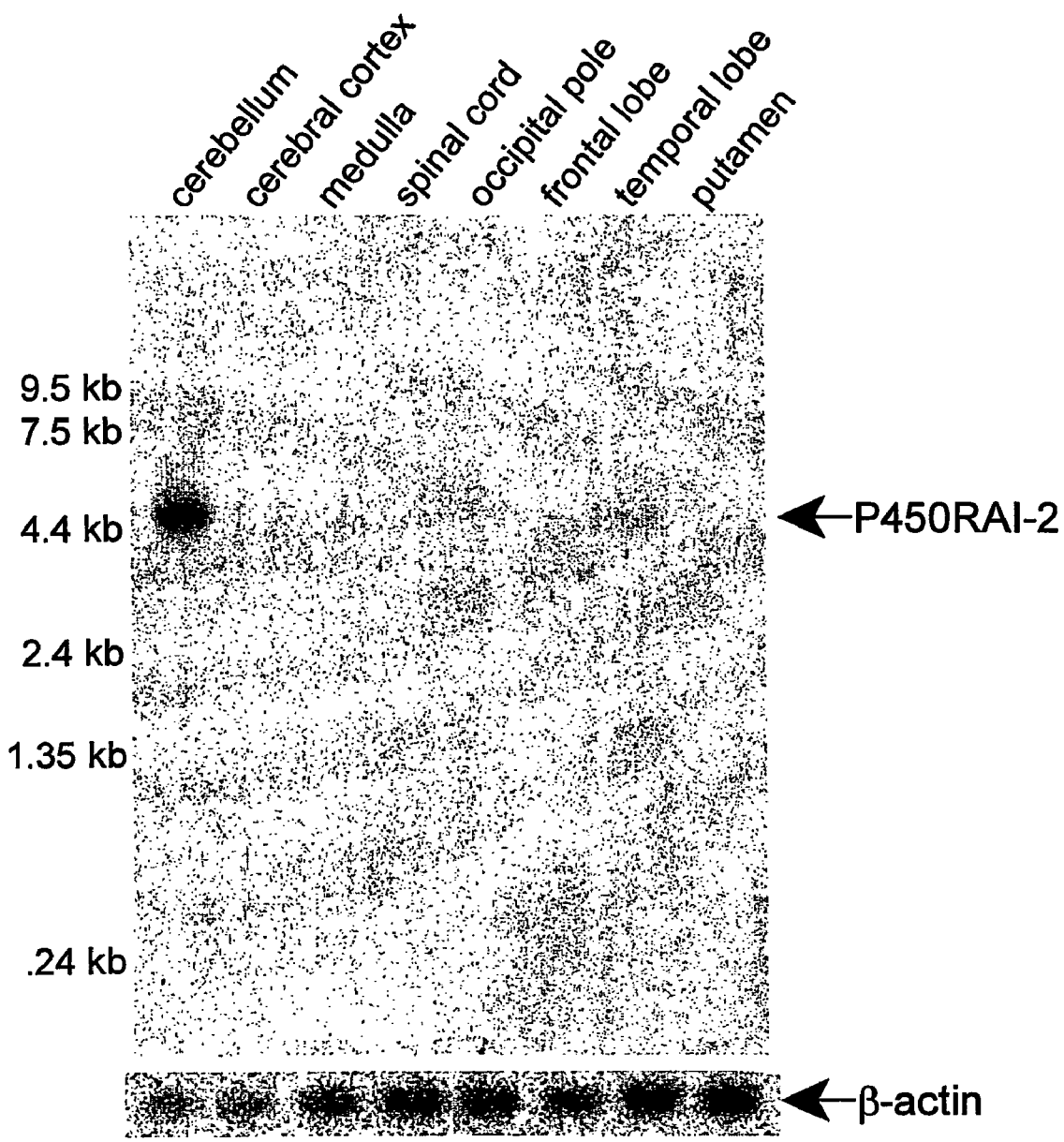

FIG. 4 illustrates the results. P450RAI-2 appears to be expressed in a variety of tissues in differing levels (other data not shown) and at higher levels in tissues including kidney, lung, liver, spleen, fetal spleen, skeletal muscle, thymus, peripheral blood leukocyte, lymph node, bone, stomach, placenta, duodenum and pituitary gland. However, samples from human brain including pons (FIG. 4A, sample h1) and left and right cerebellum (FIG. 4A, samples a2 and b2 respectively) clearly show the highest levels of expression. FIG. 4C depicts the tissue map of the 76 tissue samples. In comparison, a similar blot probed with P450RAI-1 shows low level expression in most of the tissues with the absence of a distinct signal in any of the corresponding tissues from human brain (data not shown). Blots shown in FIG. 4A and 4B are representative of multiple hybridization experiments. Two independent blots were utilized and each blot was hybridized with probes for P450RAI-2, P450RAI-1 and ubiquitin control FIG. 4B in order to verify the results.

A human Northern blot (FIG. 4D)(Clontech, CA) comprising mRNAs from various brain tissues was also probed with P450RAI-2 [SEQ ID NO. 4] according to the manufacturers directions. A hybridizing transcript of greater than 4.4 Kb was seen and is consistent with the size predicted by the cDNA clone isolated from human retina and from the predicted exons of the genomic clone that was identified. Consistent with the dot blot analyses, considerably higher levels of expression of transcripts for P450 RAI-2 are seen in the cerebellum. Lower but detectable levels of expression are observed in cerebral cortex, medulla, occipital pole, frontal lobe and temporal lobe. Other data from a Northern blot comprising mRNAs from multiple tissues indicated various levels of expression of P450RAI-2 in brain, heart, skeletal muscle, spleen, kidney, liver and small intestine. [Data not shown]

Example 3

Inducibility of P450RAI-2

The regulation of P450RAI-2 expression by various retinoids was checked in three different human cell lines, SKMES, CALU-1 and MCF-7. See FIGS. 5A (P450RAI-2 probe), B (blot was stipped and re-probed with β-actin) and C is ethidium bromide stained gel showing 18S and 28S RNAs. Tissue culture cells were incubated with each retinoid for 12 hours, total RNA prepared and a northern blot performed. The blot was hybridized with SEQ ID NO:4 using ExpressHyb (Clontech, CA) according to the manufacturer's directions at 65° C. The blot was washed as follows: 2×SSPE & 0.1% SDS two washes of 5 minutes each; 1×SSPE & 0.1% SDS one wash of 15 minutes at 65° C.; 0.1×SSPE & 0.1×SDS one wash of 15 minutes at 65° C. The blot was exposed to film for 66 hours. P450RAI-2 was found to be induced in MCF-7 cells in response to both all-trans retinoic acid and 13-cis retinoic acid. Whether or not 9-cis retinoic acid induces expression of P450RAI-2 is not clear from these results. It is known that aliquots of both 9-cis and 13-cis retinoic acid are frequently contaminated with all-trans retinoic acid.

Figure 6:
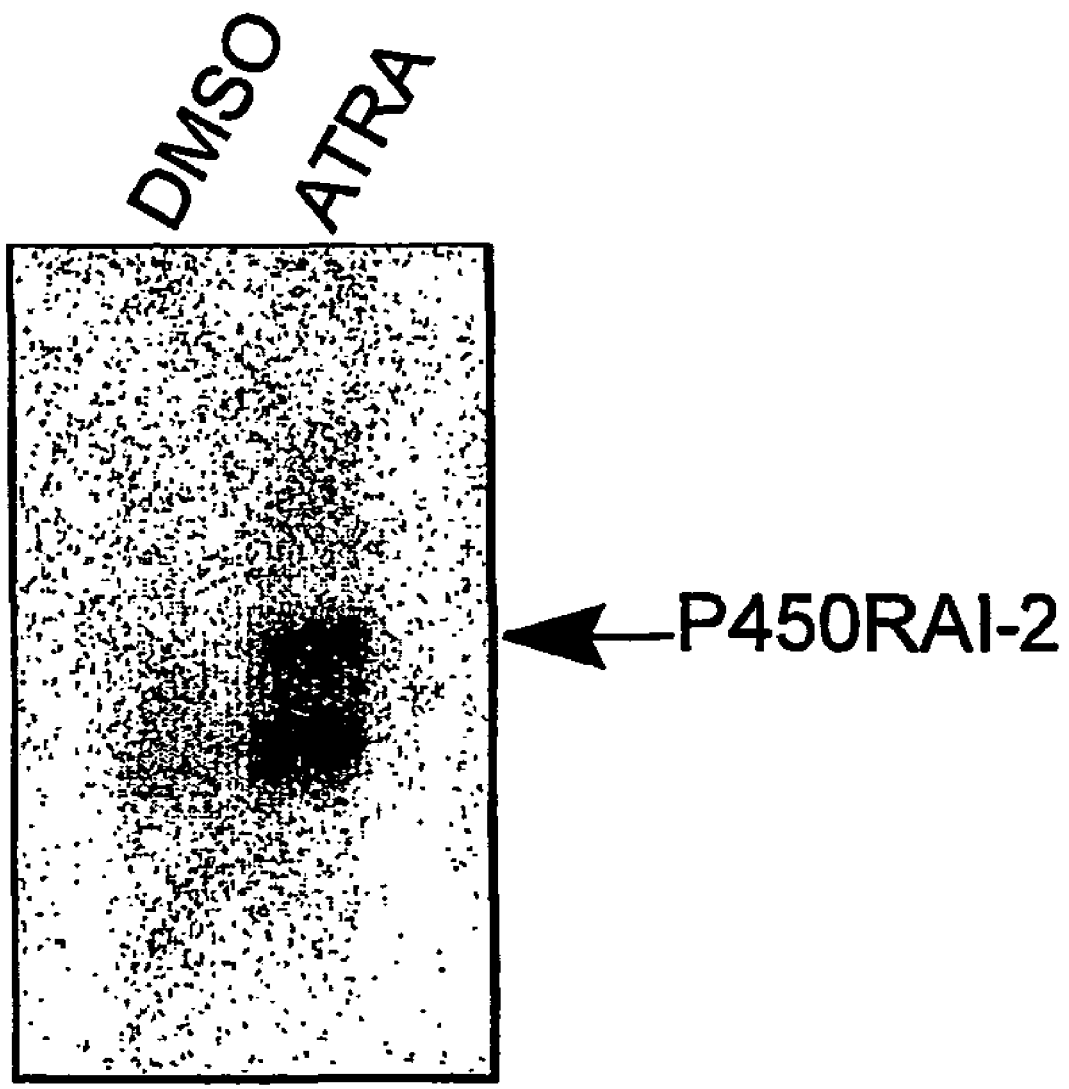
FIG. 6 is similar to FIG. 5 except that the cells, HPK1A-RAS, were treated with either DMSO or all-trans retinoic acid.

P450RAI-2 expression was found to be inducible in the human keratinocyte cell line HPK1A-RAS. Cells in culture were incubated with all-trans retinoic acid at a final concentration of $10^{-6}$ M for 12 hours. Total RNA was prepared and a northern blot performed. The blot was hybridized at 65° C. using PerfectHyb (Sigma, MO) according to the manufacturer's directions. The blot was washed as follows: 2×SSC & 0.1% SDS two washes of 5 minutes each at room temperature; 1×SSC & 0.1% SDS one wash of 15 minutes at 65° C.; 0.1×SSC & 0.1% SDS three washes of 15 minutes each at 65° C. The blot was exposed to X-ray film overnight. The results are shown in FIG. 6.

The potential induction of mRNAs for P450RAI-2 in response to all-trans-RA was also evaluated.

Tissue culture cells were incubated with 1 μM all-trans-RA dissolved in dimethylsufoxide (DMSO) or DMSO alone for 12 hours, total RNA prepared and a northern blot analysis performed. The blot was hybridized at 65° C. using ExpressHyb (Clontech, CA) according to the manufacturers directions. The blot was washed as follows: 2×SSPE & 0.1% SDS two washes of 5 minutes each; 1×SSPE & 0.1% SDS one wash of 15 minutes at 65° C.; 0.1×SSPE & 0.1×SDS one wash of 15 minutes at 65° C. The blot was exposed to X-ray file for 66 hours.

RT-PCR was performed using 1 μg total RNA and the Advantage One-Step RT-PCR kit (Clontech, CA). The final primer concentrations were 45 μM for the P450RAI-2 primers and 11.25 μM for the GAPDH-specific primers. The thermal cycling program for cDNA synthesis and PCR amplification was 1 cycle at 50° C. for 1 hr, 1 cycle at 94° C. for 5 min, followed by 30 cycles of 94° C. for 30 sec, 65° C. fo sec, 68° C. for 1 min, and a final cycle for 68° C. for 2 min. The P450RAI-2 upstream amplification primer was 5'-TCCCTGCCTGTCGACCTGCCCTTC-3' (SEQ ID NO: 29) and the downstream primer was 5'-GACACTCCAGC-CTTTGGGGATCTG-3' (SEQ ID NO: 30). The upstream and downstream primers to detect human glyceraldehyde-3-phsophate dehydrogenase mRNA were respectively, 5'-TGAAGGTCGGAGTCAACGGATTTGGT-3' (SEQ ID NO:31) and 5'-CATGTGGGCCATGAGGTCCACCAC-3' (SEQ ID NO:32).

The RT-PCR products were electrophoresed on a 1.2% agarose gel and blotted onto Hybond-N$^+$ membrane (Amersham Pharmacia Biotech, UK). Hybridization was performed at 42° C. using ExpressHyb hybridization buffer (Clontech Laboratories Inc., CA) and probed with an interal P450RAI-2-specific oligonucleotide, 5'-GTGTGCCCTCG-CAGGGGCAGCCGCCACTGTGC-3' (SEQ ID NO: 33) that had been end-labeled using γ[$^{32}$P]ATP and T4 polynucleotide kinase. The membrane was subsequently stripped and re-probed with an internal-end labeled P450RAI-1-specific oligonucleotide, 5'-CGCCTCGGATGCCCG-CAGCCC-GCAGATCTTGG-3' (SEQ ID NO: 34) The membrane was again stripped and re-probed with an internal GAPDH oligonucleotide. The final wash for all hydbridizations was 0.1×SSC/0.1%, 50° C., 15 min, blots were exposed to Kodak X-Omat AR film (Eastman Kodak Co., NY).

Figure 7A:
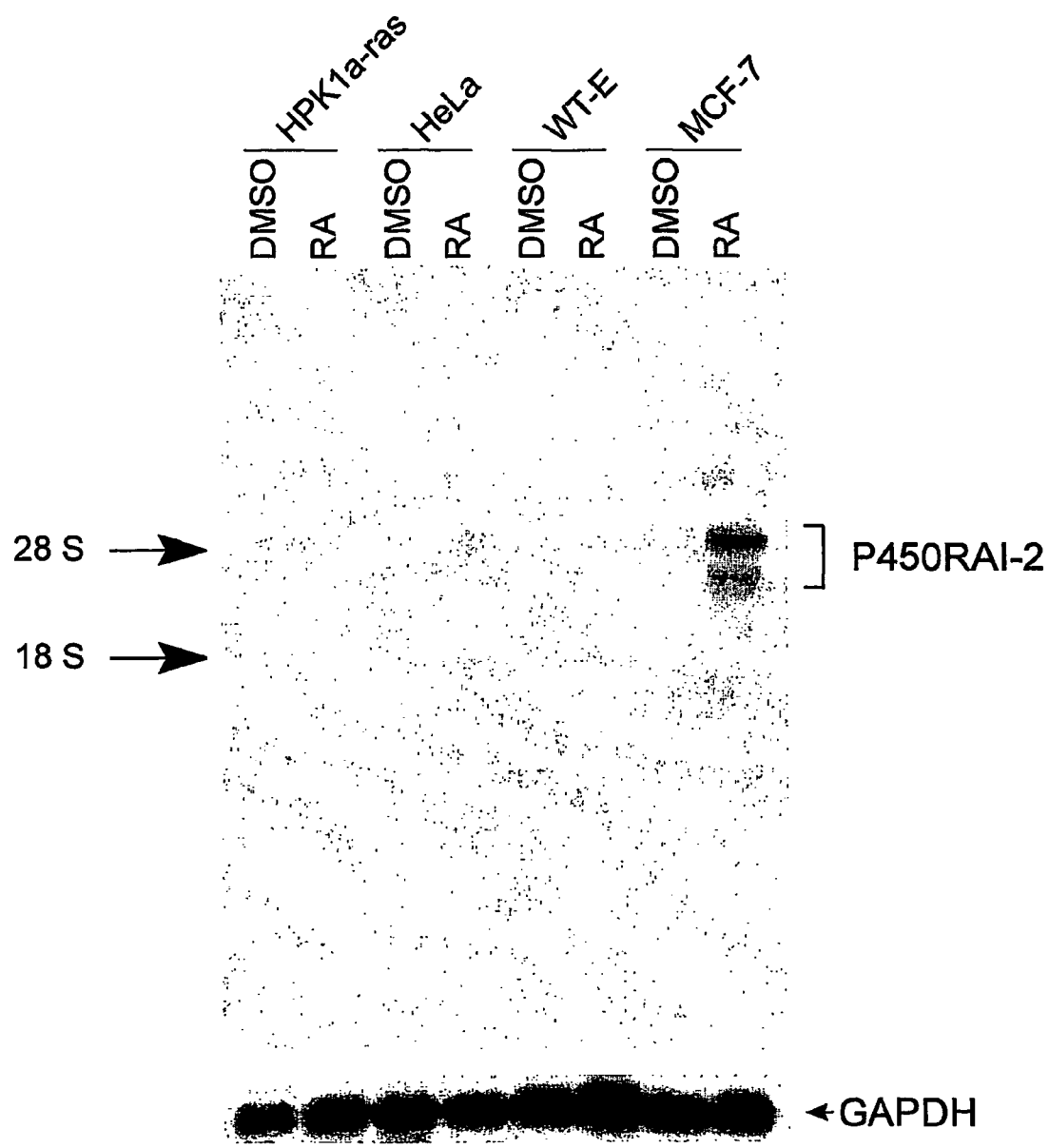
FIG. 7 All-trans-RA induction of P450RAI-2 expression. Northern blot analysis (A) of cultured cells treated with all-trans-RA or vehicle (DMSO). P450RAI-2 hybridizing transcripts are identified. The positions of 28S and 18S ribosomal RNA are indicated along with the ethidium bromide stained gel showing the relative abundance of RNA in all samples. Multiple other cell lines were tested using semiquantitative RT-PCR and southern blotting (B). Transcripts for P450RAI-2 are regulated in a cell specific manner. P450RAI-2 is constitutively expressed in SK-MES-1 and SW900 and possibly WTE; inducible in MCF-7, HPK1a-ras and HeLa; and undetectable in SK-Luci-6, V79 or NB4. A timeline of induction of mRNAs, for P450RAI-2 in HPK1a-ras cells (C). Within 2 hours of addition of all-trans-RA maximal induction of transcripts for P450RAI-2 is observed. GAPDH controls are. shown below for each RNA sample analyzed.

Several human cell lines in culture were tested for expression and induction of expression of P450RAI-2 by treating cells with 1 μM all-trans-RA or DMSO for 12 hours followed by Northern blot and RT-PCR anaylses (FIG. 7A). Of the four cell lines tested by Northern analysis, three (HPK1a-ras, HeLa and MCF-7) show induction of P450RAI-2 transcripts in response to all-trans-RA with MCF-7 showing the strongest induction.

Figure 7B:
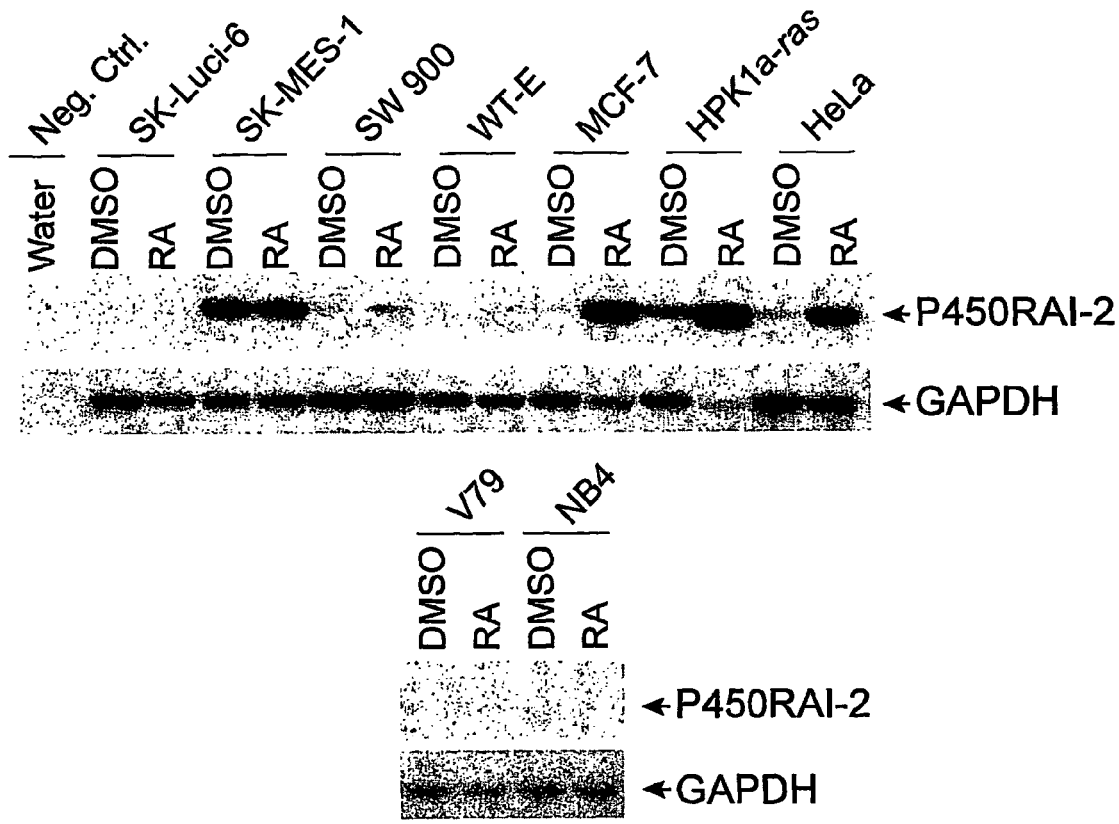

Reverse transcription polymerase chain reaction (RT-PCR) analyses of transcripts from both control and all-trans-RA treated cultured cells demonstrate several important findings. As with P450RAI-1, P450RAI-2 shows multiple distinct modes of regulation of expression (FIG. 7B). NB4, V79, and SK-Luci-6 cells appear to have little or no perceptible transcripts for P450RAI-2 in either vehicle or all-trans-RA treated cells. Several cell lines, including MCF-7, HeLa, HPK1a-ras and WT-E show evidence for inducible expression of P450RAI-2 when cells are exposed to 1 µM all-trans-RA. Interestingly, SKMES-1 and SW900, shows constitutive expression of P450RAI-2 in both treated and untreated samples.

Figure 7C:
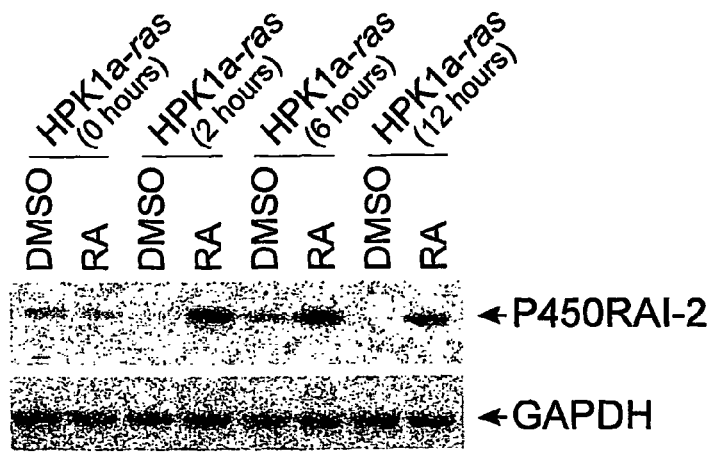

Using RT-PCR we also evaluated a brief time course of induction of PCR products corresponding to mRNA transcripts for P450RAI-2 in HPK1a-ras cells. These results (FIG. 7C) indicate that, at least in one cell line, transcripts for P450RAI-2 can be induced by all-trans-RA within 2 hours post-addition of inducer suggesting a direct transcriptional mechanism of induced.

Example 4

P450RAI-2 Homologs

The existence of homologs of P450RAI-2 in other species was explored. SEQ ID NO. 4 and the BLASTN algorithm was used in a search of the NCBI EST database. Initially, three homologs were identified, one each from mouse, rat and zebrafish. The nucleotide sequences of these clones, SEQ ID NO.6, (mouse) SEQ ID NO.7 (rat) and SEQ ID NO.8 (zebrafish) show extensive similarity to SEQ ID NO.5. The corresponding amino acid sequences of the mouse and zebrafish are given as SEQ ID NOs.11 and 12, respectively.

The clones for mouse, zebrafish and rat are all partial cDNAs and encoding portions corresponding to portions of the full-length coding sequence of the human cDNA (SEQ ID NO. 4). The zebrafish amino acid sequence, which shows homology to P450RAI-2, contains 167 amino acid residues. Of the 167 amino acids, 115 are identical to the human CYP26A sequence (i.e., when the amino acids are aligned using the Omiga software program (Oxford Molecular, Campbell, Calif.), version. 1.13, with the default parameter settings for protein alignments, 115 are the same), giving a homology of about 68 percent. The rat sequence shows nucleotide homology to the 3'-untranslated region of human P450RAI-2 so no conclusion about the degree of homology to the coding region of P450RAI-2 can be made. The mouse amino acid sequence shows an absolute conservation with the human counterpart. Over a stretch of 92 amino acids. beginning with the potential start methionine of the human P450RAI-2, all 92 amino acids are conserved between the mouse and human. At the nucleotide level there is 93.1 percent homology between the mouse and human. This degree of homology is exceptionally high, but this is a preliminary result in the sense that the full-length mouse sequences have yet to be obtained. The open reading frame of the mouse nucleotide sequence extends at least 111 amino acids upstream of the putative initial methionine in human P450RAI-2, raising a possible question as to the true origin of the mouse sequence.

Further searching of the NCBI Mouse EST database using the human P450RAI-2 sequence revealed three mouse EST clones, AW488377.1 (SEQ ID NO:18) which corresponds to human cDNA nucleotides 271–831, AW047279.1 (SEQ. ID. NO:19) which corresponds to human cDNA nucleotides 1–276 and includes 5' UTR ATG is underlined in bold, wherein the sequence should be read backwards in antisense from this point, and EST BE864840.1 (SEQ. ID. NO:20) which corresponds to human cDNA nucleotides 1–118 and includes 5'UTR; ATG is marked. In sequencing clone AW488377, the inventors identified a novel sequence included therein, SEQ ID NO: 26. A further rat EST, SEQ ID NO: 27 was also identified that corresponds to human P450RAI-2 nucleotides 1–388.

The ESTs were used to search the HTGS database wherein genomic mouse clone AC022779.3 was identified, potentially comprising the complete mouse nucleotide coding sequence of P450RAI-2. Using techniques similar to that used to identify the intro/exon boundaries of human P450RAI-2, the mouse done was aligned with the human P450RAI-2 cDNA to detect similarities. Five of Six putative mouse exon sequences were identified: SEQ ID NO: 21 (corresponds to exon 1, mouse sequence 185832–186036). SEQ ID NO: 22 (corresponds to exon 2, mouse sequence 189360–166590), SEQ ID NO: 23 (corresponds to exon 3, mouse sequence 196630–196905, SEQ ID NO: 24 (corresponds to exon 4, mouse sequence 197146–197303), and SEQ ID NO: 25 (corresponds to axon 6, mouse sequence 90745–90366).

Example 5

Metabolism of all-trans Retinoic Acid by P450RAI-2 Analysis of all-trans-RA Metabolism by HPLC 48 hours post-ransfection, cells were washed twice with DMEM medium (without serum) and then incubated in 0.5 ml DMEM medium containing 10% FBS and either 100 nM radiolabelled all-trans-RA (0.1 µCi/ml[$^3$H]-RA; 5 nCi/nmol) or unlabelled 1 µM all-trans-RA. After incubation for 3 hours at 37° C., in a light protected environment, total lipids were extracted as described previously by Bligh and Dyer [1957] as modified in White and Petkovich [1996b]. The aqueous soluble retinoid metabolites were quantified using β-scintillation counting. The organic soluble metabolites were dried under nitrogen gas, resuspended in 100 µl acetonitrile:water:acetic acid in the ratio 50:50:0.5 and analyzed by HPLC. HLPC was performed using a reverse phase column (150×4.6 mm C18 Zorbax-SB, Hewlett Packard) at a flow rate of 1 ml/min. The Mobile phase contained 10 mM ammonium acetate and consisted of an isocratic elution for 2 min with solvent A (acetonitrile; water: acetic acid 50:50: 0.5) followed by a linear gradient over 18 min from solvent A to solvent B (acetonitrile: water: acetic acid 90:10:0.04) and then an isocratic elution with solvent B for an addition 5 min. Effluent from the HPLC column flowed directly to a radioflow detector LB (EG&G Berthold). The retinoids were detected at a wavelength of 351 nm and the ultraviolet spectrum of each metabolite peak was determined using photodiode array detection. Radioactivity as well as ultraviolet spectrum data was analyzed using Millenium 32 software (Waters, Mass.). Aqueous soluble radioactivity (FIGS. 14A and B) was calculated by integration of selected regions of the chromatograms. Three regions of the chromatograms were defined which represent: (I) the substrate peak (all-trans-RA); (ii) peaks with retention times between 8 and 12 minutes (4-OH region); and more polar peaks with retention times between 2 and 6 minutes (polar region).

Example 5A

Retinoic acid as a substrate of P450RAI-2 was studied. The full-length human P450RAI-2 cDNA was cloned into the eukaryotic expression vector pcDNA 3.1 (Invitrogen, CA). Exponentially growing COS-1 cells were plated in triplicate into 6 well plates and transiently transfected with 1 ug of pcDNA 3.1, pcDNA3.1-P450RAI-1, or pcDNA3.1-P450RAI-2 using Fugene 6 transfection reagent with 3 ul per sample as described by the manufacturer (Roche Molecular Biochemicals, IN) and then incubated with nanomolar concentrations of [11,12-$^3$H]all-trans retinoic acid or micromolar concentrations of non-radioactive all-trans retinoic acid. COS-1 cells are an African green monkey kidney "fibroblast-like" cell line. The cell line was maintained in DMEM supplemented with 10% FBS at 37° C. in an atmosphere of 5% $CO_2$ and 95% air.

Figure 8A:
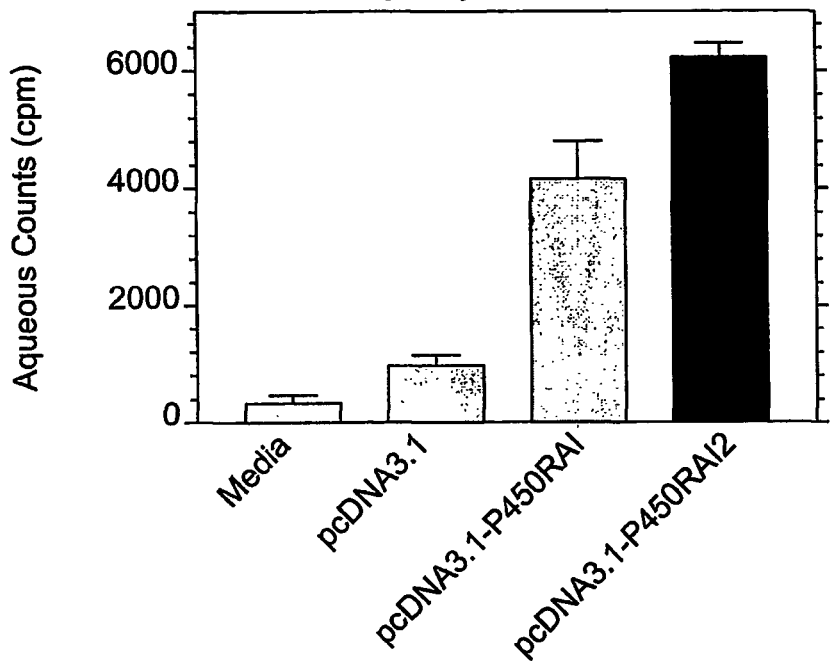
FIG. 8A shows the total aqueous soluble radioactivity measured using aliquots of the aqueous soluble extracts from media alone, as well as cells transfected with pcDNA3.1, pcDNA3.1-CYP26A (human) (i.e., P450RAI) or pcDNA-P450RAI-2. Aqueous soluble extracts were subjected to β-scintillation counting.
Figure 8B:
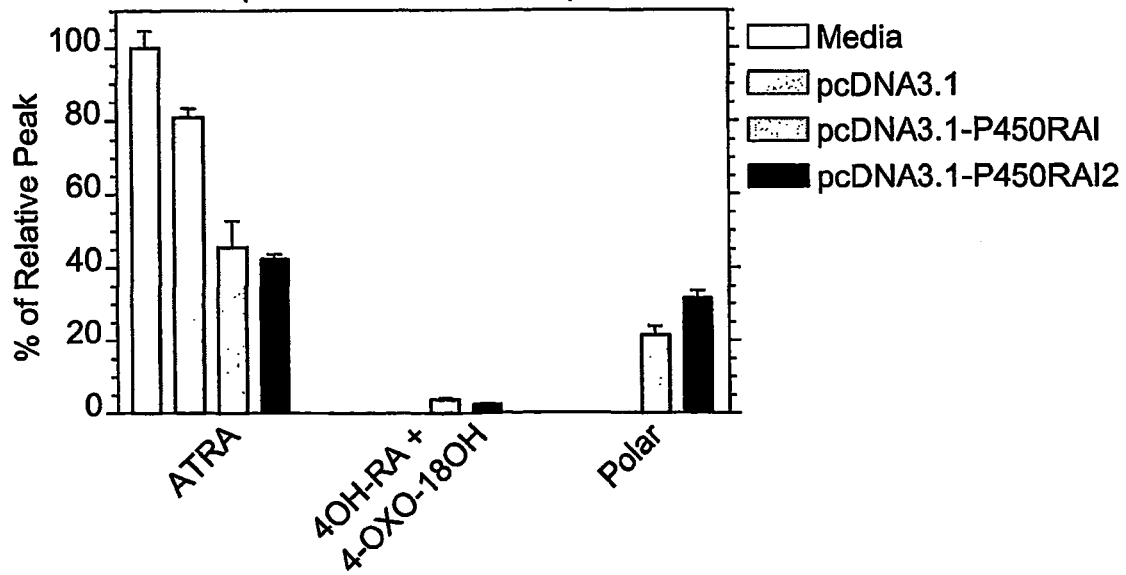
FIG. 8B shows a summary of the peak integration analysis performed after HPLC on the organic soluble radioactivity. Samples were the same as in FIG. 8A. Cells transfected with either pcDNA3.1-CYP26A (human) or pcDNA3.1-P450RAI-2 show a decrease in all-trans retinoic acid substrate with a concomitant increase in the production of 4-OH-retinoic acid, 4-oxo-retinoic acid and more polar peaks.
Figure 9:
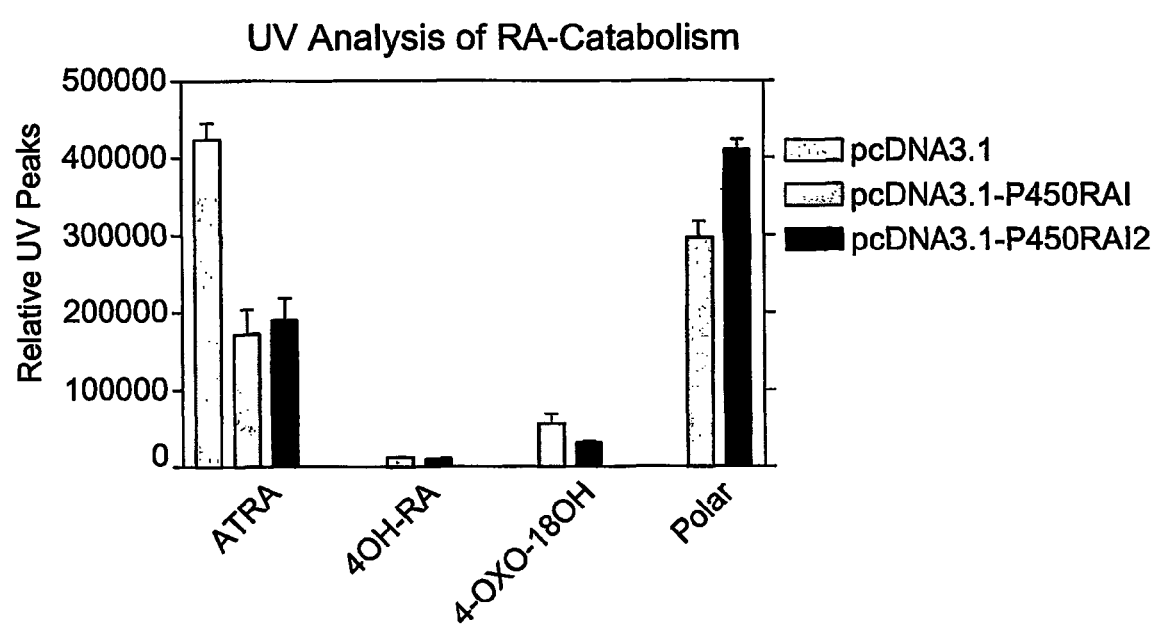
FIG. 9 shows the same analysis as FIG. 8B except that cells were treated with 1 µM non-radioactive all-trans-retinoic acid.
Figure 10:
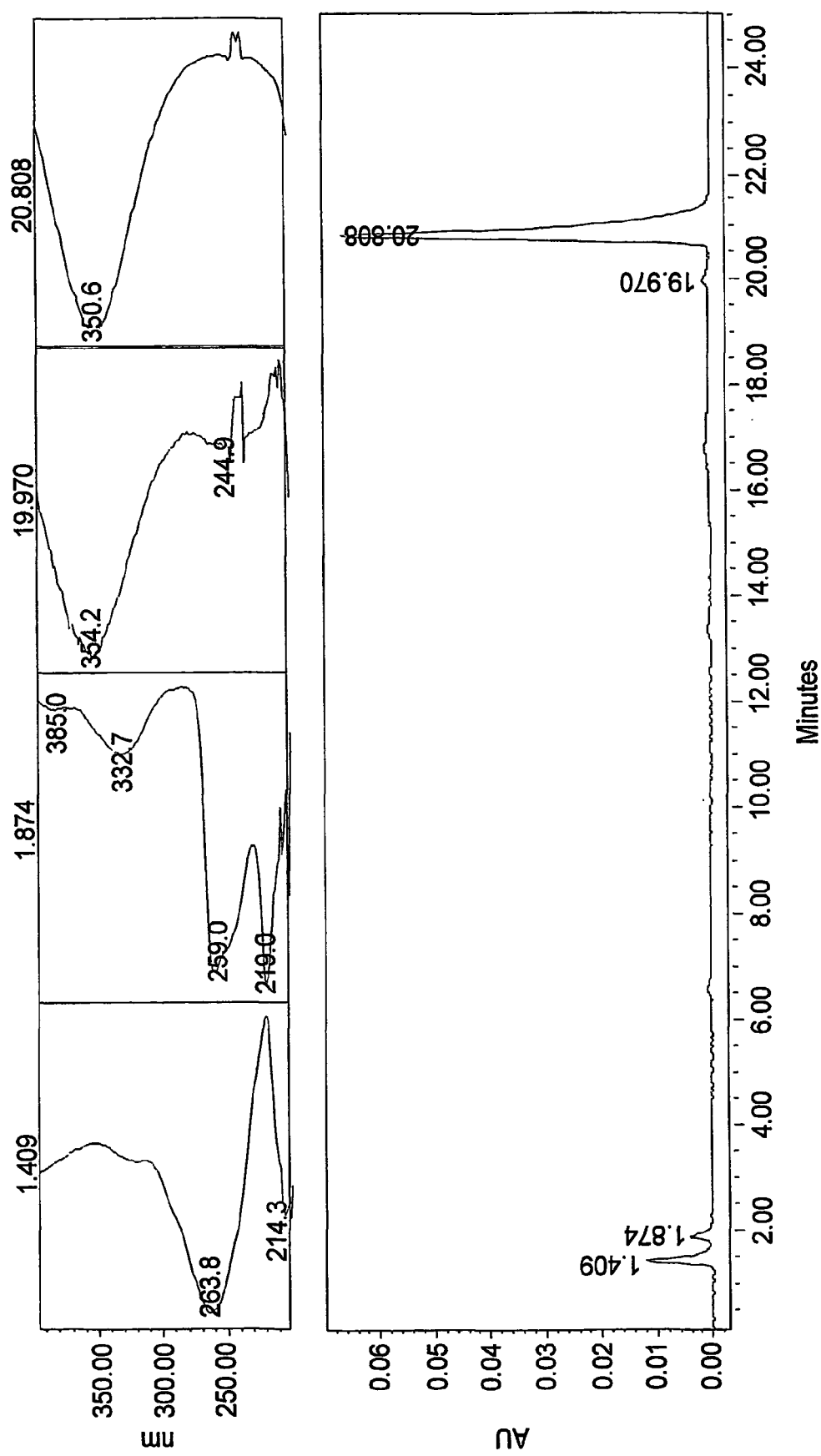
FIG. 10 shows a control HPLC trace from media alone in the absence of the COS-1 cells. An all-trans-retinoic acid substrate peak is observed at 20.808 minutes. Peaks at 1.409 and 1.874 are contaminants not characteristic of retinoids. The top panel shows photo diode array detection of the peaks. Retinoids have characteristic UV maxima in the range of about 320 to about 380 nM.
Figure 11:
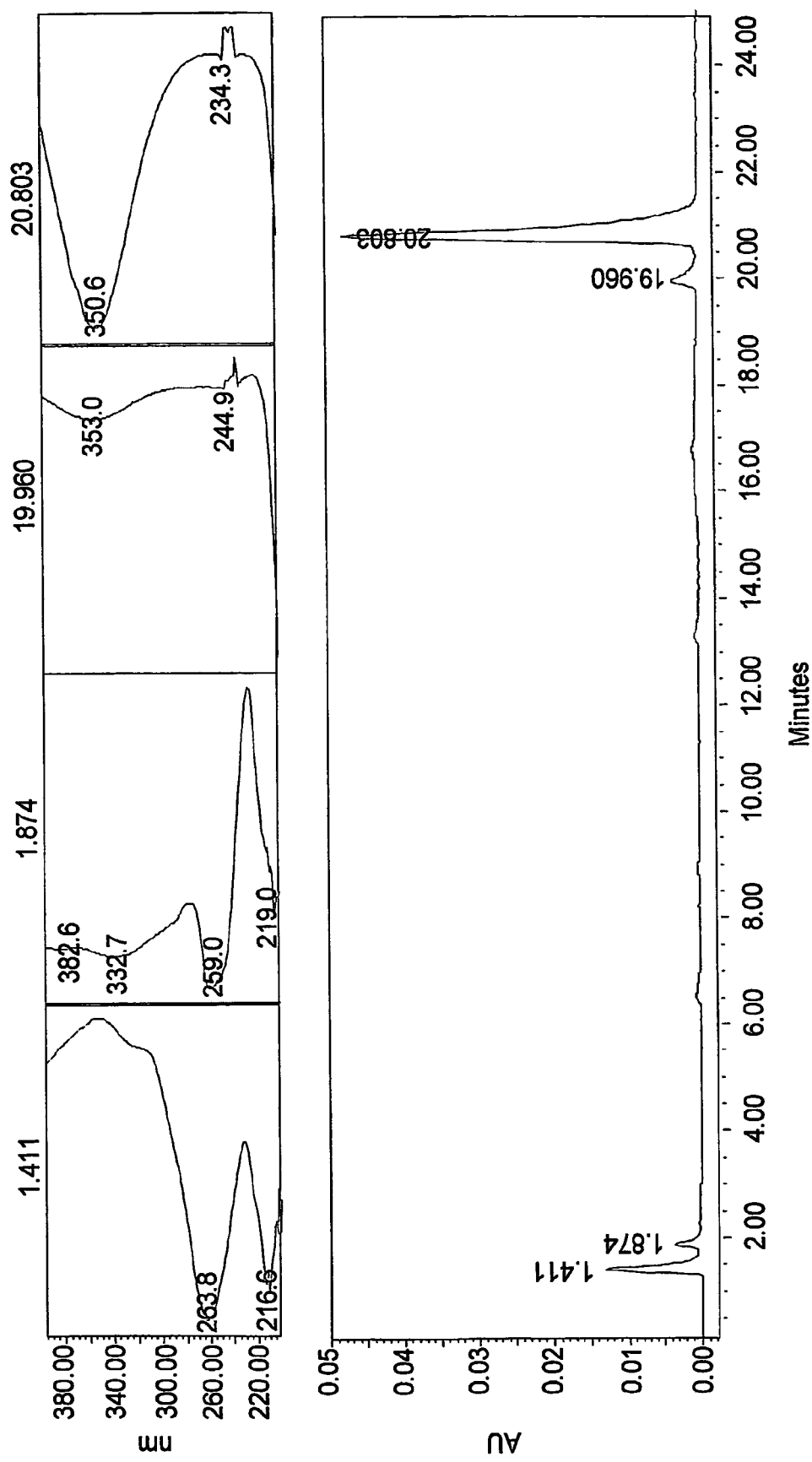
FIG. 11 is similar to FIG. 10 except that the sample is from COS-1 cells transfected with the pcDNA3.1 plasmid alone.
Figure 12:
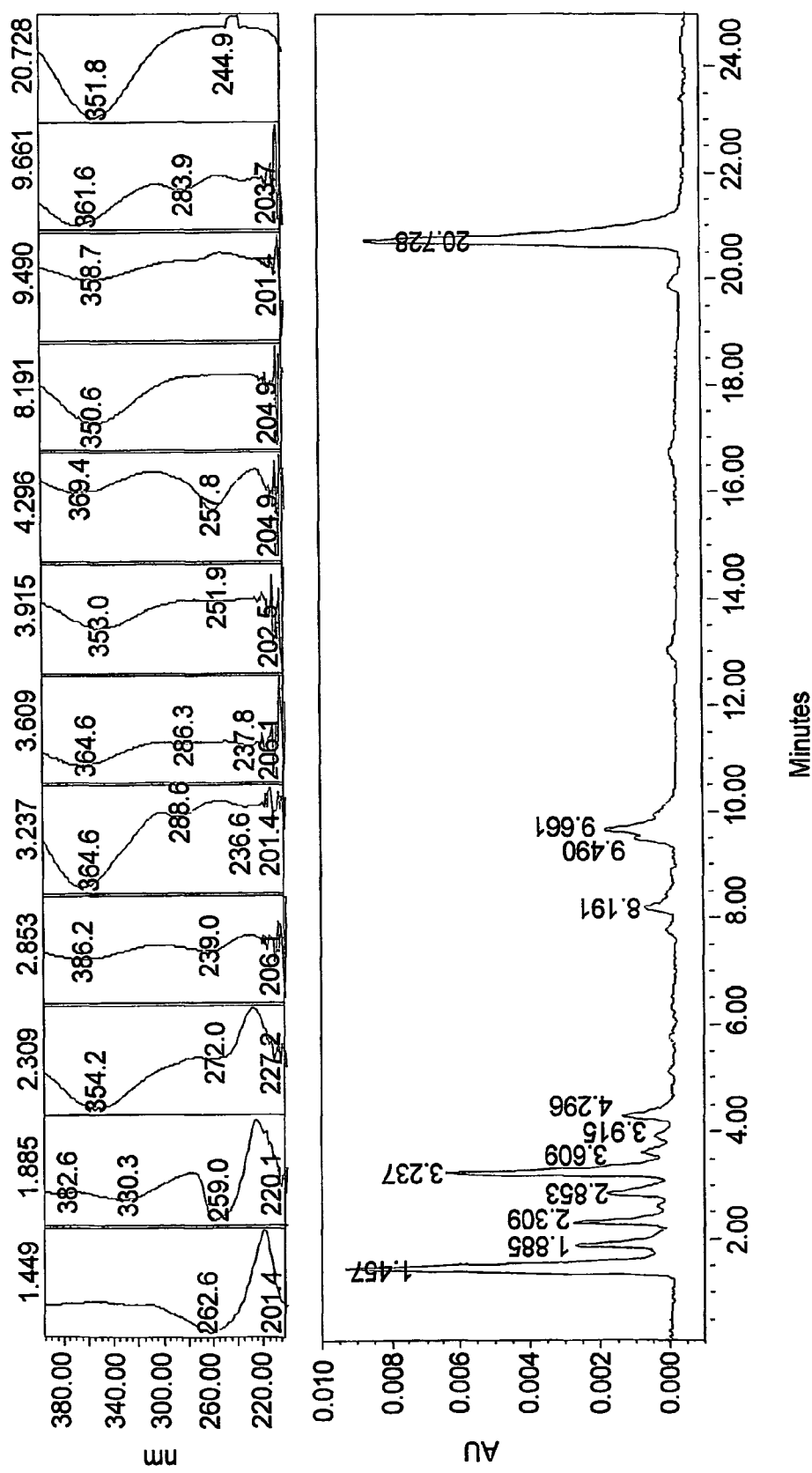
FIG. 12 is similar to FIG. 10 except that the sample is from COS-1 cells transfected with pcDNA3.1-P450RAI. Multiple more polar peaks characteristic of retinoids are generated in these cells. Peaks which co-elute with standards for 4-OH-retinoic acid and 4-oxo-retinoic acid were observed at 8.191 and 9.661 minutes respectively. Additional peaks which have not been characterized are also evident.
Figure 13:
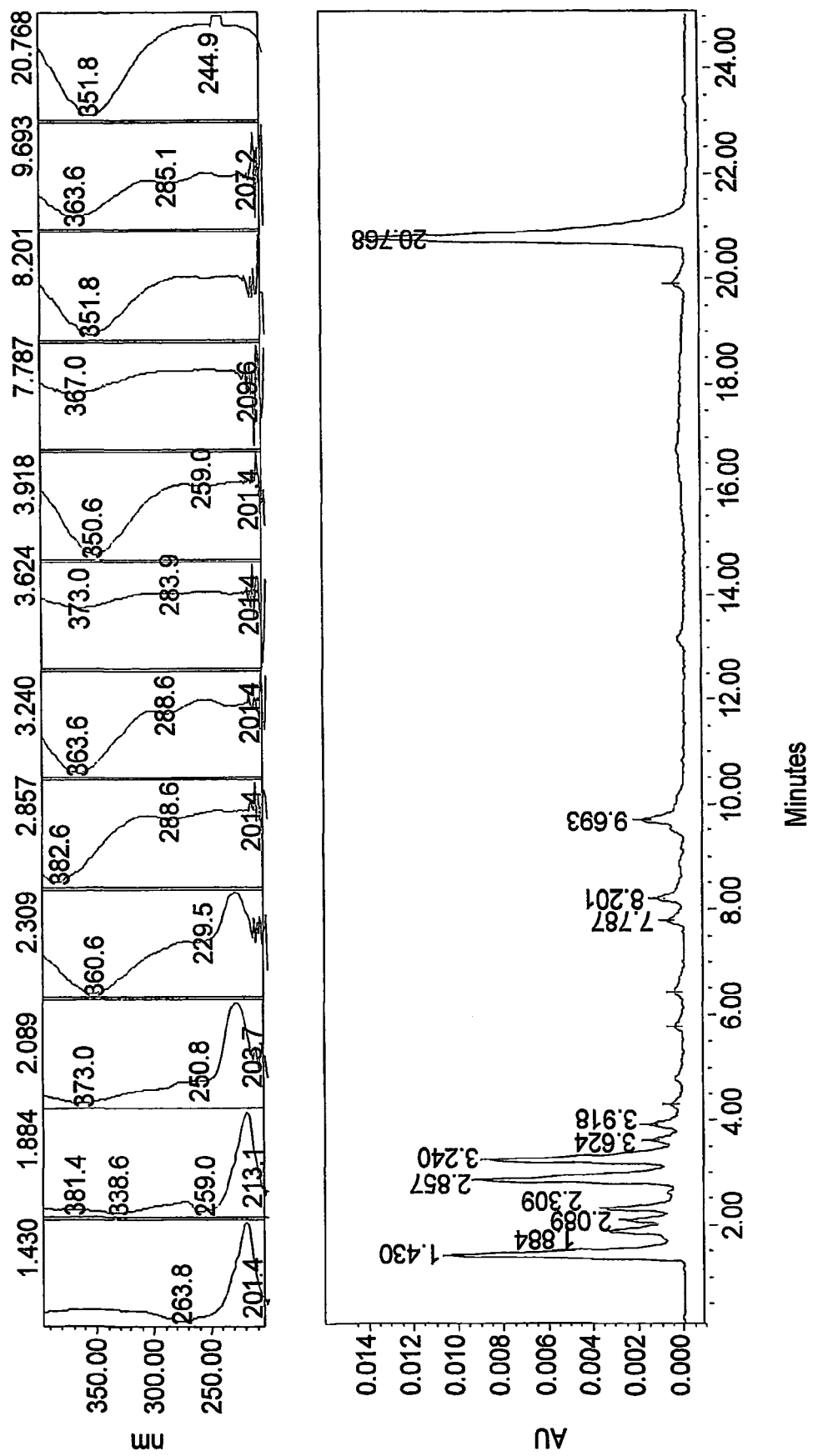
FIG. 13 is similar to FIG. 12 except that the sample is from COS-1 cells transfected with pcDNA3.1-P450RAI-2.

P450RAI-2 expression in COS-1 cells promoted the rapid conversion of RA into both lipid- and aqueous-soluble metabolites. See FIGS. 8 to 13. Fractions of total lipid extracts of transfected cells were initially separated by reverse-phase HPLC on Zorbax-SB C18 column (Hewlett Packard). HPLC conditions used a linear gradient of 50% acetonitrile, 49.9% $H_2O$, 0.1% acetic acid to 90% acetonitrile, 9.9% $H_2O$, 0.1% acetic acid with a flow rate of 1 ml/minute. Radioactivity was detected using a Berthold RadioFlow monitor. Using these conditions standard retinoids eluted at the following times: all-trans retinoic acid—20.5 minutes; 4-OH-retinoic acid—8.1 minutes; 4-oxo-retinoic acid—9.6 minutes; and 18-OH-retinoic acid—9.9 minutes. Comparison between extracts from pcDNA 3.1 and pcDNA 3.1-P450RAI-2 cells indicated that P450RAI-2 significantly increased all-trans retinoic acid metabolism. Incubation of P450RAI-2 transfected cells with micromolar concentrations of all-trans retinoic acid resulted in the production of multiple more polar peaks, some of which co-eluted with the standard retinoids. FIG. 8A shows an increase in aqueous-soluble radioactivity in P450RAI-2 transfected cells compared to media or pcDNA alone. FIG. 8B shows that there was an increase in lipid-soluble metabolites of all-trans retinoic acid when P450RAI-2 was transfected into the COS-1 cells. Metabolism of micromolar concentrations of non-radioactive all-trans retinoic acid was also evaluated. Transfected cells and controls were exposed to 1 micromolar all-trans retinoic acid for 3 to 4 hours and then analyzed for metabolism. Photo-diode array detection of HPLC-separated peaks are shown in FIGS. 10 to 13. FIG. 10 shows a background profile of media alone. FIG. 12 shows COS-1 cells transfected with the pcDNA plasmid alone. FIG. 12 shows the generation of more polar products when P450RAI (human) is transfected. In comparison, in FIG. 13, P450RAI-2 also causes the rapid metabolism of all-trans retinoic acid substrate to polar metabolites, several of which have the same retention times as the retinoid standards for 4-OH-retinoic acid and 4-oxo-retinoic acid. Although similar, there appear to be some differences in the ratios of individual metabolites in the profiles generated by P450RAI-2 compared to P450RAI.

Example 5B

Figure 14A:
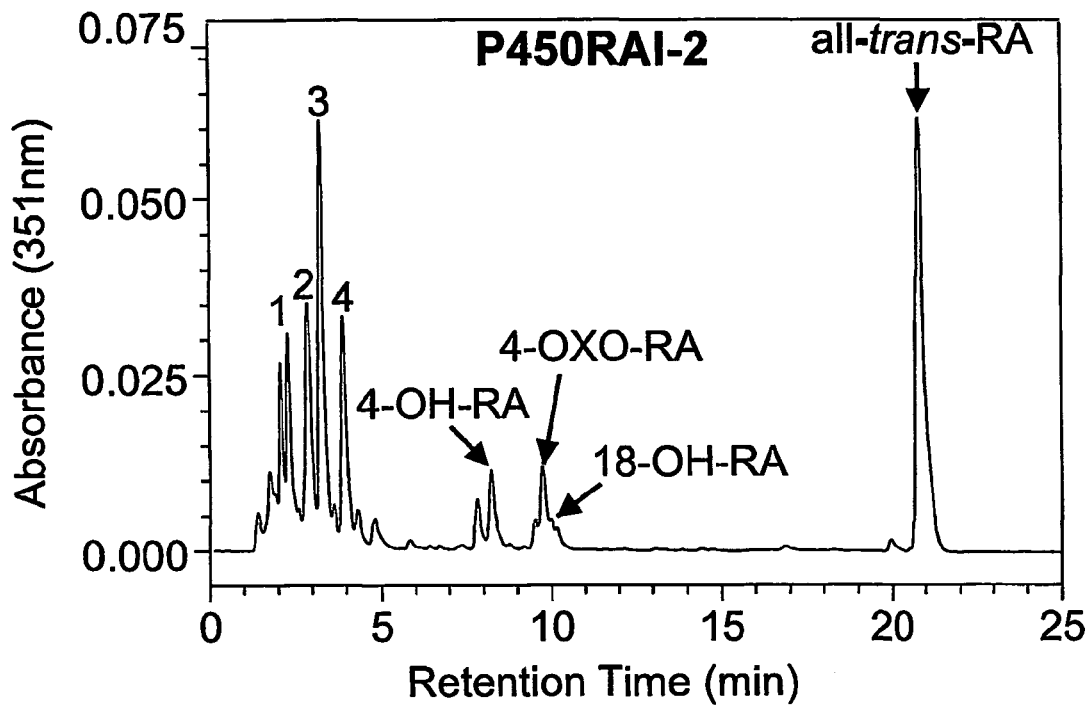
FIG. 14 shows HPLC analysis of all-trans-RA metabolism. COS-1 cells were transiently transfected with pcDNA3.1-P450RAI-2 (A), pcDNA3.1-P450RAI-1 (B) or pcDNA3.1 alone (C) and exposed to µM all-trans-RA for 3 hours. Incubation with RA was followed by total lipid extraction of the media and subsequent HPLC analysis using a reverse-phase system. Expression of either P450RAI-2 or P450RAI-1 in cells causes disappearance of all-trans-RA substrate (compare C to A or B) in addition to the generation of more polar metabolic products. Identities of the retinoids. labeled as all-trans-RA, 4-OH-RA, 4-oxo-RA and 18-OH-RA (A and B) were verified by co-elution with known standards and comparison of the spectral properties of the peaks using photodiode array detection. Multiple polar peaks are observed in P450RAI-2 expressing cells exposed to all-trans-RA. Peaks labeled 1–4 (A) have spectral properties characteristic of retinoids, specifically a UV maxima of between 320 and 350 nm. The exact identity of these polar metabolites remains to be established.
Figure 14B:
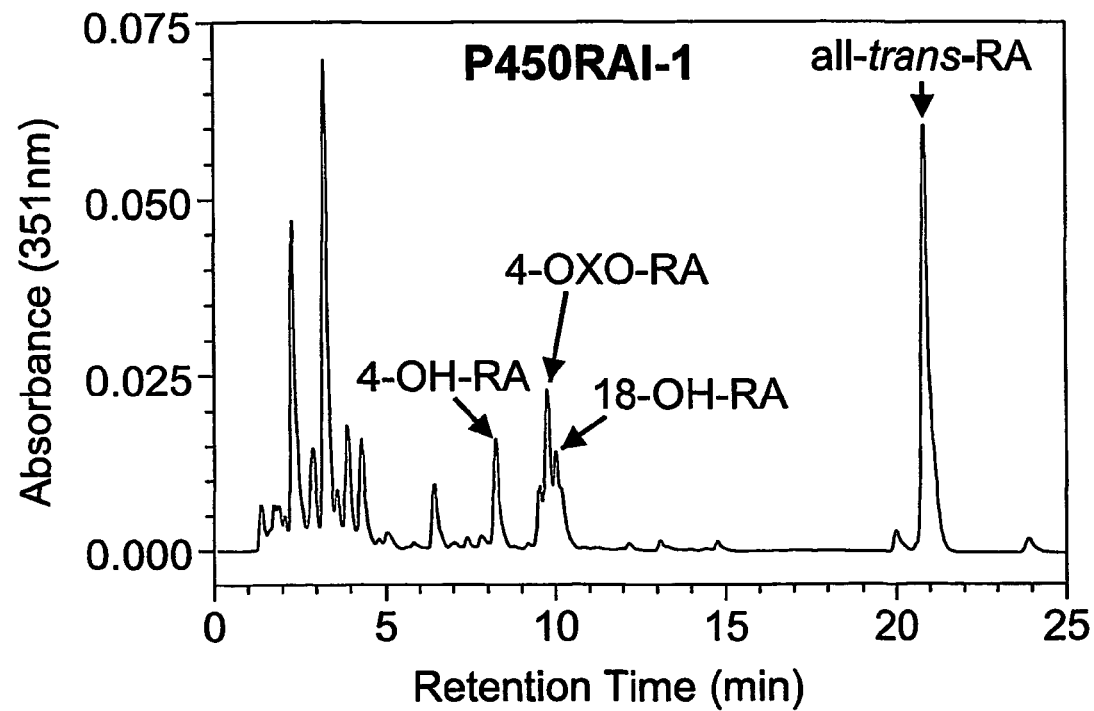
Figure 14C:
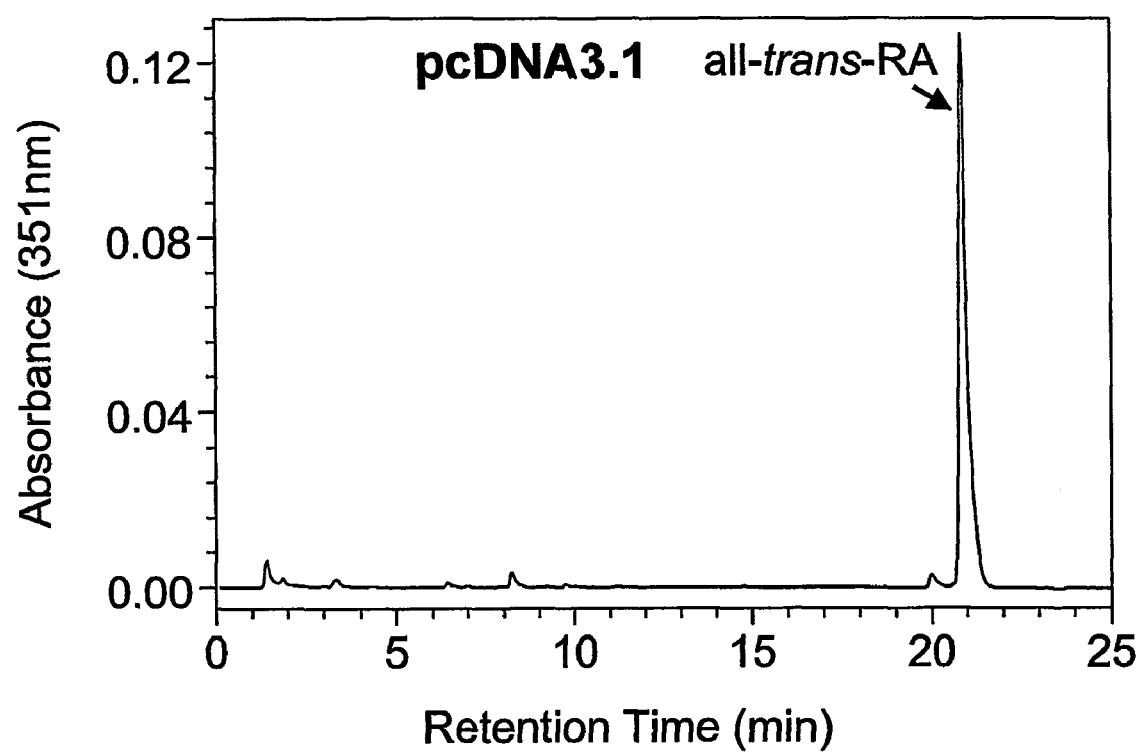

COS-1 cells were transfected with either plasmid (pcDNA3.1-P450RAI-2 or pcDNA3.1-P450RAI-1). The cells were then incubated with, all-trans-RA substrate over a 3 hour incubation period. The all-trans-RA substrate was extensively metabolized to more polar aqueous soluble products (FIGS. 14 and 15). HPLC analysis using photodiode array detection was performed on samples prepared from transfected cells trated with 1 μM unlabelled all-trans-RA. FIGS. 14A, B and C show comparative chromatograms of the lipid-soluble extracts from pcDNA3.1-P450RAI-2 (FIG. 14A), pcDNA3.1-P450RAI-1 (FIG. 14B) and pcDNA3.1 transfected cells (FIG. 14C). In both pDNA3.1-P450RAI-2 and pcDNA3.1-P450RAI-1 transfected cells the generation of multiple more polar peaks is observed. There is also a significant decrease in all-trans-RA substrate when compared to pcDNA3.1 controls (compare RA peaks in FIGS. 14A, B,with C). Peaks labelled as 4-OH-retinoic acid, 4-oxo retinoic acid and 18-OH-retinoic and co-elute with standards of and show characteristics UV spectra of these metabolites. Additionally, multiple unidentified peaks (labeled 1–4; FIG. 14A) which show maxima characteristic of retinoids (data not shown) are generated and appear to be qualitatively similar in both P450RAI-2 and P450RAI-1 samples compared to controls.

Figure 15A:
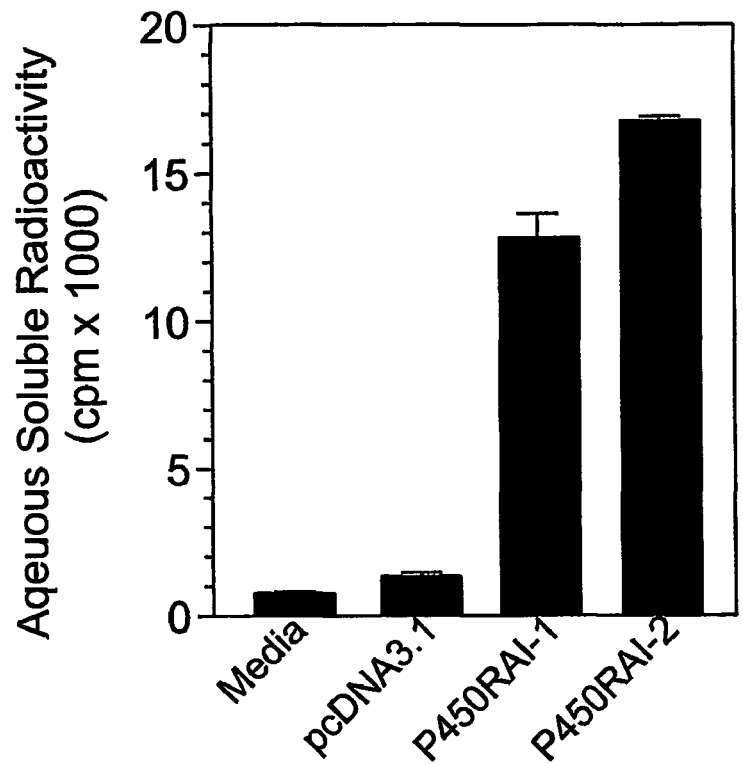
FIG. 15 shows metabolism of all-trans-RA. COS-1 cells transiently transfected with pcDNA3.1 -P450RAI-2, pcDNA3.1-P450RAI-1 or pcDNA3.1 alone and exposed to 100 nM [$^3$H]all-trans-RA for 3 hours. Conversion of all-trans-RA to aqueous-soluble metabolites is observed in P450RAI-2 or P450RAI-1 expressing cells compared to pcDNA vector or media alone control samples (A). Using HPLC analysis with subsequent β-scintillation counting was used to evaluate the lipid-soluble retinoids generated from P450RAI-2 or P450RAI-1 expressing cells. Fractions from chromatography were grouped into three regions, all-trans- RA substrate, 4-OH region and polar region allowed quantification of the retinoid metabolites. Levels of all-trans-RA remaining after incubation were substantially decreased in P450RAI-2 or P450RAI-1 transfected cells compared to controls (B). Additionally, there is an increase in radioactivity representing both the 4-OH and polar regions (B).

To evaluate the efficiency of P450RAI-2 at more physiological concentration of substrate, P450RAI-1 transfected cells were exposed to 100 mM radiolablled (spec. act.) all-trans-retinoic acid (FIGS. 15A and B). In these cells, 34±0.2% of the all-trans-RA substrate is converted to aqueous-soluble products compared to 26±1.5% in the P450RAI-1 transfected cells (FIG. 15A). Controls, including media alone or pcDNA3.1 tranfected cells, show 1.6±0.1% (media alone) and 2.7±0.2% (pcDNA3.1) conversion of substrate to aqueous radioactivity.

Figure 15B:
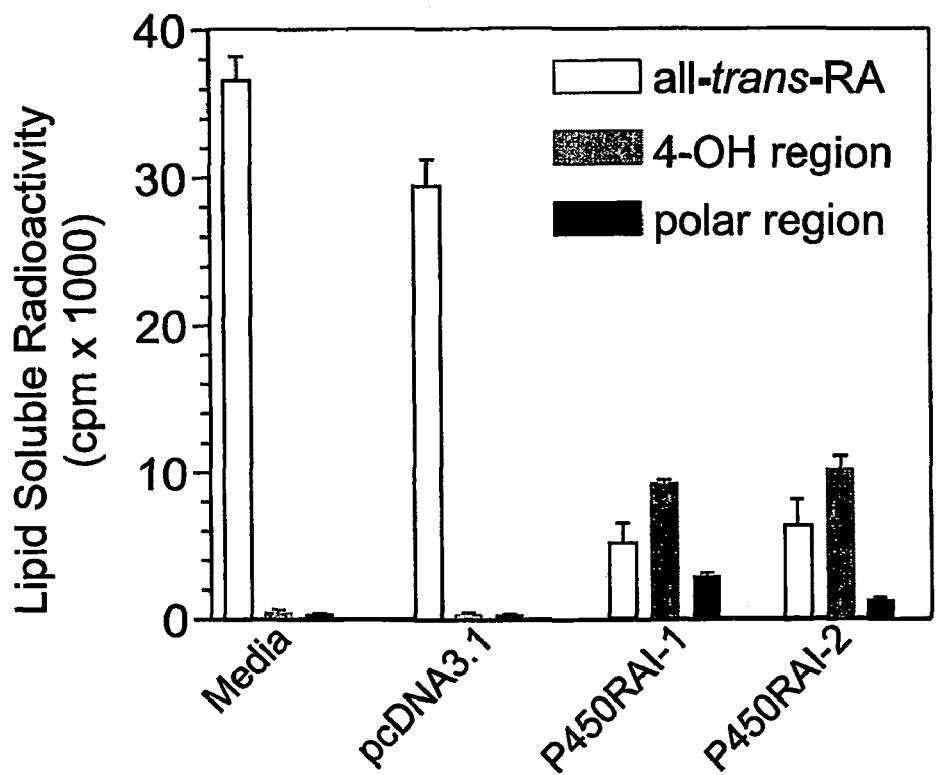

The radioactivity remaining in the organic soluble fraction in the transfected cells exposed to 100 nM [$^3$H all-trans-retinoic acid (FIG. 15B) was also evaluated. HPLC analysis identified many more polar metabolites in both the P450RAI-2 and P450RAI-1 transfected cells compared to controls (data not shown). In media from cells transfected with pcDNA3.1-P450RAI-2 or pcDNA3.1-P450RAI-1 a high degree of disappearance of substrate compared to controls was observed. As well, there is a concomitant increase in the more polar lipid-soluable retinoid metabolites which elute in both the 4-OH and polar regions of the chromatograms. These results clearly indicate that expression of either P450RAI-2 or P450RAI-1 causes substantial metabolism of all-trans-RA to more polar metabolites (FIG. 15B).

Example 6

Retinoid Substrate Specificity of P450RAI-2

Given the presence of two unique enzymes P450RAI-1 and P450RAI-2, with the capacity to rapidly metabolize all-trans-RA the specificity of these two enzymes were evaluated. Interestingly, both P450RAI-1 and P450RAI-2 show approximately equal efficiencies at metabolizing all-trans-RA (FIG. 15 and 16 A-D). Competition assays were also performed to evaluate the ability of five retinoids, all-trans-RA, 9-cis-RA, 13-cis-RA, retinal and retinol to compete out P450RAI-2 or P450RAI-1 mediated all-trans-RA metabolism (FIG. 16). The non-specific cytochrome P450 inhibitor, ketoconazole, was also tested.

COS-1 cells were transfected with either pcDNA3.1-P450RAI-1 or pcDNA3.1-P450RAI-2 in 6-well tissue culture plates as described above. 48 hours post-transfection cells were harvested, pooled, washed with DMEM medium and replated into duplicate 48-well plates with $5\times10^5$ cells per well. The cells were incubated in 0.2 ml DMEM medium containing 0.05 μCi/ml[$^3$H]-RA (final concentration 2 nM) in the present or absence of increasing concentrations of the each unlabelled retinoids (all-trans-RA, 9-cis-RA, 13-cis-RA, retinol, retinal). Control cells were incubated with increasing concentration of ketoconazole. After incubation for 3 hours at 37° C., the retinoids were extracted using the Bligh and Dyer [1957] procedure and the aqueous soluable RA-metabolites were counted in a scintillation counter as described above.

These compeition studies indicated that P450RAI-1 and, -2 exhibit comparable substrate specificities with all-trans-RA being the preferred substrate for both enzymes having $ID_{50}$ values of approximately 3.0 μM for P450RAI-2 and 2.5 μM for P450RAI-1. The other retinoids show varying abilities to compete out metabolism of all-trans-RA by P450RAI-2 and P450RAI-1 in the following rank order: 9-cis-RA>13-cis-RA>retinal≧retinol (see Table 1 for interpolated $ID_{50}$ values). Using microsomes prepared from stably-transfected P450RAI-1 cells we have also found the same relative levels of competition suggesting that the differences in $ID_{50}$ values are not due differences in cellular uptake of the retinoids (data not shown).

TABLE 1

INTERPOLATED $ID_{50}$ VALUES

|  | P450RAI-1 | P450RAI-2 |
| --- | --- | --- |
| All-trans-RA | 2.5 | 3 |
| 9-cis-RA | 32 | 25 |
| 13-cis-RA | >75 | 55 |
| Retinol | >100 | >100 |
| Retinol | >100 | >100 |
| Ketoconzole | 16 | 12 |

Figure 16A:
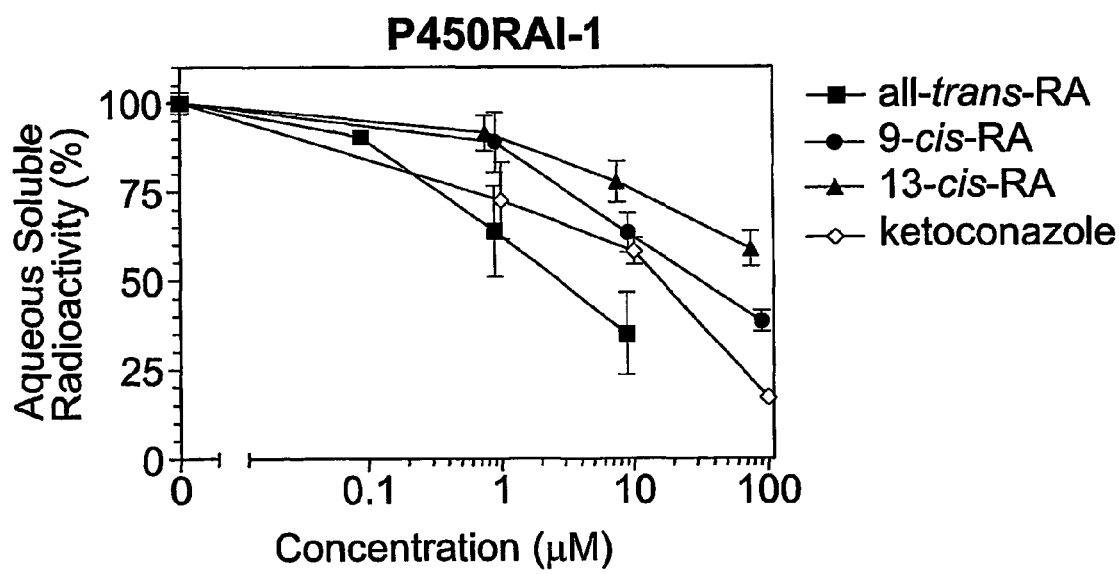
FIGS. 16 A–E is competitive inhibition of P450RAI-mediated all-trans-RA metabolism. COS 1 cells transiently transfected with pcDNA3.1-P450RAI-2, pcDNA3.1-P450RAI-1 or pcDNA3.1 alone were used to assess the ability of several retinoids to competitively inhibit all-trans-RA metabolism. Cells were exposed to 2 nM [$^3$H]all-trans-RA with increasing concentrations of unlabelled competitor and assayed for generation of aqueous soluble radioactivity. Panels C and D show cells expressing P450RAI-2 with panels A and B show cells expressing P450RAI-1.9-cis-RA and 13-cis-RA (top panels 16A and 16C) are less effective than all-trans-RA as competitors for either P450RAI-2 or P450RAI-1.
FIG. 16E shows [$^3$]-RA-metabolism inhibition assay using microsomes prepared from Hela-CYP26B (stable) cells. Microsomes (5 micograms) were incubated with [$^3$H]-RA and increased concentration o funlabeled all-trans-RA, 9-cis-RA, 13-cis-RA and ketoconazole. Retinol and retinal were similarly tested (bottom panels 16B and 16D) and found to be less effective competitors. For comparison, the nonspecific cytochrome P450 inhibitor ketoconazole is shown in each panel.
Figure 16B:
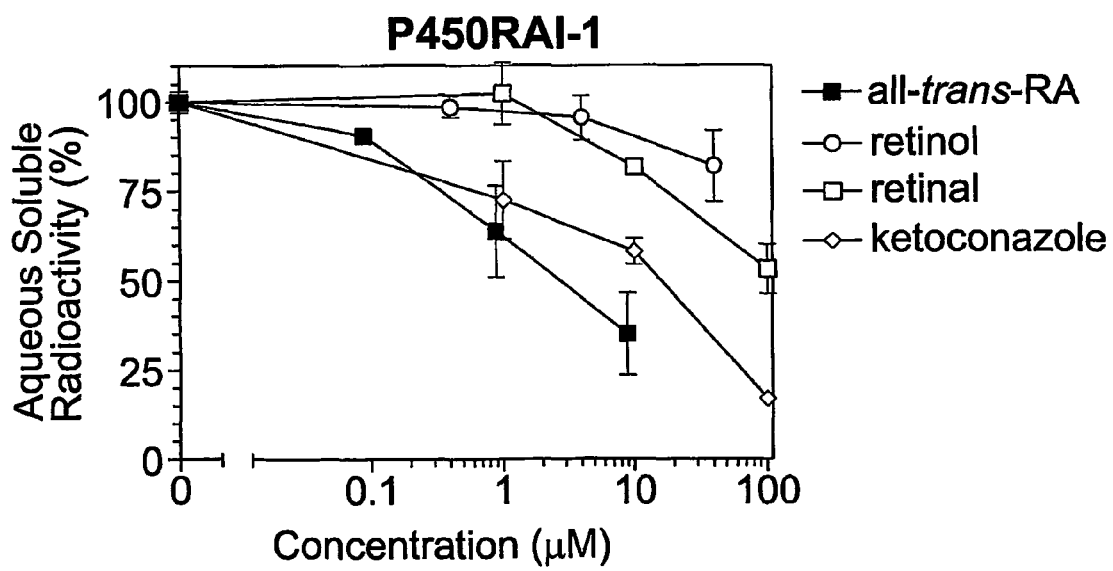
Figure 16C:
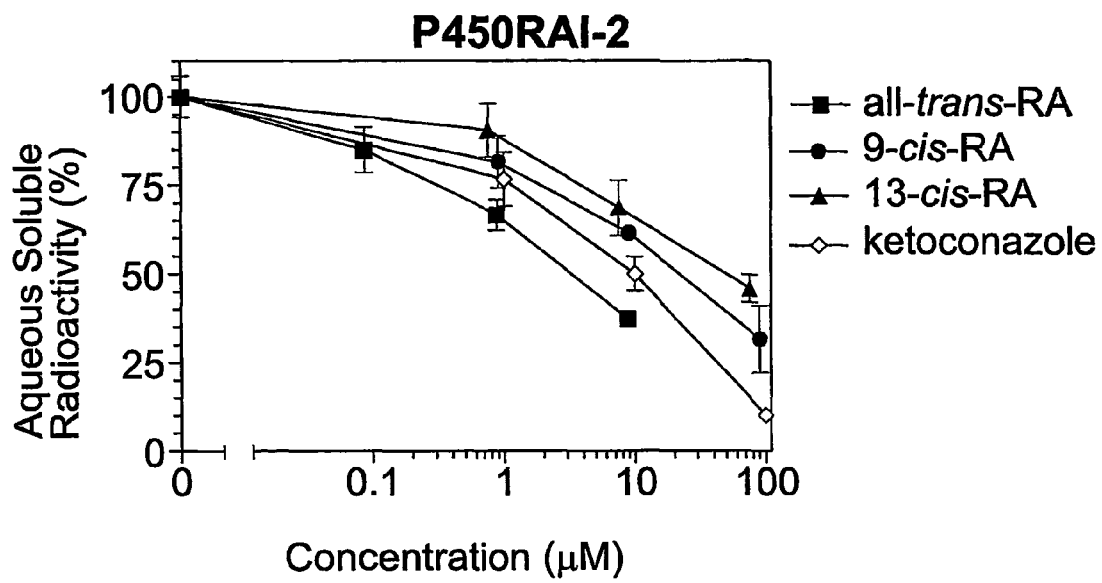
Figure 16D:
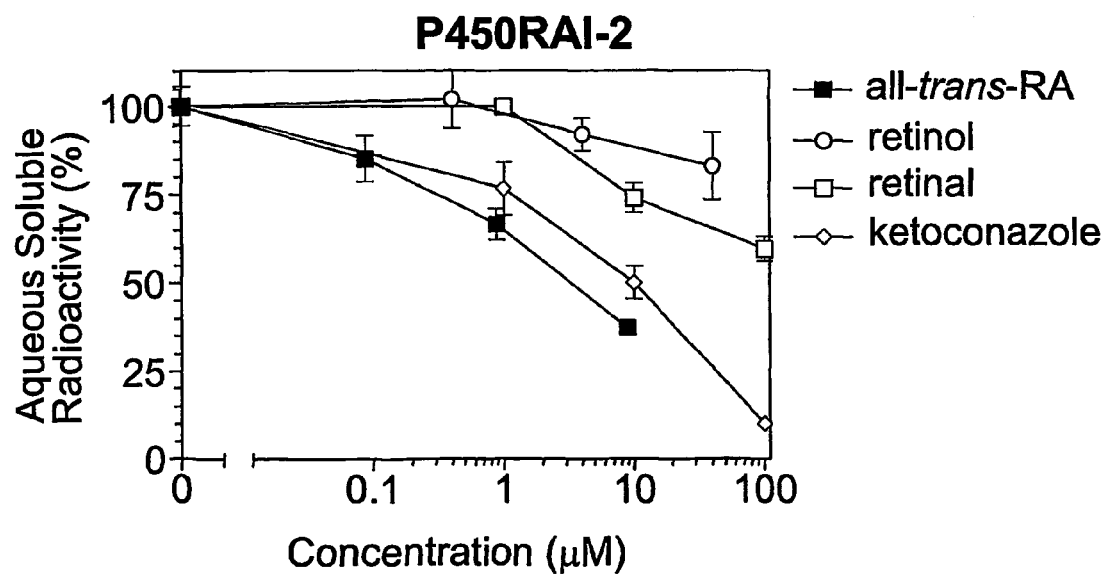
Figure 16E:
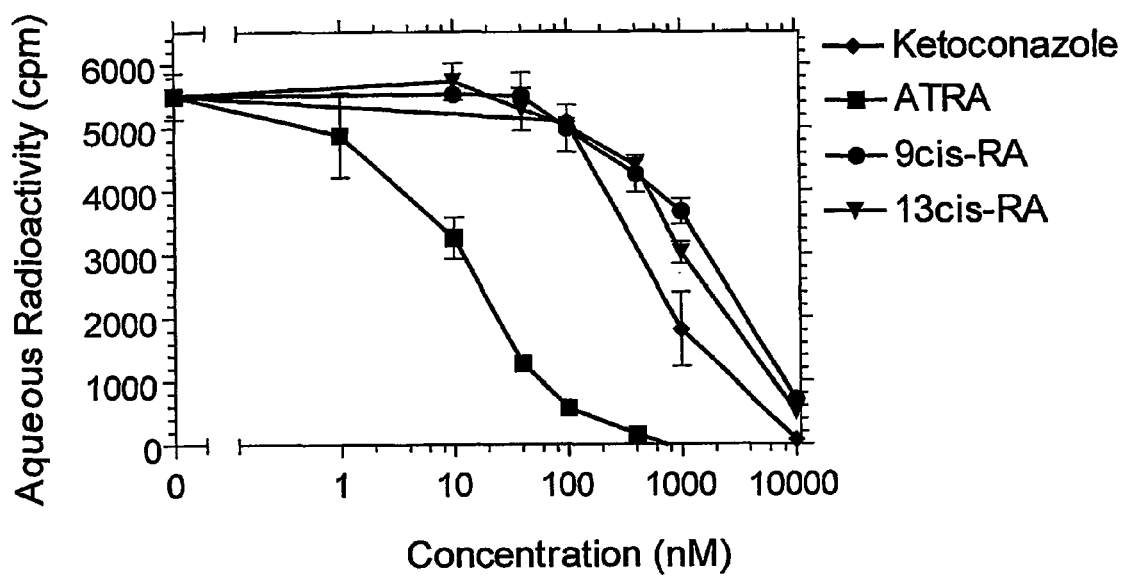

FIG. 16E also illustrates a substrate competition in Mammalian micorsomes. [$^3$H]-RA-metabolism inhibition assay was carried outusing microsomes prepared from Hela-CYP26B (stable) cells. Briefly, microsomes (5 μg) were incubated with [$^3$H]-RA and increased concentration of unlabeled all-trans-RA (ATRA), 9-cis-RA, 13-cis-RA, or ketoconazole. The reaction was started by adding NADPH for 1 hour at 37° C. and then total reinoids were extracted using Bligh-Dyer procedure and water-soluble metabolites counted. The results in FIG. 16E show that ATRA is the high affinity substrate for CYP26B (P450RAI-2). 13-cis-RA did not compete at lower concentrations. Ketoconazol is an inihibitor of CYP26B.

Example 7

Expression of P450RAI-1 and P450RAI-2 in Human Cells

Figure 17B:
FIG. 17 shows Northern blot (A) and RT-PCR (B) results for total RNA samples from the various cell samples designated.
Figure 17A:
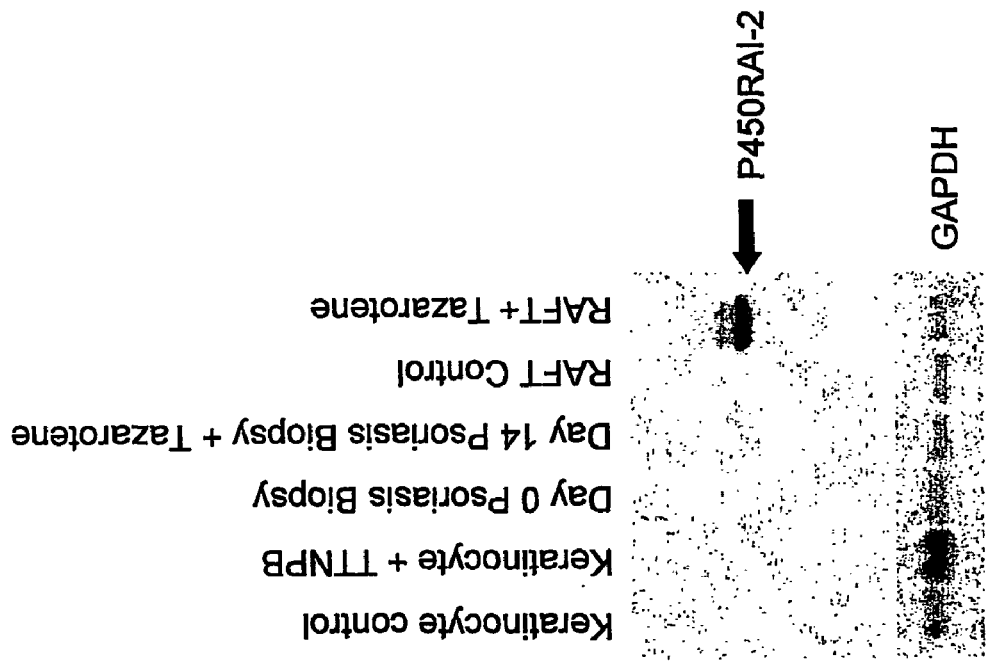
Figure 18A:
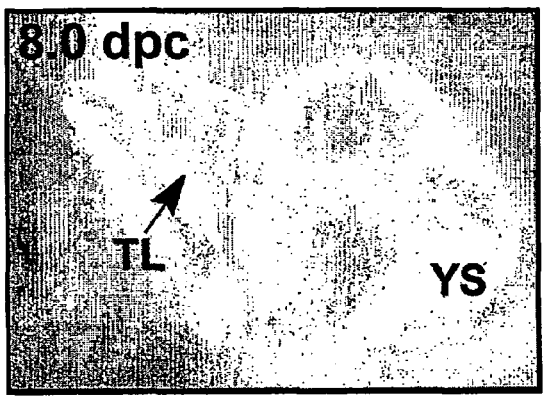
FIG. 18 shows expression of P450RAI-2 in 8.0 and 8.5 dpc mouse embryos. (A) 8.0 dpc lateral view. No apparent staining. (B) 8.0 dpc, dorsal view. Staining at anterior end of neutral folds. (C) 8.5 dpc, lateral view. Expression is evident, possibly in presumptive rhombmeres 2, 5, and 6. (D) 8.5 dpc, dorsal view, rhombomere expression of RAI2 is clearly evident. TL: Tail; YS Yolk Sac; NF: Folds; pr: Presumptive Rhombomeres.
Figure 18B:
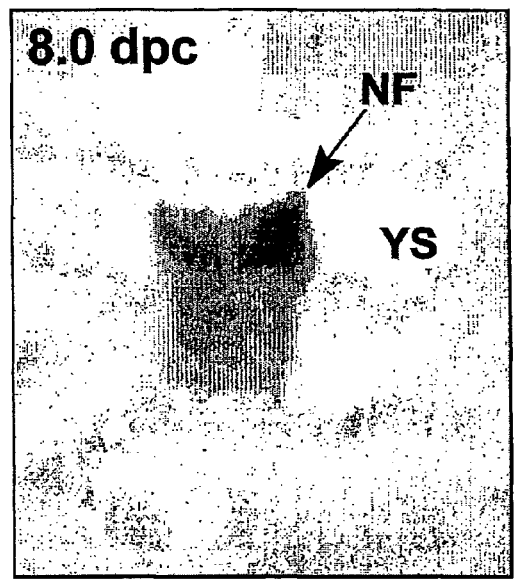
Figure 18C:
Figure 18D:
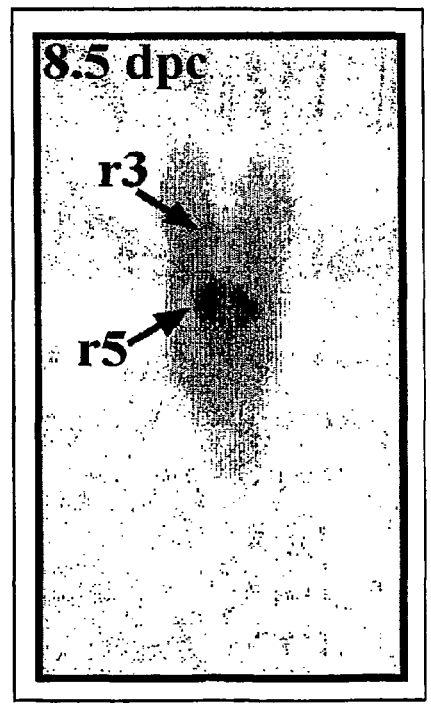
Figure 19A:
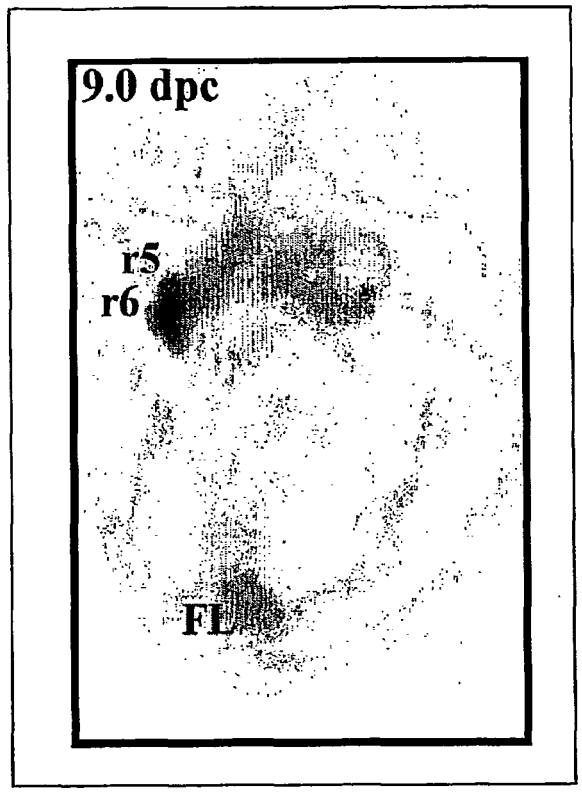
FIG. 19 shows expression of P450RAI2 in 9.0 and 10.5 dpc mouse embyros. (A) 9.0 dpc, lateral view. Specific staining is visible in the eye, and rhombomeres 5 and 6. Diffuse staining is visible where the hind bud is beginning to form. (B) 9.0 dpc, dorsal view. Rhombomeres 5 and 6 show RAI2 expression. (C) 10.5 dpc, lateral view. The otic vesicle and eye are stained. (D) 10.5 dpc, dorsal view. Specific staining is observed in both otic vesicles as well as as the hind linb bud. HL: hind limb bud; OV: Otic Vesicle.
Figure 19B:
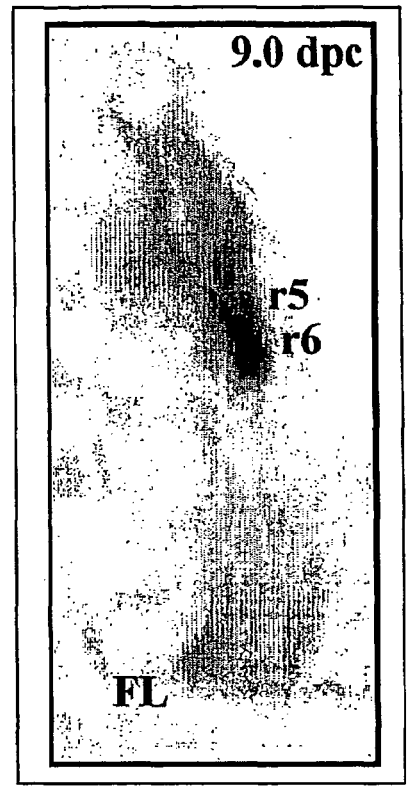
Figure 19C:
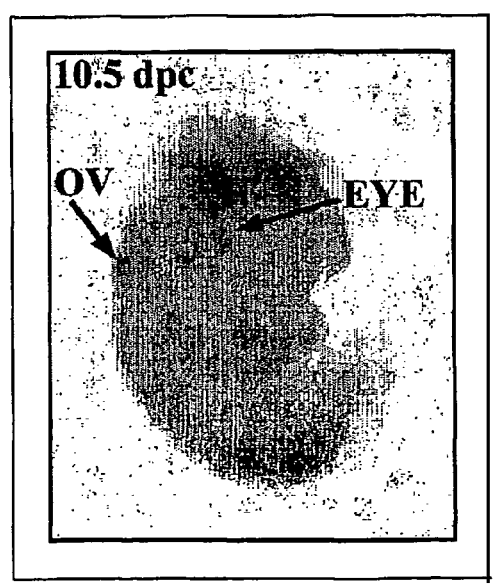
Figure 19D:
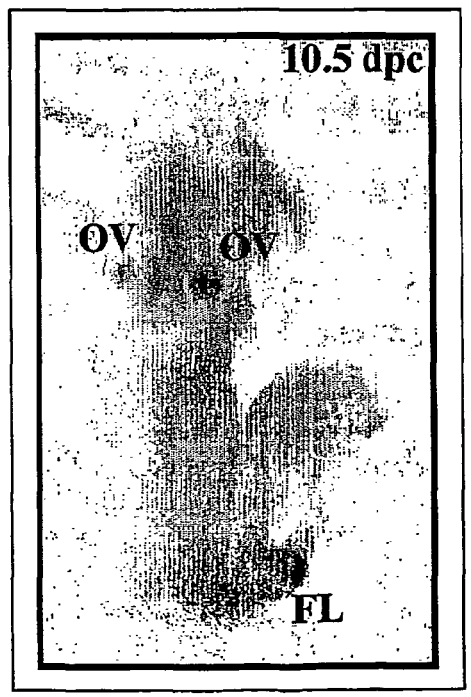

Total RNA aliquots (10 μg) were electrophoresed on a 1.0% formaldehyde-agarose gel and a northern blot performed. The gel was photographed under ultraviolet light and then blotted on Hybond ECL nitrocellulose membrane (Amersham Pharmacia Biotech, UK) and fixed to the membrane by baking at 80° C. for 2 hours under vacuum. Prehybridization and hybridization steps were performed using ExpressHyb (Clontech, CA) according to the manufacturer's directions. Three individual cDNA fragments were labeled with α-[$^3$]dATP using the Prime-A-Gene Labeling System (Promega, WI). The probes were as follows; P450RAI-1 762-1217 bp of SEQ ID NO:13, full length P450RAI-2 SEQ ID NO:4 and a human glyceraldehyde-3-phosphate dehydrogenase (GAPDH) PCR fragment. The blot was hybidized with P450RAI-2, washed two times for 5 minutes in 2×SSPE, 0.1% SDS at room temperature, then washed once at 65° C. for 10 minutes in 1×SSPE, 0.1% SDS and a final wash for 15 minutes at 65° C. in 0.1×SSPE, 0.1% SDS. The blot was exposed at −70° C. for 48 hours to Kodak X-Omat AR film (Eastman Kodak Company, NY). FIG. 17A shows P450RAI-2 expression was induced in the RAFT sample treated with Tazarotene. P450RAI-2 appears to also be expressed in the Day 14 Psoriasis Biopsy sample treated with Tazarotene. The blot was stripped by washing two times for 30 minutes in boiling 0.5% SDS and exposed to film overnight to ensure proper removal of probe. The above protocol was repeated for P450RAI-1 and GAPDH. The P450RAI-1 and GAPDH blots were exposed for 96 and 4 hours respectively. Two separate hybridizations with a P450RAI-1 probe did not produce any bands on the northern blot.

RT-PCR was performed using 1 ug of total RNA and the Advantage One-Step RT-PCR kit (Clontech, CA). The final primer concentrations were 45 μM for the P450RAI-1 and P450RAI-2 primers and 11.25 μM for the GAPDH-specific primers. Two separate sets of reactions were performed using the primer sets, P450RAI-1/GAPDH and P450RAI-2/GAPDH. The thermal cycling program for cDNA synthesis and PCR amplification was 1 cycle at 50° C. for 1 hour, 1 cycle at 94° C. for 5 minutes, followed by 30 cycles of 94° C. for 30 seconds, 65° C. for 30 seconds, 68° C. for 1 minute and a final cycle of 68° C. for 2 minutes. The P450RAI-1, P450RAI-2 and GAPDH upstream and downstream amplification primers sets were 5'-GCCTTCGAGGAAATGAC-CCG-3' (SEQ ID NO: 35) and 5'-CTGGATGCATC-CTCTGGGTG-3' (SEQ ID NO: 36), 5'-GTCTACCAGCAGTTTGTGGAC-3' (SEQ ID NO: 37) and 5'-AGTCCAGGTAGCGCAGCCCACT-3' (SEQ ID NO: 38), 5'-TGAAGGTCGGAGTCAACGGATTTGGT-3' (SEQ ID NO: 39) and 5'-CATGTGGGCCATGAGGTC-CACCAC-3' (SEQ ID NO: 40) respectively. Total RNA isolated from MCF-7 cells treated with all-trans-RA was used as a positive control. FIG. 17B also shows expression of P450RAI-2 in the Tazarotene treated RAFT sample. Both the Psoriasis samples show PCR products corresponding to P450RAI-2.

Example 8

Expression of P450RAI-2 in Mouse Embryos

Probe synthesis: All in situ hybridization experiments were performed using an antisense copy of mouse EST AW488377.1 [SEQ ID NO:18] labelled with digoxigenin. The EST was cloned into pT7T3D, linearized with HindIII, and transcription was initiated from the T7 promoter. RNA labeling reactions were performed using DIG RNA labeling mix (Roche) as per instructed by the kit insert.

In Situ Hybridization: Mice were sacrificed by cervical dislocation, and embryos were dissected in 1×PBS, before being left to fix overnight in 4% paraformaldehyde at 4° C. The next day, embryos were washed twice with PBT (1×PBS, 0.1% Tween-20) for 5 minutes at 4° C. Embryos were washed 5 minutes each with 25, 50, 75% methanol in PBT, then twice with 100% methanol and then stored at −20° C. To rehydrate embryos, they were taken through the previous methanol series in reverse and washed twice with PBT. Then embryos were treated with 10 μg/mL proteinase K in PBT for the following times: 8.5 dpc (days post coitum)—no treatment; 9.5 dpc—3 minutes; 10.5 dpc—4 minutes; 11.5 dpc-5 minutes. 3 washes of 2 mg/mL glycine in PBT were performed for 5 minutes each. Embryos were refixed in 0.2% glutaraldehyde/4% paraformaldehyde in PBT for 20 minutes, and then washed twice with PBT for 5 min. 1 mL of prehybridization solution (5×SSC, 1% SDS, 5 μg/mL Yeast tRNA, μg/mL heparin) was added, and embryos were incubated at 70° C. After 1 hour, prehybridization solution was replaced with 1 mL of fresh solution containing 1 μg digoxigenin-labeled probe and left to hybridize overnight at 70° C. The next day, embryos were washed twice with prehybridization solution for 30 minutes at 70° C. Embryos were washed for 20 minutes at 70° C. with a 1:1 mix of prehybridization solution and 1×MABT (DIG Wash and Block Buffer Set, Roche). After 3 rinses with MABT, embryos were washed twice for 30 minutes at 70° C. with MABT. To preblock embryos, 1×MABT/2% Blocking Reagent (DIG Wash and Block Buffer Set, Roche) was added. After an hour, solution was removed and replaced with 1×MABT/2% Blocking Reagent/20% sheep serum and left for 1 hour. Next, 1×MABT/2% Blocking Reagent/20% sheep serum/0.0005 Anti-Digoxigenin Antibody coupled to Alkaline Phosphatase (Roche) was added at left overnight at 4° C. The next day, embryos were rinsed 3 times with 1×MABT with 2 mM levamisole, and washed five times for 1 hour in 1×MABT/2 mM levamisole. Two washes of 10 minutes each were performed in NTMT (100 mM NaCl, 100 mM Tris-HCl, pH=9.5, 50 mM $MgCl_2$, 2 mM levamisole). 1 mL of fresh NTMT was added along with 3.5 µL BCIP and 4.5 µL NBT (Gibco), and colour reaction was allowed to proceed in the dark. When complete, embryos were rinse twice with PBT, and refixed overnight at 4° C. in 0.2% glutaraldehyde/4% paraformaldehyde. The next day, embryos were washed for 1 hour in 1:1 CMFeT:glycerol before transfer to 4:1 CMFeT:glycerol until ready to photograph.

FIG. 18 illustrates P450RAI-2 in 8.0 and 8.5 dpc mouse embryos. (A) 8.0 dpc lateral view. No apparent staining. (B) 8.0 dpc, dorsal view. Staining at anterior end of neutral folds. (C) 8.5 dpc, lateral view. Expression is evident, possibly in presumptive rhombmeres 2, 5, and 6. (D) 8.5 dpc, dorsal view, rhombomere expression of RAI2 is clearly evident. TL: Tail; YS Yolk Sac; NF: Folds; pr: Presumptive Rhombomeres.

FIG. 19 illustrates P450RAI2 in 9.0 and 10.5 dpc mouse embyros. (A) 9.0 dpc, lateral view. Specific staining is visible in the eye, and rhombomeres 5 and 6. Diffuse staining is visible where the hind bud is beginning to form. (B) 9.0 dpc, dorsal view. Rhombomeres 5 and 6 show RAI2 expression. (C) 10.5 dpc, lateral view. The otic vesicle and eye are stained. (D) 10.5 dpc, dorsal view. Specific staining is observed in both otic vesicles as well as the hind limb bud. HL: hind limb bud; OV: Otic Vesicle.

Figures 20A, 20B, 20C:
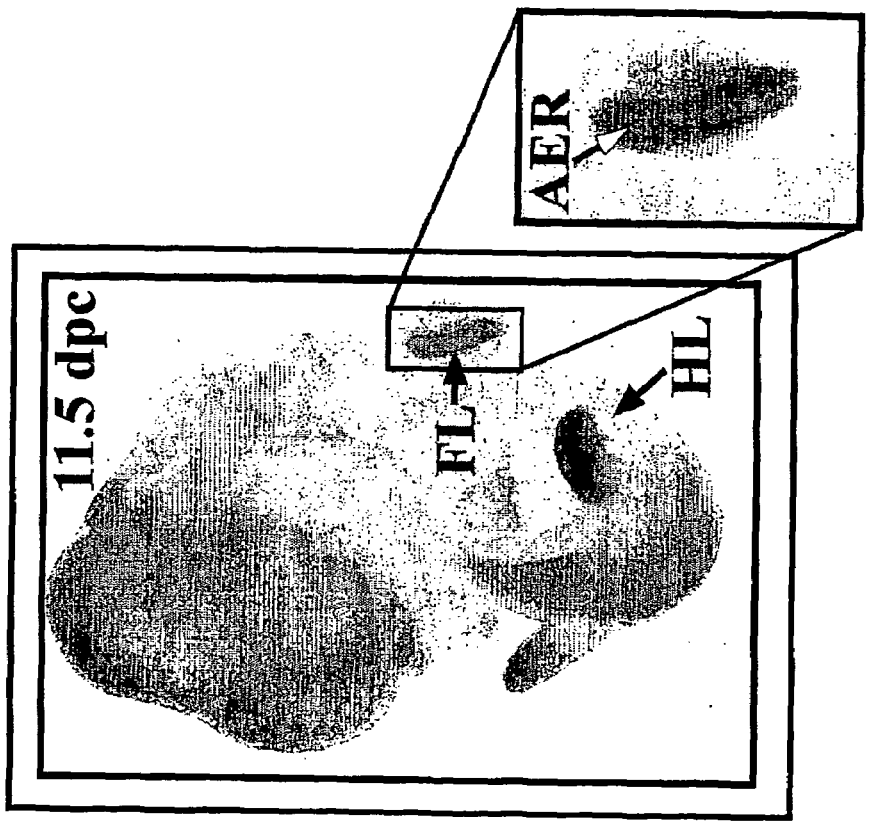
FIG. 20 shows expression of P450RAI2 staining in 11.5 dpc mouse embryo(A) 11.5 dpc, lateral view, staining is visible in both the fore and hindlimb bud. (B) 11.5 dpc, ventral view. Expression of RAI2 in both limb buds (C) Close up of forelimb bud, showing a lack of expression in the apical ectodermal ridge FL: Forelimb bud; HL: Hindlimb bud; AR: Apical Ectodermal Ridge.
Figure 21A:
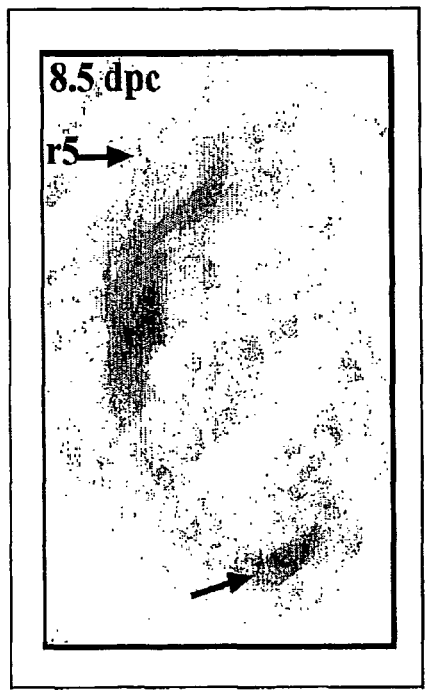
FIG. 21 shows P450RAI2 staining in embryos treated with Retinoic Acid (A) 8.5 dpc, lateral view, staining is observed in rhombomere 5 and the tail mesoderm as indicated by the arrow. (B) 8.5 dpc, dorsal view clearly showing P450RAI2 expression in rhombomere 5. (C) 9.5 dpc, lateral view, expresion of P450RAI2 is observed in rhombomeres 5 and 6, the developing hindlinb, somites and posterior mesoderm. (D) 9.5.dpc, dorsal view, expression is evidenct in rhombomeres 3,5 and 6 and in trunk ectoderm as indicated by the arrow. r: rhombomere,; HL; Limb bud.
Figure 21B:
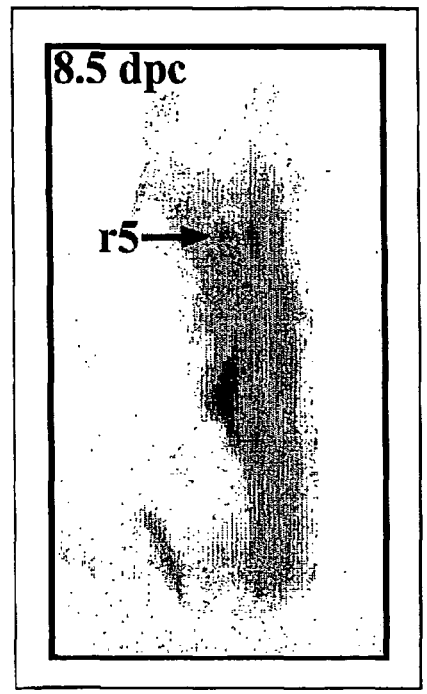
Figure 21C:
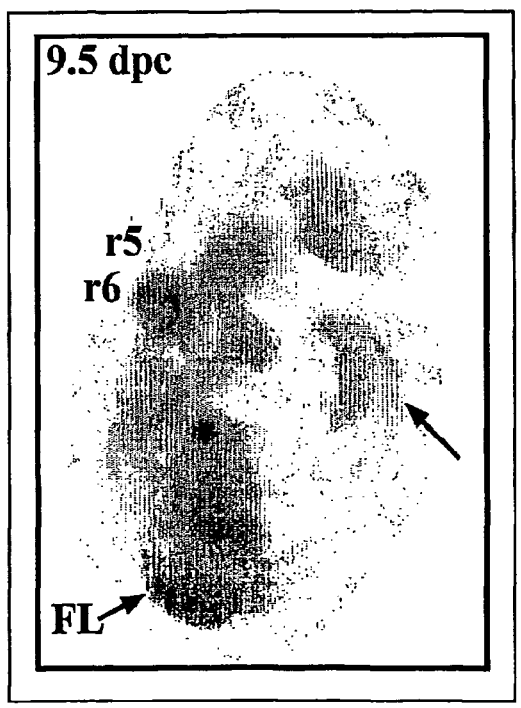
Figure 21D:
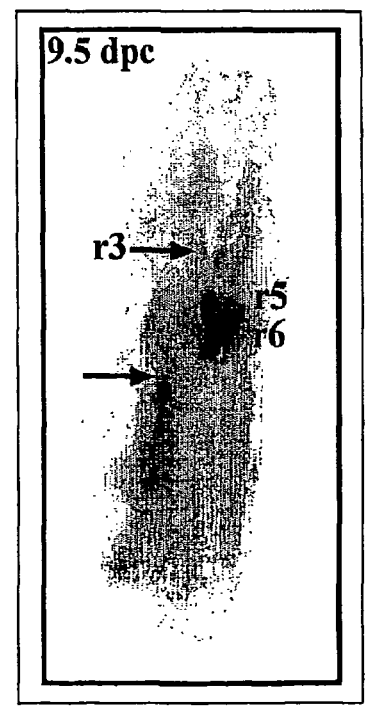

FIG. 20 illustrates P450RAI2 staining in 11.5 dpc mouse embryo(A) 11.5 dpc, laterial view, staining is visible in both the fore and hindlimb bud. (B) 11.5 dpc,ventral view. Expression of P450RA12 in both limb buds (C) Close up of forelimb bud, showing a lack of expression in the apical ectodermal ridge FL: Forelimb bud; HL: Hindlimb bud; AR: Apical Ectodermal Ridge.

FIG. 21 illustrates P450RAI-2 Staining in Embryos Treated with Retinoic Acid (A) 8.5 dpc, lateral view, staining is observed in rhombomere 5 and the tail mesoderm as indicated by the arrow. (B) 8.5 dpc, dorsal view clearly showing P450RAI2 expression in rhombomere 5. (C) 9.5 dpc, lateral view, expression of P450RAI2 is observed in rhombomeres 5 and 6, the developing hindlinb, somites and posterior mesoderm. (D) 9.5 dpc, dorsal view, expression is evidenct in rhombomeres 3,5 and 6 and in trunk ectoderm as indicated by the arrow. r: rhombomere,; HL; Limb bud.

FIG. 22 illustrates P450RAI-2 expression in 11.5 dpc embryos treated with retinoic acid. (A) 11.5 dpc, lateral view, P450RAI2 expression is observed in both the developing hind and fore limb. (B) 11.5 dpc, ventral view, as in embryos untreated with retinoic acid, P450RAI2 expression is not observed in the aptical ectodermal ridge.

Example 9

Assays using Cell Lines Expressing Different P450RAI's

P450RAI-1 and -2 expression plasmids can be used to generate transfected cells. Plasmid vectors such as pcDNA3.1 (Invitrogen, CA) are used to express cDNA of interest in the cells. Cells such as COS-1 or Hela could be used as the host for this purpose. Cells are then exposed to either low concentrations (picomolar) of a radioactive agent (substrate) or higher concentrations (micromolar) of non-radioactive agent (substrate) and the metabolic profile determined (see Example 5 and international patent publication No. WO 97/49815 in which all-trans retinoic acid is a substrate but other retinoid or retinoid type compounds can be used). The time of incubation of the cells can vary from 1 hour to 24 or 48 hours depending on the amount of agent and levels of expression of the protein of interest. The representative metabolite profiles are determined using phase extraction and HPLC. In the case of radioactive substrate B-scintillation counting can also be used if the metabolites produced segregate preferentially into one phase, as in the case of P450RAI-1 and RAI-2 when looking at all-trans retinoic acid metabolism. In comparative testing of potential modulators of P450RAI-1 or P405RAI-2, the modulators could be added to the cells at the same time as the substrate. Specificity of the modulator is determined by examining the degree to which its addition affects either the disappearance of substrate or the production of metabolites.

Example 10

Preparation of Antibodies

Polyclonal Antibodies

Figure 24:
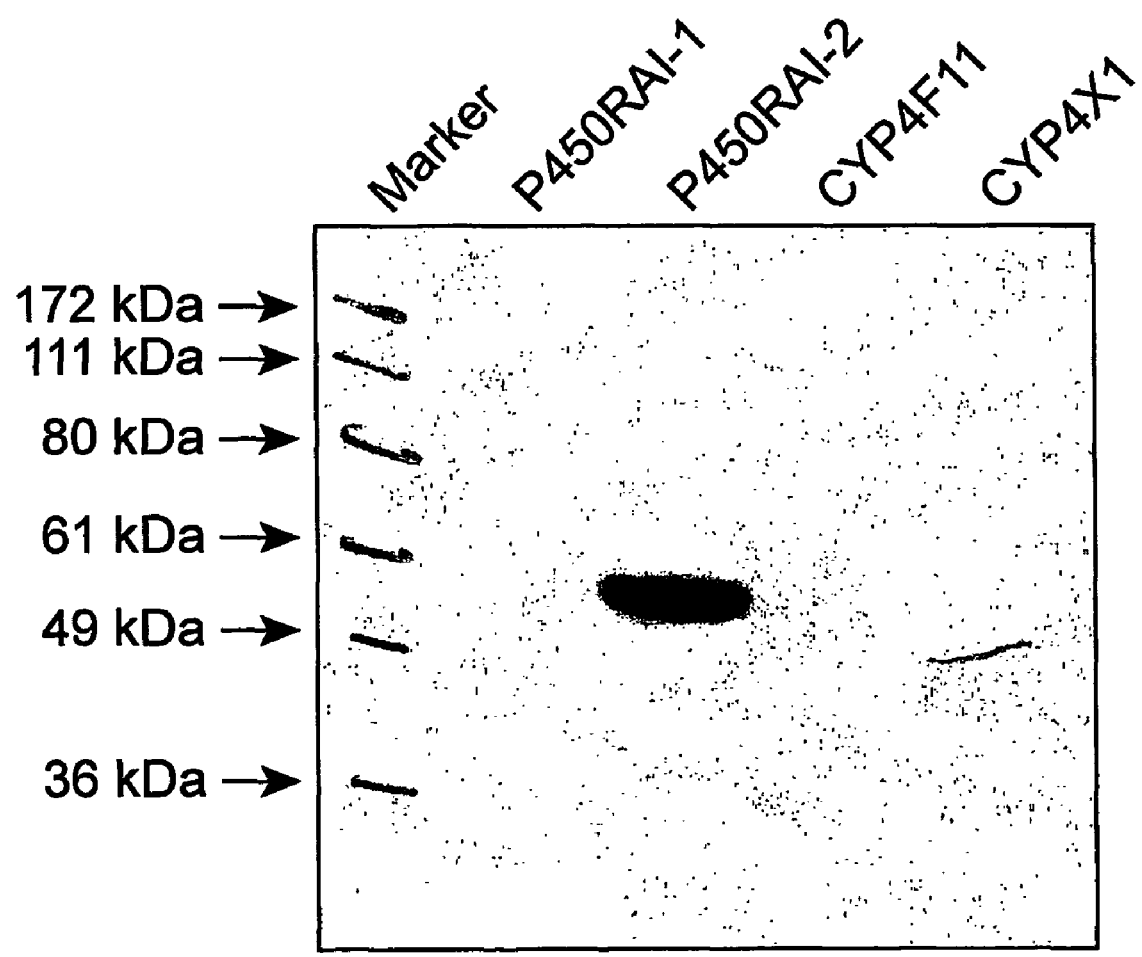
FIG. 24 is an immunoblot indicating P450RAI-2 specificity of the polyclonal antibody made against CYP26B (P450RAI-2) as compared to other cytochromes (CYP26A, CYP4F11, and CYP4X1).

A polyclonal antibody specific to P450RAI-2 was produced using standard methodology outlined herein. Whole cell lysates of Sf9 insect cells expressing his-tagges CYP26A CYP26B, CYP4511 and CYP4X1 were loaded onto a Western gel and probed with primary antibody, polyclonal antiserum 60350 used at a dilution of 1:300. The secondary antibody was HRP conjugated donkey anti-rabbit Ig used at 1:10,000. Results shown in FIG. 24 indicate that the polyclonal antiserum 60350 produced by the present inventors is specific for CYP26B (P450RAI-2) on the immunoblot.

Monoclonal Antibodies

Monoclonal antibodies (Mab's) specific for P450RAI-2 are useful, for example, for diagnostic purposes such as for determining P450RAI-2 protein levels in the identification of normal and tumor tissues which metabolize RA. To produce these antibodies, purified P450RAI-2 protein is prepared. The human P450RAI-2 protein is produced in bacterial cells as a fusion protein with glutathione-S-transferase using the vector pGEX2 (Pharmacia). This permits purification of the fusion protein by GSH affinity chromatography. In another approach, P450RAI-2 is expressed as a fusion protein with the bacterial maltose binding domain. The fusion protein is thus recovered from bacterial extracts by passing the extract over an amylose resin column followed by elution of the fusion protein with maltose. For this fusion construct, the vector pMalC2, commercially available from New England Biolabs, is used. This vector has been used in the past, for example, to overexpress nuclear receptor proteins which were recovered in high yields for functional studies and the production of receptor specific antisera [Ohno, 1993]. The preparation of a second fusion protein is also useful in the preliminary screening of MAb's.

The generation of hybridomas expressing monoclonal antibodies recognizing P450RAI-2 protein is carried out as follows: BALB/c mice are injected intraperitoneally with protein/adjuvant three times at one-month intervals, followed by a final injection into the tail vein shortly prior to cell fusion. Spleen cells are harvested and fused with NS-1 myeloma cells (American Type Culture Collection, Rockville, Md.) using polyethylene glycol 4000 according to standard protocols [Kennett, 1979; Mirski, 1989]. The cell fusion process is carried out as described in more detail below.

The fused cells are plated into 96-well plates with peritoneal exudate cells and irradiated spleen cells from BALB/Ccmice as feeder layers and selection with hypoxanthine, aminopterin, and thymidine (HAT medium) is performed.

An ELISA assay is used as an initial screening procedure. 1–10 μg of purified P450RAI-2 (cleaved from the fusion protein) in PBS is used to coat individual wells, and 50–100 μl per well of hybridoma supernatants is incubated. Horseradish peroxidase-conjugated anti-mouse antibodies are used for the colorimetric assay.

As a secondary screening, cells which exhibit no detectable expression of P450RAI-2 message and no detectable RA metabolizing activity in the absence of retinoic acid, but in which P450RAI-2 exposure to RA induces expression of P450RAI-2, are used.

Positive hybridomas are cloned by limiting-dilution and grown to large-scale for freezing and antibody production. Various positive hybridomas are selected for usefulness in western blotting and immunohistochemistry, as well as for cross reactivity with P450RAI-2 proteins from different species.

The selected MAb's are useful for monitoring the levels of expression of P450RAI-2 protein following RA treatment in cell culture and in tissues. P450RAI-2 protein expression may be a prognostic indicator for determining whether a particular tumor will respond to RA treatment. There is also a wide intersubject variability in baseline RA metabolism and there is evidence suggesting that subjects with a high rate of RA metabolism have a higher incidence of squamous or large cell cancers of the lung [Rigas, 1996]. Once useful antibodies are characterized, these antibodies are used to survey tumor tissue samples for P450RAI-2 expression.

Protocol for Production of Mouse Hybridomas

Fusion

Feeder cells (spleen and peritoneal exudate cells) are plated. 24 to 48 hours before fusion, mouse myeloma cells are taken off drug (8-azaguanine 20 μg/ml) and counted to ensure that there are at least $50 \times 10^6$ cells. 2 g of PEG 4000 are autoclaved in a glass tube for 15 minutes and maintained at 60° C. for use or alternatively stored at room temperature and remelted in a 60° C. water bath when needed.

BALB/c mice are immunized as per desired schedule. The final injection is given intravenously in the tail vein. Fusion of immunized spleen cells is carried out 3 or 4 days after the intravenous injection. Spleen from each animal is collected separately; eye sera for ELISA if desired.

A single cell suspension is prepared using a Teflon pestle and decanting connective tissue. The suspension is washed 1× in serum-free medium. Each spleen has about $10 \times 10^6$ cells. The myeloma cells are collected, counted and washed in serum-free medium.

The cells are then fused. A small beaker of water, and serum-free medium (37° C.) are prepared and the PEG melted at 50–60° C. The immunized spleen cells and myeloma cells are mixed in a 50 ml TC tube (recommended ratios vary from 1:1 to 2:1) and the cells are washed once with serum-free medium. The supernatant is carefully discarded. 2.4 ml pre-warmed serum-free medium is added immediately with pipette to the melted PEG and mixed, maintaining the temperature at 37° C. in beaker of warm water. The PEG should be light pink. If it is yellow, another aliquot should be used. 0.5–1.0 ml of PEG is added dropwise to the cell pellet over 1 minute with gentle rotation of the tube or gentle stirring to ensure mixing. The tip of the addition pipette is placed directly over the cell pellet. The tube is swirled gently in 37° C. water bath for 90 seconds with the blunt end of a 3 ml pipette tip and 10 ml warm serum-free medium added slowly over 6–10 minutes while rotating tube gently to bring the volume up to 20–50 ml. The tube is maintained at 37° C. for at least 20 minutes to obtain cell fusion and then the cells are washed 2× with serum-free medium. The cells are centrifuged and gently resuspended in 100 ml of pre-warmed medium +10–20% PBS. 100 μl/well aliquotted in 96-well plates. Assuming one spleen fused with $100 \times 10^6$ cells myeloma fusion partner, about 10 plates are needed. On the following day, 100 μl medium is removed and 100 μl 2×HAT added. Feed with 1×HAT medium for 1 to 3 weeks, then feed with HT medium (i.e., remove ½ HAT medium and replace with equal volume HT medium).

Preparation of Peritoneal Exudates and Spleen Feeder Cells

A sacrificed mouse is sprayed with 70% alcohol, skin is nicked and torn apart, with care being taken not to cut the peritoneum. The peritoneum is lifted with forceps and a needle is introduced; 5 ml of serum-free medium is slowly injected. The abdomen is massaged and the fluid is slowly sucked up, collected in a sterile tube and kept on ice. The volume is brought up to 5 ml. The spleen is obtained and placed in a sterile tube containing serum-free medium. The spleen is gently mashed with a sterile Teflon pestle. Clumps are allowed to settle and the cells are decanted into a clean tube, care being taken to avoid including connective tissue, in order to minimize fibroblast growth. The sample is irradiated at 4500 R. Cells are washed once with serum-free medium, placed into 96-well plates [one spleen/10 plates (approximately $2–5 \times 10^5$ cells/well) and peritoneal exudate cell suspension (PECS) ($<3 \times 10^3$ cells/well) in a total volume of 100 μl/well] and incubated at 37° C. until ready to be used. They can also be stored in sterile tube overnight at 4° C.

Example 11

Expression of P450RAI-2 and P450RAI-1 In Normal and Tumour Lung Cells

Materials and Methods

The RNA from human lung samples, both normal and tumour (non-small cell cancer), were generously donated by Dr. Tsai from the Ontario Cancer Institute, Toronto, Canada. The RNA was received in 100% ethanol. The RNA was precipitated using standard protocols, resuspended in DEPC-treated water and stored at −70° C. until use.

The RNA samples were analyzed spectrophotometrically (260/280 ratios) (BeckmanDU 640 Spectrophotometer, USA), and the RNA (1 μg per sample) was run on an RNA formaldehyde gel withsthidium bromide to visualize the 18S and 28S bands, using a ChemiImager 4000 and Multi Image™ Light Cabinet (Alpha Innotech Corp., USA).

RT-PCT was initially attempted using the Thermoscript RT kit, followed by PCR according to standard lab conditions; however, results were inconsistent and unsuccessful with this method. RT-PCR was successfully conducted using the TIATANIUM™ Step RT-PCR Kit (CLONETECH Laboratories, Inc., CA, USA) and a Mastercycler™ gradient Thermo Cycler (Eppendorf Scientific, Inc. Westbury, N.Y., USA) Total RNA (0.5 µg) was reverse transcribed at 50° C. for 1 hour and PCR amplification of entire cDNA conducted accoding tot he kit, in a total volume of 25 µl. 45 picomoles of primer pairs specific for human P450 CYP26A1 (5'-GGC TGC CTC TCT AAC CTG CAC-3 (SEQ. ID. NO. 42); 5'GAT CAG AGA TOT GGC TGC TGC ACT G-3' (SEQ. ID. NO. 43))and human P450 CYP26B1 (SEQ. ID. NOs. 41 and 38, although SEQ. ID. NO. 37 can be used also in place of SEQ. ID. NO. 41); human P450 CYP26C1 (5'-GCA AGG GAC CAG CTG CAT COG CAC CTG-3 (SEQ. ID. NO. 44); 5'-CTC GTG COT GTC CCG GAT GCT ATA C-3' (SEQ. ID. NO. 45) and an alternative antisence primer containing the 8F exon 5'GGA ATG GGC TAT GCC TCT GA-3' (SEQ. ID. NO. 46) and human β-actin (5'ATC TGG CAC CAC ACC TTC TAC AAT GAG CTG CG-3' (SEQ. ID. NO. 47), 5'CGT CAT ACT CCT GCT TGC TGA TCC ACA TCT GC-3' (SEQ. ID. NO. 48) (Takizawa et al, Am. J. Respir. Crit. Care Med.163, 1476–1483); were used to yield 550 bp, 450 bp, 555 bp, 850 bp and 800 bp approximated sized cDNA products, respectively.

RNA from human breast cancer cell line, MCF-7, treated with DMSO alone or retinoic acid in DMSo was used as a positive control, in addition to the mouse liver RNA and mouse β-actin primers supplied with the kit. PCR was performed at 94° C. for 5 min. followed by 35 cycles of 99° C. for 30 sec., 65° C. for 30 sec., and 72° C. for 1 min., with a final 72° C. extension for 5 min. The amplified cDNA fragments were separated on a 1% agarose gel containng ethidium bromaide, and visualized using a ChemiImager 4000 and Multi Image™ Light Cabinet (Alpha Innotech Corp.,USA).

The RT-PCR products (5 µL/sample) were run on 1% agarose gels for use in Sothern blotting to confirm product. The gels were soaked in ethidium bromide/1×TAE solution for 10 minutes prior to transfer setup to allow cisulaization of DNA, Alkaline southern blotting was conducted using a downward capillary action setup with a sponge soaked in the alkaline 0.4 M NaOH transfer solution and transfer run overnight. After disassembly, the gels were visualized to ensure complete transfer occurred. The blots were soaked in 2×SSC, and let to dry at 80° C. for 2 hours; blots were wrapped and stored at 4° C. until use.

Full length DNA probes for CYP26A1 AND CYP26B1 AND CYP26C1 were radioactively labeled using the Prime-A-Gene kit Stratagene). Prehybridization and hybridization of the blots was done using the QuickHyb™ Hybridization Solution exposed using the Storm PhophoImager system (molecular Dynamics, USA); blots were also exposed radiographically with X-OMAT film with similar results.

Figure 23:
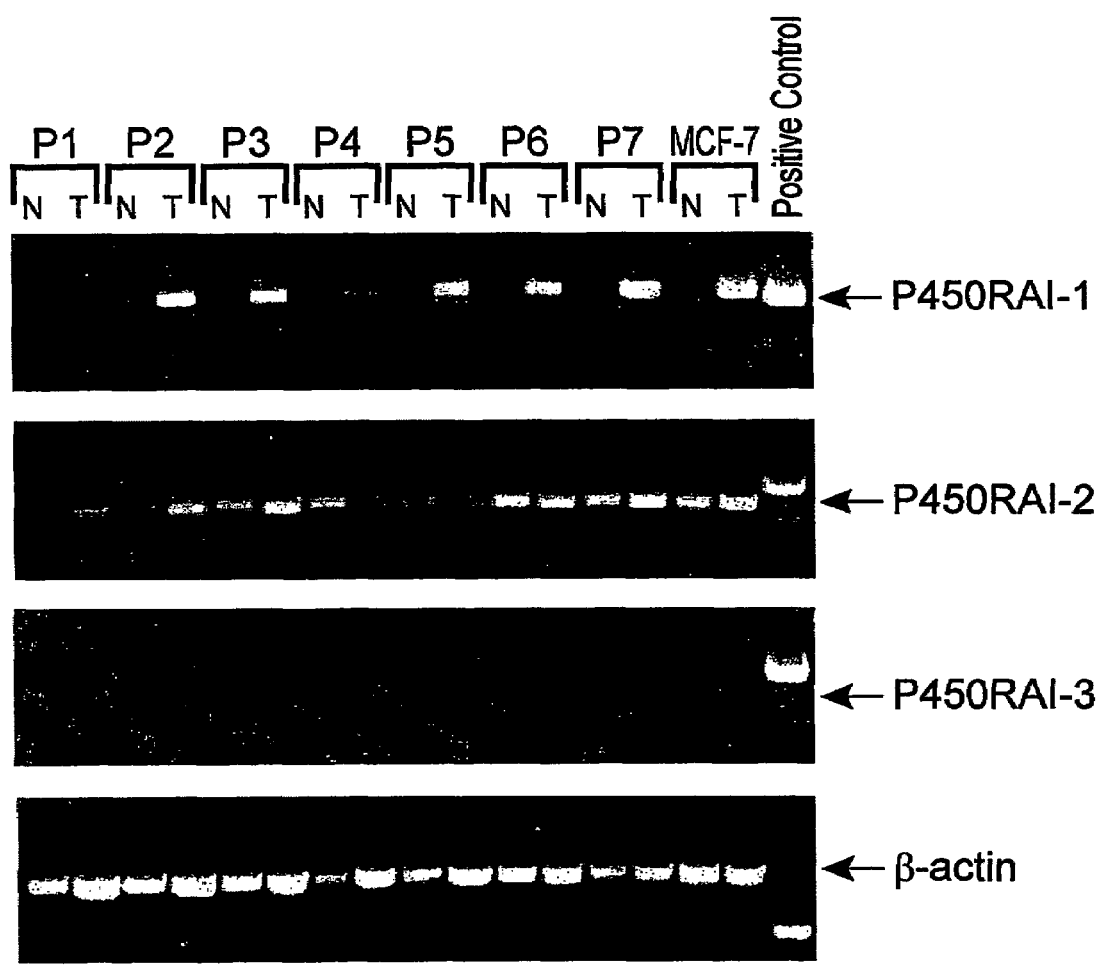
FIG. 23 shows P450RAI2 (CYP26B), P450RAI-1 (CYP26A) and P450RAI-3 (CYP26C) expression in normal (N) and tumour (T) lung tissue. B-actin is a control.

The results can be seen in FIG. 23. The results from the same normal and tumour lung tissue from seven patients can be seen. CYP26B1 (P450RAI-2) can be seen in both normal and tumour tissue. However, the tumour tissue appears to have increased levels of CYP 26B 1 expression compared to the normal tissue. The MCF-7 RNA expressed Cyp26B1 in DMSO alone and increased levels in the reinoic acid in DMSO treated cells, as was expected.

CYP26A1 was not or minimal expressed in normal lung tissue but there was strong induction in tumour tissue. The MCF-7 RNA with DMSo alone does not express P450 CYP26A1 while the MCF-7 RNA treated with reinoic acid in DMSO had strongly induced expression of CYP26A1, as expected.

There did nt appear to be any expression of Cyp26C in either normal or tumour luing tissue.

β-actin was chosen as an internal control housekeeping gene, since previous studies indicated that this was a more stable control for the experimental system. As can be seen from the figure, β-actin was uniform for all samples, indicating that the changes in CYP26 expression levels observed were true.

The southern blots (not shown) did indicate that that the amplified products for CYP26A1 and CYP26B 1 wre indeed the specific SYP26 targets.

Thus, these results indicate that P450RAI-1 and P450RAI-2 may be involved in lung cancer and inhibitors or antagonists of these cytochromes may be beneficial in the treatment of lung cancer. Further, screening tissue for P450RAI-1 and P450RAI-2 expression may assist in the diagnosis and potential early detection of lung cancer orpotential thereof.

Example 12

Expression of P450RAI-2 and P450RAI-2 In Retina and Breast Cancer Cells

Figure 25:
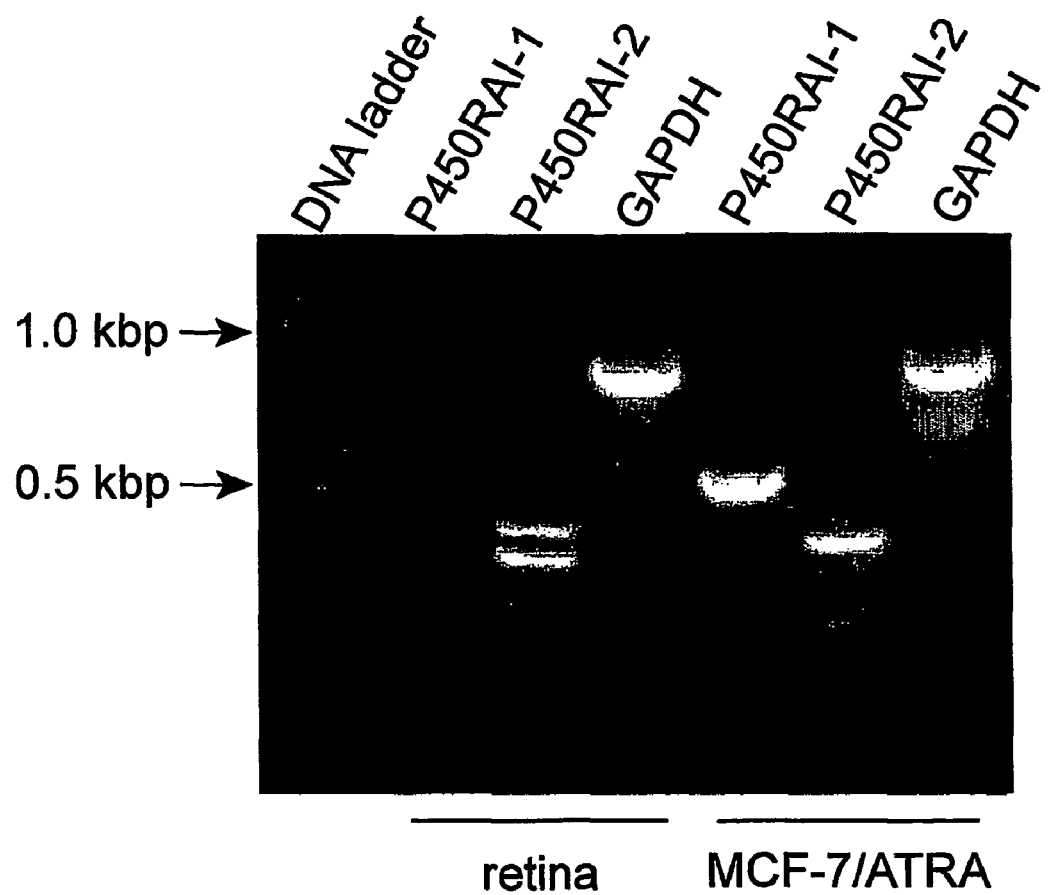
FIG. 25 shows the RT-PCR assay of CYP26A (P450RAI-1) and CYP26B (P450RAI-2) expression in human retina and MCF-7 cells.

1 µg of total RNA was RT-PCR amplified (35 cycles) in the rpesence of primers specific for human CYP26A, human 26B (SEQ. ID. NOs. 37 ro 38) or huma GAPDH, respectively. PCR products were then fractionated on 1.6% agarose gel and cisualized by ethidium bromaide staining. Following products were expected: 0.55 kpb CYP26A fragment, 0.45 kbp CYPSB fragment and 0.95 kBN GAPDH fragment. One can see in FIG. 25 the expression of P450RAI-2 (CYP26B) in human retina and MCF-7 cells.

Example 13

Screening Potential Modulators of P450RAI-2

Antisense nucleic acids or oligonucleotides (RNA or preferably DNA) that inhibit cellular RA-induced P450RAI-2 production can be used to inhibit metabolism of RA by P450RAI-2 [Monia, 1996]. Antisense oligonucleotides, typically 15 to 20 bases long, bind to the sense mRNA or pre mRNA region coding for the protein of interest, which can inhibit translation of the bound mRNA to protein. The cDNA sequence encoding human P450RAI-2 can thus be used to design a series of oligonucleotides which together span a large portion, or even the entire cDNA sequence. These oligonucleotides can be tested to determine which provides the greatest inhibitory effect on the expression of the protein [Stewart, 1996]. This can be done by exposing cells to the various oligonucleotides and measuring subsequent changes in human P450RAI-2 activity or by using antibodies to screen for inhibition of P450RAI-2 synthesis. The most suitable mRNA target sites include 5'- and 3'-untranslated regions as well as the initiation codon. Other regions might be found to be more or less effective. Alternatively, an antisense nucleic acid or oligonucleotide may bind to P450RAI-2 DNA coding or regulatory sequences.

Rather than reducing RA metabolism by inhibiting P450RAI-2 gene expression at the nucleic acid level, activity of the P450RAI-2 protein may be directly inhibited by binding to an agent, such as, for example, a suitable small molecule or a monoclonal antibody.

The present invention thus includes a method of screening drugs for their effect on activity (i.e., as a modulator, preferably an inhibitor) of a retinoic acid inducible protein. The method includes exposing the protein to a prospective inhibitor (or modulating) drug and determining the effect on protein activity. The measured activity might be hydroxylation of a retinoid, particularly all-trans retinoic acid, or hydroxylation of a retinoic acid, particularly all-trans retinoic acid, at the 4 position of the β-ionone ring thereof. For screening drugs for use in humans, P450RAI-2 itself is particularly useful for testing the effectiveness of such drugs. Prospective drugs could also be tested for inhibition of the activity of other P450 cytochromes, which are desired not to be inhibited. In this way, drugs which selectively inhibit P450RAI-2 over other P450s could be identified.

Another system for screening for potential modulators, preferably inhibitors, of a P450RAI-2 protein includes a stably transfected cell line having incorporated therein DNA of a reporter gene (e.g., β-galactosidase, firefly luciferase, or the like) and of the P450RAI-2, in which expression of both genes is inducible by exposure of the cells to RA. Expression of the reporter gene provides a measure of the induction of the expression system and therefore provides an indication of the amount of RA present. Exposure of the cells to RA leads to RA metabolism and, with time, such metabolism leads to a decrease in the degree of induction which is indicated by the reporter protein. Exposure of the cells to RA in the presence of an agent that inhibits P450RAI-2 metabolism of RA results in decreased RA metabolism, whereas exposure of the cells to RA in the presence of an agent that does not inhibit P450RAI-2 metabolism of RA has no effect on RA metabolism. A comparison of expression of the reporter gene in the presence of RA alone and in the presence of both RA and a potential inhibitory drug thus gives a measure of the effectiveness of the drug in inhibiting metabolism of RA by the P450RAI-2 protein.

One system for screening for potential inhibitors of a P450RAI-2 protein includes a cell line in which the endogenous P450RAI-2 gene is not present or not functional or not expressed. In this cell line, a cytochrome P450RAI-2 expression vector and an RA-inducible reporter gene are incorporated such that exposure of the cell line to RA results in metabolism of RA by the expressed P450RAI-2 protein and a degree of induction of the reporter gene based on remaining active RA. The addition of an inhibitor of P450RAI-2 will decrease the rate of metabolism/degradation of RA and therefore increase the activation/induction of the RA sensitive reporter gene.

Another system for screening of potential inhibitors (or other modulators) using the same cell line would be to add radioactive substrate to the cells along with the potential inhibitors (or modulators). Addition of the radioactive substrate, which could be all-trans retinoic acid, causes the production of radioactive metabolites. Using a phase extraction procedure, such as that described herein, the amount of these metabolites can be measured. The addition of an inhibitor will cause a decrease in the generation of the radioactive metabolites, which can be measured using β-scintillation counting or HPLC.

The invention thus provides a system for screening potential inhibitors of RA catabolism by a P450RAI-2 protein. The system includes a transfected cell line having incorporated therein DNA of a reporter gene, for example the luciferase gene exemplified above, in which expression of the reporter gene is inducible by exposure of the cells to RA. In this system, the P450RAI-2 gene is omitted, that is the reporter gene is under the control of the native promoter for the P450RAI-2 gene. Expression of the reporter gene provides a measure of the induction of the expression system and therefore provides an indication of the amount of mRNA produced in response to exposure of the cells to RA. Exposure of the cells to RA in the presence of an agent that inhibits induction of the expression system indicates that the agent is a potential inhibitor of RA catabolism, i.e., provides a measure of the effectiveness of the agent as a drug in inhibiting the expression of P450RAI-2 gene and thus metabolism of RA.

There is the possibility that cellular retinoic acid-binding protein (CRABP) [Adamson, 1993] is involved in binding of a retinoid substrate to a P450RAI-2 protein of the present invention. The effect of the presence of CRABP, derivatives, synthetic fragments or analogs thereof could thus be determined according to screening methods of the present invention; effectiveness of such agents in enhancing RA metabolism can also be determined.

The present invention allows the skilled artisan to prepare bispecific antibodies and tetrameric antibody complexes. Bispecific antibodies can be prepared by forming hybrid hybridomas [Staerz, 1986a &b].

The present invention includes three types of compounds related to retinoids: those that inhibit enzymatic activity of P450RAI-2, thereby inhibiting metabolism of RA; those retinoids that evade metabolism by P450RAI-2; and those compounds that repress induction of P450RAI-2 gene expression.

Compositions of the invention are administered to subjects in a biologically compatible form suitable for pharmaceutical administration in vivo. By "biologically compatible from suitable for administration in vivo" is meant a form of the composition to be administered in which any toxic effects are outweighed by the therapeutic effects of the composition. The term "subject" is intended to include living organisms in which a desired therapeutic response can be elicited, e.g. mammals. Examples of subjects include human, dogs, cats, mice, rats and transgenic species thereof. Administration of a therapeutically active amount of the therapeutic compositions of the present invention is defined as an amount effective, at dosages and for periods of time necessary to achieve the desired result. For example, a therapeutically active amount of a compound that inhibits catabolism of RA by a P450RAI-2 protein may vary according to factors such as the disease state, age, sex, and weight of the individual, as well as target tissue and mode of delivery. Dosage regimes may be adjusted to provide the optimum therapeutic response. For example, several divided doses may be administered daily or the dose may be proportionally reduced as indicated by the exigencies of the therapeutic situation.

Compounds of the present invention, such as those that are found to inhibit metabolism of RA by P450RAI-2 enzymes and that are useful as anticancer agents and in the treatment, amelioration, or prevention of skin disorders for which retinoic acid is useful, for example, may be used topically. In this regard they may be included in compositions for therapy in animals, including humans, for premalignant epithelial cell lesions, as a prophylaxis against tumor promotion in epithelial cells and treatment for dermatoses such as ichthyoses, follicular disorders, benign epithelial disorders, and other proliferative skin diseases, such as acne, psoriasis, eczema, atopic dermatitis, nonspecific dermatitis and the like.

Topical compositions are usually formulated with a pharmaceutically acceptable carrier in liquid, semi-solid or solid form. A pharmaceutically acceptable carrier is a material that is nontoxic and generally inert and does not affect the functionality of the active ingredients adversely. Such materials are well known and include those materials sometimes referred to as diluents or vehicles (excipients) in the pharmaceutical formulation arL The carrier may be organic or inorganic in nature. Examples of pharmaceutically acceptable carriers are water, gelatin, lactose, starch, mineral oil, cocoa butter, dextrose, sucrose, sorbitol, mannitol, gum, acacia, alginates, cellulose, talc, magnesium stearate, polyoxyethylene sorbitan monolaurate, and other commonly used pharmaceutical carriers. In addition to an active ingredient and carrier, the formulation may contain minor amounts of additives such as flavoring agents, coloring agents, thickening or gelling agents, emulsifiers, wetting agents, buffers, stabilizers, and preservatives such as antioxidants.

Certain compositions may be administered enterally. For oral administration, suitable forms are, for example, tablets, pills, syrups, suspensions, emulsions, solutions, powders and granules.

As anti-tumor agents or as part of an anti-tumor formulation, for example, compounds of the present invention can be used in a similar manner to retinoids used for treating various tumours, such as all-trans retinoic acid. The dose to be administered, whether a single dose, multiple does or daily dose, will of course vary with the particular compound employed because of the varying potency of the active ingredient, the chosen route of administration, the size of the recipient, the type of tumor, and the nature of the patient's condition. The dosage to be administered is not subject to definite bounds, but it will usually be an effective amount, or the equivalent on a molar basis of the pharmacologically active free form produced from a dosage formulation upon the metabolic release of the active drug to achieve its desired pharmacological and physiological effects. An oncologist sldlled in the art of cancer treatment will be able to ascertain without undue experimentation, appropriate protocols for the effective administration of the compounds of this present invention.

Nucleic acids which encode proteins having biological activity of a P450RAI-2 protein can be used to generate either transgenic animals or "knock out" animals which, in turn, are useful in the development and screening of therapeutically useful reagents. A transgenic animal (e.g., a mouse) is an animal having cells that contain a transgene, which transgene was introduced into the animal or an ancestor of the animal at a prenatal, e.g., an embryonic stage. A transgene is a DNA which is integrated into the genome of a cell from which a transgenic animal develops. In one embodiment, a human P450RAI-2 cDNA, comprising the nucleotide sequence shown in SEQ ID NO:4, or an appropriate variant or subsequence thereof, can be used to generate transgenic animals that contain cells which express human P450RAI-2 protein. Methods for generating transgenic animals, particularly animals such as mice, have become conventional in the art are described, for example, in U.S. Pat. Nos. 4,736,866 and 4,870,009. In a preferred embodiment, plasmids containing recombinant molecules of the invention are microinjected into mouse embryos. In particular, the plasmids are microinjected into the male pronuclei of fertilized one-cell mouse eggs; the injected eggs are transferred to pseudo-pregnant foster females; and, the eggs in the foster females are allowed to develop to term. [Hogan, 1986]. Alternatively, an embryonal stem cell line can be transfected with an expression vector comprising nucleic acid encoding a protein having P450RAI-2 activity, and cells containing the nucleic acid can be used to form aggregation chimeras with embryos from a suitable recipient mouse strain. The chimeric embryos can then be implanted into a suitable pseudopregnant female mouse of the appropriate strain and the embryo brought to term. Progeny harboring the transfected DNA in their germ cells can be used to breed uniformly transgenic mice.

Typically, particular cells would be targeted for P450RAI-2 transgene incorporation by use of tissue specific enhancers operatively linked to the P450RAI-2 encoding gene. For example, promoters and/or enhancers which direct expression of a gene to which they are operatively linked preferentially in cardiac muscle cells can be used to create a transgenic animal which expresses a P450RAI-2 protein preferentially in cardiac muscle tissue. Examples of suitable promoters and enhancers include those which regulate the expression of the genes for cardiac myosin and cardiac actin. Transgenic animals that include a copy of an P450RAI-2 transgene introduced into the germ line of the animal at an embryonic stage can also be used to examine the effect of increased P450RAI-2 expression in various tissues.

The pattern and extent of expression of a recombinant molecule of the invention in a transgenic mouse is facilitated by fusing a reporter gene to the recombinant molecule such that both genes are co-transcribed to form a polycistronic mRNA. The reporter gene can be introduced into the recombinant molecule using conventional methods such as those described in Sambrook et al., [Sambrook,1989]. Efficient expression of both cistrons of the polycistronic mRNA encoding the protein of the invention and the reporter protein can be achieved by inclusion of a known internal translational initiation sequence such as that present in poliovirus mRNA. The reporter gene should be under the control of the regulatory sequence of the recombinant molecule of the invention and the pattern and extent of expression of the gene encoding a protein of the invention can accordingly be determined by assaying for the phenotype of the reporter gene. Preferably the reporter gene codes for a phenotype not displayed by the host cell and the phenotype can be assayed quantitatively. Examples of suitable reporter genes include IacZ ($-galactosidase), neo (neomycin phosphotransferase), CAT (chloramphenicol acetyltransferase) dhfr (dihydrofolate reductase), aphIV (hygromycin phosphotransferase), lux (luciferase), uidA ($-glucuronidase). Preferably, the reporter gene is lacZ which codes for $-galactosidase. $-galactosidase can be assayed using the lactose analogue X-gal (5-bromo-4-chloro-3-indolyl-b-D-galactopyranoside) which is broken down by $-galactosidase to a product that is blue in color [Old].

Although experimental animals used in the preferred embodiment disclosed are mice, the invention should not be limited thereto. It can be desirable to use other species such as, for example, rats, hamsters, rabbits and sheep.

The transgenic animals of the invention can be used to investigate the molecular basis of RA metabolism. The transgenic animals of the invention can also be used to test substances for the ability to prevent, slow or enhance RA metabolism. A transgenic animal can be treated with the substance in parallel with an untreated control transgenic animal.

Cells from the transgenic animals of the invention can be cultured using standard tissue culture techniques. In particular, cells carrying the recombinant molecule of the invention can be cultured and used to test substances for the ability to prevent, slow or enhance RA metabolism.

Additionally, the non-human homologs of genes encoding proteins having P450RAI-2 activity can be used to construct a "knock out" animal which has a defective or altered P450RAI-2 gene. For example, with established techniques, a portion of murine genomic P450RAI-2 DNA (e.g., an exon), can be deleted or replaced with another gene, such as a gene encoding a selectable marker which can be used to monitor integration. The altered P450RAI-2 DNA can then be transfected into an embryonal stem cell line. The altered P450RAI-2 DNA will homologously recombine with the endogenous P450RAI-2 gene in certain cells and clones containing the altered gene can be selected. Cells containing the altered gene are injected into a blastocyst of an animal, such as a mouse, to form aggregation chimeras as described for transgenic animals. Chimeric embryos are implanted as described above. Transmission of the altered gene into the germline of a resultant animal can be confirmed using standard techniques and the animal can be used to breed animals having an altered P450RAI-2 gene in every cell [Lemoine, 1996]. Accordingly, a knockout animal can be made which cannot express a functional P450RAI-2 protein. Such a knockout animal can be used, for example, to test the effectiveness of an agent in the absence of a P450RAI-2 protein.

The antisense nucleic acids and oligonucleotides of the invention are useful for inhibiting expression of nucleic acids (e.g. mRNAs) encoding proteins having P450RAI-2 activity. Since proteins having P450RAI-2 activity are associated with metabolism of agents which can act on the cell, e.g., RA, decreasing expression of such proteins can increase sensitivity of the cell to such agents. Antisense nucleic acids can be introduced into a drug resistant cell in culture to inhibit P450RAI-2 expression. One or more antisense nucleic acids, such as oligonucleotides, can be added to cells in culture media, typically, for example, at 200 µg/ml.

The antisense nucleic acids of the invention, or oligonucleotides thereof, can thus be used in gene therapy to correct or prevent retinoic acid or other retinoid resistance in a subject. For example, antisense sequences can be used to render retinoic acid or other retinoid resistant malignant cells sensitive to chemotherapeutic agents. Administration of antisense nucleic acids to a subject may be most effective when the antisense nucleic acid is contained in a recombinant expression vector which allows for continuous production of antisense RNA. Recombinant molecules comprising an antisense nucleic acid or oligonucleotide thereof, can be directly introduced into tissues, including lung tissue in vivo, using delivery vehicles such as liposomes, retroviral vectors, adenoviral vectors and DNA virus vectors. A delivery vehicle can be chosen which can be targeted to a cell of interest in the subject (e.g. a retinoid resistant tumor cell). Antisense nucleic acids can also be introduced into isolated cells, such as those of the haematopoietic system, ex vivo using viral vectors or physical techniques such as microinjection and electroporation or chemical methods such as coprecipitation and incorporation of DNA into liposomes, and such cells can be returned to the donor. Recombinant molecules can be delivered in the form of an aerosol or by lavage.

Accordingly, the invention provides a method for inhibiting retinoic acid or other retinoid resistance of a resistant cell by introducing into the resistant cell a nucleic acid which is antisense to a nucleic acid which encodes the protein identified as SEQ ID NO:5.

The nucleic acids of the invention can further be used to design ribozymes which are capable of cleaving a single-stranded nucleic acid encoding a protein having P450RAI-2 activity, such as an mRNA. A catalytic RNA (ribozyme) having ribonuclease activity can be designed which has specificity for a P450RAI-2-encoding mRNA based upon the sequence of a nucleic acid of the invention. For example, a derivative of a Tetrahymena L-19IVS RNA can be constructed in which the base sequence of the active site is complementary to the base sequence to be cleaved in a P450RAI-2-encoding mRNA. [Cech a and b]. Alternatively, a nucleic acid of the invention could be used to select a catalytic RNA having a specific ribonuclease activity from a pool of RNA molecules [Bartel, 1993].

The isolated nucleic acids and antisense nucleic acids of the invention can be used to construct recombinant expression vectors as described previously. These recombinant expression vectors are then useful for making transformant host cells containing the recombinant expression vectors, for expressing protein encoded by the nucleic acids of the invention, and for isolating proteins of the invention as described previously. The isolated nucleic acids and antisense nucleic acids of the invention can also be used to construct transgenic and knockout animals as described previously.

The isolated proteins of the invention are useful for making antibodies reactive against proteins having P450RAI-2 activity, as described previously. Alternatively, the antibodies of the invention can be used to isolate a protein of the invention by standard immunoaffinity techniques. Furthermore, the antibodies of the invention, including bispecific antibodies are useful for diagnostic purposes.

Molecules which bind to a protein comprising an amino acid sequence shown in SEQ ID NO:5 can also be used in a method for killing a cell which expresses the protein, wherein the cell takes up the molecule. Preferably, the cell is a tumor cell. Destruction of such cells can be accomplished by labeling the molecule with a substance having toxic or therapeutic activity. The term "substance having toxic or therapeutic activity" as used herein is intended to include molecules whose action can destroy a cell, such as a radioactive isotope, a toxin (e.g. diphtheria toxin or ricin), or a chemotherapeutic drug, as well as cells whose action can destroy a cell, such as a cytotoxic cell. The molecule binding to the P450RAI-2 can be directly coupled to a substance having a toxic or therapeutic activity or may be indirectly linked to the substance. In one example, the toxicity of the molecule taken up by the cell is activated by P450RAI-2 protein.

The invention also provides a diagnostic kit for identifying tumor cells comprising a molecule which binds to a protein comprising an amino acid sequence shown in SEQ ID NO:5, for example, for incubation with a sample of tumor cells; means for detecting the molecule bound to the protein, unreacted protein or unbound molecule; means for determining the amount of protein in the sample; and means for comparing the amount of protein in the sample with a standard. Preferably, the molecule is a monoclonal antibody. In some embodiments of the invention, the detectability of the molecule which binds to P450RAI-2 is activated by said binding (e.g., change in fluorescence spectrum, loss of radioisotopic label). The diagnostic kit can also contain an instruction manual for use of the kit.

The invention further provides a diagnostic kit for identifying tumor cells comprising a nucleotide probe complementary to the sequence, or an oligonucleotide fragment thereof, shown in SEQ ID NO:4, for example, for hybridization with mRNA from a sample of tumor cells; means for detecting the nucleotide probe bound to mRNA in the sample with a standard. The diagnostic kit can also contain an instruction manual for use of the kit.

Discussion of Results

The present inventors have have identified a novel retinoic acid metabolizing cytochrome P450. Consequently, at least two genes, encoding all-trans-RA metabolizing enzymes P450RAI-1 [White, J. A., et al. (1997), White, J., et al. (1998)] and P450RAI-2 are expressed in humans. The predicted amino acid sequences of these enzymes (P450RAI-1 and P450RAI-2) are 42% similar overall. Regions corresponding to functional domains such as those for heme binding and putative substrate binding exhibit the highest degrees of similarity. P450RAI-1 and -2 are also conserved across species from zebrafish to humans suggesting that these enzymes may be functionally distinct [White, J. A., et al. (1997), Nelson, D. (1999); White, J. A. et al. (1996)]. The genomic structures of these two genes are quite distinct-, P450RAI-1 is comprised of 7 exons while P450RAI-2 has 6 and there is no clear evidence of conserved intron/exon boundaries between the two genes [White, J., et al. (1998); Nelson, D. (1999)], These data support the possibility that these genes diverged from a common ancestral gene prior to the emergence of mammals.

P450RAI-2 can metabolize all-trans-RA with efficiency comparable to that of P450RAI-1. HPLC analysis comparing these enzymes reveals their striking similarities with respect to conversion of all-trans-RA into 4-OH— and 4-oxo RA and characteristic secondary products. Moreover, P450RAI-1 and P450RAI-2 share surprisingly similar specificities for retinoids as determined by our competition studies. The all-trans metabolite of RA is clearly the preferred substrate for both enzymes with a rank- order of: all-trans-RA>9 cis RA>13 cis. Other retinoids such as retinol and retinaldehyde are very poor competitors suggesting that they are unlikely to be natural substrates for these enzymes under normal physiological conditions. This is in contrast to a recent report suggesting that P450RAI (CYP26A) may be involved in the activation step of retinol [Lane, M., et al. (1999)]. These similarities would suggest that, at least with respect to metabolic activity, these enzymes may be equivalent. Although this is somewhat surprising given their differences in sequence, there are many RA binding proteins—RARs, RXRs, CRABPs—which are widely different in primary amino acid sequences. It is possible that the differences in sequence reflect differences in the abilities of these enzymes to interact with other proteins such as CRABPs which have been proposed to modify all-transRA metabolic activities in cells [Boylan, J. & Gudas, L. (1992); Napoli, J. (1996)].

Although the enzymatic activities of P450RAI-1 and -2 may be similar, it appears that their tissue specific expression is not. Tissue dot blot and northern blot analyses indicate that in the adult, P450RAI-2 is broadly expressed at low levels in most tissues but is predominantly expressed in brain tissues, notably pons and cerebellum. P450RAI-1, on the other hand, does not show appreciable expression in any of the human brain tissues evaluated. During development numerous studies have indicated that the role of P450RAI-1 is to regulate local levels of all-trans-RA and restrict certain tissues from all-trans-RA activity. Developing retina exhibit an exquisite pattern of coordinated expression of P450RAI-1, and the all-trans-RA synthesizing enzymes RALDH-2 and ALDH-1 [McCafferty et al., (1999)]. Given that the EST corresponding to P450RAI-2 (accession # AA012833) was derived from an adult retinal library suggests that this enzyme may also play a role in the balance of all-trans-RA in retinal tissue.

Expression of P450RAI-2 in adult human brain suggests that all-trans-RA may play an important homeostatic role in brain tissue. In this regard, it has recently been shown that all-trans-RA signaling pathways may be important for memory and learning since RARP/RXR(X knockout mice have impaired long-term potentiation and limited ability to negotiate a water-maze [Chiang, M. Y., (1998)]. If all trans-RA signaling pathways are involved in maintenance of higher order brain function then the regulation and function of enzymes like P450RAI-2 will be important regulators of these pathways. The high level of expression of P450RAI-2 in adult cerebellum suggests that it is protecting this tissue from exposure to RA. Of note, developing cerebellum is highly sensitive to the teratogenic effects of RA [Lammer, E. J., (1985); Lammer, E. & Armstrong, D. (1992)]. Also, Yamamoto et al. [Yamamoto, M., et al. (1998)], have reported evidence that RA may be synthesized from retinol in the choroid plexus of developing cerebellum, and that RA injected into the cerebellum is rapidly metabolized. These findings support the notion of an important role for RA metabolism in cerebellum during development which may also extend into adulthood. It is likely that this metabolism is mediated by P450RAI-2.

Studies of several cell lines in culture indicate that P450RAI-2 expression, similar to that of P450RAI-1, is regulated by all-trans-RA. For example, the induction by all-trans-RA of P450RAI-2 expression in the breast epithelial adenocarcinoma cell line MCF-7 is comparable to that of P450RAI-1. Interestingly, the transcriptional elements required for RA-induction of P450RAI-2 may be different from those for induction of P450RAI-1-, inspection of genomic sequence immediately upstream of the first exon of P450RAI-2 has not revealed any elements previously demonstrated to mediate a retinoid induction of transcription, whereas we have identified a functional, conserved, canonical RA response element (RARE) within the first 200 bp of the P450RAI-1 promoter (M.P.; unpublished). Comparative studies of induction of these two genes at the transcriptional level will help to discriminate possible similarities in their regulation.

RA metabolism may be implicated in certain disease states such as dermatological conditions angiogenesis, immunological disorders, and cancer. The present work suggests that certain brain functions may also depend on normal retinoid metabolism. There is interest in inhibiting this activity to increase the cell sensitivity to the differentiating or apoptotic affects of all-trans-RA ; recent clinical trials with all-trans-RA metabolism inhibitors suggest that this may be a viable approach to treat diseases which respond positively to retinoids. The identification of a second P450RAI provides another potentially useful target for rational drug design.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirey.

REFERENCES

Particulars of references cited above are given below. All of the listed references are incorporated herein by refer11ence.

Abu-Abed, S. S., Beckett, B. R., Chiba, H., Chithalen, J. V., Jones, G., Metzger, D., Chambon, P., and Petkovich, M. (1998). Mouse P450RAI (CYP26) expression and retinoic acid-inducible retinoic acid metabolism in F9 cells are regulated by retinoic acid receptor gamma and retinoid X receptor alpha. Journal of Biological Chemistry 273, 2409–15.

Achkar, C. C., Derguini, F., Blumberg, B., Langston, A., Arthur, A. L., Speck, J., Evans, R. M., Bolado, Jr., J. Nakanishi, K. and Buck, J. (1996) 4-Oxoreinol, a new natural ligand and transactivator of the retinoic acid receptors. Proc. Natl. Acad. Sci. USA 93,4879–84.

Adamson, P. C., Boylan, J. F., Balis, F. M., Murphy, R. F., Godwin, K. A., Gudas, L. J. and Poplack, D. G. (1993). Time course of induction of metabolism of all-trans retinoic acid and the up-regulation of cellular retinoic acid-binding protein. Cancer Research 53, 472–476.

Akimenko, M. A. and Ekker, M. (1995a). Anterior duplication of the Sonic hedgehog expression pattern in the pectoral fin buds of zebrafish treated with retinoic acid. Developmental Biology 170, 243–7.

Akimenko, M. A., Johnson, S. L., Westerfield, M. and Ekker, M. (1995b). Differential induction of four msx homeobox genes during fin development and regeneration in zebrafish. Development 121, 347–57.

Bartel, D. and Szostak, J. W. (1993). Science 261, 1411–1418.

Blaner, W. (1994). Retinol and retinoic acid metabolism. In: The Retinoids. (M. Sporn, Roberts, A. and Goodman, D. S., Editors) Raven Press, Inc.: New York.

Bligh, E. G. and Dyer, W. J. (1957). A rapid method of total lipid extraction and purification. Canadian Journal of Biochemistry 37, 911–917.

Blumberg, B., Bolado, Jr., J., Derguini, F., Craig, A. G., Moreno, T. A., Chakravarti, D., Heyman, R. A., Buck, J. and Evans, R. M. (1996) Novel retinoic acid receptor ligands in Xenopus embryos. Proc. Natl. Acad. Sci. USA 93, 4873–78.

Boss et al., U.S. Pat. No. 4,816,397.

Boylan, J. & Gudas, L. (1992) J. Biol. Chem. 267, 21486–21491

Boylan, J. F., Lufkin, T., Achkar, C. C., Taneha, R., Chambon, P. and Gudas, L. J. (1995). Targeted Disruption of Retinoic Acid Receptor a (RARa) and RARg Results in Receptor-Specific Alterations in Retinoic Acid-Mediated Differentiation and Retinoic Acid Metabolism. Mol. Cell Biol. 15, 843–851.

Butler, W. B., and Fontana, J. A. (1992). Responses to retinoic acid of tamoxifen-sensitive and -resistant sublines of human breast cancer cell line MCF-7. Cancer Research 52, 6164–7.

Cabilly et al. U.S. Pat. No. 4,816,567.

Cech et al., (a) U.S. Pat. No. 4,987,071.

Cech et al., (a) U.S. Pat. No. 5,116,742.

Chambon, P. (1995). The molecular and genetic dissection of the retinoid signaling pathway. [Review]. Recent Progress in Hormone Research 50, 317–32.

Chambon, P. (1996) Faseb J. 10, 940–954

Chiang, M. Y., Misner, D., Kempermann, G., Schikorski, T., Giguere, V., Sucov, H. M., Gage, F. H, Stevens, C. F. & Evans, R. M. (1998) Neuron 21, 1353–1361.

Chomienne, C., Fenaux and Degos, L. (1996). Retinoid differentiation therapy in promyelocytic leukemia. FASEB J. 1025–1030.

Chytil, F. (1984). Retinoic acid: Biochemistry, toxicology, pharmacology, and therapeutic use. Pharmacol. Rev. 36, 93–99.

Cole et al. (1985). Monoclonal Antibodies in Cancer Therapy. Allen R. Bliss, Inc.

Creech Kraft, J., Schuh, T., Juchau, M. R. and Kimelman, D. (1994). Temporal distribution, localization and metabolism of all-trans retinol, didehydroretinol and all-trans retinal during Xenopus development. Biochem. J. 301, 111–119.

De Coster, R., Wouters, W. and Bruynseels, J. (1996). P450-dependent enzymes as targets for prostate cancer therapy. J. Ster. Biochem. Mol. Biol. 56, 133–43.

Duell, E. A., Astrom, A., Griffiths, C. E., Chambon, P. and Voorhees, J. J. (1992). Human skin levels of retinoic acid and cytochrome p450-derived 4-hydroxyretinoic acid after topical application of retinoic acid in vivo compared to concentrations required to stimulate retinoic acid receptor-mediated transcription in vitro. Journal of Clinical Investigation 90, 1269–74.

Fiorella, P. D., Giguère, V. and Napoli, J. L. (1993). Expression of Cellular Retinoic Acid-binding Protein (Type II) in *Escherichia coli*. The Journal of Biological Chemistry 268, 21545–21552.

Formelli, F., Barua, A. and Olson,J. (1996). Bioactivities of N-(4-hydroxyphenyl) retinimide and retinoyl B-glucuronide. FASEB J. 10, 1014–1024.

Frolik, C. A., Roberts, A. B., Tavela, T. E., Roller, P. P., Newton, D. L. and Sporn, M. B. (1979). Isolation and identification of 4hydroxy- and 4-oxoretinoic acid. In vitro metabolites of all-trans retinoic acid in hamster trachea and liver. Biochemistry 18, 2092–7.

Fujii, H., Sato, T., Kaneko, S., Gotoh, O., Fujii-Kuriyama, Y., Osawa, K., Kato, S., and Hamada, H. (1997). Metabolic inactivation of retinoic acid by a novel P450 differentially expressed in developing mouse embryos. EMBO Journal 16, 4163–73.

Gudas, L., Sporn, M. and Roberts, A. (1994). Cellular biology and biochemistry of the retinoids. In: The Retinoids. (M. Sporn, Roberts, A. and Goodman, D. S., Editors) Raven Press, Inc.: New York.

Guengerich, (1991) *J. Biol. Chem.* 266:10019–10022

Higgins, D. G. and Sharp, P. M. (1989). Fast and sensitive multiple sequence alignments on a microcomputer. CABIOS 5, 151–153.

Higgins, D. G., Bleasby, A. J., and Fuchs, R. (1991). CLUSTAL V: improved software for multiple sequence alignment. CABIOS 8, 189–191.

Hogan, B. et al., (1986). A Laboratory Manual, Cold Spring Harbor, N.Y., Cold Spring Harbor Laboratory.

Hollermann, T., Chen, Y., Grunz, H., and Pieler, T. (1998). Regionalized metabolic activity establishes boundaries of retinoic acid signalling. European Molecular Biology Organization 17,7361–7372.

Hong, W. (1994). Retinoids and human cancer. In: The Retinoids. (M. Sporn, Roberts, A. and Goodman, D. S., Editors) Raven Press, Inc.: New York Houbenwcyl, (1987). Methods of Organic Chemistry, ed. E. Wansch. Vol. 15 I and II. Thieme, Stuttgart.

Hozumi, N and Sandhu, J. S. (1993). Recombinant antibody technology, its advent and advances. Cancer Invest. 11, 714–723.

Huse et al., (1989). Science 246, 1275 –1281.

Iulianella, A., Beckett, B., Petkovich, M., and Lohnes, D. (1999). A molecular basis for retinoic acid-induced axial truncation. Developmental Biology 205, 33–48.

Jones, G., Ramshaw, H., Zhang, A., Cook, R., Byford, V., White, J. & Petkovich, M (1999) Endocrinology 140, 3303–3310.

Kennett, R. (1979). Cell fusion. Methods Enzymol. 58, 345–359.

Kohler and Milstein. (1975). Nature 256, 495–497.

Kozbor et al. (1983). Immunol. Today 4, 72.

Lammer, E. j., Chen, D. T., Hoar, R. M., Agnish, N. D., Benke, P. J., Braun, J. T., curry, C. J., Fernhoff, P. M., Grix, A. J., Lott, I. T. & et, a. l. (1985) N. Engl. J. Med. 313, 837–841.

Lammer, E. & Armstrong, D. (1992) in Retinoids in normal development and teratogenesis, ed. Morris-Kay, G. (Oxford University Press, Oxford), pp. 281–295.

Lane, M., Chen, A., Roman, S., Derguini, F. & Gudas, L. (1999) Proc. Natl. Acad. Sci. USA 96, 13524–13529.

Lemoine, N. R. and Cooper, D. N. (1996). Gene Therapy, Human Molecular Genetics Series, BIOS Scientific Publishers, Oxford, U.K.

Leo et al. (1989). Metabolism of retinol and retinoic acid by human liver cytochrome P450IIC8. Arch. Biochem. Biophys. 269, 305–312.

Lippman, S. M., Heyman, R. A., Kurie, J. M., Benner, S. E. and Hong, W. K. (1995). Retinoids and chemoprevention: clinical and basic studies. J. Cellular Biochem. Supplement 22, 1–10.

Lotan, R. M. (1995). Squamous differentiation and retinoids. Cancer Treat. Res. 74, 43–72.

Lotan, R. (1996). Retinoids in Cancer Chemoprevention. Faseb J. 10, 1031–1039.

Maden, M. and Holder, N. (1992). Retinoic acid and development of the central nervous system. [Review]. Bioessays 14, 431–8.

Mangelsdorf, D. J. and Evans, R. M. (1995). The RXR Heterodimers and Orphan Receptors. Cell 83, 841–850.

Merrifield, (1964]. J. Am. Chem. Assoc. 85, 2149–2154.

McCafferty et al., (1990). Nature 348, 552–554.

Mirski, S. and Cole, S. P. C. (1989). Antigens associated with multidrug resistance in H69AR, a small cell lung cancer cell line. Cancer Res. 49, 5719–5724.

Monia, B. P., Johnston, J. F., Geiger, T., Muller, M. and Fabbro, D. (1996). Antitumor activity of a phosphorothioate antisense oligodeoxynucleotide targeted against C-raf kinase. Nature Medicine 2, 668–75.

Moon, R. C., Mehta, R. G. and Rao, K. V. N. (1994). Retinoids and cancer in experimental animals. In: The Retinoids. (M. Sporn, Roberts, A. and Goodman, D. S., Editors) Raven Press, Inc.: New York.

Morriss-Kay, G. M. (1996). Embryonic development and pattern formation. FASEB J. 10, 961–968.

Morrison et al., (1985). Proc. Natl. Acad. Sci. USA 81, 6851.

Muindi, J. R. F., Frankel, S. R., Huselton, C., DeGrazia, F., Garland, W., Young, C. W. and Warrell, R. P., Jr. (1992). Clinical pharmacology of oral all-trans retinoic acid in patients with acute promyelocytic leukemia. Cancer Research 52, 2138–2142.

Muindi, J. R., Young, C. W. and Warrell, R. J. (1994a). Clinical pharmacology of all-trans retinoic acid. Leukemia 8, 1807–1812.

Muindi, J. R., Young, C. W. and Warrell, R. J. (1994b). Clinical pharmacology of all-trans retinoic acid. Leukemia 8, s16–s21.

Napoli, J. L., Boerman, M. H., Chai, X., Zhai, Y. and Fiorella, P. D. (1995). Enzymes and binding proteins affecting retinoic acid concentrations. J. Ster. Biochem. Mol. Biol. 53, 497–502.

Napoli, J. (1996). Retinoic acid biosynthesis and metabolism. FASEB J. 10, 993–1001.

Nebert et al. (1989), *DNA* 8:1–13

Nelson, D. et al (1996), *Phamacogenetics* 6:1–42

Nelson, D. (1999a) *Arch. Biochem. Biophys* 369: 1–10

Nelson, D. (1999b) Arch. Biochem. Biophys. 371, 345–347.

Niederreither, K., Subbarayan, V., Dolle, P. & Chambon, P. (1999) Nature Genetics 21, 444–448.

Old, R. W. and Primrose, S. B., In: Principles of Gene Manipulation. An Introduction to Genetic Engineering, 4th ed. Oxford University Press. 63–66.

Ohno, C. K. and Petkovich, M. (1993). FTZ-F1 beta, a novel member of the *Drosophila* nuclear receptor family. Mechanisms of Development 40, 13–24.

Pijnappel, W. W., Hendriks, H. F., Folkers, G. E., van den Brink, C., Dekker, E. J., Edelenbosch, C., van der Saag, P. and Durston, A. J. (1993). The retinoid ligand 4-oxo-retinoic acid is a highly active modulator of positional specification. Nature 366, 340–4.

Ray, W. J., Bain, G., Yao, M., and Gottlieb, D. I. (1997). CYP26, a novel mammalian cytochrome P450, is induced by retinoic acid and defines a new family. Journal of Biological Chemistry 272, 18702–8.

Reddy, A. P., Chen, J., Zacharewski, T., Gronemeyer, H., Voorhees, J. J. and Fisher, G. J. (1992). Characterization and purification of human retinoic acid receptor-g1 over-expressed in the baculovirus-insect cell system. Biochem. J. 287, 833–840.

Rigas, J., Miller, V., Zhang, Z. F., Klimstra, D., Tong, W., Kris, M. and Warrell, R. (1996). Metabolic phenotypes of retinoic acid and the risk of lung cancer. Cancer Res. 56, 2692–2696.

Roberts, A. B., Nichols, M. D., Newton, D. L. and Sporn, M. B. (1979a). In vitro metabolism of retinoic acid in hamster intestine and liver. Journal of Biological Chemistry 254, 6296–302.

Roberts, A. B., Frolik, C. A., Nichols, M. D. and Sporn, M. B. (1979b). Retinoid-dependent induction of the in vivo and in vitro metabolism of retinoic acid in tissues of the vitamin A-deficient hamster. Journal of Biological Chemistry 254, 6303–9.

Sambrook, J., Fritsch E. F. and Maniatis, T. (1989). Molecular Cloning: A Laboratory Manual. Cold Spring Harbor Lab Press, Cold Spring Harbor, New York.

Staerz & Bevan (1986a). Proc. Natl. Acad. Sci. USA) 83, 1453.

Staerz & Bevan (1986b). Immunology Today 7, 241.

Stewart, A. J., Canitrot, Y., Baracchini, E., Dean, N. M., Deeley, R. G., and Cole, S. P. C. (1996). Reduction of Expression of the multidrug resistance protein (MRP) in human tumor cells by antisense phophorothioate oligo-nucleotides. Biochem. Pharamcol. 51, 461–469.

Swindell, E., Thaller, C., Sockanathan, S., Petkovich, M., Jessell, T. & Eichele, G. (1999) Dev. Biol. 216, 282–296.

Takatsuka, J., Takahashi, N. and De Luca, L. M. (1996). Retinoic Acid Metabolism and Inhibition of Cell Proliferation: An Unexpected Liaison. Cancer Research 56, 675–678.

Takeda et al., (1985). Nature 314, 452.

Tanaguchi et al., European Patent Publication EP171496.

Teng, et al., (1982) Meth. Enzymol. 92. 3–16.

Thompson, J. D., Higgins, D. G., and Gibson, T. J. (1994). CLUSTAL W: improving the sensitivity of progressive multiple sequence alignment through sequence weighting, positions-specific gap penalties and weight matrix choice. Nucleic Acids Research 22, 4673–4680.

Van Wauwe, J. P., Coene, M. -C., Goossens, J., Van Nijen, G., Cools, W. and Lauwers, W. (1988). Ketoconazole inhibits the in vitro and in vivo metabolism of all-trans retinoic acid. The Journal of Pharmacology and Experimental Therapeutics 245, 718–722.

Van Wauwe, J. P., Coene, M. -C., Goossens, J., Cools, W. and Monbaliu, J. (1990). Effects of cytochrome P450 inhibitors on the in vivo metabolism of all-trans-retinoic acid in rats. The Journal of Pharmacology and Experimental Therapeutics 252, 365–369.

Van Wauwe, J., Van Nyen, G., Coene, M., Stoppie, P., Cools, W., Goossens, J., Borghgraef, P. and Janssen, P. A. J. (1992). Liarazole, an Inhibitor of Retinoic Acid Metabolism, Exerts Retinoid-Mimetic Effects in Vivo. The Journal of Pharmacology and Experimental Therapeutics 261, 773–779.

Ward et al., (1989). Nature 341. 544–546.

Warrell, R. J. (1994). Applications for retinoids in cancer therapy. Seminars in Hematol. 31, 1–13.

Warrell, R. J., Maslak, P., Eardley, A., Heller, G., Miller, W. J. and Frankel, S. R. (1994). Treatment of acute promyelocytic leukemia with all-trans retinoic acid: an update of the New York experience. Leukemia 8, 929–933.

White, J. A., Boffa, M. B., Jones, B. and Petkovich, M. (1994). A zebrafish retinoic acid receptor expressed in the regenerating caudal fin. Development 120, 1861–72.

White, J. A., Guo, Y., Baetz, K., Beckett-Jones, B., Bonasoro, J., Hsu, K., Dilworth, J., Jones, G., and Petkovich, M. (1996a). Identification of the retinoic acid-inducible all trans retinoic acid 4-hydroxylase. Journal of Biological Chemistry 271, 29922–29927.

White, J. & Petkovich, M. (1996b) Met. Mol. Biol. 89, 389–404.

White, J. A., Beckett-Jones, B., Guo, Y. D., Dilworth, F. J., Bonasoro, J., Jones, G., and Petkovich, M. (1997). cDNA cloning of human retinoic acid-metabolizing enzyme (hP450RAI) identifies a novel family of cytochromes P450. Journal of Biological Chemistry 272, 18538–41.

White, J., Beckett, B., Scherer, S., Hebrick, J. and Petkovick, M. (1998) Genomics 48, 270–272.

Williams, J. B. and Napoli, J. L. (1987). Inhibition of retinoic acid metabolism by imidazole antimycotics in F9 embryonal carcinoma cells. Biochemical Pharmacology 36, 1386–1388.

Wouters, W., van, D. J., Dillen, A., Coene, M. C., Cools, W. and De, C. R. (1992). Effects of liarazole, a new antitumoral compound, on retinoic acid-induced inhibition of cell growth and on retinoic acid metabolism in MCF-7 human breast cancer cells. Cancer Research 52, 2841–6.NCES Yamamoto, M., Drager, U., Ong, D. & McCaffery, P. (1998) Eur. J. Biochem. 257, 344–350.

What is claimed is:

1. An isolated antibody to a cytochrome P450 retinoic acid metabolizing peptide-2 (P450RAI-2) comprising the amino acid sequence of SEQ. ID. NO. 5.

2. The isolated antibody of claim 1 to an immunogenic portion or epitope of SEQ. ID. NO. 5.

3. The isolated antibody of claim 1, wherein the antibody is polyclonal.

4. The isolated antibody of claim 1, wherein the antibody is monoclonal.

5. A kit for determining the presence of a P450RAI-2 protein comprising an amino acid sequence as identified by SEQ ID NO: 5, said kit comprising an antibody to said protein linked to a reporter system, wherein the reporter system produces a detectable response when a predetermined amount of the protein and the antibody are bound together.

6. The kit of claim 5 wherein the antibody is the antibody of claim 2.

* * * * *

SEQUENCE LISTING

```
<160> NUMBER OF SEQ ID NOS: 48

<210> SEQ ID NO 1
<211> LENGTH: 30
<212> TYPE: PRT
<213> ORGANISM: Artificial Sequence
<220> FEATURE:
<223> OTHER INFORMATION: typical heme binding motif found in all
                        Cytochrome P450s

<400> SEQUENCE: 1

Lys Lys Glu Thr Phe Ile Pro Phe Gly Ile Gly Lys Arg Val Cys Met
1               5                   10                  15

Gly Glu Gln Leu Ala Lys Met Glu Leu Phe Leu Met Phe Val
            20                  25                  30

<210> SEQ ID NO 2
<211> LENGTH: 194
<212> TYPE: DNA
<213> ORGANISM: Artificial Sequence
<220> FEATURE:
<223> OTHER INFORMATION: clone from soares retinc N2b4 H2 library
<220> FEATURE:
<221> NAME/KEY: misc_feature
<222> LOCATION: (36)..(36)
<223> OTHER INFORMATION: n is any nucleic acid
<220> FEATURE:
<221> NAME/KEY: misc_feature
<222> LOCATION: (85)..(85)
<223> OTHER INFORMATION: n is any nucleic acid
<220> FEATURE:
<221> NAME/KEY: misc_feature
<222> LOCATION: (180)..(180)
<223> OTHER INFORMATION: n is any nucleic acid
<220> FEATURE:
<221> NAME/KEY: misc_feature
```

<222> LOCATION: (188)..(188)
<223> OTHER INFORMATION: n is any nucleic acid

<400> SEQUENCE: 2

| | | | | |
|---|---|---|---|---|
| ggtgtccgga | cctgcctggg | caagcacctg | gccaanctgt | tcctgaaggt gaaggcggtg | 60 |
| gagctggcta | gcaccagccg | ctttnagctg | gccacacgga | ccttcccccg catcaccttg | 120 |
| gtccccgtcc | tgcaccccgt | ggatggcctc | agcgtcaagt | tctttggcct ggactccaan | 180 |
| cagaaagnga | tatc | | | | 194 |

<210> SEQ ID NO 3
<211> LENGTH: 11358
<212> TYPE: DNA
<213> ORGANISM: Homo sapiens

<400> SEQUENCE: 3

| | | | | | |
|---|---|---|---|---|---|
| gttcagagtg | aggttggctg | cctcatttaa | agccatgcat | ggatttaagt gccagagtca | 60 |
| tgtatttaac | cattctgtgc | ctcagtttcc | tcatctataa | actgagtaat aacacatcac | 120 |
| tggattaaaa | gaaactatgt | atataaagct | ttagaactgt | gtctggcaca tagcttagtc | 180 |
| tcagtaggat | ttagccttta | actgactctc | gtttgctgac | acatgaggct ctgggctgg | 240 |
| gagcagcgtc | ctgggtacc | ccgatctgcc | aggcccagta | gctgcagtcc tagggatcat | 300 |
| gactcacagg | tactctgggg | gaaccacttc | agaacctctg | cctcccctcc caggctgggg | 360 |
| tggctgggcc | aatggaatga | cctcagccag | gaggaatgag | gggcgcggag tctgtaggca | 420 |
| ggcccctgcc | taccctgga | gcatccgcag | ccccggcttg | cattcgctcc ctagcaggtg | 480 |
| accacagcca | acaggacccc | agggtcacc | ctggtgactc | actgtagtct cttgatccag | 540 |
| accttgttca | agggacctcc | cagcctcttc | cttctgcagc | ccactgctta aaagttgatc | 600 |
| ccagccccat | taccctttgac | ctatagctga | gacctcaagc | tggcctctga ctaatgcatg | 660 |
| accctgatct | ttgactgacc | tctgaccctg | gccgtgact | ggctttgatt cagacagtcg | 720 |
| cagttctggc | ctctgctggg | ccctggccct | ggctgcagat | ggaccattg cacagacatg | 780 |
| aaagacactc | aggggtttc | tgggctgatc | tcctctcagc | accgcatctc cctcccttca | 840 |
| gatctcctgg | ctccaggctg | aagtgctccg | cctgccaggc | agcctggctc cctgaaggtg | 900 |
| gggagtgcct | gtctgccccc | cttgctggga | gaggcccaca | tggagaggag gcctcagcct | 960 |
| tagagaagat | acaggtggat | tctgctggtg | ttatctcttt | agtccacttc tcagtgatgc | 1020 |
| ctcctaagga | gcatccttcc | tccagcccct | gctggctaca | gctcccagat gaaagggaac | 1080 |
| ccacaacccc | cgccaccact | gttgccctgc | cattagacac | ttttccggga gcttcctaag | 1140 |
| agcagcaaca | aagcttccca | gctggaccaa | gtttctgtag | acagaacac ggcaatcaga | 1200 |
| ccgggagagc | cccatggtca | ggagttgtgt | ctcagtcacc | catggtgggg cgggggggg | 1260 |
| cccaaggagg | ggctaagagc | aacttgcgtg | ctgcagttga | acacacttgg accctaacct | 1320 |
| tggctccact | atttactagc | tgtgtgtctt | tgggccaatc | tctgaacctc tctgaactca | 1380 |
| gtttcctcac | ctgcaaaacg | gggccagtgg | cattacttac | tgcagaatga tgaagatgga | 1440 |
| atgggctaca | ctctgggaag | ccccaagcat | gtctggcact | tgtacttgct cagtagatgt | 1500 |
| cagtggtcag | ggatagtctg | tccctagcac | atcaggggtt | ccacagggca gggcagctca | 1560 |
| gtgaggctga | gatctttacc | cctgcagaag | cagggttttc | tcactgaaga gggtcagaag | 1620 |
| gcaatgtcta | atctagcctc | ccctgccccgc | ccttgctcct | tgtagcttct cagggactct | 1680 |
| gggcctgcag | ggctcagccc | aacctctcca | cagagctctc | ctctgtccctt caccgtaaga | 1740 |

```
aagcctctcc tcctcagcct tacctattta tgtctacccg tccttcctgg gttgcctgac    1800
ccaacccacc ccctgcagga agcttctgag ggtgacgtct gccagggcct ggctcttgaa    1860
agctaagtca caaaagccag ggctgatcct ccactgtgga tggccttgct gtgatccctg    1920
gctgcctggt tctcctgaga cagtgaggat cagggcccgg cctgccccgg caccatggac    1980
cctagggtgg ggccagggtg agacgtgttt cctgaacctg agccaccagg ccggggcat     2040 ctccattgca ctcattgccc aagcaggtac tcaaactgcc ctcagaaggg tttggtttct    2100
tttcctctct tttcagttaa ttaaatcaat taagtcattt tgagtcattc ctgttggcca    2160
cttgggcctt tctccttagc gaggcctgat tcattaaggc agcaggacag atgccaaggt    2220
cagccatgac gtcatgatcc ggggtcacac ttcctgtggg cggagaagag agccatacag    2280
gcacccaggg cgtgccccag gactgacctc tggggaggga cccagagagt aaggatatgg    2340
gtccccgtgg ggtcacttgg ccaaagcaag tcatgaactt aggctgccac ccatgttttc    2400
agtcagcctc aagcattctt caagggtttc cttgacgcca ggtgctgggg gaggatgaaa    2460
agatggttca gtgcctcccg aagatgccct ttttattagg ttgatttcaa agtagtgtg    2520 gccttttaat ggcagaaacc acaattactt ttgcaccaac ttgtacctta gctgctagga    2580
gcccagatag aaagttaacc cttaatcaca cgatctgtgt tagcccctgt gtttggcgta    2640
tttgagtctt tctttctcct cttgaatttt tatgtattat catttttgt tagcagcatt     2700 atatgcatgt attctatggt aagctacttc atgtcctctt tggaagtagg tagagtataa    2760
atcataagtc aattaatggg gcctggagaa actcatagac catcaagagg gactcatgca    2820
aacatcctat acctttcccc cttggatgga gaaaacctca agcgacaggg tgtgaaaacg    2880
tgagtcttct ggggcctgaa cacctggaaa caaattgcag ctgcaatctt cagttgagga    2940
gaaagggagt aggggcctgg gctcaaacgg cagctctctg cggaaggaaa ctggccgggg    3000
tttaaggtct caagccctga ctgccggtcc cagctccacc tgtctctggc agtgggaccc    3060
tgggaagatt ctcttgcccc ttgggcctct gtttatctaa gtgttaaacg gatttgatga    3120
ggggcctgac cttggctctt atggggctgc tttgaggctc ccttgagcca aagagtggat    3180
ttagtgattt ctctggtcag agctggtttg cccactaatc ttgctgctca aagaagaaac    3240
gggagagttt gctcaggctg ggaaggccac ctactctcag cttctaggag agaaatctat    3300
tatataaatg actgtcccct gacccccgag agacccacta cccatctgag gccccatgct    3360
ctctggccac tgcctccctg ctggcctggg ttcctccatg ccacactccc agcatccaag    3420
ggtgaccgag catgtgagtc agggctggct ccgacttcct tgaagcgggg tcctgctcct    3480
tagcatgggg tgccctccct aggctctggg caagaaaagc ctgccgggtg agctgagaga    3540
agctttccgg gcacatctcc tgacctgaa aggggctcag tgggccgcga cacacctgcc     3600
tcctagtgat gctctgcaga tagcatcatg gtcacagtca atatttattg agcacatgtt    3660
aatccacaca ccagccccat gagtcaagta ccattattaa cttaatttta caaataagcg    3720
aactgaggca tgaagagatt atgtcacaca gttaggaaat ggcagattac tagttctctt    3780
ttccattaca gtctactgat gcctattcac tcagtcacac tgtaagtatt gattgagcgc    3840
atactgtgtg ccagatgcta aggatccttt aaagaacaag atagataaaa agccctgccc    3900
tcctggtgct aacattctag agggaggaga gagacaataa acagcaaaca tagacgcatg    3960
acagagtatg ttagaaggtc atatgaggtt tggggaaaaa caaggagag tcaagtggat     4020 caggtctgct gccagggaag ggtgttcaa tggaagtgcg gaggccgagg agagcctggg    4080
ttcagccaag acttgaagga ggtcagggag ggagcgtgtg gctgcctggg agaaagacat    4140
```

```
gcatgggccc tgagagagga gctgaacaca gcaagggtg cttcggctgg agaggaggga    4200
gaagggcctg agaaccgaga ggtaatggag gacacagcat gcagggccct gtcggccatt    4260
gtaaggtctt ttgagttttt ttcccaaaac cgagttggtt ttattgcaag aatagaacgg    4320
tgcactgccc tcgaggcttt gccttttact ctgaagcttc tgtggagttt gggccccaag    4380
ggaccagacc tgacttgagg tttaaaagga tccctctggc tgcagcaggg aatgctgatg    4440
gtgggcggcg ggggggggg gggtggtggt ggcaaagcgt gggacagagt gacccagagg    4500
aggcttcctc gatggcccag aggaccacag gacctggacc agtgaggaag aggtgaagca    4560
agcatcagtg gaattctgga tctgcttttga aggtggcacc agagtatttg ctgctggatt    4620
ggctgtgggg tagagagaaa gagaggagtc caaattttgg gcctgaacaa ctggaaggat    4680
ggagctgcct tttactggga tacagggtga aggaggttct tttgtggcat tcggggatga    4740
tcagagtttc atattgggca tgcagggttt gagctgccta gtgtgcattc taggcagagt    4800
tctagggaca gcagctggcc atgccagtgg gaggtatagg gagacagagg tcacagctga    4860
ggacctccct caggtcacac tcctgtcaga gcaggatgga ctcttaggga ctgccgagga    4920
agcacagcag caagtggtca ggccacacag ctggcaaatg gcagggctgg ggctgcaacc    4980
ccgggctgtt cccaggtgct cctgtctcct gcagccactg cctcccatcc acacccacgt    5040
caggaggagc ggctgggggcc gactgagtcc accaccccct ttaccagagg aggaaactag    5100
gcctacgtga ttgcctgggc acacaccgag gacgagcagc agagctggaa cccgggcctc    5160
cctgacttgg ggttcagaga ttatgcatga caagatagca ctcgtgaagg cgccccgaca    5220
ggtctggaat gtgggagtga gtgtggtggt gatgattatt gtgccccatt ggctggccag    5280
gggcgcattt tggcaggatt gccctcttac ccagtgaggg ctgggaccca actcatgttc    5340
ttcctgctgg gagaggccca ggcccctggg tggggcccc acattcagtc cctgccttcc    5400
tgattcatcc cagctctctt ggaggcctga gtcactttt ttccaggtga gagctgcctg    5460
tttggcaaat tcctggattt caggggaaga aataggaact cctgcccagg gttggtctta    5520
tgcacaggta aggcaggcag caacccacgt ctgccccaaa tccctgccct ggcctggaat    5580
tcactcactt gtctatctat ccatggggcc agccatttct gagtaatgat ctccattctg    5640
atattcagta ttttgcagtt tgcaaaacac tttcaaatac gggtagtcct attttgtgga    5700
tgagaagact gaggctcaga gaagggaaag gctgtttcaa gagggcccag ctgggaaaca    5760
gggagccagg gtgcagtccc aggcttgtct gacacaggag ttcttccatt tacagtcact    5820
actgtcccca catctggtcg ccatttccaa ctctttgccc caattctctg agctagggaa    5880
ggaagctgtg accttcaaga agtctgattc cccttgcact gtgggtaaca ggagaaggag    5940
gaggcatgga cactgaagaa cagtctcgag gacaactgca cagccaggtc tggagagcgg    6000
ccgtgggaga agccttgagt gggttgagtg cccagcagct ccgtggaggc tatcacaaga    6060
atatcagaga agcgaggtgg gtaggaggcg ttctggacag ggaagcagcc agcagaatgg    6120
gatgaactta cattcagggg ccaggaacat aaggtatgtg tatgagtggg caggagggtc    6180
aggttgcaga agtttctgaa tgcctatgga atgttcgggg cagtactggt gaggggccca    6240
gggctgctcc ctcttccccc aggaagcctt cctgcgctaa ctcctctggt tcctcagccc    6300
cggccggctc tcttcccca ggcacagcct gtacttggag acttcctggg tcatgtcctc    6360
tctcccaggg aacagggcaa ggggccgctc gtaggatacc taccttactg atagagatcg    6420
tgggaagtta ggaagccaga gtctttctca agaaggatca gggcttggag ggagggccaa    6480
```

-continued

```
ccctacagac aggcagactg tattcctcga ggtgtatgca gacgtctctt ctccaaagag   6540
cccctgattg catgttacag tgcccagagt tccagcagag gtgattcaca ctttcggaca   6600
gggcacatcc cctcaccaca gatgaatttc cttgaaagga tactgctgca cccatcactg   6660
taaatggcac cagcaaatag tttcttccct gggtagggggg ctgggggaag tgggagcaga   6720
gaagagggtg accggagaac ctcaagggaa ggtgggggtag cagagacacc ttgggccact   6780
tcatatccgt gctataggaa gaccgtgtct atttggagcc tccacaataa tccatcctca   6840
ctctttacca atgccctaac agctagttca gatttgcctt gtttcaatca aattcctagt   6900
gggtctcggg cttcttagta tagggggtgc aggggctgat tcagggcacc atgaagaggg   6960
tttttgaaaa ccagtttccc tcggcaggta gaacctaatt cagagaaagg caatctgggc   7020
atctgtcagg tagccagtca gtagtgggca caaacggttc aagctggaaa taggatgcta   7080
cctaactcag gtttcactgt gaccacgtcg ctataactga caaaatgcaa ataagctcca   7140
ctcccactga tgtagacaac gccctggagt agaattaaaa aaagaaaacg ttgtgccaac   7200
ctattttgat tgtgtacttc tgcaataagg atgcacatgt tgcatggcac gattatatgc   7260
cacgcctctc acctgggacc cagactcaaa gctgcaaccg acccaaatcc tgcaaccaaa   7320
taatacctgg tgcatacggc tctgcttttt gagaaagggt gatataaagc ttagagtctt   7380
tgacatgact ctcagacaca gatccagttt aggaaaacaa agaccaagat cttgaggcag   7440
gctgggcatg gtggctcacg cctgtactcc tagcactttg ggaggccaag gcaggaggac   7500
cccttgaatt taggagtttg agaccagcct ggacaacaca gtgggatgct gtctctacaa   7560
aaaataaaaa gttagccagg ggtggtggta gccaggtgca cttgtagtcc tggctactca   7620
ggaggctgag gtgggtggat tgcttgaaac tgggaggtca aggctttgag ccatgattat   7680
gccactgcac tccagcctgg gcaacagagt gagaccctgt aaaaaacaa aacaaaacca   7740
aaacaaaaac aaaaaaactt gaggtgttgg cagtgagtga ccacgaacca gaataaaaca   7800
atttttaaat atgctgtaaa taagccttag taatgatgtg tatataagtt agaggatgtg   7860
gctataagtg gccagttata aaagtgggga agattataaa atgaagacaa tttcaaataa   7920
ggaaaaatat attacattac ttcaacttgt taattcctta ttctgaacat aaaaacatat   7980
gtaatttata ttgtttgaaa acctgtttct ttccatttct cctgaataaa agatagataa   8040
gccaaaattt tagcggttta ttgagatcac caaattatta gccatcatgg gttgaccagc   8100
tgccttgttc ctccctgatg agaatggtgg gtgaaatcga ggctgcttgc ggcgtgtgga   8160
aaagccaagt ggaggcaact cagcttcaag tctgtgctat ggcaacatat gtgcttctca   8220
ttagtgattt acatcacaag atctagcagc gggtctaata gttttttgtat aataatttct   8280
gcattgggat gagcgttttt gatatttcaa gatgtggatg agcgttttttg atatttcaag   8340
atgtcttctc aactgtaatg atatgaaaat atctgatttc gattgctaac aaagtcacag   8400
gtacttttac atacttttgt ggtttgttgt ctccacacat aactgaaaga aagttgagtt   8460
aggcgttggt gaaaataatg gtgtaatttt ctccgcattc aatccccaaa tcccctacat   8520
tctctccttg gacgtccagt gggttaatgg agcccaggtc aggtggtccc tgaagttccc   8580
cacaatctct gcccacagga cagacgcctg gagtgagagg ctctggggct gaactcccca   8640
tggagggctc tgtctctctg acccactctt aagtgctcct ttcctccctc tgaaatagac   8700
aatgccctgt gtccgcctc ctcacactct cccgtggagg ctgctccttc atggctctcg   8760
actctgtcca ctcctgccca cctgcccctc tgagtcaggg cccaggcct gggctgctgt   8820
ggagcctccc gacagtctgc tagctcctct ctggtggact cccattggtt ccccacatgg   8880
```

```
taaccagtgg gatgttaagt tgtagagttc atcatgtcac tctctgctta aagtccttca    8940
atggttcccc agtacccta gggtaggaac aagaacttga cttttgtccc caaggccggc    9000
ccacgctgcc tcccatctcc cactaggccc tccgtagca ccctggccac cttgcacttc    9060
ctggctcatg ccatgtgcct ctctgccagg cccttggcac tcaccgttcc ctctgtctgg    9120 cccctacct cgctctgccc catagcttgt gaactcagct ctctcgcaga catcactttc    9180
tccaggagat gcccctgctc tctgtggagc ccccattcca cacctgctgc tctgctcaag    9240
gctggtttgt tagaacatgc attttgtctt tcacattggg gatgtctgga agcccttga    9300 tgctacaaaa gggcatgggg tgggggcac caggaacatc ccgctgcctg ggaggaccac    9360
ccagcatgcg gacaactctg gatcaaggct tgtgctgacg ttaggagatt ggagggcctg    9420
aaaggcgatg ctaacacagt gctggaaacc caggcccatg ggcctgtggt gtgggcgga    9480 ggcaggctgc cctccaggtg tggagcagag caagcactgt tctgcgggc tctcctggca    9540 ccatgaactt tgggtttaaa tcccctaatg ccattgcaac tttactttc tttgattaat    9600 atcatttccc cactagacta taagttccaa ggaggcaaag atggcattgg tggccagcat    9660
ctagcatgtg cccgcctgca gtgggagttc gaaagttgct attgaaggaa tgtccgagtt    9720
ctctcttccc tattcacaga aaagccctcc ggctccttct gtccctcttt gtttccccct    9780
gccttttgag agtctgcaca cccttggctg ggttttgtgg gtatttcccc attaactggc    9840
taagtcatcc cttactcgtt tttcaggagg gctgctggtg actcagaccc ggtgtggctg    9900
ggcctggctc tgagggagct cctgagagcc tgagtagatg ctcaacaaac atgtgccgag    9960
ttgagcctca gccaagcttg gaggcagagg gatggacagg atgacttggc tgcaggaggg   10020
tgagtccttg gaggagggaa aagacaggtc aggtgactga gaacagggtt cgattcccgg   10080
tcaggtgact ctggggaagg tgctgggtg tctatggagt ttcacacccc atgatctggg   10140
ctgggtgctc cagataggat cctggcacac ccccggcggc ctgcccccac ctgctcctgg   10200
ggcaggggca acaggtgggg cccacttatc gccaaccagg ccagcaggtg gagccagcct   10260
ggccctgggg agatggcaat agcacaggca ctcctcagtg gaaaatcacc acaccacacg   10320
gcctcctcct gggaacggga acagaaaggc ctggaagata tgggccagaa gtgtgtgggc   10380
ctgtgcaaag agctcaggct cccctcaaac tgggtaggc gggtgggcct tccctctatg   10440
gtgccacatg tgggcagttc tcaggctggg tcggagtgag ccgagggtca gtcctcagcc   10500
ccatggatcc aggccctcca gggcttagg aagcatctgc agtctccttt taggcccttg   10560
agatttcaaa ttacgtctaa tcacaactcg cagggctaga cctactccac ttgtgatccc   10620
ataatgtctg ctggactccc agcttgggtg tagcagtgtc cttggcaagg gccagcttga   10680
gggccgaggg cactgaacac ttttttattg gggcaatggc tgctggcccc tttacggtca   10740
aggtgtgcag actgagaagt gtccatatca cttgctaatt gctttgctcg aacatgaaga   10800
cttggacata agaaatacgt gcacacactc agagcatact ctgcacatgt tttcacacct   10860
atgtccacac atgaagacat tttctcacat aaccacagac aaaactgtgc cccagtgcac   10920
acggatgcac agaggcctgc gtggaaatcc atgcccatgc ctcggacacc tcacagtctc   10980
ggtatgcagg ctgagcacca caatcctgtc ctggagctgg ggagtcatgc ctctttcctt   11040
ccagtccctt ttctatgcac ttacaaagca tacttgcatt tgaattattt gtaccatttt   11100
gtatctcatg tcatgaaaca ctctctgtaa acatcatttt aaatcattgc ataatctacc   11160
atcatatggg tggaccgtaa tttatttgac caatcccta ttgttggaca tgtgagttgt   11220
```

| | | | | |
|---|---|---|---|---|
| attccatttt | tcacaacact | gtgtgtaaat | ctttatccac | ctgtctgatg | atttccttgg | 11280 |
| gctggcctcc | tagaagtcgc | aatactgagc | caaagggtaa | gactgtttta | aaggcctttg | 11340 |
| aatcatgttg | ctgaattc | | | | 11358 |

<210> SEQ ID NO 4
<211> LENGTH: 1598
<212> TYPE: DNA
<213> ORGANISM: Homo sapiens

<400> SEQUENCE: 4

| | | | | | |
|---|---|---|---|---|---|
| atgctctttg | agggcttgga | tctggtgtcg | gcgctggcca | ccctcgccgc | gtgcctggtg | 60 |
| tccgtgacgc | tgctgctggc | cgtgtcgcag | cagctgtggc | agctgcgctg | ggccgccact | 120 |
| cgcgacaaga | gctgcaagct | gcccatcccc | aagggatcca | tgggcttccc | gctcatcgga | 180 |
| gagaccggcc | actggctgct | gcagggttct | ggcttccagt | cgtcgcggag | ggagaagtat | 240 |
| ggcaacgtgt | tcaagacgca | tttgttgggg | cggccgctga | tacgcgtgac | cggcgcggag | 300 |
| aacgtgcgca | agatcctcat | gggcgagcac | cacctcgtga | gcaccgagtg | gcctcgcagc | 360 |
| acccgcatgt | tgctgggccc | caacacggtg | tccaattcca | ttggcgacat | ccaccgcaac | 420 |
| aagcgcaagg | tcttctccaa | gatcttcagc | cacgaggccc | tggagagtta | cctgcccaag | 480 |
| atccagctgg | tgatccagga | cacactgcgc | gcctggagca | gccaccccga | ggccatcaac | 540 |
| gtgtaccagg | aggcgcagaa | gctgaccttc | gcatggcca | tccgggtgct | gctgggcttc | 600 |
| agcatccctg | aggaggacct | tgggcacctc | tttgaggtct | accagcagtt | tgtggacaat | 660 |
| gtcttctccc | tgcctgtcga | cctgcccttc | agtggctacc | ggcggggcat | tcaggctcgg | 720 |
| cagatcctgc | agaaggggct | ggagaaggcc | atccgggaga | agctgcagtg | cacacagggc | 780 |
| aaggactact | ggacgcccct | ggacctcctc | attgagagca | gcaaggagca | cgggaaggag | 840 |
| atgaccatgc | aggagctgaa | ggacgggacc | ctggagctga | tctttgcggc | ctatgccacc | 900 |
| acggccagcg | ccagcacctc | actcatcatg | cagctgctga | agcaccccac | tgtgctggag | 960 |
| aagctgcggg | atgagctgcg | ggctcatggc | atcctgcaca | gtggcggctg | ccctgcgag | 1020 |
| ggcacactgc | gcctggacac | gctcagtggg | ctgcgctacc | tggactgcgt | catcaaggag | 1080 |
| gtcatgcgcc | tgttcacgcc | catttccggc | ggctaccgca | ctgtgctgca | gaccttcgag | 1140 |
| cttgatggtt | tccagatccc | caaaggctgg | agtgtcatgt | atagcatccg | ggacacccat | 1200 |
| gacacagcgc | ccgtgttcaa | agacgtgaac | gtgttcgacc | ccgatcgctt | cagccaggcg | 1260 |
| cggagcgagg | acaaggatgg | ccgcttccat | tacctcccgt | tcggtggcgg | tgtccggacc | 1320 |
| tgcctgggca | gcacctggc | caagctgttc | ctgaaggtgc | tggcggtgga | gctggctagc | 1380 |
| accagccgct | ttgagctggc | tacacggacc | ttccccccgca | tcaccttggt | ccccgtcctg | 1440 |
| caccccgtgg | atggcctcag | cgtcaagttc | tttggcctgg | actccaacca | gaacgagatc | 1500 |
| ctgccggaga | cggaggccat | gctgagcgcc | acagtctaac | ccaagaccca | cccgcctcag | 1560 |
| cccagcccag | gcagcggggt | ggtggttgtg | ggaggtag | | 1598 |

<210> SEQ ID NO 5
<211> LENGTH: 512
<212> TYPE: PRT
<213> ORGANISM: Homo sapiens

<400> SEQUENCE: 5

Met Leu Phe Glu Gly Leu Asp Leu Val Ser Ala Leu Ala Thr Leu Ala
1               5                   10                  15

```
Ala Cys Leu Val Ser Val Thr Leu Leu Leu Ala Val Ser Gln Gln Leu
         20                  25                  30

Trp Gln Leu Arg Trp Ala Ala Thr Arg Asp Lys Ser Cys Lys Leu Pro
         35                  40                  45

Ile Pro Lys Gly Ser Met Gly Phe Pro Leu Ile Gly Glu Thr Gly His
 50                  55                  60

Trp Leu Gln Gly Ser Gly Phe Gln Ser Ser Arg Arg Glu Lys Tyr
 65                  70                  75                  80

Gly Asn Val Phe Lys Thr His Leu Leu Gly Arg Pro Leu Ile Arg Val
                 85                  90                  95

Thr Gly Ala Glu Asn Val Arg Lys Ile Leu Met Gly Glu His His Leu
             100                 105                 110

Val Ser Thr Glu Trp Pro Arg Ser Thr Arg Met Leu Leu Gly Pro Asn
         115                 120                 125

Thr Val Ser Asn Ser Ile Gly Asp Ile His Arg Asn Lys Arg Lys Val
 130                 135                 140

Phe Ser Lys Ile Phe Ser His Glu Ala Leu Glu Ser Tyr Leu Pro Lys
145                 150                 155                 160

Ile Gln Leu Val Ile Gln Asp Thr Leu Arg Ala Trp Ser Ser His Pro
                 165                 170                 175

Glu Ala Ile Asn Val Tyr Gln Glu Ala Gln Lys Leu Thr Phe Arg Met
             180                 185                 190

Ala Ile Arg Val Leu Leu Gly Phe Ser Ile Pro Glu Glu Asp Leu Gly
         195                 200                 205

His Leu Phe Glu Val Tyr Gln Gln Phe Val Asp Asn Val Phe Ser Leu
     210                 215                 220

Pro Val Asp Leu Pro Phe Ser Gly Tyr Arg Arg Gly Ile Gln Ala Arg
225                 230                 235                 240

Gln Ile Leu Gln Lys Gly Leu Glu Lys Ala Ile Arg Glu Lys Leu Gln
                 245                 250                 255

Cys Thr Gln Gly Lys Asp Tyr Leu Asp Ala Leu Asp Leu Leu Ile Glu
             260                 265                 270

Ser Ser Lys Glu His Gly Lys Glu Met Thr Met Gln Glu Leu Lys Asp
         275                 280                 285

Gly Thr Leu Glu Leu Ile Phe Ala Ala Tyr Ala Thr Thr Ala Ser Ala
 290                 295                 300

Ser Thr Ser Leu Ile Met Gln Leu Leu Lys His Pro Thr Val Leu Glu
305                 310                 315                 320

Lys Leu Arg Asp Glu Leu Arg Ala His Gly Ile Leu His Ser Gly Gly
                 325                 330                 335

Cys Pro Cys Glu Gly Thr Leu Arg Leu Asp Thr Leu Ser Gly Leu Arg
             340                 345                 350

Tyr Leu Asp Cys Val Ile Lys Glu Val Met Arg Leu Phe Thr Pro Ile
         355                 360                 365

Ser Gly Gly Tyr Arg Thr Val Leu Gln Thr Phe Glu Leu Asp Gly Phe
 370                 375                 380

Gln Ile Pro Lys Gly Trp Ser Val Met Tyr Ser Ile Arg Asp Thr His
385                 390                 395                 400

Asp Thr Ala Pro Val Phe Lys Asp Val Asn Val Phe Asp Pro Asp Arg
                 405                 410                 415

Phe Ser Gln Ala Arg Ser Glu Asp Lys Asp Gly Arg Phe His Tyr Leu
             420                 425                 430

Pro Phe Gly Gly Gly Val Arg Thr Cys Leu Gly Lys His Leu Ala Lys
```

```
              435             440             445
Leu Phe Leu Lys Val Leu Ala Val Glu Leu Ala Ser Thr Ser Arg Phe
    450                 455                 460

Glu Leu Ala Thr Arg Thr Phe Pro Arg Ile Thr Leu Val Pro Val Leu
465                 470                 475                 480

His Pro Val Asp Gly Leu Ser Val Lys Phe Phe Gly Leu Asp Ser Asn
                485                 490                 495

Gln Asn Glu Ile Leu Pro Glu Thr Glu Ala Met Leu Ser Ala Thr Val
            500                 505                 510
```

<210> SEQ ID NO 6
<211> LENGTH: 616
<212> TYPE: DNA
<213> ORGANISM: Mus musculus

<400> SEQUENCE: 6

```
cggccgcccc agtaagtgtg tcttgaaaac gttgccatac ttctcccggc gcgacgactg     60
gaagccggaa ccctgtagca accagtgacc agtctctccg atgagcggga atcccatgga    120
gcccttgggg atgggcagct tgcagctctt gtcgcgggtg gcagcccagc gcagctgcca    180
cagctgctgc gacaccgcca gcagcagcgt cacggacacc aggcacgcgg cgagggtggc    240
cagcgccgac accaactcca agccttcaaa cagcatgttg gcagccgctt ggggggattgg   300
ctgtgcggtc gcgatggggg aggggagggg ccggaccaga gtgacggggg aggggaggct    360
gcggcagggg gtcctggcac ccctcggaga aacccaggag atggggccga ggggaagggg    420
ctggaggctg cgaggtgatc gaagagagag aggaaaaaga ttgcctgggg aggccttggc    480
tccaaacact ttgcccagga ggaattattt tatagaagtg actcttccca tcctccgcca    540
tcaaagcccc aagcccagaa ttccttctgc cctacaacca atacagtcta aagcaatctg    600
aaaatggact tgccga                                                    616
```

<210> SEQ ID NO 7
<211> LENGTH: 464
<212> TYPE: DNA
<213> ORGANISM: rattus

<400> SEQUENCE: 7

```
tttttttttt ttttgtgag tccccacagt ttattatgga agccaataaa agagcacatt      60
gagtatttca caaatgcag gacattcgtt gttgtaatat gcaacgtgga atattatata     120
tacatcaaaa ccacacgaca gccaagacac acacacaagc accagctcat accaagacga    180
gacacacaag tgcttttttca atattaaaac aactgtgata aagcatatt aatattttga    240
aacatgttta caataaagaa caattcatat tttactaaat aacaaatatt taacagcaaa    300
aactttaaac taaatatcta ttttgaatta taacaaaata gtacttataa tagtttataa    360
agacggacac aaaattataa catttatgaa aaaaagtttt gtgtataaa ataacagaaa     420
cctgtgcagg gtcaaaacgg ttgcccagaa tgcacacgcc agcg                     464
```

<210> SEQ ID NO 8
<211> LENGTH: 503
<212> TYPE: DNA
<213> ORGANISM: Danio rerio

<400> SEQUENCE: 8

```
ggttcttatg ggagagcaca gcctggtcac tgtggactgt ccccaaagca ccagcactct     60
tctgggcga aacagtttgg ccaactcaat aggagacatc catcgcaaaa ggaggaagat     120
```

```
ctttgctaaa gttttagcc atgaggctct ggaaagctac ctgcccaaga tccagcaggt    180
cattcaggag accctacgtg tgtggagctc aatcctgac cccatcaatg tgtatcgcga    240
gtcccagcgg ctatccttca acatggctgt acgcgtgctc ctgggtttcc gcatcccaga    300
agaagagatg cactgtttgt tcagcacctt ccaggagttt gtggagaacg tcttcagtct    360
tcccatcgac ctgccattta gtggttacag aaagggtatt cgagcaagag actcactcca    420
aaaaagcata gagaaagcca tcagagagaa accactccac acacagggga aagattacac    480
tgatgctctt gatgtgcttc tag                                            503
```

```
<210> SEQ ID NO 9
<211> LENGTH: 26
<212> TYPE: DNA
<213> ORGANISM: Artificial Sequence
<220> FEATURE:
<223> OTHER INFORMATION: PCR amplify fragment

<400> SEQUENCE: 9
caacatgctc tttgagggct tggatc                                         26

<210> SEQ ID NO 10
<211> LENGTH: 27
<212> TYPE: DNA
<213> ORGANISM: Artificial Sequence
<220> FEATURE:
<223> OTHER INFORMATION: PCR amplify fragment

<400> SEQUENCE: 10
ctacctccca caaccaccac cccgctg                                        27

<210> SEQ ID NO 11
<211> LENGTH: 203
<212> TYPE: PRT
<213> ORGANISM: Mus musculus

<400> SEQUENCE: 11
```

```
Arg Gln Val His Phe Gln Ile Ala Leu Asp Cys Ile Gly Cys Arg Ala
 1               5                  10                  15

Glu Gly Ile Leu Gly Leu Gly Leu Trp Arg Arg Met Gly Arg Val Thr
                20                  25                  30

Ser Ile Lys Phe Leu Leu Gly Lys Val Phe Gly Ala Lys Ala Ser Pro
            35                  40                  45

Gly Asn Leu Phe Pro Leu Ser Leu Arg Ser Pro Arg Ser Leu Gln Pro
        50                  55                  60

Leu Pro Leu Gly Pro Ile Ser Trp Val Ser Pro Arg Gly Ala Arg Thr
 65                  70                  75                  80

Pro Cys Arg Ser Leu Pro Ser Pro Val Thr Leu Val Arg Pro Ser Pro
                85                  90                  95

Pro Pro Ser Arg Thr Ala Gln Pro Ile Pro Gln Ala Ala Ala Asn Met
            100                 105                 110

Leu Phe Glu Gly Leu Glu Leu Val Ser Ala Leu Ala Thr Leu Ala Ala
        115                 120                 125

Cys Leu Val Ser Val Thr Leu Leu Ala Val Ser Gln Gln Leu Trp
        130                 135                 140

Gln Leu Arg Trp Ala Ala Thr Arg Asp Lys Ser Cys Lys Leu Pro Ile
145                 150                 155                 160

Pro Lys Gly Ser Met Gly Phe Pro Leu Ile Gly Glu Thr Gly His Trp
                165                 170                 175
```

```
Leu Leu Gln Gly Ser Gly Phe Gln Ser Ser Arg Arg Glu Lys Tyr Gly
            180                 185                 190

Asn Val Phe Lys Thr His Leu Leu Gly Arg Pro
        195                 200
```

<210> SEQ ID NO 12
<211> LENGTH: 167
<212> TYPE: PRT
<213> ORGANISM: Danio rerio

<400> SEQUENCE: 12

```
Val Leu Met Gly Glu His Ser Leu Val Thr Val Asp Cys Pro Gln Ser
1               5                   10                  15

Thr Ser Thr Leu Leu Gly Arg Asn Ser Leu Ala Asn Ser Ile Gly Asp
            20                  25                  30

Ile His Arg Lys Arg Arg Lys Ile Phe Ala Lys Val Phe Ser His Glu
        35                  40                  45

Ala Leu Glu Ser Tyr Leu Pro Lys Ile Gln Gln Val Ile Gln Glu Thr
    50                  55                  60

Leu Arg Val Trp Ser Ser Asn Pro Asp Pro Ile Asn Val Tyr Arg Glu
65                  70                  75                  80

Ser Gln Arg Leu Ser Phe Asn Met Ala Val Arg Val Leu Leu Gly Phe
                85                  90                  95

Arg Ile Pro Glu Glu Met His Cys Leu Phe Ser Thr Phe Gln Glu
            100                 105                 110

Phe Val Glu Asn Val Phe Ser Leu Pro Ile Asp Leu Pro Phe Ser Gly
        115                 120                 125

Tyr Arg Lys Gly Ile Arg Ala Arg Asp Ser Leu Gln Lys Ser Ile Glu
    130                 135                 140

Lys Ala Ile Arg Glu Lys Pro Leu His Thr Gln Gly Lys Asp Tyr Thr
145                 150                 155                 160

Asp Ala Leu Asp Val Leu Leu
                165
```

<210> SEQ ID NO 13
<211> LENGTH: 1494
<212> TYPE: DNA
<213> ORGANISM: Homo sapiens
<220> FEATURE:
<221> NAME/KEY: CDS
<222> LOCATION: (1)..(1491)

<400> SEQUENCE: 13

```
atg ggg ctc ccg gcg ctg ctg gcc agt gcg ctc tgc acc ttc gtg ctg      48
Met Gly Leu Pro Ala Leu Leu Ala Ser Ala Leu Cys Thr Phe Val Leu
1               5                   10                  15 ccg ctg ctg ctc ttc ctg gct gcg atc aag ctc tgg gac ctg tac tgc      96
Pro Leu Leu Leu Phe Leu Ala Ala Ile Lys Leu Trp Asp Leu Tyr Cys
            20                  25                  30 gtg agc ggc cgc gac cgc agt tgt gcc ctc cca ttg ccc ccc ggg act     144
Val Ser Gly Arg Asp Arg Ser Cys Ala Leu Pro Leu Pro Pro Gly Thr
        35                  40                  45 atg ggc ttc ccc ttc ttt ggg gaa acc ttg cag atg gta ctg cag cgg     192
Met Gly Phe Pro Phe Phe Gly Glu Thr Leu Gln Met Val Leu Gln Arg
    50                  55                  60 agg aag ttc ctg cag atg aag cgc agg aaa tac ggc ttc atc tac aag     240
Arg Lys Phe Leu Gln Met Lys Arg Arg Lys Tyr Gly Phe Ile Tyr Lys
65                  70                  75                  80
```

-continued

| | |
|---|---|
| acg cat ctg ttc ggg cgg ccc acc gta cgg gtg atg ggc gcg gac aat<br>Thr His Leu Phe Gly Arg Pro Thr Val Arg Val Met Gly Ala Asp Asn<br>                      85                      90                95 | 288 |
| gtg cgg cgc atc ttg ctc gga gac gac cgg ctg gtg tcg gtc cac tgg<br>Val Arg Arg Ile Leu Leu Gly Asp Asp Arg Leu Val Ser Val His Trp<br>            100                  105                110 | 336 |
| cca gcg tcg gtg cgc acc att ctg gga tct ggc tgc ctc tct aac ctg<br>Pro Ala Ser Val Arg Thr Ile Leu Gly Ser Gly Cys Leu Ser Asn Leu<br>            115                  120                125 | 384 |
| cac gac tcc tcg cac aag cag cgc aag aag gtg att atg cgg gcc ttc<br>His Asp Ser Ser His Lys Gln Arg Lys Lys Val Ile Met Arg Ala Phe<br>        130                  135                140 | 432 |
| agc cgc gag gca ctc gaa tgc tac gtg ccg gtg atc acc gag gaa gtg<br>Ser Arg Glu Ala Leu Glu Cys Tyr Val Pro Val Ile Thr Glu Glu Val<br>145                  150                155                160 | 480 |
| ggc agc agc ctg gag cag tgg ctg agc tgc ggc gag cgc ggc ctc ctg<br>Gly Ser Ser Leu Glu Gln Trp Leu Ser Cys Gly Glu Arg Gly Leu Leu<br>                  165                170                175 | 528 |
| gtc tac ccc gag gtg aag cgc ctc atg ttc cga atc gcc atg cgc atc<br>Val Tyr Pro Glu Val Lys Arg Leu Met Phe Arg Ile Ala Met Arg Ile<br>        180                  185                190 | 576 |
| cta ctg ggc tgc gaa ccc caa ctg gcg ggc gac ggg gac tcc gag cag<br>Leu Leu Gly Cys Glu Pro Gln Leu Ala Gly Asp Gly Asp Ser Glu Gln<br>            195                  200                205 | 624 |
| cag ctt gtg gag gcc ttc gag gaa atg acc cgc aat ctc ttc tcg ctg<br>Gln Leu Val Glu Ala Phe Glu Glu Met Thr Arg Asn Leu Phe Ser Leu<br>        210                  215                220 | 672 |
| ccc atc gac gtg ccc ttc agc ggg ctg tac cgg ggc atg aag gcg cgg<br>Pro Ile Asp Val Pro Phe Ser Gly Leu Tyr Arg Gly Met Lys Ala Arg<br>225                  230                235                240 | 720 |
| aac ctc att cac gcg cgc atc gag cag aac att cgc gcc aag atc tgc<br>Asn Leu Ile His Ala Arg Ile Glu Gln Asn Ile Arg Ala Lys Ile Cys<br>                  245                250                255 | 768 |
| ggg ctg cgg gca tcc gag gcg ggc cag ggc tgc aaa gac gcg ctg cag<br>Gly Leu Arg Ala Ser Glu Ala Gly Gln Gly Cys Lys Asp Ala Leu Gln<br>            260                  265                270 | 816 |
| ctg ttg atc gag cac tcg tgg gag agg gga gag cgg ctg gac atg cag<br>Leu Leu Ile Glu His Ser Trp Glu Arg Gly Glu Arg Leu Asp Met Gln<br>        275                  280                285 | 864 |
| gca cta aag caa tct tca acc gaa ctc ctc ttt gga gga cac gaa acc<br>Ala Leu Lys Gln Ser Ser Thr Glu Leu Leu Phe Gly Gly His Glu Thr<br>290                  295                300 | 912 |
| acg gcc agt gca gcc aca tct ctg atc act tac ctg ggg ctc tac cca<br>Thr Ala Ser Ala Ala Thr Ser Leu Ile Thr Tyr Leu Gly Leu Tyr Pro<br>305                  310                315                320 | 960 |
| cat gtt ctc cag aaa gtg cga gaa gag ctg aag agt aag ggt tta ctt<br>His Val Leu Gln Lys Val Arg Glu Glu Leu Lys Ser Lys Gly Leu Leu<br>                  325                330                335 | 1008 |
| tgc aag agc aat caa gac aac aag ttg gac atg gaa att ttg gaa caa<br>Cys Lys Ser Asn Gln Asp Asn Lys Leu Asp Met Glu Ile Leu Glu Gln<br>            340                  345                350 | 1056 |
| ctt aaa tac atc ggg tgt gtt att aag gag acc ctt cga ctg aat ccc<br>Leu Lys Tyr Ile Gly Cys Val Ile Lys Glu Thr Leu Arg Leu Asn Pro<br>        355                  360                365 | 1104 |
| cca gtt cca gga ggg ttt cgg gtt gct ctg aag act ttt gaa tta aat<br>Pro Val Pro Gly Gly Phe Arg Val Ala Leu Lys Thr Phe Glu Leu Asn<br>        370                  375                380 | 1152 |
| gga tac cag att ccc aag ggc tgg aat gtt atc tac agt atc tgt gat<br>Gly Tyr Gln Ile Pro Lys Gly Trp Asn Val Ile Tyr Ser Ile Cys Asp<br>385                  390                395                400 | 1200 |

-continued

```
act cat gat gtg gca gag atc ttc acc aac aag gaa gaa ttt aat cct      1248
Thr His Asp Val Ala Glu Ile Phe Thr Asn Lys Glu Glu Phe Asn Pro
                405                 410                 415 gac cga ttc agt gct cct cac cca gag gat gca tcc agg ttc agc ttc      1296
Asp Arg Phe Ser Ala Pro His Pro Glu Asp Ala Ser Arg Phe Ser Phe
            420                 425                 430 att cca ttt gga gga ggc ctt agg agc tgt gta ggc aaa gaa ttt gca      1344
Ile Pro Phe Gly Gly Gly Leu Arg Ser Cys Val Gly Lys Glu Phe Ala
        435                 440                 445 aaa att ctt ctc aaa ata ttt aca gtg gag ctg gcc agg cat tgt gac      1392
Lys Ile Leu Leu Lys Ile Phe Thr Val Glu Leu Ala Arg His Cys Asp
    450                 455                 460 tgg cag ctt cta aat gga cct cct aca atg aaa acc agt ccc acc gtg      1440
Trp Gln Leu Leu Asn Gly Pro Pro Thr Met Lys Thr Ser Pro Thr Val
465                 470                 475                 480 tat cct gtg gac aat ctc cct gca aga ttc acc cat ttc cat ggg gaa      1488
Tyr Pro Val Asp Asn Leu Pro Ala Arg Phe Thr His Phe His Gly Glu
                485                 490                 495 atc tga                                                              1494
Ile
```

<210> SEQ ID NO 14
<211> LENGTH: 1850
<212> TYPE: DNA
<213> ORGANISM: Danio rerio
<220> FEATURE:
<221> NAME/KEY: CDS
<222> LOCATION: (88)..(1563)

<400> SEQUENCE: 14

```
tgtcgccgtt gctgtcggtt gctgtcggac gctgtctcct ctccagaagc ttgttttcg       60 ttttggcgat cagttgcgcg cttcaac atg ggg ctg tac acc ctt atg gtc acc     114
                                Met Gly Leu Tyr Thr Leu Met Val Thr
                                  1               5 ttt ctc tgc acc atc gtg cta ccc gtt tta ctc ttt ctc gcc gcg gtg      162
Phe Leu Cys Thr Ile Val Leu Pro Val Leu Leu Phe Leu Ala Ala Val
10                  15                  20                  25 aag ttg tgg gag atg tta atg atc cga cga gtc gat ccg aac tgc aga      210
Lys Leu Trp Glu Met Leu Met Ile Arg Arg Val Asp Pro Asn Cys Arg
                30                  35                  40 agt cct cta ccg cca ggt acc atg ggc ttg ccg ttc att gga gaa acg      258
Ser Pro Leu Pro Pro Gly Thr Met Gly Leu Pro Phe Ile Gly Glu Thr
            45                  50                  55 ctc cag ctg atc ctc cag aga agg aag ttt ctg cgc atg aaa cgg cag      306
Leu Gln Leu Ile Leu Gln Arg Arg Lys Phe Leu Arg Met Lys Arg Gln
        60                  65                  70 aaa tac ggg tgc atc tac aag acg cac ctc ttc ggg aac ccg act gtc      354
Lys Tyr Gly Cys Ile Tyr Lys Thr His Leu Phe Gly Asn Pro Thr Val
75                  80                  85 agg gtg atg gga gct gat aat gtg agg cag att ctg ctg ggc gaa cac      402
Arg Val Met Gly Ala Asp Asn Val Arg Gln Ile Leu Leu Gly Glu His
90                  95                  100                 105 aag ctg gtg tct gtt cag tgg cca gca tca gtg aga acc atc ctg ggc      450
Lys Leu Val Ser Val Gln Trp Pro Ala Ser Val Arg Thr Ile Leu Gly
                110                 115                 120 tct gac acc ctc tcc aat gtc cat gga gtt caa cac aaa aac aag aaa      498
Ser Asp Thr Leu Ser Asn Val His Gly Val Gln His Lys Asn Lys Lys
            125                 130                 135 aag gcc att atg agg gcg ttc tct cga gat gct ctg gag cac tac att      546
Lys Ala Ile Met Arg Ala Phe Ser Arg Asp Ala Leu Glu His Tyr Ile
```

```
              140                 145                 150
ccc gtg atc cag cag gag gtg aag agc gcc ata cag gaa tgg ctg caa       594
Pro Val Ile Gln Gln Glu Val Lys Ser Ala Ile Gln Glu Trp Leu Gln
    155                 160                 165 aaa gac tcc tgc gtg ctg gtt tat cca gaa atg aag aaa ctc atg ttt       642
Lys Asp Ser Cys Val Leu Val Tyr Pro Glu Met Lys Lys Leu Met Phe
170                 175                 180                 185 cgg ata gct atg aga atc ctg ctt ggt ttt gaa cca gag caa ata aag       690
Arg Ile Ala Met Arg Ile Leu Leu Gly Phe Glu Pro Glu Gln Ile Lys
                190                 195                 200 acg gac gag caa gaa ctg gtg gaa gct ttt gag gaa atg atc aaa aac       738
Thr Asp Glu Gln Glu Leu Val Glu Ala Phe Glu Glu Met Ile Lys Asn
            205                 210                 215 ttg ttc tcc ttg cca atc gac gtt cct ttc agt ggt ctg tac agg ggt       786
Leu Phe Ser Leu Pro Ile Asp Val Pro Phe Ser Gly Leu Tyr Arg Gly
        220                 225                 230 ttg agg gca cgc aat ttc att cac tcc aaa att gag gaa aac atc agg       834
Leu Arg Ala Arg Asn Phe Ile His Ser Lys Ile Glu Glu Asn Ile Arg
    235                 240                 245 aag aaa att caa gat gac gac aat gaa aac gaa cag aaa tac aaa gac       882
Lys Lys Ile Gln Asp Asp Asp Asn Glu Asn Glu Gln Lys Tyr Lys Asp
250                 255                 260                 265 gcc ctt cag ctg ttg atc gag aac agc aga aga agt gac gaa cct ttt       930
Ala Leu Gln Leu Leu Ile Glu Asn Ser Arg Arg Ser Asp Glu Pro Phe
                270                 275                 280 agt ttg cag gcg atg aaa gaa gca gct aca gag ctt cta ttt gga ggt       978
Ser Leu Gln Ala Met Lys Glu Ala Ala Thr Glu Leu Leu Phe Gly Gly
            285                 290                 295 cat gaa acc acc gcc agc act gca acc tca ctt gtc atg ttt ctg ggt      1026
His Glu Thr Thr Ala Ser Thr Ala Thr Ser Leu Val Met Phe Leu Gly
        300                 305                 310 ctg aac aca gaa gtg gtg cag aag gtc aga gag gag gtt cag gag aag      1074
Leu Asn Thr Glu Val Val Gln Lys Val Arg Glu Glu Val Gln Glu Lys
    315                 320                 325 gtt gaa atg ggc atg tat aca cct gga aag ggc ttg agt atg gag ctg      1122
Val Glu Met Gly Met Tyr Thr Pro Gly Lys Gly Leu Ser Met Glu Leu
330                 335                 340                 345 ttg gac cag ctg aag tac act gga tgt gtg att aaa gag act ctt aga      1170
Leu Asp Gln Leu Lys Tyr Thr Gly Cys Val Ile Lys Glu Thr Leu Arg
                350                 355                 360 atc aac cct cct gtt ccc gga gga ttc aga gtc gca ctc aaa acc ttt      1218
Ile Asn Pro Pro Val Pro Gly Gly Phe Arg Val Ala Leu Lys Thr Phe
            365                 370                 375 gaa ttg aat ggt tac caa att cct aaa gga tgg aac gtc att tac agc      1266
Glu Leu Asn Gly Tyr Gln Ile Pro Lys Gly Trp Asn Val Ile Tyr Ser
        380                 385                 390 atc tgt gac acg cac gat gtg gcc gac gtc ttt cca aac aaa gag gag      1314
Ile Cys Asp Thr His Asp Val Ala Asp Val Phe Pro Asn Lys Glu Glu
    395                 400                 405 ttc cag ccg gag aga ttc atg agc aaa ggt ctg gag gac ggg tcc agg      1362
Phe Gln Pro Glu Arg Phe Met Ser Lys Gly Leu Glu Asp Gly Ser Arg
410                 415                 420                 425 ttt aac tac atc ccc ttc gga gga gga tcc agg atg tgt gtg ggc aaa      1410
Phe Asn Tyr Ile Pro Phe Gly Gly Gly Ser Arg Met Cys Val Gly Lys
                430                 435                 440 gag ttc gcc aaa gtg tta ctc aag atc ttt tta gtt gag tta acg cag      1458
Glu Phe Ala Lys Val Leu Leu Lys Ile Phe Leu Val Glu Leu Thr Gln
            445                 450                 455 cat tgc aat tgg att ctc tca aac gga ccc ccg aca atg aaa aca ggc      1506
```

```
                His Cys Asn Trp Ile Leu Ser Asn Gly Pro Pro Thr Met Lys Thr Gly
                    460                 465                 470 ccg act att tac cca gtg gac aat ctc cct acc aaa ttc act agt tat         1554
Pro Thr Ile Tyr Pro Val Asp Asn Leu Pro Thr Lys Phe Thr Ser Tyr
    475                 480                 485 gtc aga aat tagcctaacc ggagctttgt acatatgttt ttattttaga                 1603
Val Arg Asn
490 tgaactgtga tgtattggat attttctatt ttgtttatat aaagcagatg tgtatataag       1663 tctatgcgag gaagcgaaaa cgagggcact actttctcat ggatcactgt aatgctacag       1723 agtgtctgtg atgtatattt ataatgtagt tgtgttatat agcttttgta ctgtatgcaa       1783 cttatttaac tcgctcttta tctcatgggt tttatttaat aaaacatgtt cttacaaaaa       1843 aaaaaaa                                                                 1850

<210> SEQ ID NO 15
<211> LENGTH: 2677
<212> TYPE: DNA
<213> ORGANISM: Homo sapiens
<220> FEATURE:
<221> NAME/KEY: misc_feature
<222> LOCATION: (856)..(856)
<223> OTHER INFORMATION: n is any nucleic acid
<220> FEATURE:
<221> NAME/KEY: misc_feature
<222> LOCATION: (861)..(861)
<223> OTHER INFORMATION: n is any nucleic acid

<400> SEQUENCE: 15
gatcccagat ctgcctattg cgcccgatgc cccgaggctc tctcttggac tctggccctg         60
agttcttctg cgcgatcctt cggagacgtc tggaggcctg ctttatgcat ctctcttgga        120
cctcagtttc cccacacgtg ggaggaggca gctggacgat tcctgaaagg actttcccct       180
gcttcctcat cacgtggaag agagcccacc cggcacctgg aaatggaaag ccagtgaagg        240
ctgctttggg ccggggcakc gggtgggacc gggcgggagg gattccaaag agaccgccgg        300
gaaggctaga gcttggaatt ccggctcctc ggagtcctgg ccctccccca ccgccgcctc        360
ggagctcagc acaccttgga tggggaggc gggcagctcc tagccccgca ccccaggagg        420
cgcgctcgga gggaagccgc caccgccgcc gcctctgcct cggcgcggaa caaacggtta       480
aagattttgg gccascgcct ccgcgggggg aggagccagg ggccccaatc ccgcaattaa        540
agatgaactt tgggtgaact aattgtctga ccaaggtaac gtgggcagca acctgggccg       600
cctataaagc ggcagcgccg tggggtttga agcgctggcg gcggcggcag gtggcgcggg        660
aggtcgcggc gcgccatggg gctcccggcg ctgctggcca gtgcgctctg caccttcgtg       720
ctgccgctgc tgctcttcct ggctgcgatc aagctctggg acctgtactg cgtgagcggc        780
cgcgaccgca gttgtgccct cccattgccc ccgggactaa tsggsttccc cttcttttggg      840 gaaaccttgc agatgntact ncaggtaagg gagggtgggg cgggacaggc tgcttccccg       900
gagcccggcg cggctctggg cttctgctga agtcggggta ggcgccccg ggaggcatgc        960 tattgcggct aggagcaggg ctggcgggag cgcggcgctc cccggmkymc sctcawgcsc      1020
rcwwktmwcc tccgcctymc tcccamagcg garsaarwkc ykgmrgatga agcgcaggaa      1080
atacggcttc atctacaaga cgcatctgtt cgggcggccc accgtacggg tgatgggcgc      1140
ggacaatgtg cggcgcatct tgctcggaga gcaccggctg gtgtcggtcc actggccagc      1200
gtcggtgcgc accattctgg gatctggctg cctctctaac ctgcacgact cctcgcacaa      1260
```

```
gcagcgcaag aaggtgggggg caggaggcga cggctggaca gggaggggga ccccatttat    1320
gagcggaatt ccggctgatg gatgctaggc gcgggctagc agcttgaggt gggctaggac    1380
cctctgccag ctccaggtta gctttcccag ctcggagagt gccatgtgtc tggcaggact    1440
gggggtgtct ggaagggggac ggcggtagac gagagggggcg gatggaggct tttaacgctg  1500
tccccctcctc gggactcagg tgattatgcg ggccttcagc cgcgaggcac tcgaatgcta   1560
cgtgccggtg atcaccgagg aagtgggcag cagcctggac cagtggctga gctgcggcga   1620
gcgcggcctc ctggtctacc ccgaggtgaa gcgcctcatg ttccgaatcg ccatgcgcat    1680
cctactgggc tgcgaacccc aactggcggg cgacggggac tccgagcagc agcttgtgga   1740
ggccttcgag gaaatgaccc gcaatctctt ctcgctgccc atcgacgtgc ccttcagcgg   1800
gctgtaccgg gtaagggcgg caaacgggct gcggactagg ggcgcgggac ctgggcgtct   1860
gctcaccgcc gcgcgctctc tgcgctcagg gcatgaaggc gcggaacctc attcacgcgc   1920
gcatcgagca gaacattcgc gccaagatct gcgggctgcg ggcatccgag gcgggccagg   1980
gctgcaaaga cgcgctgcag ctgttgatcg agcactcgtg ggagagggga gagcggctgg   2040
acatgcaggt gagtagcagc ttcagaccag gcactgcgga gtttggtccc ctggctttcc    2100
aaggcgctgt tcctggggcc cccaaagcgc gcgcctgggg cccagctttc tggagtgggc    2160
ggccggctca gactacagct atggaatccc gaaggaaggc tgagcacccc ggtcaggaga    2220
gctgcggaag gggctgcggm ggaaactggg agcatcccct agcctttamc aggtttcaaa    2280
gggaaagttg gaatttgcaa aaatgttaat aaagaacctt gcgattttaa taaaactaag    2340
actttaactc aggagtttcc ggtagrgcgg ggtcgtactc gccttactgc tccagctgaa    2400
ctaaagggac gttgcatttt gtttaaagat attgctttcc ttgactttct gtcagcaaaa    2460
catttagccc ttctagtctt ccctccagaa ctctcagttc gattctgagt aatccttctg   2520
tcaaaccgca ggcagacttg tgagaatgtg ggtctcactc tattcttagg cactaaagca    2580
atcttcaacc gaactcctct ttggaggaca cgaaaccacg gccagtgcag ccacatctct    2640
gatcacttac ctgggggctct acccacatgt tctccag                           2677
```

<210> SEQ ID NO 16
<211> LENGTH: 683
<212> TYPE: DNA
<213> ORGANISM: Homo sapiens

<400> SEQUENCE: 16

```
gatccaggtt gctgaaacat atctccatat agggcagaac aattatcaaa agcataagaa     60
ttgcagccac agcataggga agaaagagga gttttttaaac cacaacaaaa gggagaaaga   120
agagaattttt aacttacatt taattcaaaa gtcttcagag caacccgaaa ccctcctgga   180
actgggggat tcagtcgaag ggtctcctta ataacacacc cgatgtatyt aagttgttcc    240
aaaatttcca tgtccaactt gttgtcttga ttgctcttgc aaagtaaacc ctaycaaaay   300
agtcatacag aggtgaacag tyattttgtg ctccaattaa aatcagccca gcagacgtaa   360
acagggctta agtggagact aaacccaaag ggccccatga tgggagagac tgggaggggg   420
aaacagcagc taatggccat ttgcctgccc aaatccacta tctatttaca atcccaggag   480
aatgctgctc accagttaga aggaccaagt ttctccccac gcccccccac cccacactca    540
ccaccaccac ccacactaat cagctattca cactatgtat gcccttggac acaccaattc    600
aagaaaagtg gaacctatct gagaatctcc acggttcaca aaaaggtgga ggagggtag    660
gaatacaagg tcaaaccctg ccc                                           683
```

<210> SEQ ID NO 17
<211> LENGTH: 1725
<212> TYPE: DNA
<213> ORGANISM: Mus musculus
<220> FEATURE:
<221> NAME/KEY: CDS
<222> LOCATION: (25)..(1515)

<400> SEQUENCE: 17

| | | | | | | | | | | | | | | | |
|---|---|---|---|---|---|---|---|---|---|---|---|---|---|---|---|
| gcacgaggga ggctgaagcg tgcc | atg | ggg | ctc | ccg | gcg | ctg | ctg | gcc | agt | | | | | 51 |
| | Met | Gly | Leu | Pro | Ala | Leu | Leu | Ala | Ser | | | | | |
| | 1 | | | 5 | | | | | | | | | | |

| gcg | ctc | tgc | acc | ttc | gtg | ctg | ccg | ctg | ctg | ctc | ttc | ctg | gcg | gcg | ctc | 99 |
|---|---|---|---|---|---|---|---|---|---|---|---|---|---|---|---|---|
| Ala | Leu | Cys | Thr | Phe | Val | Leu | Pro | Leu | Leu | Leu | Phe | Leu | Ala | Ala | Leu | |
| 10 | | | | 15 | | | | | 20 | | | | | 25 | | |

| aag | ctc | tgg | gac | ctg | tac | tgt | gtg | agc | agc | cgc | gat | cgc | agc | tgc | gcc | 147 |
|---|---|---|---|---|---|---|---|---|---|---|---|---|---|---|---|---|
| Lys | Leu | Trp | Asp | Leu | Tyr | Cys | Val | Ser | Ser | Arg | Asp | Arg | Ser | Cys | Ala | |
| | | | 30 | | | | | 35 | | | | | 40 | | | |

| ctc | ccc | ttg | ccc | ccc | ggt | acc | atg | ggc | ttc | cca | ttc | ttt | ggg | gaa | aca | 195 |
|---|---|---|---|---|---|---|---|---|---|---|---|---|---|---|---|---|
| Leu | Pro | Leu | Pro | Pro | Gly | Thr | Met | Gly | Phe | Pro | Phe | Phe | Gly | Glu | Thr | |
| | | 45 | | | | | 50 | | | | | 55 | | | | |

| ttg | cag | atg | gtg | ctt | cag | cgg | agg | aag | ttt | ctg | cag | atg | aag | cgc | agg | 243 |
|---|---|---|---|---|---|---|---|---|---|---|---|---|---|---|---|---|
| Leu | Gln | Met | Val | Leu | Gln | Arg | Arg | Lys | Phe | Leu | Gln | Met | Lys | Arg | Arg | |
| | 60 | | | | | 65 | | | | | 70 | | | | | |

| aaa | tac | ggc | ttc | atc | tac | aag | acg | cat | ctg | ttt | ggg | cgg | ccc | acg | gtg | 291 |
|---|---|---|---|---|---|---|---|---|---|---|---|---|---|---|---|---|
| Lys | Tyr | Gly | Phe | Ile | Tyr | Lys | Thr | His | Leu | Phe | Gly | Arg | Pro | Thr | Val | |
| 75 | | | | | 80 | | | | | 85 | | | | | | |

| cgg | gtg | atg | ggc | gcg | gat | aat | gtg | cgg | cgc | atc | ttg | ctg | gga | gag | cac | 339 |
|---|---|---|---|---|---|---|---|---|---|---|---|---|---|---|---|---|
| Arg | Val | Met | Gly | Ala | Asp | Asn | Val | Arg | Arg | Ile | Leu | Leu | Gly | Glu | His | |
| 90 | | | | 95 | | | | | 100 | | | | | 105 | | |

| cgg | ttg | gtg | tcg | gtg | cac | tgg | ccc | gcg | tcg | gtg | cgc | acc | atc | ctg | ggc | 387 |
|---|---|---|---|---|---|---|---|---|---|---|---|---|---|---|---|---|
| Arg | Leu | Val | Ser | Val | His | Trp | Pro | Ala | Ser | Val | Arg | Thr | Ile | Leu | Gly | |
| | | | 110 | | | | | 115 | | | | | 120 | | | |

| gct | ggc | tgc | ctc | tcc | aac | ctg | cac | gat | tcc | tcg | cac | aag | cag | cga | aag | 435 |
|---|---|---|---|---|---|---|---|---|---|---|---|---|---|---|---|---|
| Ala | Gly | Cys | Leu | Ser | Asn | Leu | His | Asp | Ser | Ser | His | Lys | Gln | Arg | Lys | |
| | | 125 | | | | | 130 | | | | | 135 | | | | |

| aag | gtg | att | atg | cag | gcc | ttc | agc | cgc | gag | gca | ctc | cag | tgc | tac | gtg | 483 |
|---|---|---|---|---|---|---|---|---|---|---|---|---|---|---|---|---|
| Lys | Val | Ile | Met | Gln | Ala | Phe | Ser | Arg | Glu | Ala | Leu | Gln | Cys | Tyr | Val | |
| | 140 | | | | | 145 | | | | | 150 | | | | | |

| ctg | gtg | atc | gct | gag | gaa | gtc | agc | agt | tgt | ctg | gag | cag | tgg | cta | agc | 531 |
|---|---|---|---|---|---|---|---|---|---|---|---|---|---|---|---|---|
| Leu | Val | Ile | Ala | Glu | Glu | Val | Ser | Ser | Cys | Leu | Glu | Gln | Trp | Leu | Ser | |
| 155 | | | | | 160 | | | | | 165 | | | | | | |

| tgc | ggc | gag | cgc | ggc | ctc | ctg | gtc | tac | ccc | gag | gtg | aag | cgc | ctc | atg | 579 |
|---|---|---|---|---|---|---|---|---|---|---|---|---|---|---|---|---|
| Cys | Gly | Glu | Arg | Gly | Leu | Leu | Val | Tyr | Pro | Glu | Val | Lys | Arg | Leu | Met | |
| 170 | | | | 175 | | | | | 180 | | | | | 185 | | |

| ttc | cgc | atc | gcc | atg | cgc | atc | ctg | ctg | ggc | tgc | gag | ccg | ggt | cca | gcg | 627 |
|---|---|---|---|---|---|---|---|---|---|---|---|---|---|---|---|---|
| Phe | Arg | Ile | Ala | Met | Arg | Ile | Leu | Leu | Gly | Cys | Glu | Pro | Gly | Pro | Ala | |
| | | | 190 | | | | | 195 | | | | | 200 | | | |

| ggc | ggc | ggg | gag | gac | gag | caa | cag | ctc | gtg | gag | gct | ttc | gag | gag | atg | 675 |
|---|---|---|---|---|---|---|---|---|---|---|---|---|---|---|---|---|
| Gly | Gly | Gly | Glu | Asp | Glu | Gln | Gln | Leu | Val | Glu | Ala | Phe | Glu | Glu | Met | |
| | | | 205 | | | | | 210 | | | | | 215 | | | |

| acc | cgc | aat | ctc | ttc | tct | ctt | ccc | att | gac | gtg | ccc | ttt | agc | ggc | ctg | 723 |
|---|---|---|---|---|---|---|---|---|---|---|---|---|---|---|---|---|
| Thr | Arg | Asn | Leu | Phe | Ser | Leu | Pro | Ile | Asp | Val | Pro | Phe | Ser | Gly | Leu | |
| | | 220 | | | | | 225 | | | | | 230 | | | | |

| tac | cgg | ggc | gtg | aag | gcg | cgg | aac | ctt | ata | cac | gcg | cgc | atc | gag | gag | 771 |
|---|---|---|---|---|---|---|---|---|---|---|---|---|---|---|---|---|
| Tyr | Arg | Gly | Val | Lys | Ala | Arg | Asn | Leu | Ile | His | Ala | Arg | Ile | Glu | Glu | |
| | 235 | | | | | 240 | | | | | 245 | | | | | |

| aac | att | cgc | gcc | aag | atc | cgc | cgg | ctt | cag | gct | aca | gag | ccg | gat | ggg | 819 |
|---|---|---|---|---|---|---|---|---|---|---|---|---|---|---|---|---|
| Asn | Ile | Arg | Ala | Lys | Ile | Arg | Arg | Leu | Gln | Ala | Thr | Glu | Pro | Asp | Gly | |
| 250 | | | | | 255 | | | | | 260 | | | | | 265 | |

```
ggt tgc aag gac gcg ctg cag ctc ctg att gag cac tcg tgg gag agg      867
Gly Cys Lys Asp Ala Leu Gln Leu Leu Ile Glu His Ser Trp Glu Arg
            270                 275                 280 gga gag agg ctg gat atg cag gca cta aaa caa tcg tca aca gag ctc      915
Gly Glu Arg Leu Asp Met Gln Ala Leu Lys Gln Ser Ser Thr Glu Leu
        285                 290                 295 ctc ttt ggt ggt cat gaa act aca gcc agt gct gcg aca tca ctg atc      963
Leu Phe Gly Gly His Glu Thr Thr Ala Ser Ala Ala Thr Ser Leu Ile
    300                 305                 310 act tac cta gga ctc tac cca cat gtc ctc cag aaa gtt cga gaa gag     1011
Thr Tyr Leu Gly Leu Tyr Pro His Val Leu Gln Lys Val Arg Glu Glu
315                 320                 325 ata aag agc aag ggc tta ctt tgc aag agc aat caa gac aac aag tta     1059
Ile Lys Ser Lys Gly Leu Leu Cys Lys Ser Asn Gln Asp Asn Lys Leu
330                 335                 340                 345 gac atg gaa act ttg gaa cag ctt aaa tac att ggg tgt gtc att aag     1107
Asp Met Glu Thr Leu Glu Gln Leu Lys Tyr Ile Gly Cys Val Ile Lys
                350                 355                 360 gag acc ctg cga ttg aat cct ccg gtt cca gga ggg ttt cgg gtt gct     1155
Glu Thr Leu Arg Leu Asn Pro Pro Val Pro Gly Gly Phe Arg Val Ala
            365                 370                 375 ctg aag act ttt gag ctg aat gga tac cag atc ccc aag ggc tgg aat     1203
Leu Lys Thr Phe Glu Leu Asn Gly Tyr Gln Ile Pro Lys Gly Trp Asn
        380                 385                 390 gtt att tac agt atc tgt gac acc cac gat gtg gca gat atc ttc act     1251
Val Ile Tyr Ser Ile Cys Asp Thr His Asp Val Ala Asp Ile Phe Thr
    395                 400                 405 aac aag gag gaa ttt aat ccc gac cgc ttt ata gtg cct cat cca gag     1299
Asn Lys Glu Glu Phe Asn Pro Asp Arg Phe Ile Val Pro His Pro Glu
410                 415                 420                 425 gat gct tcc cgg ttc agc ttc att cca ttt gga gga ggc ctt cgg agc     1347
Asp Ala Ser Arg Phe Ser Phe Ile Pro Phe Gly Gly Gly Leu Arg Ser
                430                 435                 440 tgt gta ggc aaa gag ttt gca aaa att ctt ctt aag ata ttt aca gtg     1395
Cys Val Gly Lys Glu Phe Ala Lys Ile Leu Leu Lys Ile Phe Thr Val
            445                 450                 455 gag ctg gct agg cac tgt gat tgg cag ctt cta aat gga cct cct aca     1443
Glu Leu Ala Arg His Cys Asp Trp Gln Leu Leu Asn Gly Pro Pro Thr
        460                 465                 470 atg aag aca agc ccc act gtg tac cct gtg gac aat ctc cct gca aga     1491
Met Lys Thr Ser Pro Thr Val Tyr Pro Val Asp Asn Leu Pro Ala Arg
    475                 480                 485 ttc acc tac ttc cag gga gat atc tgatagctat ttcaattctt ggacttattt    1545
Phe Thr Tyr Phe Gln Gly Asp Ile
490                 495 gaagtgtata ttggttttttt ttaaaaatag tgtcatgttg actttattta atttctaaat  1605
gtatagtatg atatttatgt gtctctacta cagtcccgtg gtctttaaat attaaaataa  1665
tgaatttgta tgatttccca ataaagtaaa attaaaaagt gaaaaaaaaa aaaaaaaaa   1725

<210> SEQ ID NO 18
<211> LENGTH: 690
<212> TYPE: DNA
<213> ORGANISM: Mus musculus
<220> FEATURE:
<221> NAME/KEY: misc_feature
<222> LOCATION: (636)..(636)
<223> OTHER INFORMATION: n is any nucleic acid
<220> FEATURE:
<221> NAME/KEY: misc_feature
<222> LOCATION: (659)..(659)
```

<223> OTHER INFORMATION: n is any nucleic acid
<220> FEATURE:
<221> NAME/KEY: misc_feature
<222> LOCATION: (665)..(665)
<223> OTHER INFORMATION: n is any nucleic acid
<220> FEATURE:
<221> NAME/KEY: misc_feature
<222> LOCATION: (683)..(683)
<223> OTHER INFORMATION: n is any nucleic acid

<400> SEQUENCE: 18

| | | | | | |
|---|---|---|---|---|---|
| gcggccgctg | attcgtgtga | ccggtgcgga | gaatgtgcgc | aagatcctac | tgggcgaaca | 60 |
| ccagctagtg | agcaccgagt | ggccgcggag | cgcacgcgta | ctgctgggtc | caacacggt | 120 |
| ggccaattcc | attggcgaca | tccaccgcaa | caagcgcaag | gtcttctcca | agatcttcag | 180 |
| ccatgaggca | cttgagagct | acctgcccaa | gatccaactg | gtgatccagg | atacacttcg | 240 |
| agcctggagc | agccagcctg | aggccatcaa | tgtatatcag | gaggcccagc | gacttacctt | 300 |
| ccgaatggcc | gtgcgtgtgc | tgctaggctt | cagcatccct | gaggaggacc | tgggccacct | 360 |
| ctttgaggta | taccagcagt | ttgtggagaa | tgtcttctct | ctgccagtgg | acctgccctt | 420 |
| cagtggctac | cggaggggca | tccaagctcg | gcagatcctt | cagaagggcc | tagagaaggc | 480 |
| tatccgtgag | aagctgcagt | gtacccaggg | caaagactac | tcggacgccc | tggacattct | 540 |
| cattgagagc | agcaaggaac | atggcaagga | gatgaccatg | caggagctga | aggatggaac | 600 |
| cctggagttg | atcttcgcag | cctacgccac | gacggncagc | ctcgtgccga | attcttggnc | 660 |
| tcganggcca | aattccctat | agngagtcgt | | | | 690 |

<210> SEQ ID NO 19
<211> LENGTH: 616
<212> TYPE: DNA
<213> ORGANISM: Mus musculus

<400> SEQUENCE: 19

| | | | | | |
|---|---|---|---|---|---|
| cggccgcccc | agtaagtgtg | tcttgaaaac | gttgccatac | ttctcccggc | gcgacgactg | 60 |
| gaagccggaa | ccctgtagca | accagtgacc | agtctctccg | atgagcggga | atcccatgga | 120 |
| gcccttgggg | atgggcagct | tgcagctctt | gtcgcgggtg | gcagcccagc | gcagctgcca | 180 |
| cagctgctgc | gacaccgcca | gcagcagcgt | cacggacacc | aggcacgcgg | cgagggtggc | 240 |
| cagcgccgac | accaactcca | agccttcaaa | cagcatgttg | gcagccgctt | ggggattgg | 300 |
| ctgtgcggtc | cgcgatgggg | gaggggaggg | ccggaccaga | gtgacggggg | agggaggct | 360 |
| gcggcagggg | gtcctggcac | ccctcggaga | aacccaggag | atgggccga | ggggaagggg | 420 |
| ctggaggctg | cgaggtgatc | gaagagagag | aggaaaaaga | ttgcctgggg | aggccttggc | 480 |
| tccaaacact | ttgcccagga | ggaattattt | tatagaagtg | actcttccca | tcctccgcca | 540 |
| tcaaagcccc | aagcccagaa | ttccttctgc | cctacaacca | atacagtcta | agcaatctg | 600 |
| aaaatggact | tgccga | | | | | 616 |

<210> SEQ ID NO 20
<211> LENGTH: 477
<212> TYPE: DNA
<213> ORGANISM: Mus musculus

<400> SEQUENCE: 20

| | | | | | |
|---|---|---|---|---|---|
| gcgccccttc | caccttctat | cggcaagtcc | attttcagat | tgctttagac | tgtattggtt | 60 |
| gtagggcaga | aggaattctg | ggcttggggc | tttgatggcg | gaggatggga | agagtcactt | 120 |
| ctataaaata | attcctcctg | ggcaaagtgt | ttggagccaa | ggcctcccca | ggcaatcttt | 180 |

-continued

```
ttcctctctc tcttcgatca cctcgcagcc tccagcccct tccctcggc cccatctcct      240 gggtttctcc gagggtgcc aggaccccct gccgcagcct cccctccccc gtcactctgg      300
tccggccctc ccctccccca tcgcggaccg cacagccaat cccccaagcg gctgccaaca    360
tgctgtttga aggcttggag ttggtgtcgg cgctggccac cctcgccgcg tgcctggtgt    420
ccgtgacgct gctgctggcg gtgtcgcagc agctgtggca gctgcgctgg gctgcca      477
```

<210> SEQ ID NO 21
<211> LENGTH: 205
<212> TYPE: DNA
<213> ORGANISM: Mus musculus

<400> SEQUENCE: 21

```
atgctgtttg aaggcttgga gttggtgtcg gcgctggcca ccctcgccgc gtgcctggtg     60
tccgtgacgc tgctgctggc ggtgtcgcag cagctgtggc agctgcgctg gctgccacc    120 cgcgacaaga gctgcaagct gcccatcccc aagggctcca tgggattccc gctcatcgga   180
gagactggtc actggttgct acagg                                          205
```

<210> SEQ ID NO 22
<211> LENGTH: 230
<212> TYPE: DNA
<213> ORGANISM: Mus musculus

<400> SEQUENCE: 22

```
agggttccgg cttccagtcg tcgcgccggg agaagtatgg caacgttttc aagacacact     60
tactggggcg ccgctgatt cgtgtgaccg gtgcggagaa tgtgcgcaag atcctactgc    120
gcgaacacca gctagtgagc accgagtggc cgcggagcgc acgcgtactg ctgggtccca    180
acacggtggc caattccatt ggcgacatcc accgcaacaa gcgcaaggta              230
```

<210> SEQ ID NO 23
<211> LENGTH: 275
<212> TYPE: DNA
<213> ORGANISM: Mus musculus

<400> SEQUENCE: 23

```
aggtcttctc caagatcttc agccatgagg cacttgagag ctacctgccc aagatccaac     60
tggtgatcca ggatacactt cgagcctgga gcagccagcc tgaggccatc aatgtatatc    120
aggaggccca gcgacttacc ttccgaatgg ccgtgcgtgt gctgctaggc ttcagcatcc    180
ctgaggagga cctgggccac ctctttgagg tataccagca gtttgtggag aatgtcttct    240
ctctgccagt ggacctgccc ttcagtggct accgg                               275
```

<210> SEQ ID NO 24
<211> LENGTH: 157
<212> TYPE: DNA
<213> ORGANISM: Mus musculus

<400> SEQUENCE: 24

```
ggcatccaag ctcggcagat ccttcagaag ggcctagaga aggctatccg tgagaagctg     60
cagtgtaccc agggcaaaga ctactcggac gccctggaca ttctcattga gagcagcaag   120
gaacatggca aggagatgac catgcaggag ctgaagg                             157
```

<210> SEQ ID NO 25
<211> LENGTH: 380

<212> TYPE: DNA
<213> ORGANISM: Mus musculus

<400> SEQUENCE: 25

| | |
|---|---|
| ctcaacatgg cctctgtctc cggcagaatc tcattctggt tggagtccag accaaagaac | 60 |
| ttgacactga ggccatccac ggggtgcaag acggggacca gagtgatgcg agggaaggtc | 120 |
| cgggtggcca gctcgaagcg ctagtgctg gccagctcca ctgccagcac cttcaggaac | 180 |
| agcttggcca agtgcttgcc caggcaggtc cgcacgccac cgccaaacgg gaggtaatgg | 240 |
| aagcggccat ccttatcctc actgcgtgcc tgactgaagc ggtccgggtc aaacacattc | 300 |
| acgtccttga acacgggcgc tgtgtcgtga gtgtctcgga tgctatacat gacactccag | 360 |
| cccttgggga tctggaaacc | 380 |

<210> SEQ ID NO 26
<211> LENGTH: 83
<212> TYPE: DNA
<213> ORGANISM: Mus musculus
<220> FEATURE:
<221> NAME/KEY: misc_feature
<222> LOCATION: (83)..(83)
<223> OTHER INFORMATION: n is any nucleic acid

<400> SEQUENCE: 26

| | |
|---|---|
| aaggaacatg gcaaggagat gaccatgcag gagctgaagg atggaaccct ggagttgatc | 60 |
| ttcgcagcct acgccacgac ggn | 83 |

<210> SEQ ID NO 27
<211> LENGTH: 399
<212> TYPE: DNA
<213> ORGANISM: rattus

<400> SEQUENCE: 27

| | |
|---|---|
| cggccgccaa catgctgttt gagggcttgg agttggtgtc ggcgctggcc accctcgccg | 60 |
| cgtgcctggt gtccgtgacg ctgcttctgg cggtgtcgca gcagctgtgg cagctgcgct | 120 |
| gggctgccac ccgcgacaag agctgcaagc tgcctatccc caagggctcc atgggattcc | 180 |
| cgctcatcgg agagactggt cactggttgc tacagggttc cggcttccag tcgtcgcgcc | 240 |
| gcgagaagta tggcaacgtt ttcaagacac acttactggg gcggccgttg atccgtgtga | 300 |
| ccggtgcgga gaacgtgcgc aagatcctac tgggcgaaca ccagctagtg agcacggagt | 360 |
| gggcgcggag cgcacgcgtg ctgctgggac ccaacacgg | 399 |

<210> SEQ ID NO 28
<211> LENGTH: 4445
<212> TYPE: DNA
<213> ORGANISM: Homo sapiens
<220> FEATURE:
<221> NAME/KEY: CDS
<222> LOCATION: (1)..(1536)

<400> SEQUENCE: 28

| | |
|---|---|
| atg ctc ttt gag ggc ttg gat ctg gtg tcg gcg ctg gcc acc ctc gcc<br>Met Leu Phe Glu Gly Leu Asp Leu Val Ser Ala Leu Ala Thr Leu Ala<br>1               5                    10                 15 | 48 |
| gcg tgc ctg gtg tcc gtg acg ctg ctg ctg gcc gtg tcg cag cag ctg<br>Ala Cys Leu Val Ser Val Thr Leu Leu Leu Ala Val Ser Gln Gln Leu<br>               20                    25                    30 | 96 |
| tgg cag ctg cgc tgg gcc gcc act cgc gac aag agc tgc aag ctg ccc<br>Trp Gln Leu Arg Trp Ala Ala Thr Arg Asp Lys Ser Cys Lys Leu Pro<br>        35                    40                    45 | 144 |

```
atc ccc aag gga tcc atg ggc ttc ccg ctc atc gga gag acc ggc cac       192
Ile Pro Lys Gly Ser Met Gly Phe Pro Leu Ile Gly Glu Thr Gly His
 50                  55                  60 tgg ctg ctg cag ggt tct ggc ttc cag tcg tcg cgg agg gag aag tat       240
Trp Leu Leu Gln Gly Ser Gly Phe Gln Ser Ser Arg Arg Glu Lys Tyr
 65                  70                  75                  80 ggc aac gtg ttc aag acg cat ttg ttg ggg cgg ccg ctg ata cgc gtg       288
Gly Asn Val Phe Lys Thr His Leu Leu Gly Arg Pro Leu Ile Arg Val
                     85                  90                  95 acc ggc gcg gag aac gtg cgc aag atc ctc atg ggc gag cac cac ctc       336
Thr Gly Ala Glu Asn Val Arg Lys Ile Leu Met Gly Glu His His Leu
                100                 105                 110 gtg agc acc gag tgg cct cgc agc acc cgc atg ttg ctg ggc ccc aac       384
Val Ser Thr Glu Trp Pro Arg Ser Thr Arg Met Leu Leu Gly Pro Asn
            115                 120                 125 acg gtg tcc aat tcc att ggc gac atc cac cgc aac aag cgc aag gtc       432
Thr Val Ser Asn Ser Ile Gly Asp Ile His Arg Asn Lys Arg Lys Val
        130                 135                 140 ttc tcc aag atc ttc agc cac gag gcc ctg gag agt tac ctg ccc aag       480
Phe Ser Lys Ile Phe Ser His Glu Ala Leu Glu Ser Tyr Leu Pro Lys
145                 150                 155                 160 atc cag ctg gtg atc cag gac aca ctg cgc gcc tgg agc agc cac ccc       528
Ile Gln Leu Val Ile Gln Asp Thr Leu Arg Ala Trp Ser Ser His Pro
                165                 170                 175 gag gcc atc aac gtg tac cag gag gcg cag aag ctg acc ttc cgc atg       576
Glu Ala Ile Asn Val Tyr Gln Glu Ala Gln Lys Leu Thr Phe Arg Met
            180                 185                 190 gcc atc cgg gtg ctg ctg ggc ttc agc atc cct gag gag gac ctt ggg       624
Ala Ile Arg Val Leu Leu Gly Phe Ser Ile Pro Glu Glu Asp Leu Gly
        195                 200                 205 cac ctc ttt gag gtc tac cag cag ttt gtg gac aat gtc ttc tcc ctg       672
His Leu Phe Glu Val Tyr Gln Gln Phe Val Asp Asn Val Phe Ser Leu
    210                 215                 220 cct gtc gac ctg ccc ttc agt ggc tac cgg cgg ggc att cag gct cgg       720
Pro Val Asp Leu Pro Phe Ser Gly Tyr Arg Arg Gly Ile Gln Ala Arg
225                 230                 235                 240 cag atc ctg cag aag ggg ctg gag aag gcc atc cgg gag aag ctg cag       768
Gln Ile Leu Gln Lys Gly Leu Glu Lys Ala Ile Arg Glu Lys Leu Gln
                245                 250                 255 tgc aca cag ggc aag gac tac ttg gac gcc ctg gac ctc ctc att gag       816
Cys Thr Gln Gly Lys Asp Tyr Leu Asp Ala Leu Asp Leu Leu Ile Glu
            260                 265                 270 agc agc aag gag cac ggg aag gag atg acc atg cag gag ctg aag gac       864
Ser Ser Lys Glu His Gly Lys Glu Met Thr Met Gln Glu Leu Lys Asp
        275                 280                 285 ggg acc ctg gag ctg atc ttt gcg gcc tat gcc acc acg gcc agc gcc       912
Gly Thr Leu Glu Leu Ile Phe Ala Ala Tyr Ala Thr Thr Ala Ser Ala
    290                 295                 300 agc acc tca ctc atc atg cag ctg ctg aag cac ccc act gtg ctg gag       960
Ser Thr Ser Leu Ile Met Gln Leu Leu Lys His Pro Thr Val Leu Glu
305                 310                 315                 320 aag ctg cgg gat gag ctg cgg gct cat ggc atc ctg cac agt ggc ggc      1008
Lys Leu Arg Asp Glu Leu Arg Ala His Gly Ile Leu His Ser Gly Gly
                325                 330                 335 tgc ccc tgc gag ggc aca ctg cgc ctg gac acg ctc agt ggg ctg cgc      1056
Cys Pro Cys Glu Gly Thr Leu Arg Leu Asp Thr Leu Ser Gly Leu Arg
            340                 345                 350 tac ctg gac tgc gtc atc aag gag gtc atg cgc ctg ttc acg ccc att      1104
Tyr Leu Asp Cys Val Ile Lys Glu Val Met Arg Leu Phe Thr Pro Ile
```

|     |     |     |     |     |     |     |     |     |     |     |     |     |     |     |     |
| --- | --- | --- | --- | --- | --- | --- | --- | --- | --- | --- | --- | --- | --- | --- | --- |
|     |     | 355 |     |     |     | 360 |     |     |     |     | 365 |     |     |     |     |
| tcc | ggc | ggc | tac | cgc | act | gtg | ctg | cag | acc | ttc | gag | ctt | gat | ggt | ttc | 1152 |
| Ser | Gly | Gly | Tyr | Arg | Thr | Val | Leu | Gln | Thr | Phe | Glu | Leu | Asp | Gly | Phe |     |
|     | 370 |     |     |     | 375 |     |     |     |     | 380 |     |     |     |     |     |     |
| cag | atc | ccc | aaa | ggc | tgg | agt | gtc | atg | tat | agc | atc | cgg | gac | acc | cat | 1200 |
| Gln | Ile | Pro | Lys | Gly | Trp | Ser | Val | Met | Tyr | Ser | Ile | Arg | Asp | Thr | His |     |
| 385 |     |     |     |     | 390 |     |     |     |     | 395 |     |     |     |     | 400 |     |
| gac | aca | gcg | ccc | gtg | ttc | aaa | gac | gtg | aac | gtg | ttc | gac | ccc | gat | cgc | 1248 |
| Asp | Thr | Ala | Pro | Val | Phe | Lys | Asp | Val | Asn | Val | Phe | Asp | Pro | Asp | Arg |     |
|     |     |     |     | 405 |     |     |     |     | 410 |     |     |     |     | 415 |     |     |
| ttc | agc | cag | gcg | cgg | agc | gag | gac | aag | gat | ggc | cgc | ttc | cat | tac | ctc | 1296 |
| Phe | Ser | Gln | Ala | Arg | Ser | Glu | Asp | Lys | Asp | Gly | Arg | Phe | His | Tyr | Leu |     |
|     |     |     | 420 |     |     |     |     | 425 |     |     |     |     | 430 |     |     |     |
| ccg | ttc | ggt | ggc | ggt | gtc | cgg | acc | tgc | ctg | ggc | aag | cac | ctg | gcc | aag | 1344 |
| Pro | Phe | Gly | Gly | Gly | Val | Arg | Thr | Cys | Leu | Gly | Lys | His | Leu | Ala | Lys |     |
|     |     | 435 |     |     |     |     | 440 |     |     |     |     | 445 |     |     |     |     |
| ctg | ttc | ctg | aag | gtg | ctg | gcg | gtg | gag | ctg | gct | agc | acc | agc | cgc | ttt | 1392 |
| Leu | Phe | Leu | Lys | Val | Leu | Ala | Val | Glu | Leu | Ala | Ser | Thr | Ser | Arg | Phe |     |
| 450 |     |     |     |     | 455 |     |     |     |     | 460 |     |     |     |     |     |     |
| gag | ctg | gct | aca | cgg | acc | ttc | ccc | cgc | atc | acc | ttg | gtc | ccc | gtc | ctg | 1440 |
| Glu | Leu | Ala | Thr | Arg | Thr | Phe | Pro | Arg | Ile | Thr | Leu | Val | Pro | Val | Leu |     |
| 465 |     |     |     | 470 |     |     |     |     | 475 |     |     |     |     | 480 |     |     |
| cac | ccc | gtg | gat | ggc | ctc | agc | gtc | aag | ttc | ttt | ggc | ctg | gac | tcc | aac | 1488 |
| His | Pro | Val | Asp | Gly | Leu | Ser | Val | Lys | Phe | Phe | Gly | Leu | Asp | Ser | Asn |     |
|     |     |     |     | 485 |     |     |     |     | 490 |     |     |     |     | 495 |     |     |
| cag | aac | gag | atc | ctg | ccg | gag | acg | gag | gcc | atg | ctg | agc | gcc | aca | gtc | 1536 |
| Gln | Asn | Glu | Ile | Leu | Pro | Glu | Thr | Glu | Ala | Met | Leu | Ser | Ala | Thr | Val |     |
|     |     |     | 500 |     |     |     |     | 505 |     |     |     |     | 510 |     |     |     |

```
taacccaaga cccaccgcc tcagcccagc ccaggcagcg gggtggtggt tgtgggaggt   1596
agaaacctgt gtgtgggagg gggccggaac ggggagggcg agtggccccc atacttgccc   1656
tcccttgctc cccctcctg gcaaacccta cccaaagcca gtgggcccca ttcctagggc   1716
tgggctcccc ttctggctcc agcttccctc cagccactcc ccatttacca tcagctcagc   1776
ccctgggaag ggcgtggcag gggctctgca tgcccgtgac agtgttaggt gtcagcgcgt   1836
gctacagtgt ttttgtgatg ttctgaactg ctcccttccc tccgttcctt tcggacccct   1896
ttagctgggg ttgggggacg ggaagagccg tgccccttg ggcgcactct tcagcgtctc   1956
ctcctcctgc gcccccactg cgtctgccca ggaacagcat cctgggtagc agaacaggag   2016
tcaaccttgg cggggcgggg gctgcgtcca acctggagat tgcccttccc tatgccacgg   2076
ttcccaccct ccctcaccag tttggacaat ttgaaattac ctattgctgc tacttgttct   2136
gtcctctgac cttggggcaa aggagcccca ggcctgtct ccccagcatc ctccctggtg   2196
gccctgggca ggtgcactga cacccccacc ttcccatccc ctgctgaacc aggccctgtt   2256
acacacagcc gcctaaggcc cgcggctcat gtgctgcccg ccccatatt tattcactga   2316
tagagaatct tggggatgct ggggtctgga gtgaacatct cctcccttc atgccctagc   2376
ctgtgttcta gctgtcctgg cgagacttct gtgagtgaag aggaagggt ctctggtcaa   2436
acccagcccc cagggcctag ggttgaaagc cttccccggc tccgggcatt atttgggttt   2496
aatctcggag cctcactcct ggactgaagt ccggtgcctc tgccttatcc ctggtggaga   2556
tggaatgtgg cccattgcct cctccctctc tgtcaaaaa ccctgatcag gtagatttgg   2616
aggcggccac gatttcctgt ttggcccctg ttcaccccag tgcactggcc ctgactccag   2676
gcgtgagtat ggggaaggat acgggttctt ctgacgggga gcaagggcct ccgtcttccc   2736
ttccttaact ctcccccttt gccctccgcc ctgaaaaagg tgtccttgaa gtcccttcca   2796
```

```
cctctatgcc actgtctgct tagcccagct caggggtggg gaagaggcga aagcgtgggg    2856
gaggtgagcg cagcggcagt tctgcctcgg agctgattgc agggccctgt gtggtctccg    2916
gacagctgcg ggaaggctgc cgcagctgaa gctgaagagg cggctacgtg cggtttgtca    2976
gggggattgg gttgaaaact ggccagtcgg gatgactggg tgaaagagga gtagctcctg    3036
ccactggcgt tttgagtgtt ggcaatttgg gatgcctcct ggggaaggtt tccgggcgtt    3096
tggtgagtct ctagattttt ccttgctttc tgtgtttatt ggttttgat gttgtaaaag     3156 caatgaatcc cctttacaag aaaatcgaaa acacagaaga atgaaggaca tgccagtccc    3216
cgatcgctgc tgtgagcacc tcagtggctc cctcagacca gatcccgtag gcagccccac    3276
agaccgaccc tgaccccact cacagccacc ctgaagatag actataggaa cgggcccata    3336
ccacacagac tgctctccaa tccctgagtc tcagatgttt catttatttc ctacttttcc    3396
actactaaaa aacagtgtgg aatagacatt attggcaaaa ttgctcatcc ctaatcctga    3456
aaaacaggcc agaatgggta aagacttgtc aaagcttgca acatagctac atggtgcacc    3516
cggacctgta ccccctcccc ccaacacaaa accagtgtct gggaggttca ttttcccttta   3576 aactgatcca gctggccctg aaccaattgt ttttgactga gtatctagga gagcagtaag    3636
tggaacttca gacaagccca ctgggtctgg tccaggtgag gggcaggggg catgggctg     3696 ggaggtctca ggggccttcc ctgggggtgg ccagcctggt aggggggcaga aaggaaaag    3756 ctgagggggg tccctgtgag ggaggaaaga aggatcattt gccccgctgg gtctcaaagg    3816
cagtgagaag agagctgaag aaagctctgg ctggctgaca ggatccctgt gttgtaattg    3876
gtccctcctt tcagctctct agtgagatgc ccgtgtctgt gcgtgtgcgt gtgtgtttca    3936
tacagctagc attagatggg tgatgtttct tacttatcat ccctaactat tgcaacttga    3996
ccttaaaaag acaaaacccc acaaaactct tcctgccacg ggcttgcaga ttgaagcact    4056
ttcgatgttg ggcgctggcg tttgtgttct gggcaccacc gtgaccctgc ccagatggct    4116
ataatattat tttatacaca aacctttttt ttcataaatg ttataatttt gtgtctgtct    4176
ttataaacta ttataagtac tatttttgtt ataattcaaa atagatattt agtataaagt    4236
ttttgctgtt aaatatttgt tatttagtaa aatatgaatt ttgctctatt gtaaacatgg    4296
ttcaaaatat taatatgttt ttatcacagt cgttttaata ttgaaaaagc acttgtgtgt    4356
tttgttttga tatgaaactg gtaccgtgtg agtgtttttg ctgtcgtggt tttaatctgt    4416
atataatatt ccatgttgca tattaaaaa                                     4445
```

<210> SEQ ID NO 29
<211> LENGTH: 24
<212> TYPE: DNA
<213> ORGANISM: Artificial Sequence
<220> FEATURE:
<223> OTHER INFORMATION: primers and probes

<400> SEQUENCE: 29
tccctgcctg tcgacctgcc cttc                                          24

<210> SEQ ID NO 30
<211> LENGTH: 24
<212> TYPE: DNA
<213> ORGANISM: Artificial Sequence
<220> FEATURE:
<223> OTHER INFORMATION: primers and probes

<400> SEQUENCE: 30

| | |
|---|---|
| gacactccag cctttgggga tctg | 24 |

<210> SEQ ID NO 31
<211> LENGTH: 26
<212> TYPE: DNA
<213> ORGANISM: Artificial Sequence
<220> FEATURE:
<223> OTHER INFORMATION: primers and probes

<400> SEQUENCE: 31

| | |
|---|---|
| tgaaggtcgg agtcaacgga tttggt | 26 |

<210> SEQ ID NO 32
<211> LENGTH: 24
<212> TYPE: DNA
<213> ORGANISM: Artificial Sequence
<220> FEATURE:
<223> OTHER INFORMATION: primers and probes

<400> SEQUENCE: 32

| | |
|---|---|
| catgtgggcc atgaggtcca ccac | 24 |

<210> SEQ ID NO 33
<211> LENGTH: 32
<212> TYPE: DNA
<213> ORGANISM: Artificial Sequence
<220> FEATURE:
<223> OTHER INFORMATION: primers and probes

<400> SEQUENCE: 33

| | |
|---|---|
| gtgtgccctc gcagggcag ccgccactgt gc | 32 |

<210> SEQ ID NO 34
<211> LENGTH: 32
<212> TYPE: DNA
<213> ORGANISM: Artificial Sequence
<220> FEATURE:
<223> OTHER INFORMATION: primers and probes

<400> SEQUENCE: 34

| | |
|---|---|
| cgcctcggat gcccgcagcc cgcagatctt gg | 32 |

<210> SEQ ID NO 35
<211> LENGTH: 20
<212> TYPE: DNA
<213> ORGANISM: Artificial Sequence
<220> FEATURE:
<223> OTHER INFORMATION: primers and probes

<400> SEQUENCE: 35

| | |
|---|---|
| gccttcgagg aaatgacccg | 20 |

<210> SEQ ID NO 36
<211> LENGTH: 20
<212> TYPE: DNA
<213> ORGANISM: Artificial Sequence
<220> FEATURE:
<223> OTHER INFORMATION: primers and probes

<400> SEQUENCE: 36

| | |
|---|---|
| ctggatgcat cctctgggtg | 20 |

<210> SEQ ID NO 37
<211> LENGTH: 21
<212> TYPE: DNA
<213> ORGANISM: Artificial Sequence

```
<220> FEATURE:
<223> OTHER INFORMATION: primers and probes

<400> SEQUENCE: 37
gtctaccagc agtttgtgga c                                              21

<210> SEQ ID NO 38
<211> LENGTH: 22
<212> TYPE: DNA
<213> ORGANISM: Artificial Sequence
<220> FEATURE:
<223> OTHER INFORMATION: primers and probes

<400> SEQUENCE: 38
agtccaggta gcgcagccca ct                                             22

<210> SEQ ID NO 39
<211> LENGTH: 26
<212> TYPE: DNA
<213> ORGANISM: Artificial Sequence
<220> FEATURE:
<223> OTHER INFORMATION: primers and probes

<400> SEQUENCE: 39
tgaaggtcgg agtcaacgga tttggt                                         26

<210> SEQ ID NO 40
<211> LENGTH: 24
<212> TYPE: DNA
<213> ORGANISM: Artificial Sequence
<220> FEATURE:
<223> OTHER INFORMATION: primers and probes

<400> SEQUENCE: 40
catgtgggcc atgaggtcca ccac                                           24

<210> SEQ ID NO 41
<211> LENGTH: 21
<212> TYPE: DNA
<213> ORGANISM: Artificial Sequence
<220> FEATURE:
<223> OTHER INFORMATION: primers and probes

<400> SEQUENCE: 41
gtctaccagc agtttctcga c                                              21

<210> SEQ ID NO 42
<211> LENGTH: 21
<212> TYPE: DNA
<213> ORGANISM: Artificial Sequence
<220> FEATURE:
<223> OTHER INFORMATION: primer

<400> SEQUENCE: 42
ggctgcctct ctaacctgca c                                              21

<210> SEQ ID NO 43
<211> LENGTH: 25
<212> TYPE: DNA
<213> ORGANISM: Artificial Sequence
<220> FEATURE:
<223> OTHER INFORMATION: primer

<400> SEQUENCE: 43
gatcagagat gtggctgctg cactg                                          25
```

```
<210> SEQ ID NO 44
<211> LENGTH: 27
<212> TYPE: DNA
<213> ORGANISM: Artificial Sequence
<220> FEATURE:
<223> OTHER INFORMATION: primer

<400> SEQUENCE: 44
gcaagggacc agctgcatcg gcacctg                                          27

<210> SEQ ID NO 45
<211> LENGTH: 25
<212> TYPE: DNA
<213> ORGANISM: Artificial Sequence
<220> FEATURE:
<223> OTHER INFORMATION: primer

<400> SEQUENCE: 45
ctcgtgcgtg tcccggatgc tatac                                            25

<210> SEQ ID NO 46
<211> LENGTH: 20
<212> TYPE: DNA
<213> ORGANISM: Artificial Sequence
<220> FEATURE:
<223> OTHER INFORMATION: primer

<400> SEQUENCE: 46
ggaatgggct atgcctctga                                                  20

<210> SEQ ID NO 47
<211> LENGTH: 32
<212> TYPE: DNA
<213> ORGANISM: Artificial Sequence
<220> FEATURE:
<223> OTHER INFORMATION: primer

<400> SEQUENCE: 47
atctggcacc acaccttcta caatgagctg cg                                    32

<210> SEQ ID NO 48
<211> LENGTH: 32
<212> TYPE: DNA
<213> ORGANISM: Artificial Sequence
<220> FEATURE:
<223> OTHER INFORMATION: primer

<400> SEQUENCE: 48
cgtcatactc ctgcttgctg atccacatct gc                                    32
```